(12) United States Patent
Hatakeyama

(10) Patent No.: US 11,644,753 B2
(45) Date of Patent: May 9, 2023

(54) RESIST COMPOSITION AND PATTERNING PROCESS

(71) Applicant: Shin-Etsu Chemical Co., Ltd., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 154 days.

(21) Appl. No.: 17/212,275

(22) Filed: Mar. 25, 2021

(65) Prior Publication Data

US 2023/0021453 A1 Jan. 26, 2023

(30) Foreign Application Priority Data

Jun. 25, 2020 (JP) .............................. JP2020-109898

(51) Int. Cl.

| | |
|---|---|
| *G03F 7/039* | (2006.01) |
| *C08F 220/18* | (2006.01) |
| *C08F 220/28* | (2006.01) |
| *G03F 7/004* | (2006.01) |
| *C07C 211/62* | (2006.01) |
| *C07C 211/63* | (2006.01) |
| *C07C 381/12* | (2006.01) |

(52) U.S. Cl.
CPC .......... *G03F 7/0392* (2013.01); *C07C 211/62* (2013.01); *C07C 211/63* (2013.01); *C07C 381/12* (2013.01); *C08F 220/18* (2013.01); *C08F 220/283* (2020.02); *G03F 7/0045* (2013.01)

(58) Field of Classification Search
CPC ...... G03F 7/004; G03F 7/0395; G03F 7/0397; C07C 211/62; C07C 211/63
See application file for complete search history.

(56) References Cited

U.S. PATENT DOCUMENTS

| | | | |
|---|---|---|---|
| 8,921,026 B2 | 12/2014 | Hatakeyama et al. | |
| 11,187,980 B2 * | 11/2021 | Hatakeyama | ......... G03F 7/0045 |
| 11,281,101 B2 * | 3/2022 | Hatakeyama | ......... G03F 7/0392 |
| 11,415,887 B2 * | 8/2022 | Hatakeyama | ......... G03F 7/0045 |
| 11,460,773 B2 * | 10/2022 | Hatakeyama | ......... C08F 212/24 |
| 2014/0120470 A1 * | 5/2014 | Pohlers | ................. G03F 7/0046 |
| | | | 430/325 |
| 2021/0048748 A1 * | 2/2021 | Hatakeyama | ......... G03F 7/0397 |
| 2022/0260909 A1 * | 8/2022 | Hatakeyama | ............. G03F 1/76 |

FOREIGN PATENT DOCUMENTS

| | | | | |
|---|---|---|---|---|
| JP | 2001-166476 A | | 6/2001 | |
| JP | 2001-194776 A | | 7/2001 | |
| JP | 2002-226470 A | | 8/2002 | |
| JP | 2002-363148 A | | 12/2002 | |
| JP | 2012-137729 A | | 7/2012 | |
| JP | 2018036644 A | * | 3/2018 | .............. C07F 19/00 |
| WO | 2008/066011 A1 | | 6/2008 | |
| WO | WO-2012063840 A1 | * | 5/2012 | ............ C08F 220/18 |

* cited by examiner

*Primary Examiner* — Amanda C. Walke

(74) *Attorney, Agent, or Firm* — WHDA, LLP

(57) ABSTRACT

A resist composition is provided comprising a base polymer and a quencher comprising a salt compound consisting of a cyclic ammonium cation and a 1,1,1,3,3,3-hexafluoro-2-propoxide anion having a trifluoromethyl, hydrocarbylcarbonyl or hydrocarbyloxycarbonyl group bonded thereto. The resist composition has a high sensitivity and forms a pattern with improved LWR or CDU, independent of whether it is of positive or negative tone.

13 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2020-109898 filed in Japan on Jun. 25, 2020, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, 20 manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

With the progress of miniaturization in logic devices, the flash memory now takes the form of devices having stacked layers of gate, known as 3D-NAND. The capacity is increased by increasing the number of stacked layers. As the number of stacked layers increases, the hard mask used in processing of layers becomes thicker and the photoresist film also becomes thicker. While the resist for logic devices becomes thinner, the resist for 3D-NAND becomes thicker.

As the pattern feature size is reduced, approaching to the diffraction limit of light, light contrast lowers. In the case of positive resist film, a lowering of light contrast leads to reductions of resolution and focus margin of hole and trench patterns. The trend of the resist toward thicker films suggests that the thickness of resist film for previous generation devices is resumed. As more dimensional uniformity is required, the previous photoresist cannot accommodate the requirements. For preventing a reduction of resolution of resist pattern due to a lowering of light contrast as a result of size reduction, or for improving dimensional uniformity in the trend toward thicker resist film, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 and 2.

There are known amine quenchers for inviting a polarity switch under the action of acid catalyst. Patent Document 3 proposes an amine quencher having an acid labile group. This amine compound generates a carboxylic acid via the acid-aided deprotection reaction of a tertiary ester having a carbonyl group positioned on the nitrogen atom side whereby alkaline solubility increases. In this case, however, since the molecular weight on the nitrogen atom side is not increased, the acid diffusion controlling ability is low, and the contrast improving effect is faint. Patent Document 4 describes a quencher having a tert-butoxycarbonyl group which undergoes deprotection reaction with the aid of acid, to generate an amino group. This mechanism is adapted to generate a quencher upon light exposure, achieving a reverse effect to contrast enhancement. The contrast is enhanced by the mechanism that the quencher disappears or loses its quenching ability upon light exposure or under the action of acid. Patent Document 5 discloses a quencher in the form of an amine compound which cyclizes under the action of acid to form a lactam structure. The conversion of the strong base amine compound to the weak base lactam compound causes the acid to change its activity whereby the contrast is improved.

With respect to the acid labile group used in (meth) acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 6 discloses a resist composition comprising a sulfonium or iodonium salt capable of generating carboxylic acid as a quencher.

Sulfonium and iodonium salt type quenchers are photodecomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

Since a sulfonium or iodonium salt type quencher absorbs ArF radiation of wavelength 193 nm, a resist film in which the quencher is combined with a sulfonium or iodonium salt type acid generator has a reduced transmittance to that radiation. As a result, in the case of a resist film having a thickness of at least 100 nm, the cross-sectional profile of a pattern as developed becomes tapered. For resist films having a thickness of at least 100 mu, especially at least 150 nm, a highly transparent quencher is necessary.

Lowering the PEB temperature is effective for suppressing acid diffusion. However, the dissolution contrast is reduced, inviting degradations of resolution and LWR. There is the need for a resist composition of new concept featuring controlled acid diffusion and a high contrast.

CITATION LIST

Patent Document 1: JP-A 2001-194776
Patent Document 2: JP-A 2002-226470

Patent Document 3: JP-A 2002-363148
Patent Document 4: JP-A 2001-166476
Patent Document 5: JP-A 2012-137729 (U.S. Pat. No. 8,921,026)
Patent Document 6: WO 2008/066011

DISCLOSURE OF INVENTION

For the acid-catalyzed chemically amplified resist material, it is desired to develop a quencher capable of reducing the LWR of line patterns or improving the CDU of hole patterns and increasing sensitivity. To this end, it is necessary to reduce the distance of acid diffusion significantly and to increase the contrast at the same time, that is, to improve ambivalent properties at the same time.

An object of the invention is to provide a resist composition which exhibits a high sensitivity and a reduced LWR or improved CDU, independent of whether it is of positive tone or negative tone; and a pattern forming process using the same.

The inventor has found that using a salt consisting of a cyclic ammonium cation having a tertiary ester structure and a 1,1,1,3,3,3-hexafluoro-2-propoxide anion having a trifluoromethyl, hydrocarbylcarbonyl or hydrocarbyloxycarbonyl group bonded thereto as the quencher, a resist material having a reduced LWR, improved CDU, high contrast, improved resolution, and wide process margin is obtainable.

In one aspect, the invention provides a resist composition comprising a base polymer and a quencher, the quencher comprising a salt compound consisting of a cyclic ammonium cation having the formula (A-1) or (A-2) and a 1,1,1,3,3,3-hexafluoro-2-propoxide anion having bonded thereto a group selected from trifluoromethyl, hydrocarbylcarbonyl and hydrocarbyloxycarbonyl.

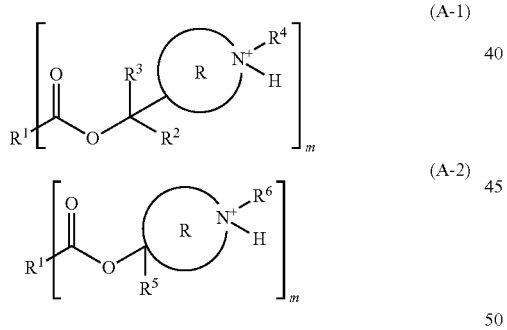

Herein m is an integer of 1 to 6.

$R^1$ is a $C_1$-$C_{30}$ hydrocarbyl group when m=1, a single bond or $C_1$-$C_{30}$ hydrocarbylene group when m=2, and a m-valent $C_1$-$C_{30}$ hydrocarbon group when m is an integer of 3 to 6, the hydrocarbyl, hydrocarbylene and m-valent hydrocarbon groups may contain at least one moiety selected from hydroxyl, thiol, ester bond, thioester bond, thionoester bond, ether bond, sulfide bond, halogen, nitro, amino, amide bond, sulfonyl, sulfonate bond, sultone ring, lactam ring, and carbonate, exclusive of an aromatic hydrocarbon group having iodine bonded to the aromatic ring.

$R^2$ and $R^3$ are each independently a $C_1$-$C_6$ saturated hydrocarbyl group, $R^2$ and $R^3$ may bond together to form a ring with the carbon atom to which they are attached, $R^4$ and $R^5$ are each independently hydrogen, a $C_1$-$C_4$ alkyl group or $C_2$-$C_{12}$ alkoxycarbonyl group, $R^5$ is a $C_1$-$C_6$ aliphatic hydrocarbyl group or $C_6$-$C_{12}$ aryl group, which may be substituted with halogen or trifluoromethyl, the ring R is a $C_2$-$C_{10}$ alicyclic group containing the nitrogen atom.

In a preferred embodiment, the 1,1,1,3,3,3-hexafluoro-2-propoxide anion having bonded thereto a group selected from trifluoromethyl, hydrocarbylcarbonyl and hydrocarbyloxycarbonyl has the formula (B).

Herein $R^7$ is a trifluoromethyl group, $C_1$-$C_{20}$ hydrocarbyloxy group or $C_2$-$C_{21}$ hydrocarbyloxycarbonyl group, the hydrocarbyl moiety in the hydrocarbyloxy group or hydrocarbyloxycarbonyl group may contain at least one moiety selected from ether bond, ester bond, thiol, cyano, nitro, hydroxyl, sultone, sulfonate bond, amide bond, and halogen.

The resist composition may further comprise an acid generator capable of generating a sulfonic acid, imide acid or methide acid, an organic solvent, and/or a surfactant.

In a preferred embodiment, the base polymer comprises recurring units having the formula (a1) or recurring units having the formula (a2).

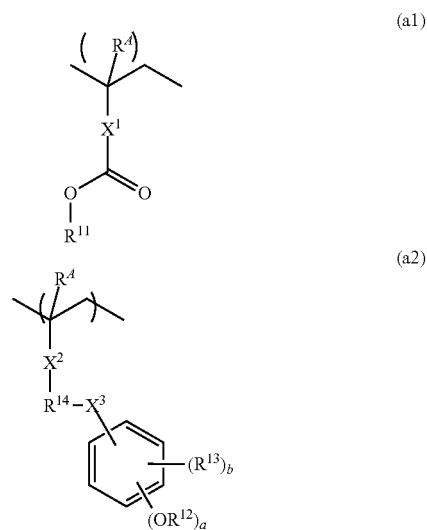

Herein $R^A$ is each independently hydrogen or methyl. $X^1$ is a single bond, phenylene, naphthylene, or a $C_1$-$C_{12}$ linking group containing an ester bond and/or lactone ring. $X^2$ is a single bond or ester bond. $X^3$ is a single bond, ether bond or ester bond. $R^{11}$ and $R^{12}$ are each independently an acid labile group. $R^{13}$ is fluorine, trifluoromethyl, cyano or $C_1$-$C_6$ saturated hydrocarbyl group. $R^{14}$ is a single bond or a $C_1$-$C_6$ alkanediyl group in which some carbon may be replaced by an ether bond or ester bond, "a" is 1 or 2, "b" is an integer of 0 to 4, and $1 \leq a+b \leq 5$.

Typically, the resist composition is a chemically amplified positive resist composition.

In another embodiment, the base polymer is free of an acid labile group. Typically, the resist composition is a chemically amplified negative resist composition.

In a preferred embodiment, the base polymer comprises recurring units of at least one type selected from recurring units having the formulae (f1) to (f3).

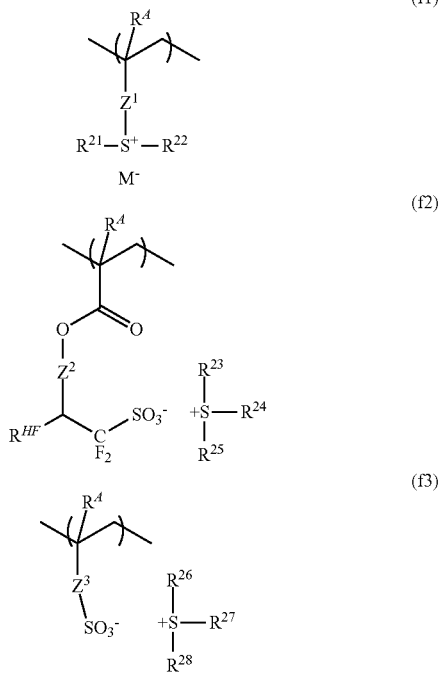

Herein $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, wherein $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ saturated hydrocarbylene group which may contain a carbonyl moiety, ester bond or ether bond. $Z^{31}$ is a single bond, methylene, ethylene, phenylene, fluorinated phenylene, —O—$Z^{31}$—, —C(=O)—O—$Z^{31}$— or —C(=O)—NH—$Z^{31}$—, wherein $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety. $R^{21}$ to $R^{22}$ are each independently halogen or a $C_1$-$C_{20}$ hydrocarbyl group which may contain a heteroatom, a pair of $R^2$ and $R^{24}$ or $R^{26}$ and $R^{27}$ may bond together to form a ring with the sulfur atom to which they are attached. $R^{HF}$ is hydrogen or trifluoromethyl. $M^-$ is a non-nucleophilic counter ion.

In another aspect, the invention provides a pattern forming process comprising the steps of applying the resist composition defined above to form a resist film on a substrate, exposing the resist film to high-energy radiation, and developing the exposed resist film in a developer.

In a preferred embodiment, the high-energy radiation is i-line of wavelength 365 nm, ArF excimer laser of wavelength 193 nm. KrF excimer laser of wavelength 248 nm, EB, or EUV of wavelength 3 to 15 nm.

Advantageous Effects of Invention

The cyclic ammonium salt compound is a quencher capable of suppressing acid diffusion by virtue of nitrogen. Since the compound also has an acid-decomposable tertiary ester structure, it is decomposed with acid in the exposed region and converted to a cyclic ammonium salt compound having a lower molecular weight. As a result, the acid in the exposed region becomes more active and the contrast is improved. There are obtained advantages including low acid diffusion, high contrast, high sensitivity, low LWR, and improved CDU. A resist composition having a high sensitivity, low LWR and improved CDU is thus designed.

DESCRIPTION OF EMBODIMENTS

As used herein, the singular forms "a," "an" and "the" include plural referents unless the context clearly dictates otherwise. The notation ($C_n$-$C_m$) means a group containing from to m carbon atoms per group. The term"group" and "moiety" are interchangeable. In chemical formulae, the broken line designates a valence bond, and Me stands for methyl and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher containing a cyclic ammonium salt compound having a tertiary ester structure.

Cyclic Ammonium Salt Compound Having Tertiary Ester Structure

The cyclic ammonium salt compound having a tertiary ester structure is a salt compound consisting of a cyclic ammonium cation having the formula (A-1) or (A-2) shown below and a 1,1,1,3,3,3-hexafluoro-2-propoxide anion having bonded thereto a group selected from trifluoromethyl, hydrocarbylcarbonyl and hydrocarbyloxycarbonyl.

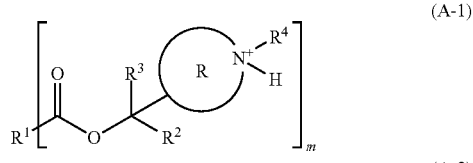

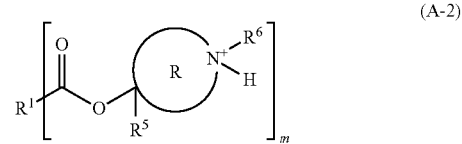

In formulae (A-1) and (A-2), m is an integer of 1 to 6, preferably an integer of 1 to 4, more preferably 1 or 2, and most preferably 1.

In formulae (A-1) and (A-2), $R^1$ is a $C_1$-$C_{30}$ hydrocarbyl group when m=1, a single bond or $C_1$-$C_{30}$ hydrocarbylene group when m=2, and a m-valent $C_1$-$C_{30}$ hydrocarbon group when m is an integer of 3 to 6. The hydrocarbyl, hydrocarbylene and m-valent hydrocarbon groups each may contain at least one moiety selected from hydroxyl, thiol, ester bond, thioester bond, thionoester bond, ether bond, sulfide bond, halogen, nitro, amino, amide bond, sulfonyl, sulfonate bond, sultone ring, lactam ring, and carbonate, but exclude an aromatic hydrocarbon group having iodine bonded to the aromatic ring.

The hydrocarbyl group may be saturated or unsaturated and straight, branched or cyclic. Examples thereof include $C_1$-$C_{30}$ alkyl groups such as methyl, ethyl, n-propyl, isopropyl, n-butyl, isobutyl, sec-butyl, tert-butyl, n-pentyl, isopentyl, sec-pentyl, 3-pentyl, tert-pentyl, neopentyl, n-hexyl, n-octyl, n-nonyl n-decyl, undecyl, dodecyl, tridecyl, tetradecyl, pentadecyl, heptadecyl, octadecyl, nonadecyl and icosyl; $C_3$-$C_{30}$ cyclic saturated hydrocarbyl groups such as cyclopropyl, cyclopentyl, cyclohexyl, norbornyl, adamantyl and cyclopentahydrophenanthrene; $C_2$-$C_{30}$ alkenyl groups such as vinyl, 1-methylvinyl, 1-propenyl, 2-propenyl, butenyl, pentenyl and hexenyl; $C_2$-$C_{20}$ alkynyl groups such as ethynyl, propynyl and butynyl; $C_3$-$C_{30}$ cyclic unsaturated aliphatic hydrocarbyl groups such as cyclopentenyl, cyclohexenyl and norbornenyl; $C_6$-$C_{30}$ aryl groups such as phenyl, naphthyl, phenanthryl, anthryl and fluorenyl; $C_7$-$C_{30}$ aralkyl groups such as benzyl and phenethyl; and combinations thereof.

The hydrocarbylene group may be saturated or unsaturated and straight, branched or cyclic. Examples thereof include groups obtained by removing one hydrogen atom from the exemplary groups illustrated above for the hydrocarbyl group. The m-valent hydrocarbon group may be saturated or unsaturated and straight, branched or cyclic. Examples thereof include groups obtained by removing (m−1) number of hydrogen atoms from the exemplary groups illustrated above for the hydrocarbyl group.

In formula (A-1). $R^2$ and $R^3$ are each independently a $C_1$-$C_6$ saturated hydrocarbyl group, and $R^2$ and $R^3$ may bond together to form a ring with the carbon atom to which they are attached. The saturated hydrocarbyl group may be straight, branched or cyclic and examples thereof include alkyl groups such as methyl, ethyl, n-propyl, isopropyl, n-butyl, isobutyl, sec-butyl, tert-butyl, n-pentyl and n-hexyl and cyclic saturated hydrocarbyl groups such as cyclopropyl, cyclobutyl, cyclopentyl and cyclohexyl.

In formulae (A-1) and (A-2), $R^4$ and $R^6$ are each independently hydrogen, a $C_1$-$C_4$ alkyl group or $C_2$-$C_{12}$ alkoxycarbonyl group. Suitable $C_1$-$C_4$ alkyl groups include methyl, ethyl, n-propyl, isopropyl, n-butyl, isobutyl, sec-butyl, and tert-butyl. Suitable $C_2$-$C_{12}$ alkoxycarbonyl groups include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, sec-pentyloxycarbonyl, tert-pentyloxycarbonyl, neopentyloxycarbonyl, n-hexyloxycarbonyl, n-heptyloxycarbonyl, n-octyloxycarbonyl, 2-ethylhexyloxycarbonyl, n-nonyloxycarbonyl, n-decyloxycarbonyl, n-undecyloxycarbonyl, n-dodecyloxycarbonyl, n-tridecyloxycarbonyl, n-pentadecyloxycarbonyl, vinyloxycarbonyl, 1-propenyloxycarbonyl, and 2-propenyloxycarbonyl.

In formula (A-2). $R^5$ is a $C_1$-$C_6$ aliphatic hydrocarbyl group or $C_6$-$C_{12}$ aryl group, which may be substituted with halogen or trifluoromethyl. The $C_1$-$C_6$ aliphatic hydrocarbyl group may be saturated or unsaturated and straight, branched or cyclic. Examples thereof include alkyl groups such as methyl, ethyl, n-propyl, isopropyl, α-butyl, isobutyl, sec-butyl, tert-butyl, n-pentyl and n-hexyl, cyclic saturated hydrocarbyl groups such as cyclopropyl, cyclobutyl, cyclopentyl and cyclohexyl, alkenyl groups such as vinyl, 1-propenyl, 2-propenyl, butenyl and hexenyl, alkynyl groups such as ethynyl, propynyl and butynyl, and cyclic unsaturated hydrocarbyl groups such as cyclohexenyl. Suitable $C_6$-$C_{12}$ aryl groups include phenyl, tolyl, xylyl, l-naphthyl and 2-naphthyl.

Among others. $R^2$ and $R^3$ are preferably $C_1$-$C_3$ alkyl groups. $R^4$ and $R^6$ are preferably hydrogen, $C_1$-$C_4$ alkyl groups or $C_2$-$C_6$ alkoxycarbonyl groups. $R^5$ is preferably a $C_1$-$C_6$ alkyl group, $C_2$-$C_4$ alkenyl group or $C_2$-$C_4$ alkynyl group.

In formulae (A-1) and (A-2), the ring R is a $C_2$-$C_{10}$ alicyclic group containing the nitrogen atom in the formula. Suitable alicyclic groups include groups corresponding to cyclic hydrocarbons such as cyclopropane, cyclopentane, cyclohexane, norbornane, and adamantane, in which one carbon is replaced by nitrogen.

Examples of the cation having formula (A-1) are shown below, but not limited thereto.

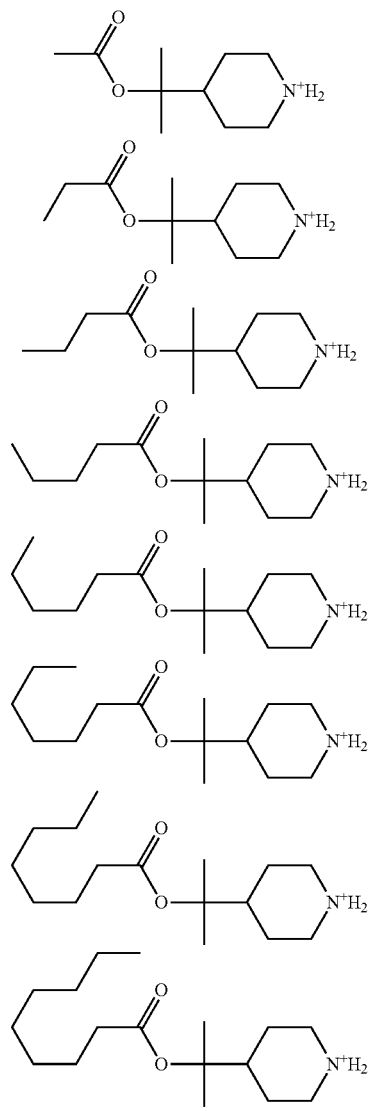

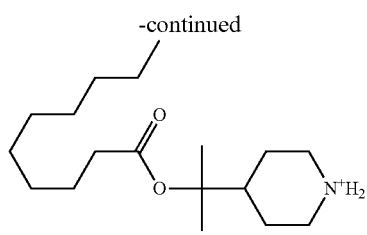
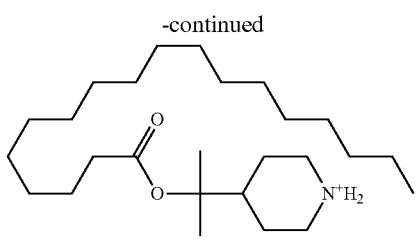
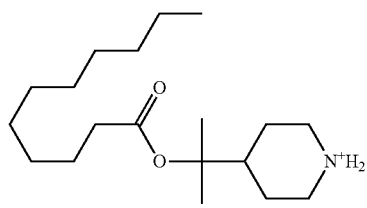
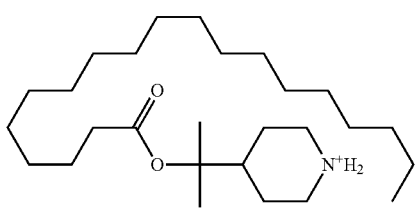
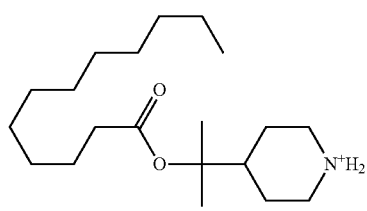
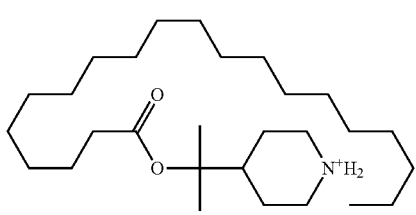
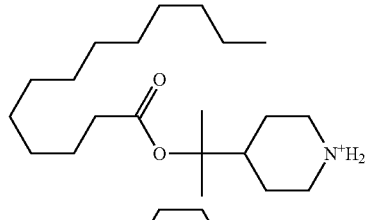
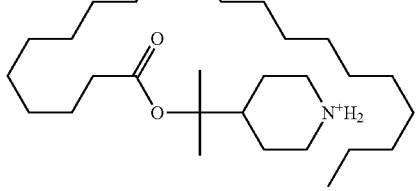
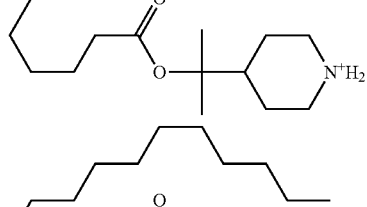
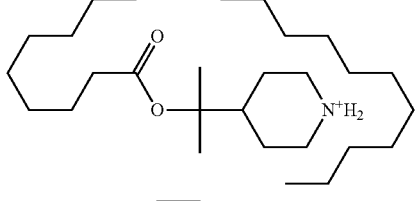
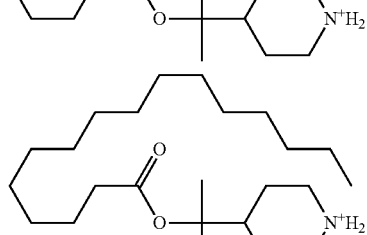
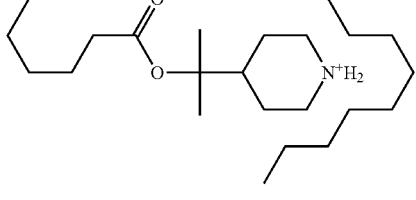
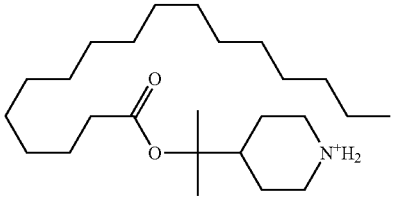

-continued
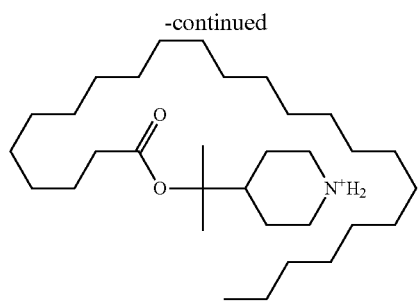
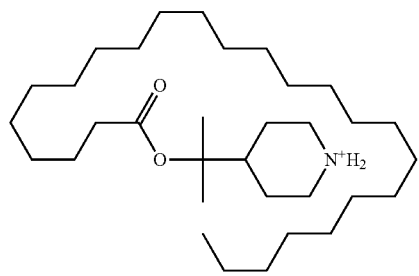
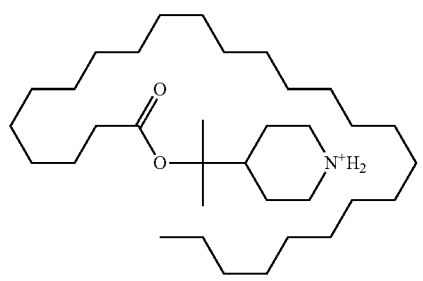
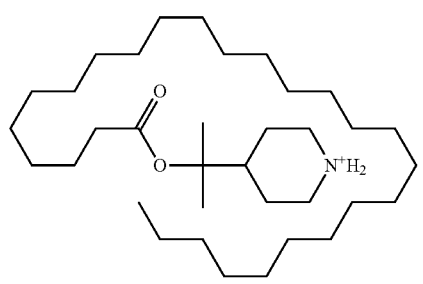
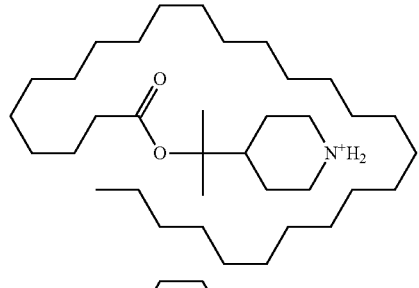
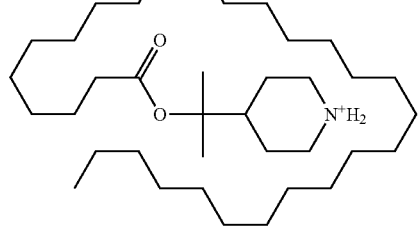
-continued
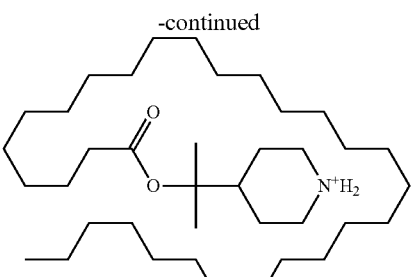

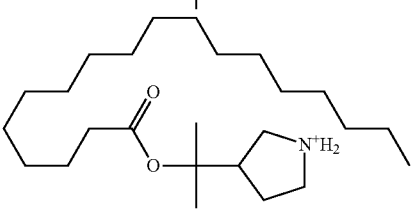
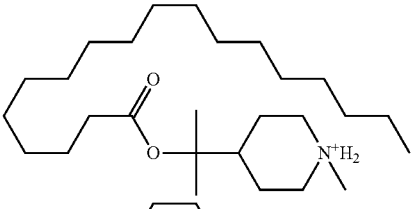
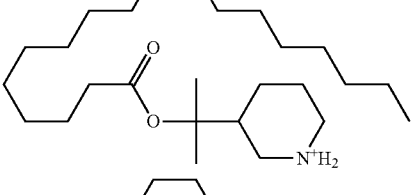
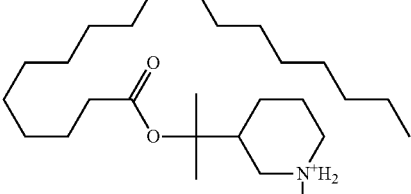
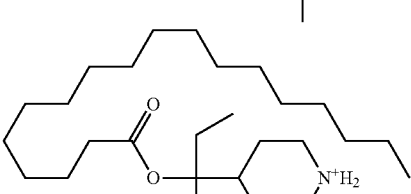
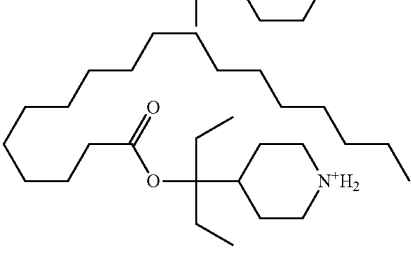

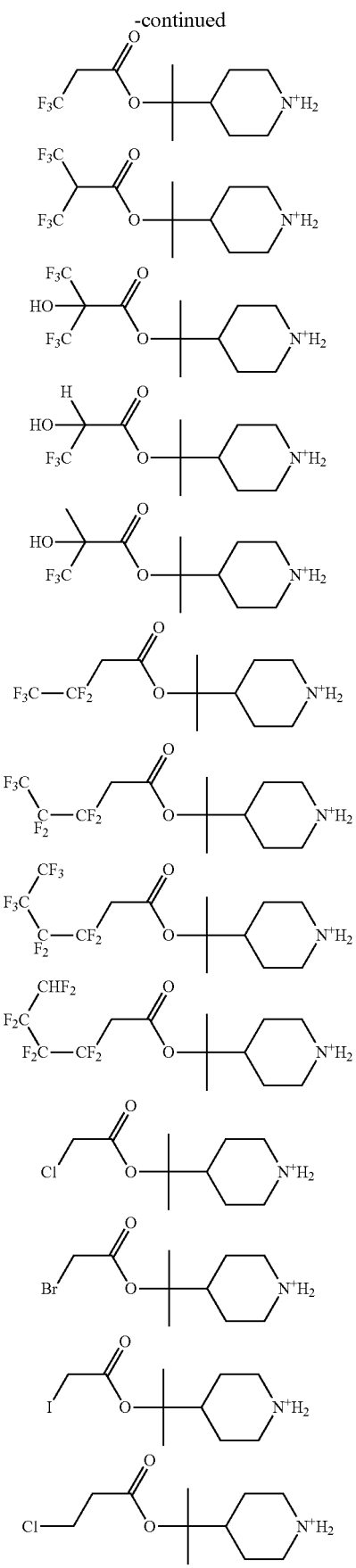
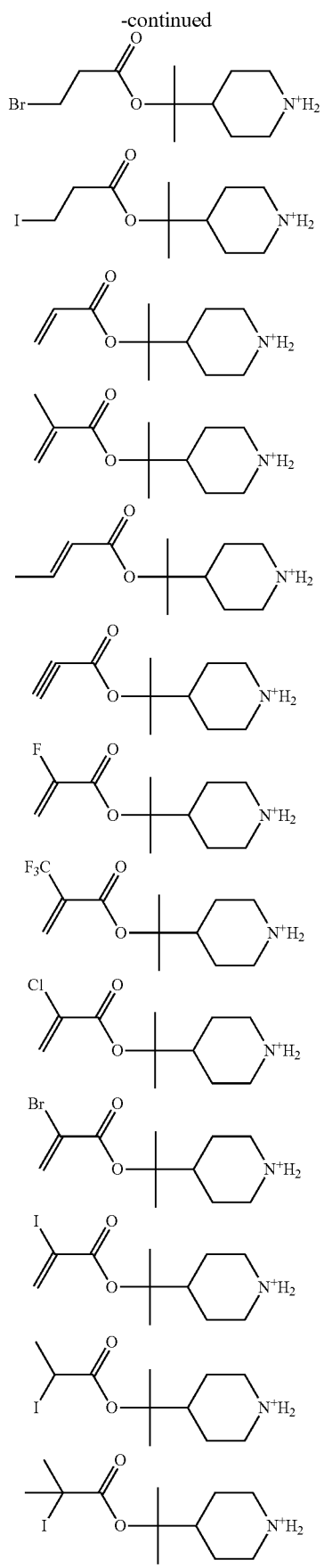

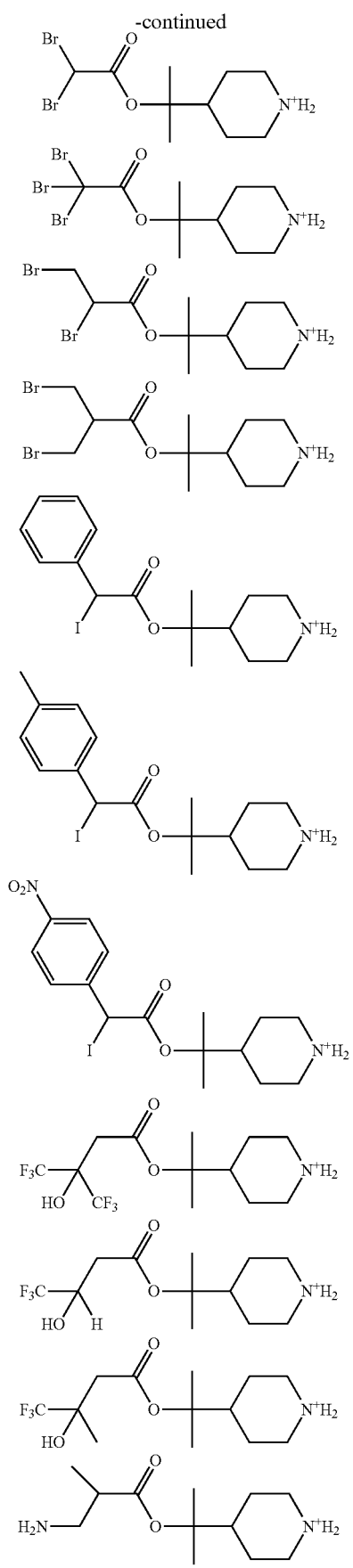
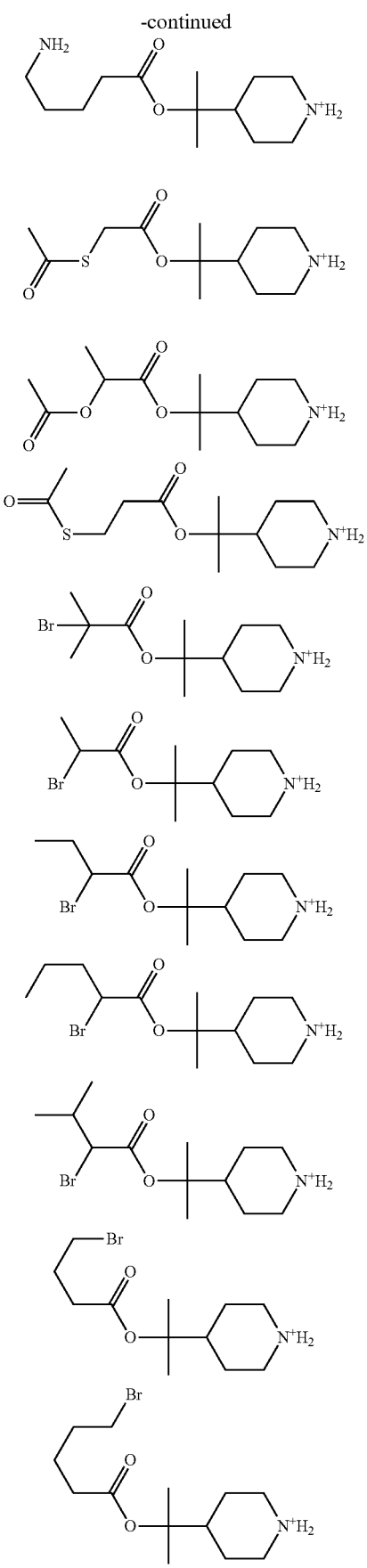

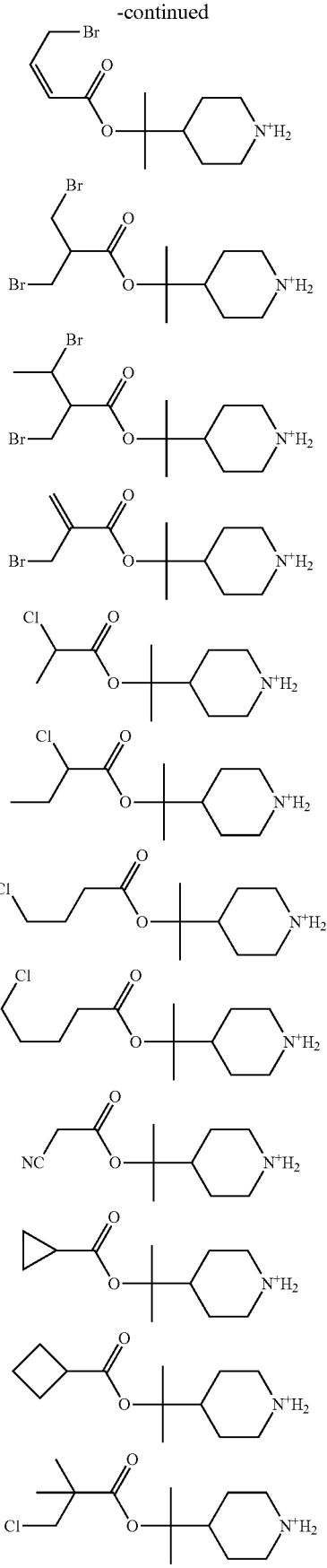
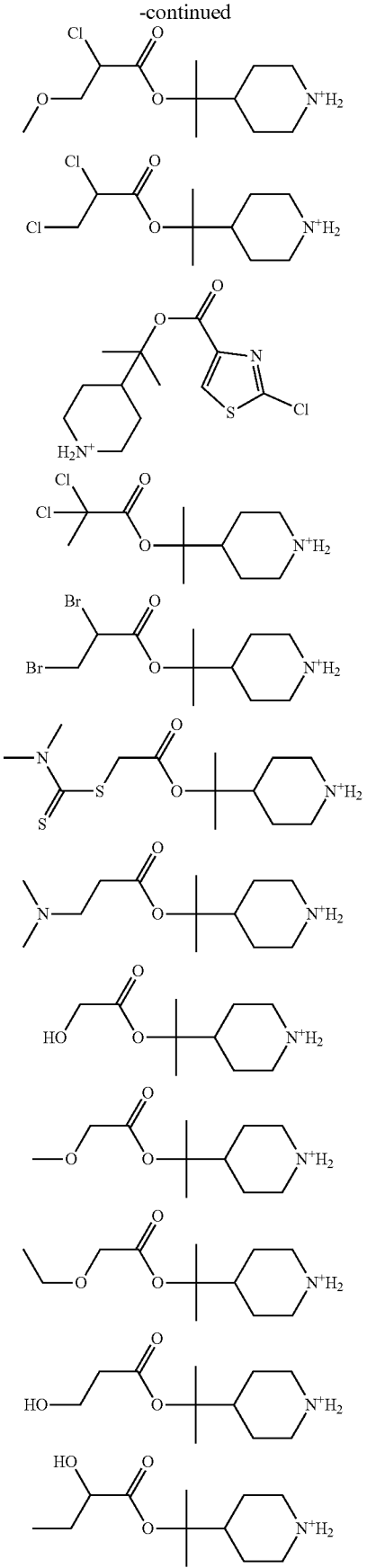

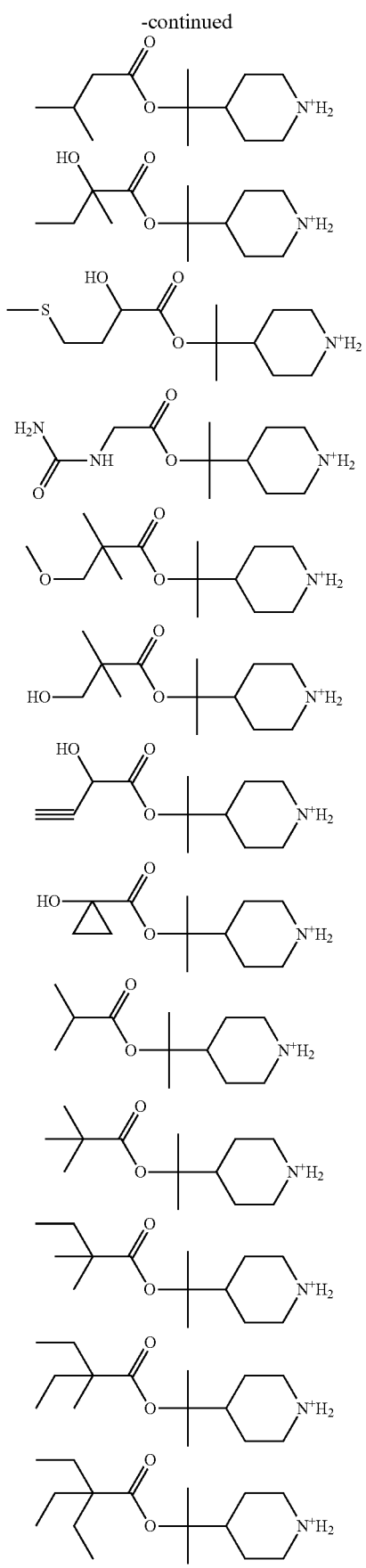
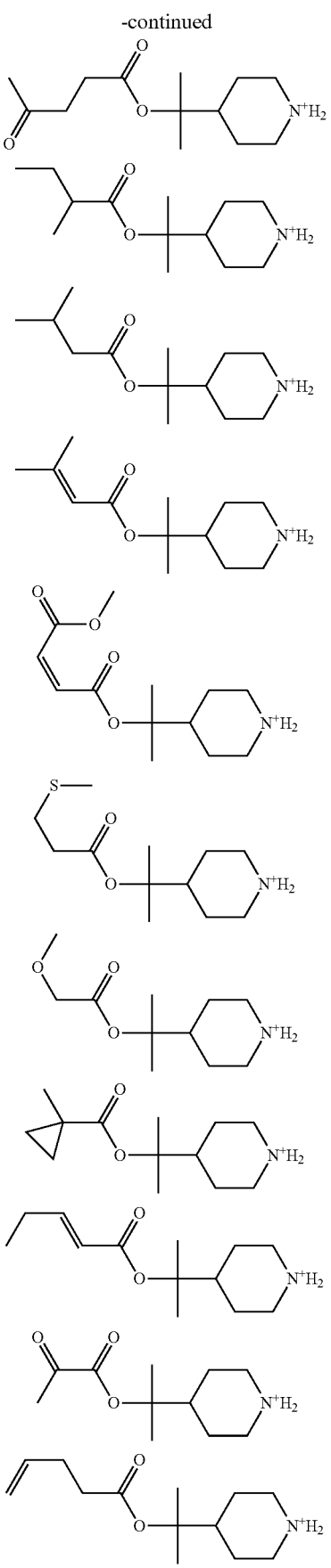

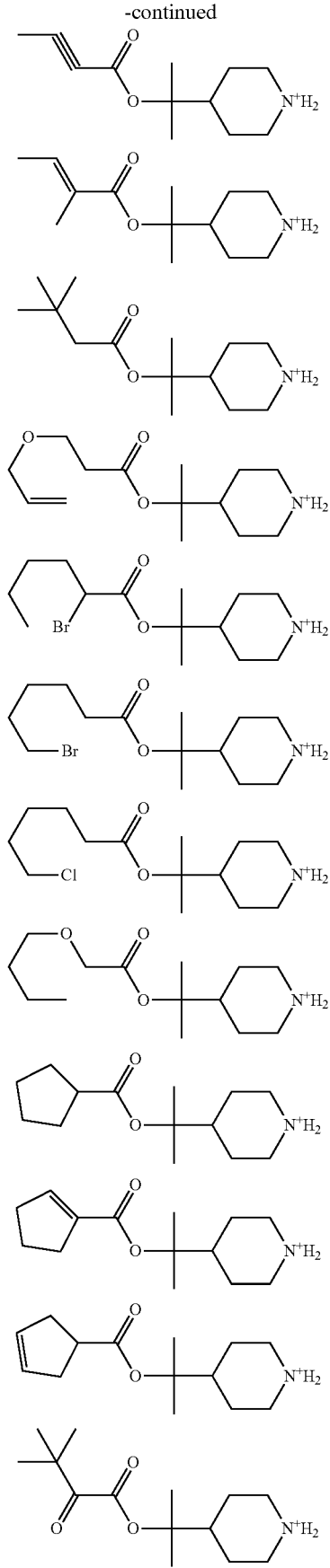
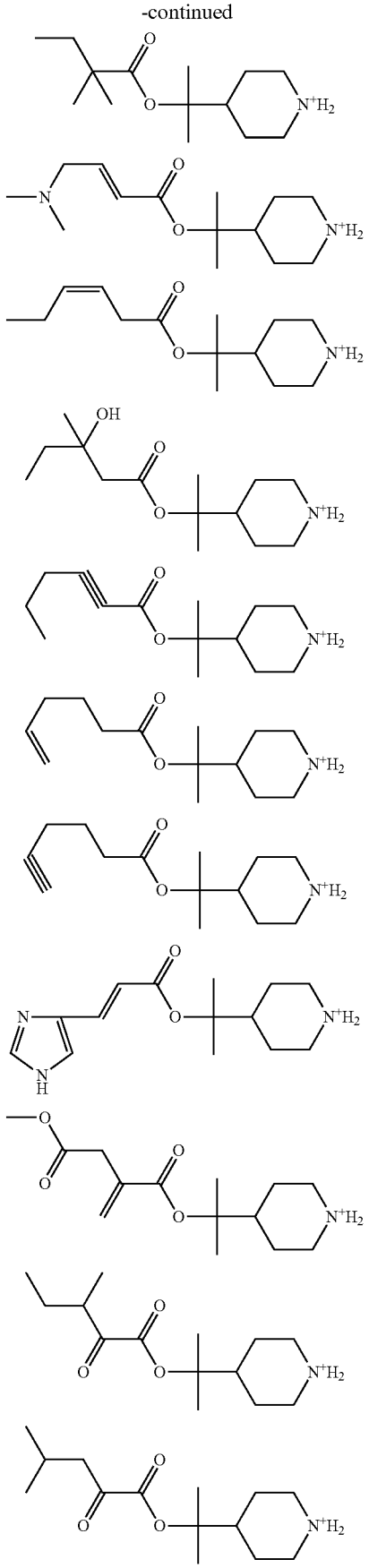

23
-continued
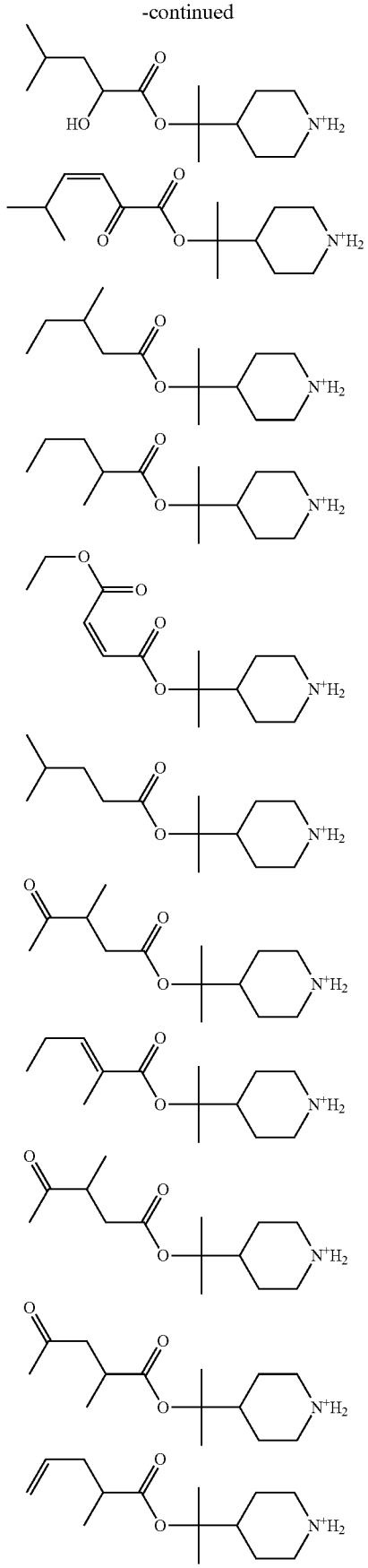
24
-continued
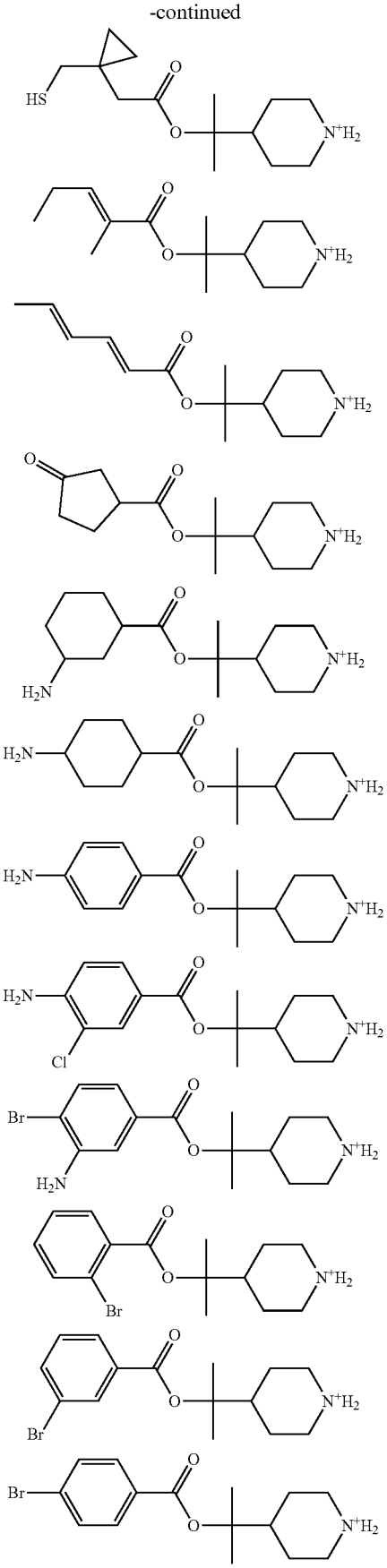

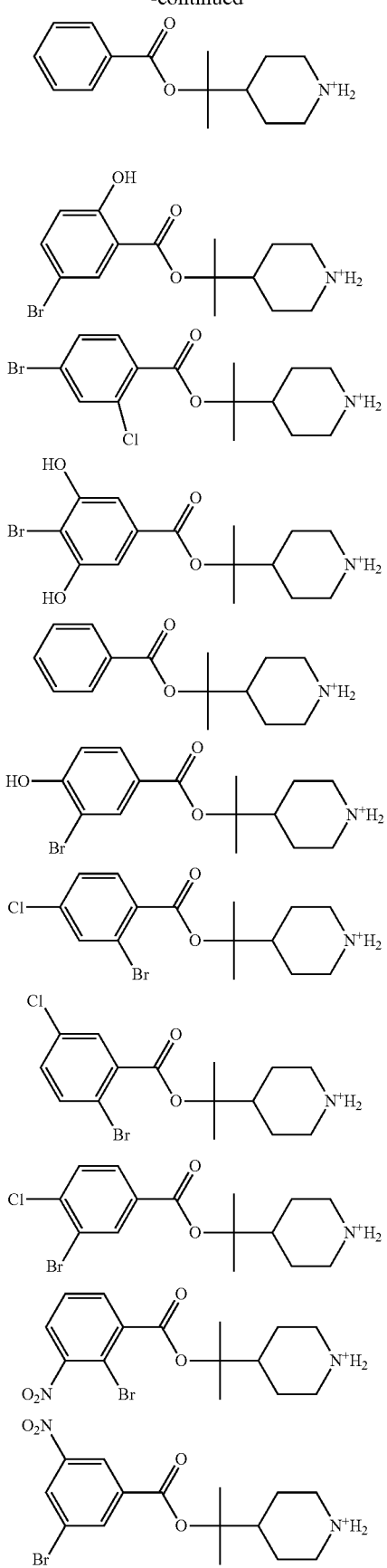
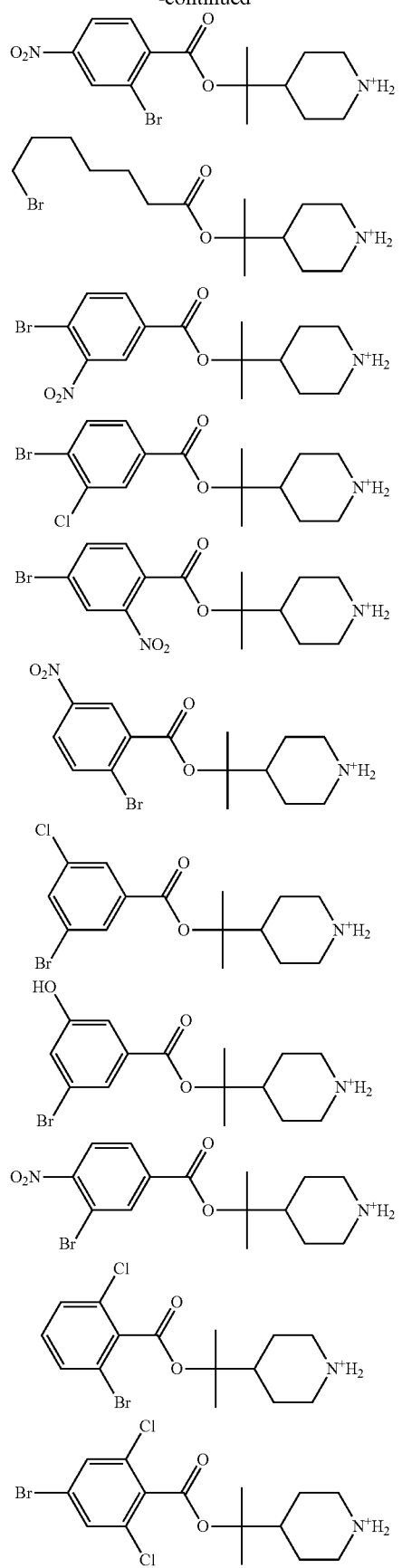

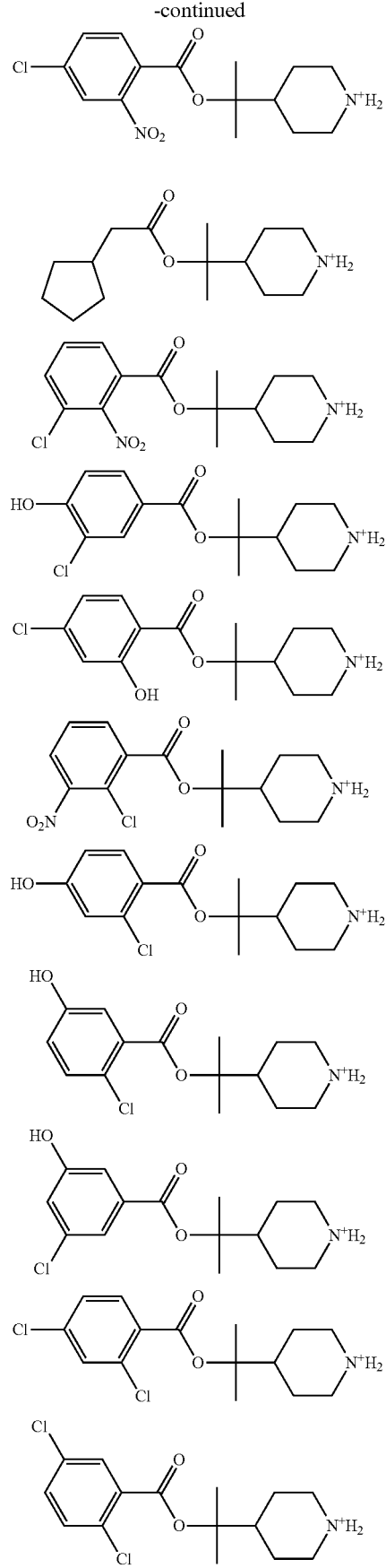

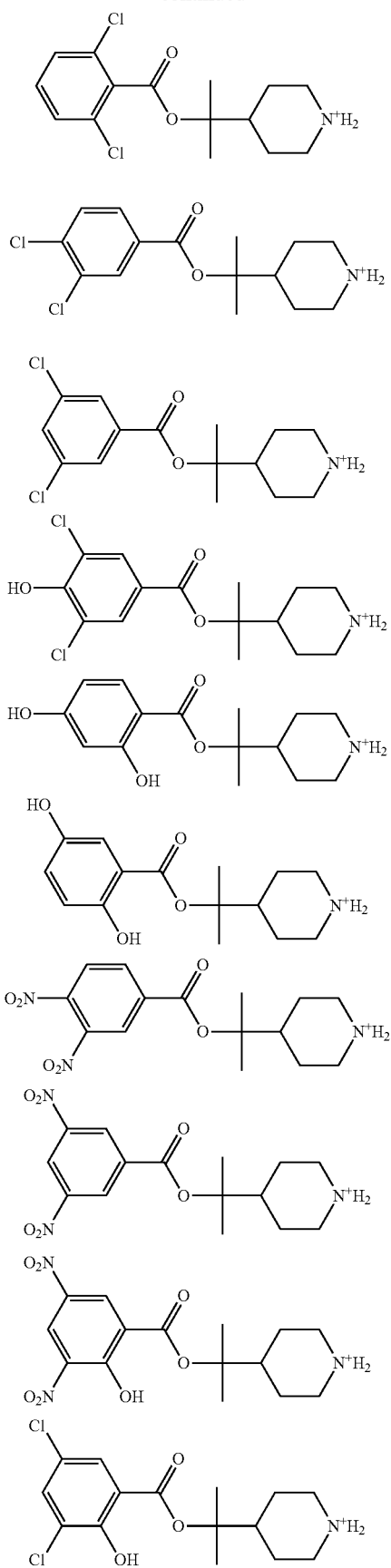
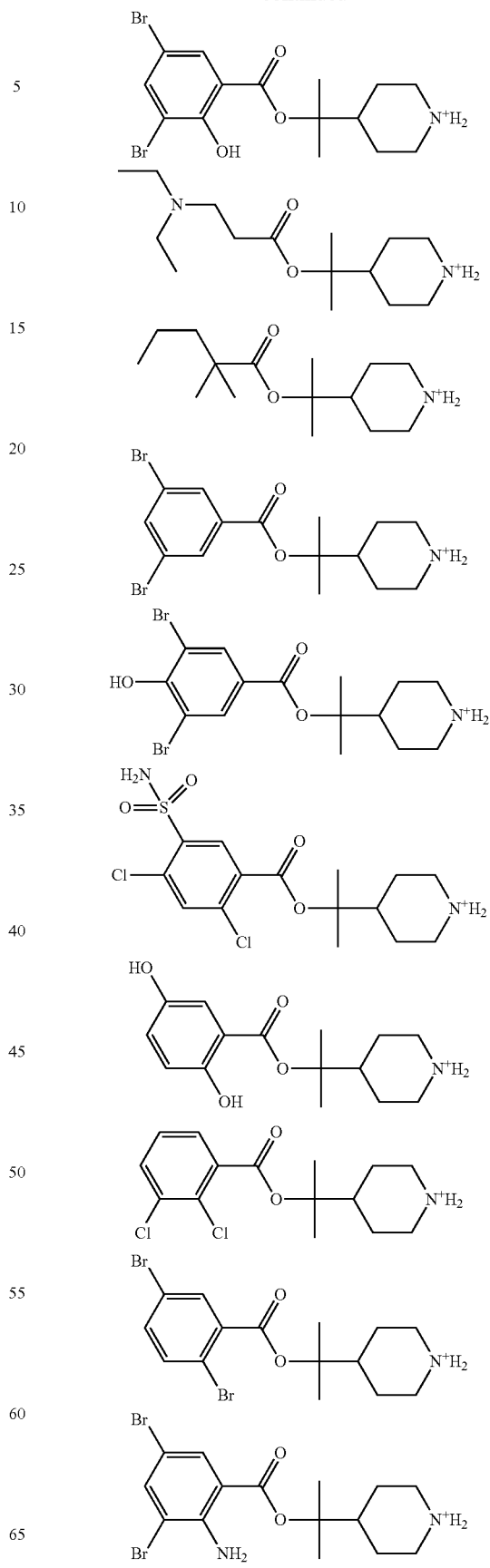

-continued
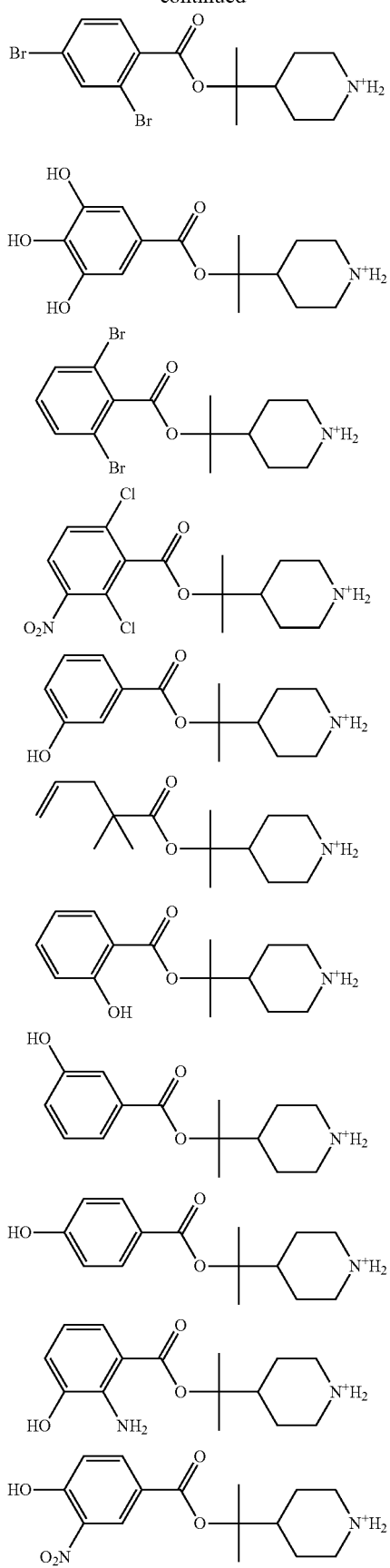
-continued
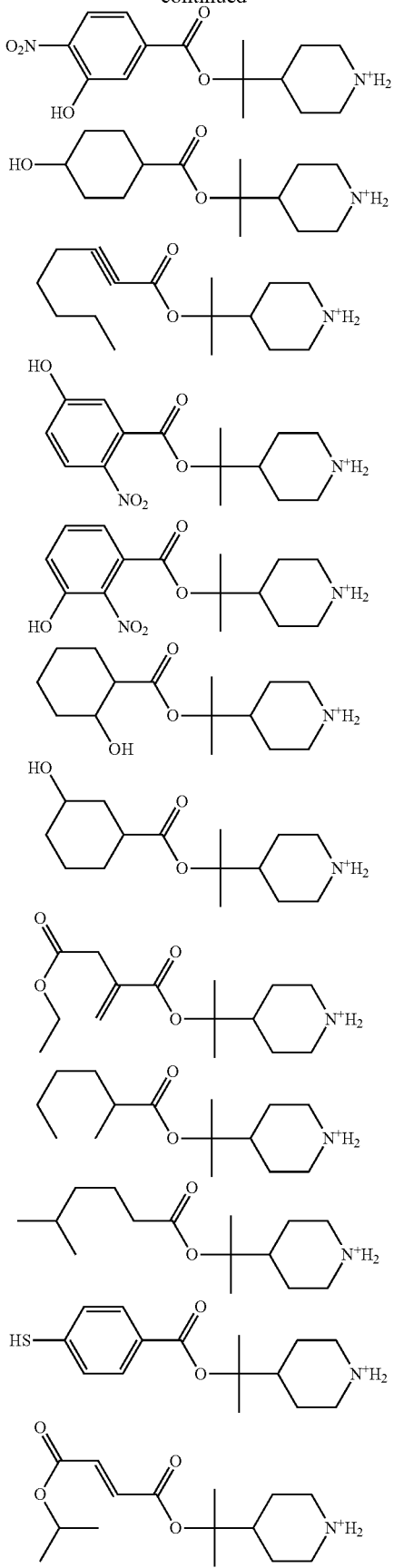

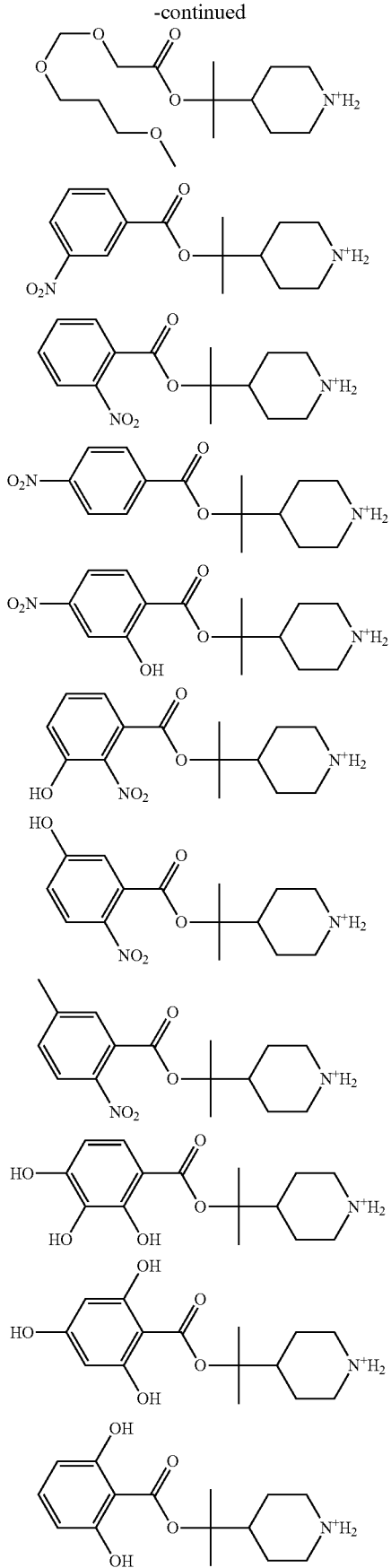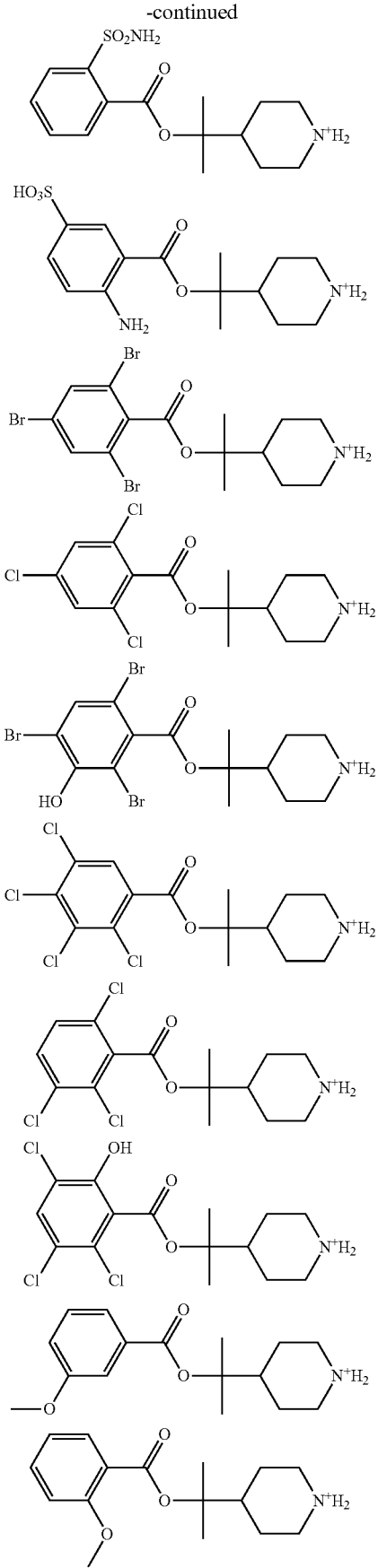

35
-continued
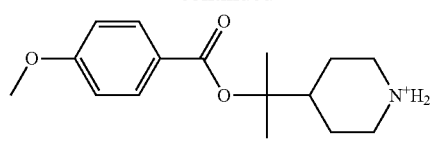
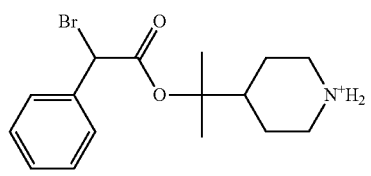
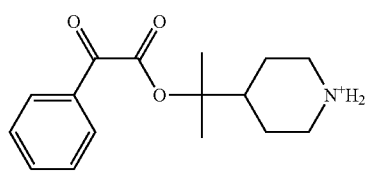
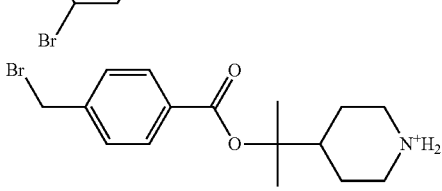
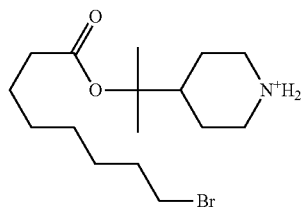
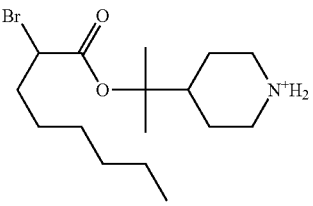
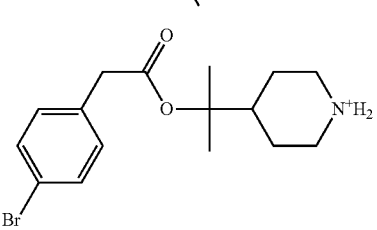
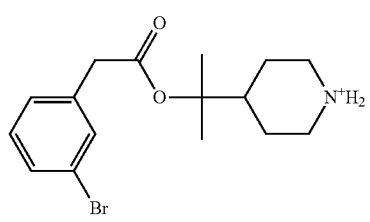
36
-continued
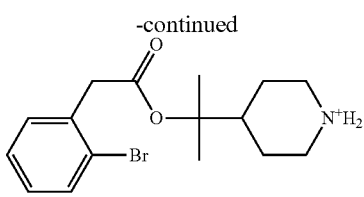
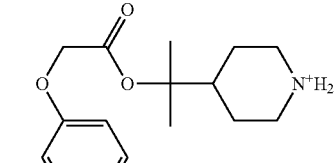
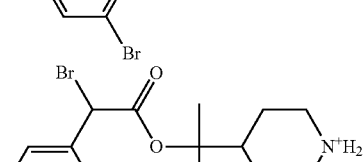
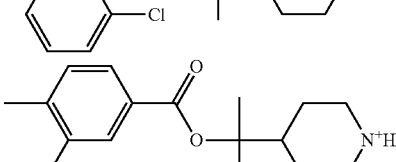
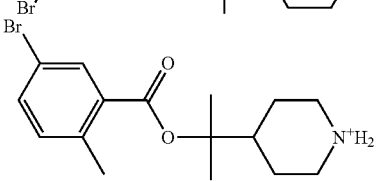
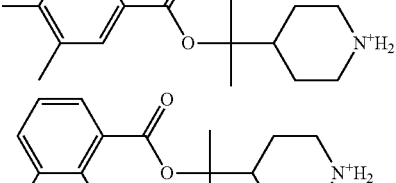
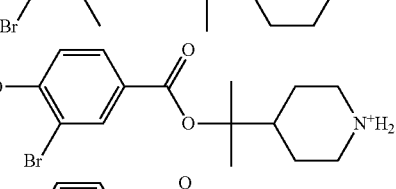
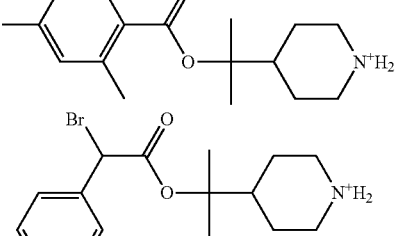
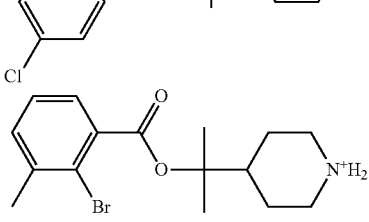

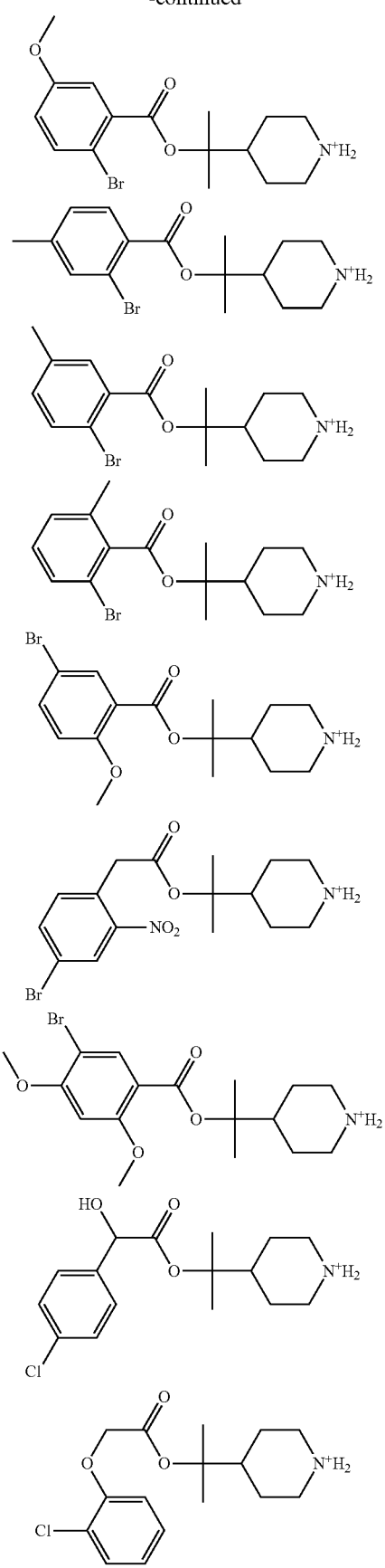
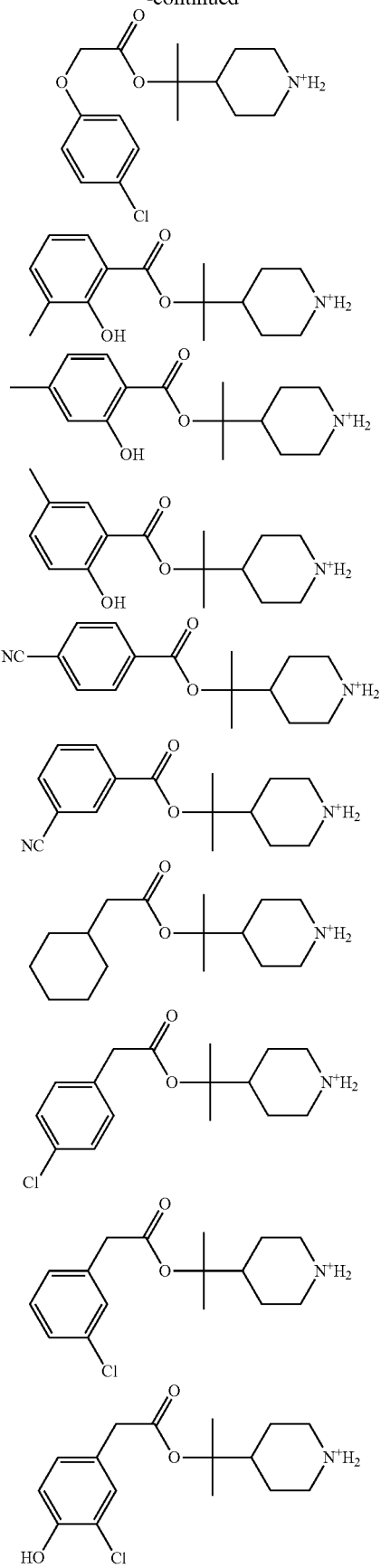

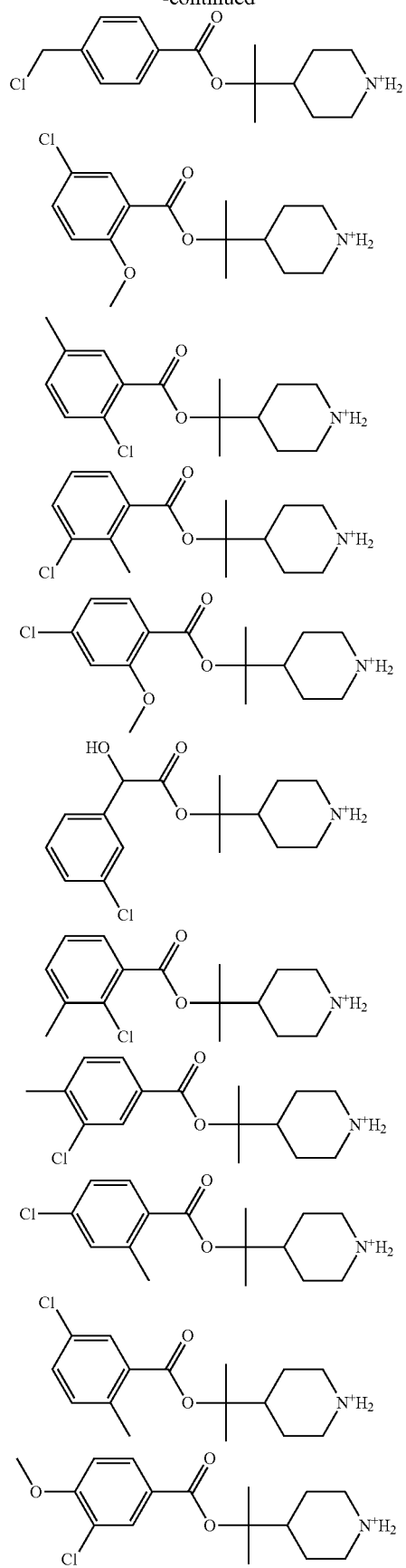
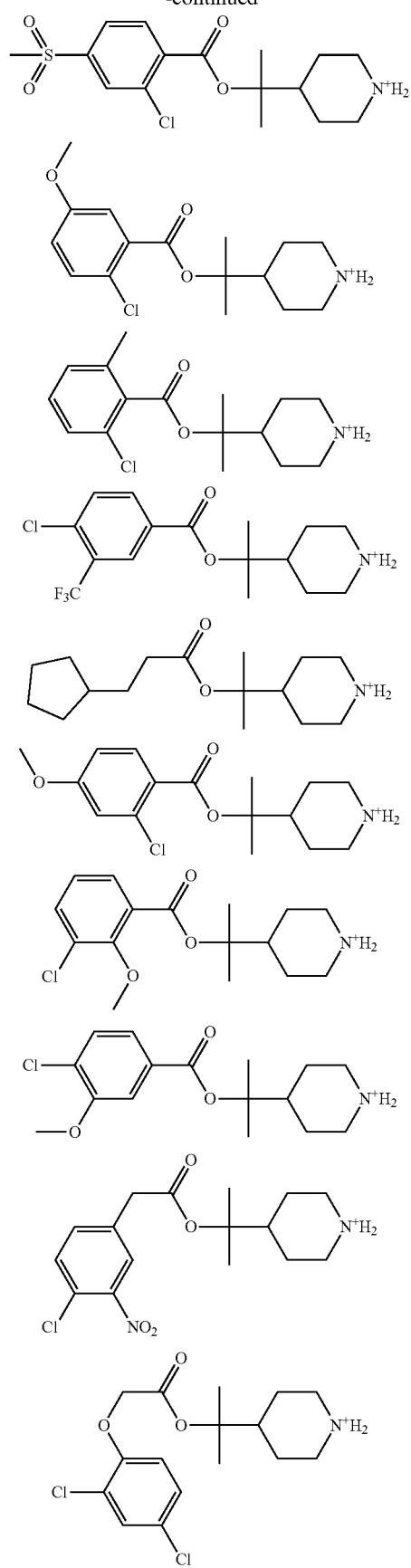

-continued
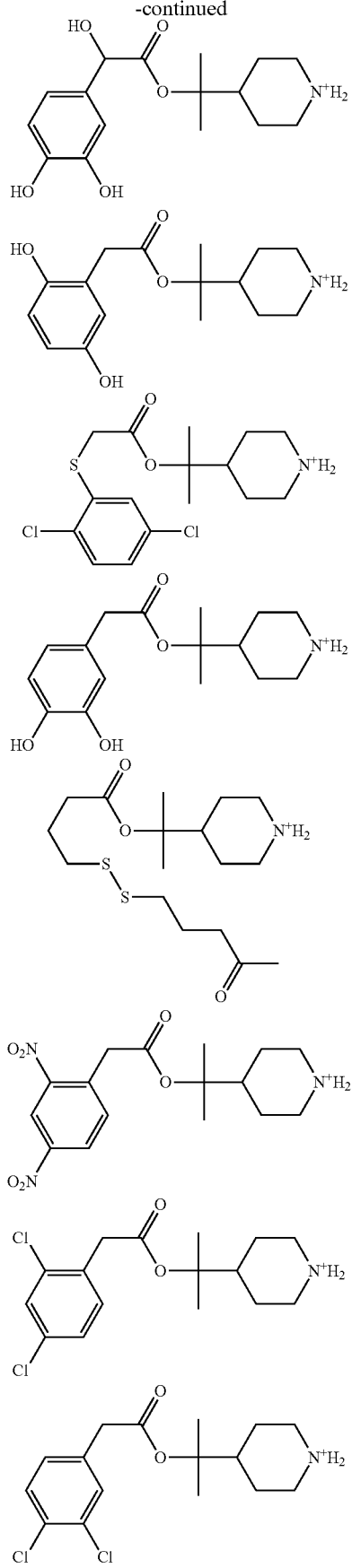
-continued
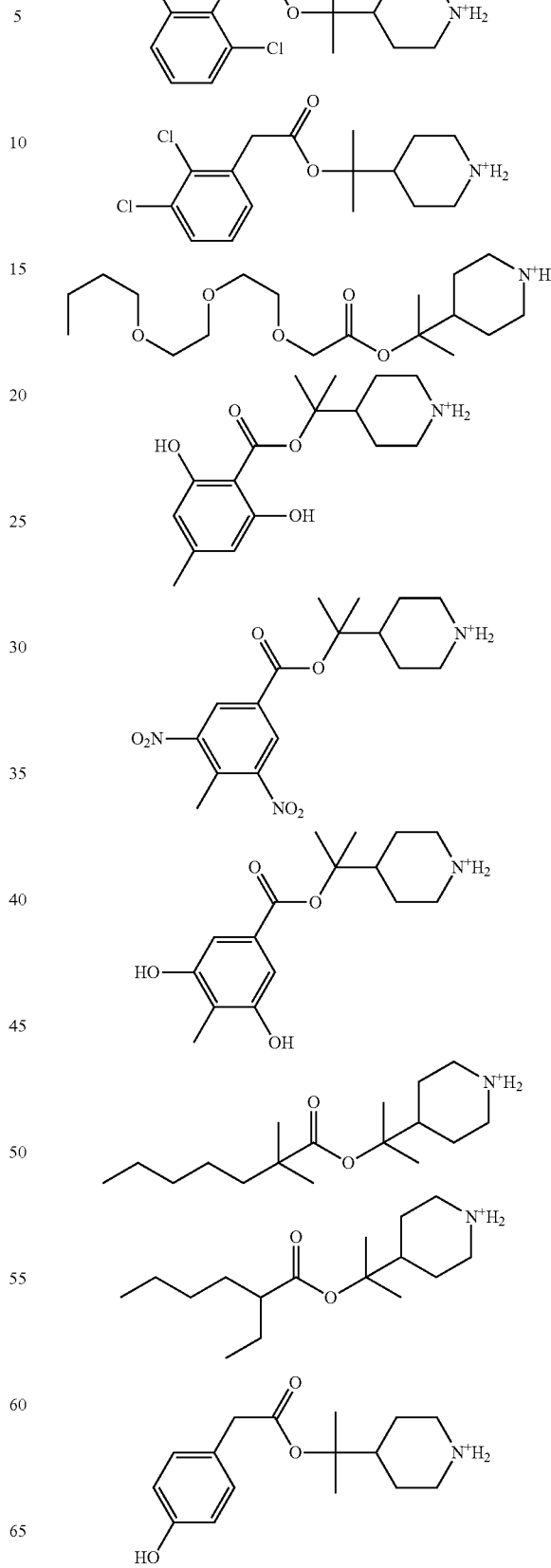

-continued
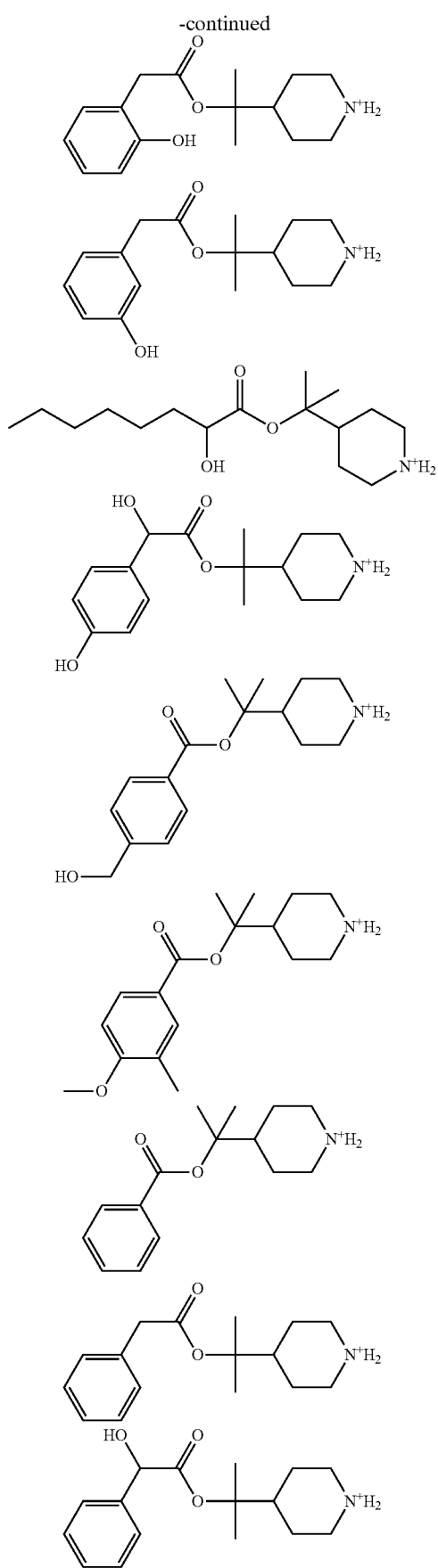
-continued
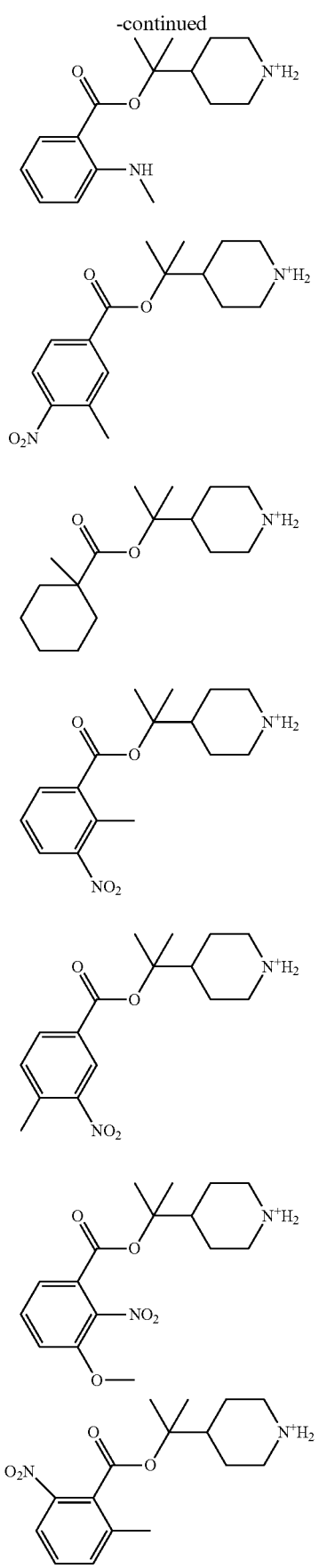

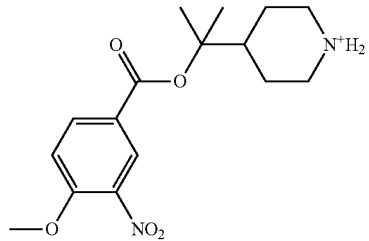
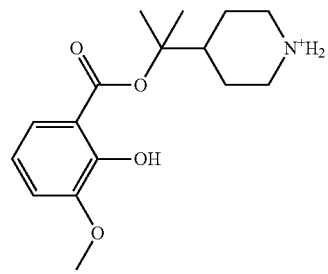
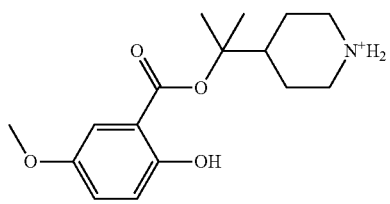
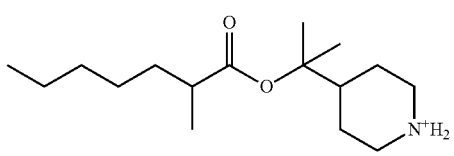
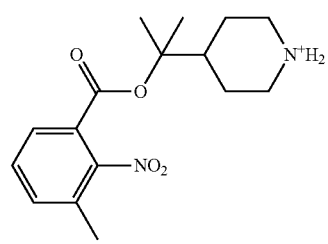
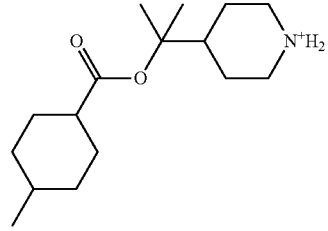
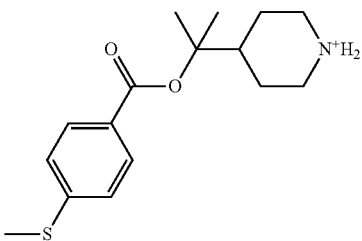
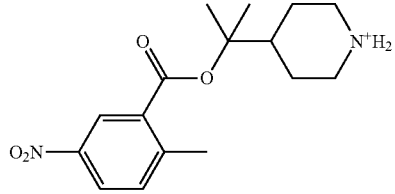
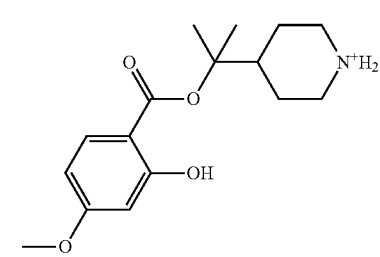
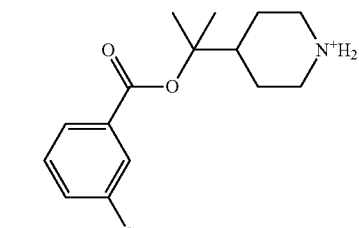
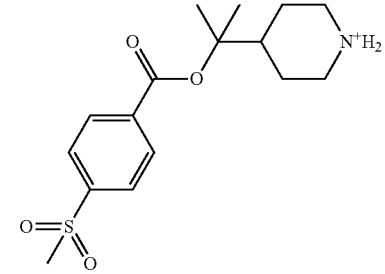
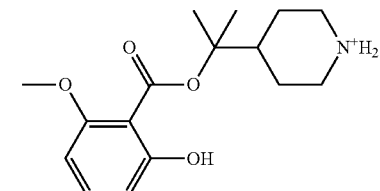
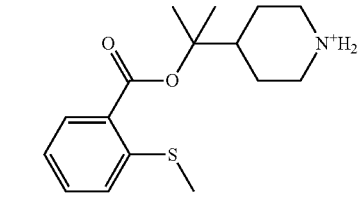
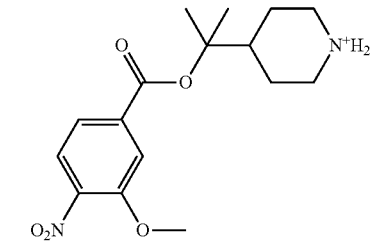

-continued
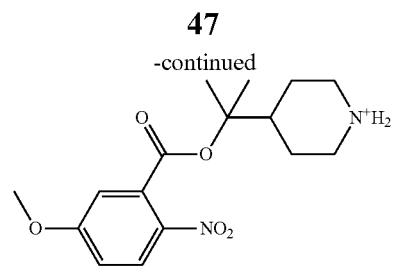
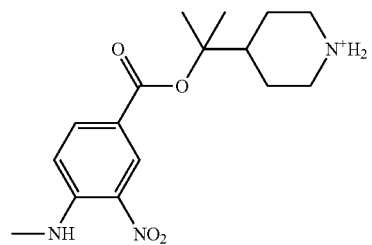
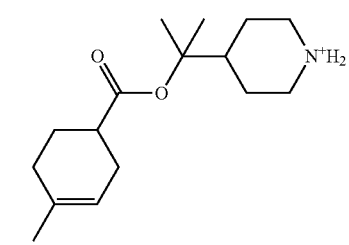
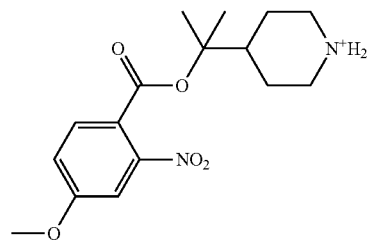
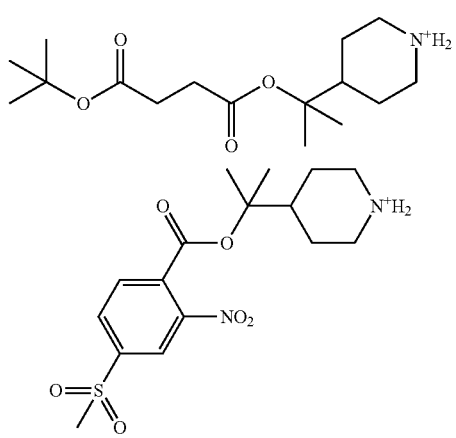
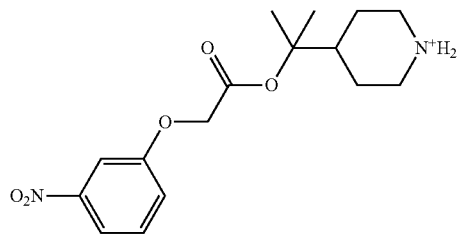
-continued
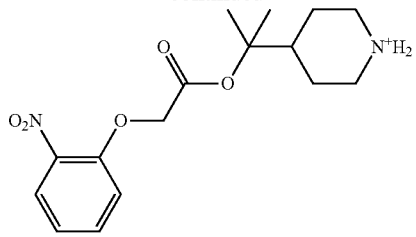
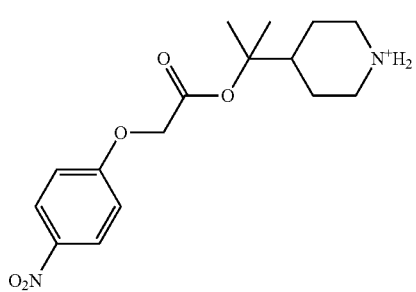
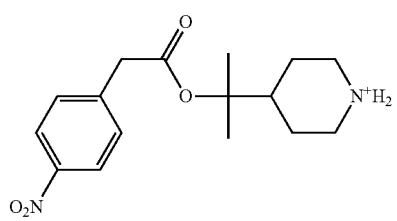
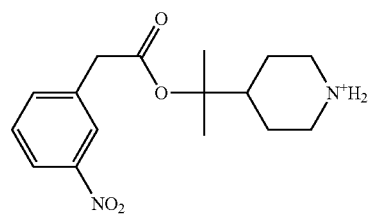
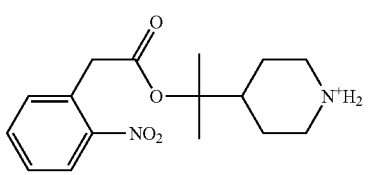
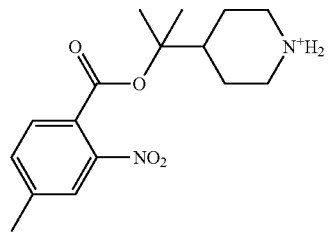
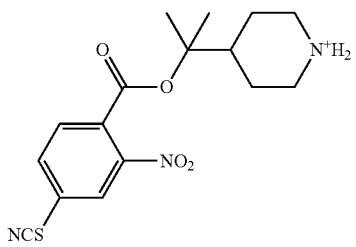

49
-continued
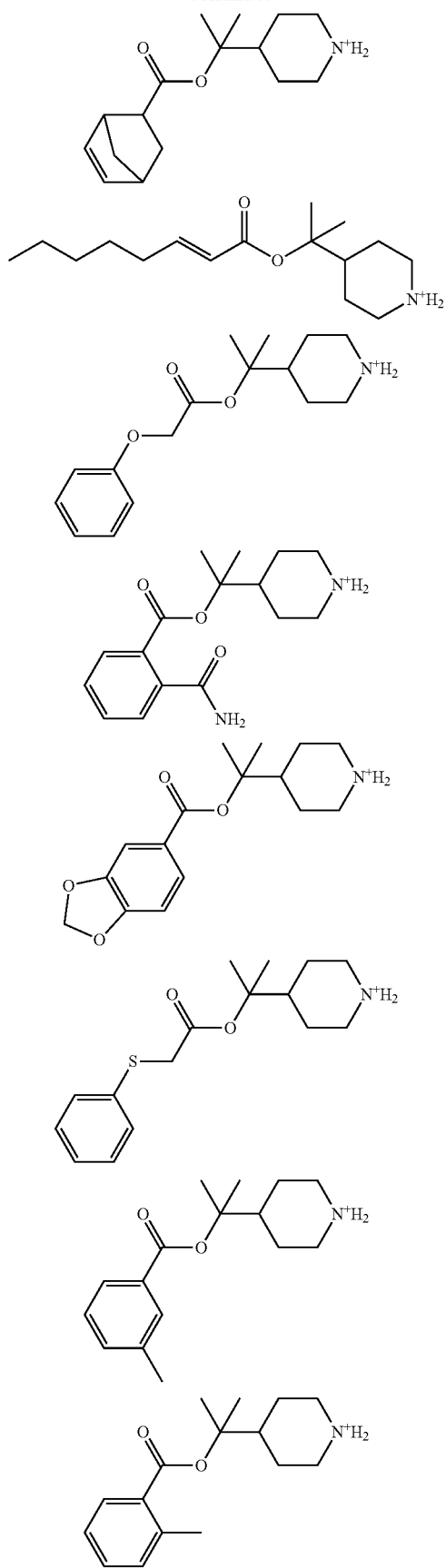
50
-continued
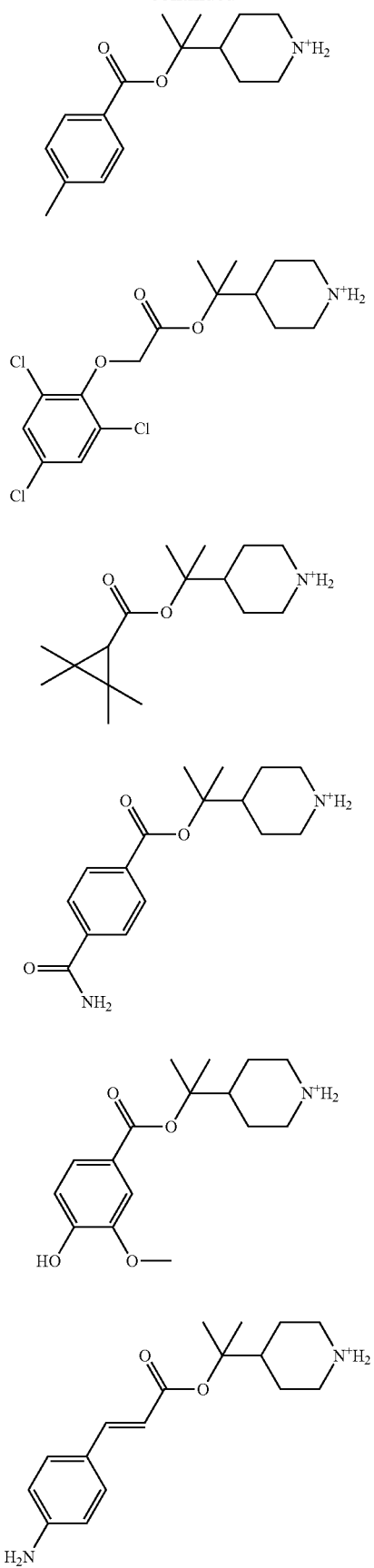

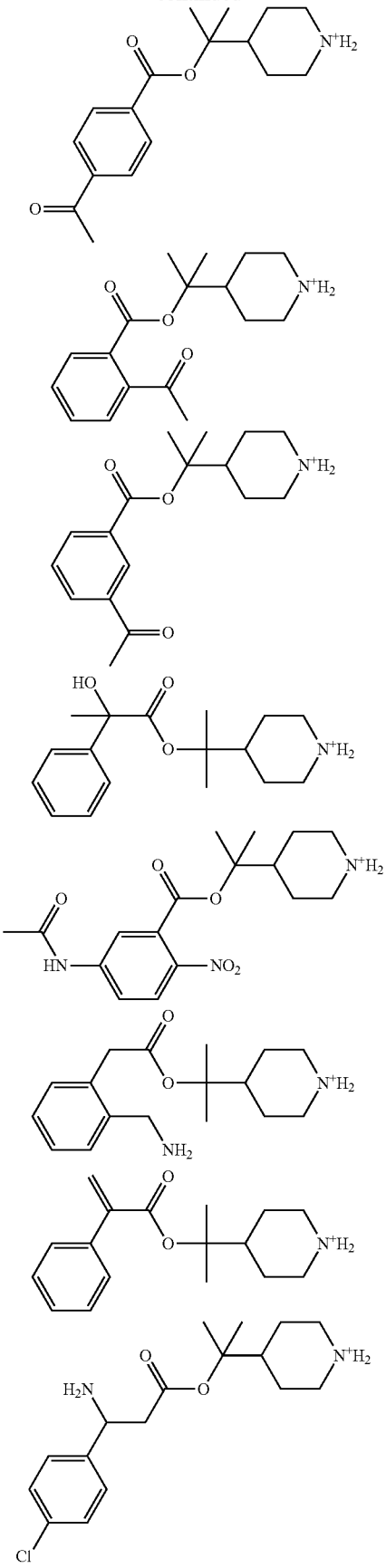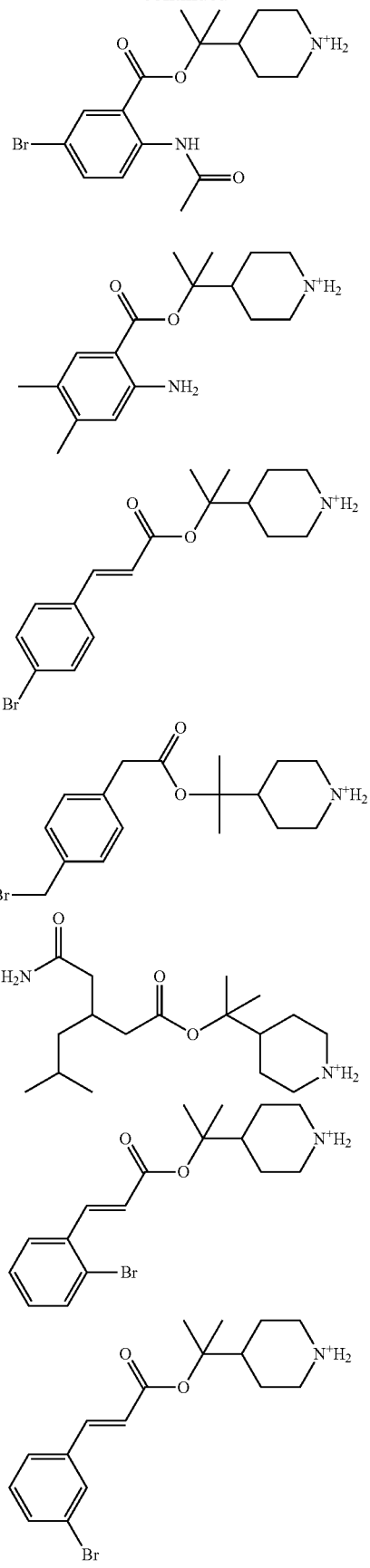

-continued

-continued
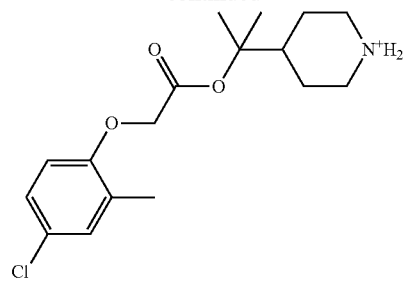
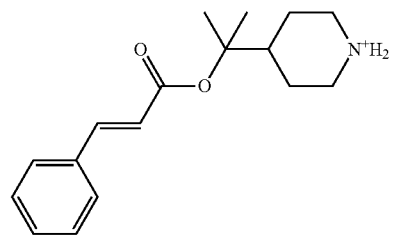
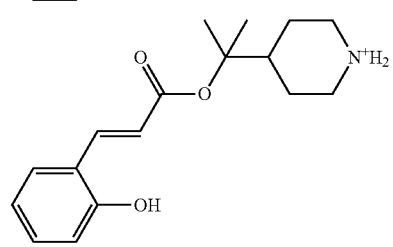
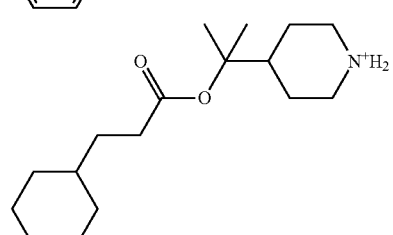
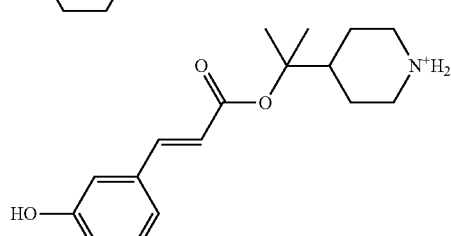
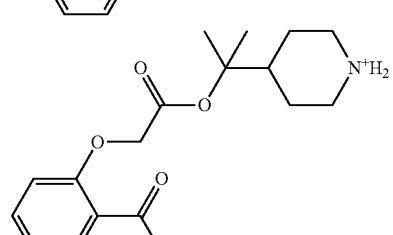
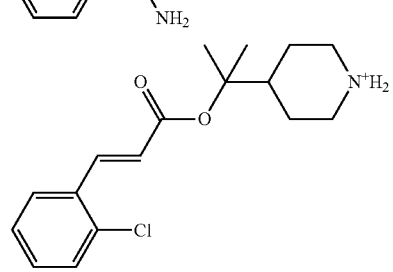
-continued
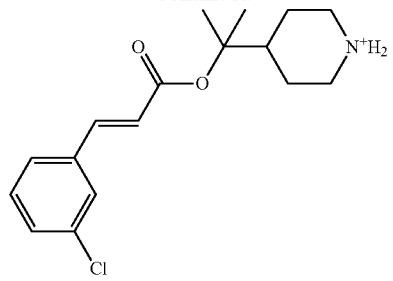
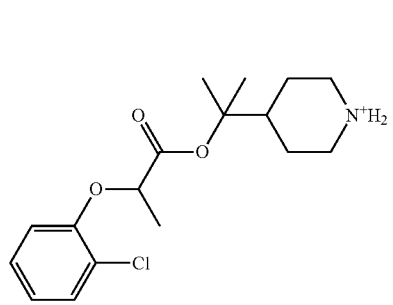
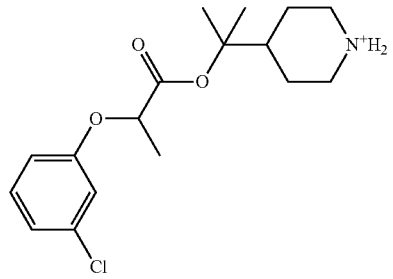
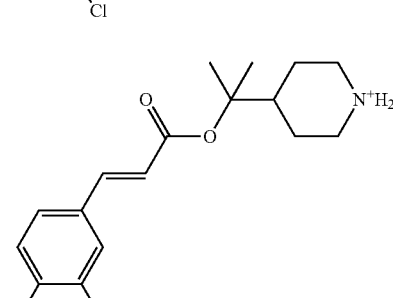
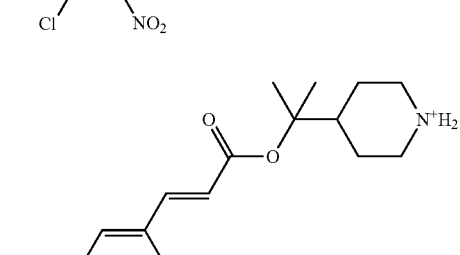
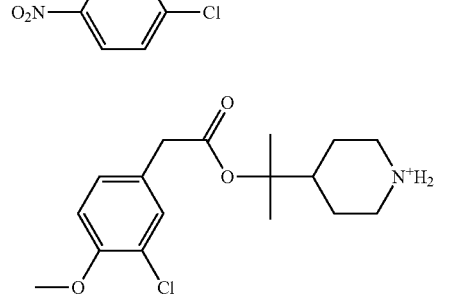

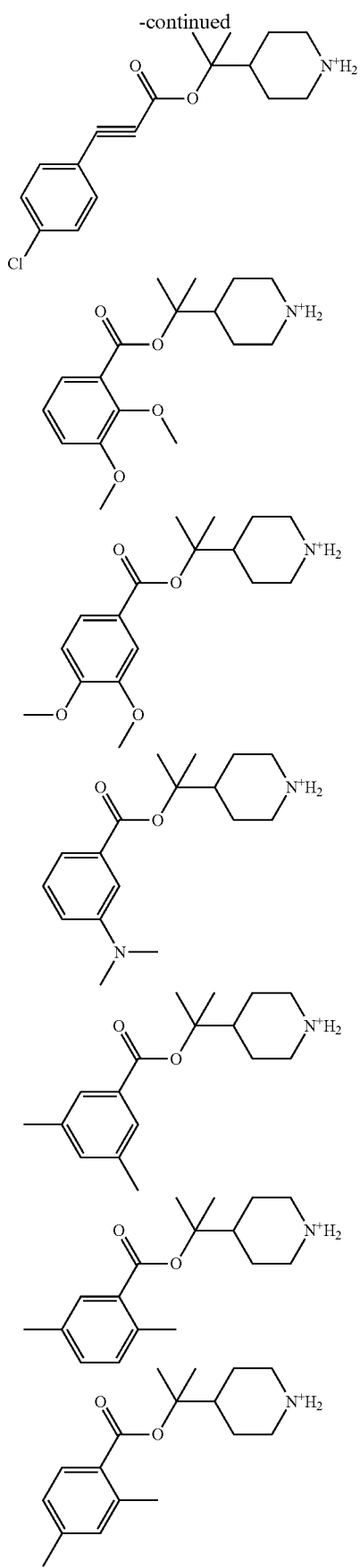
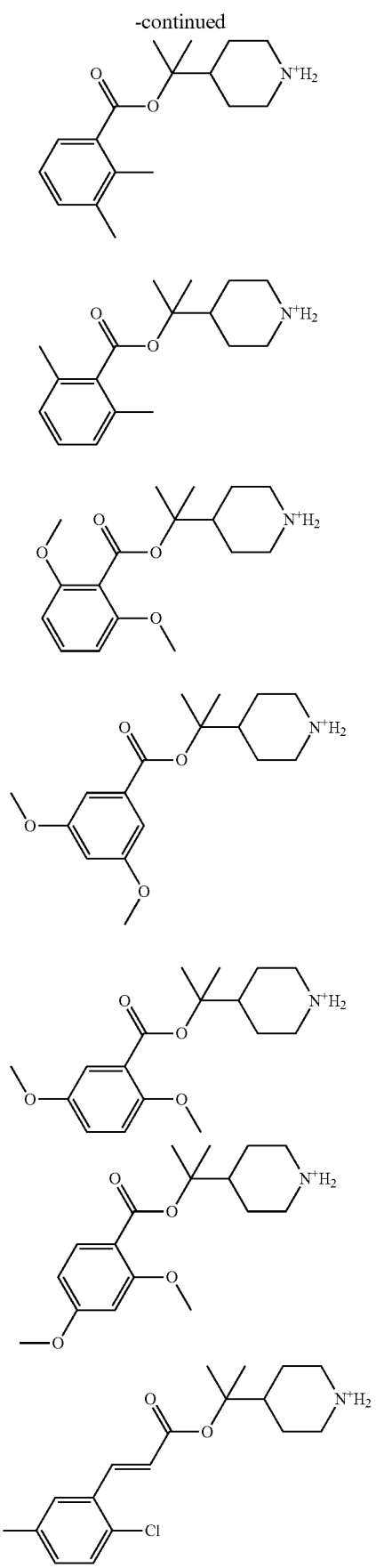

-continued
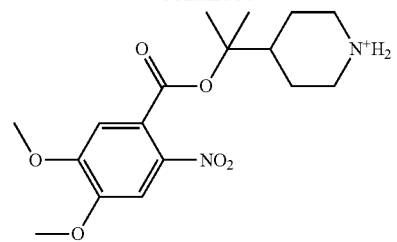
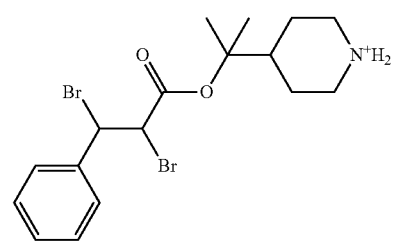
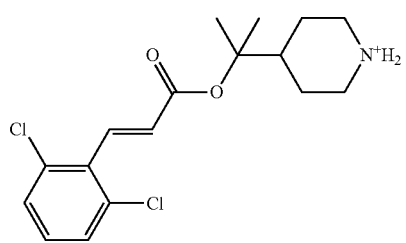
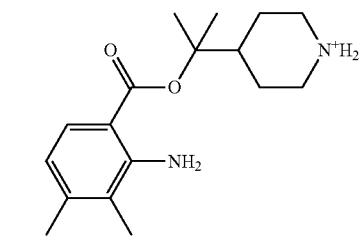
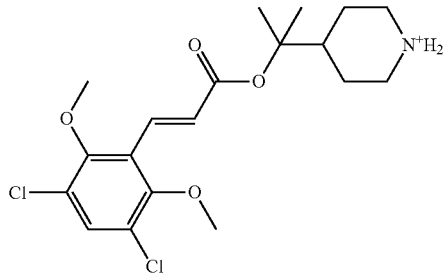
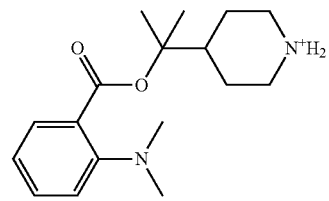
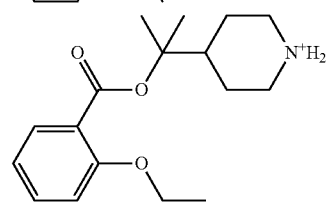
-continued
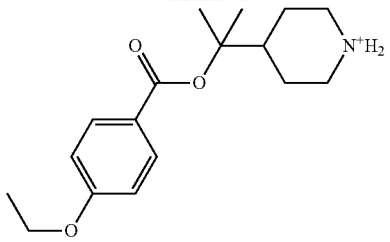
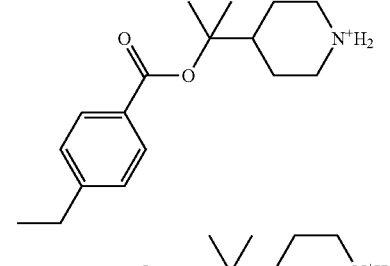
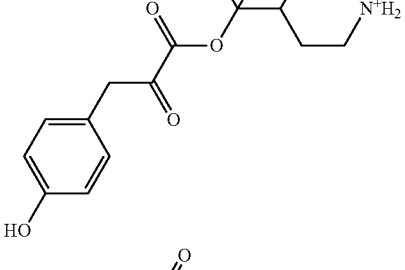
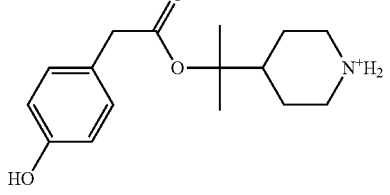
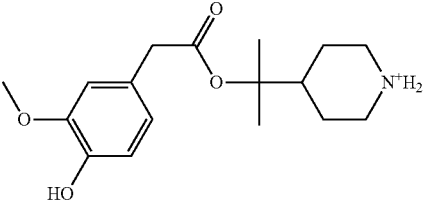
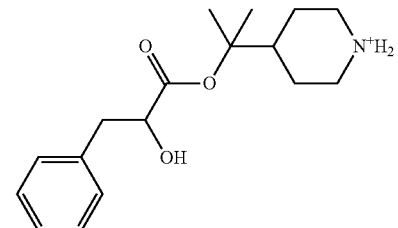
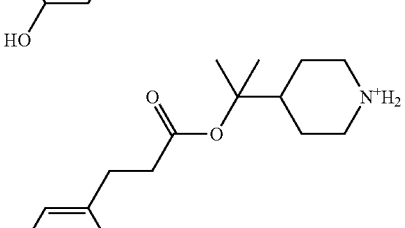

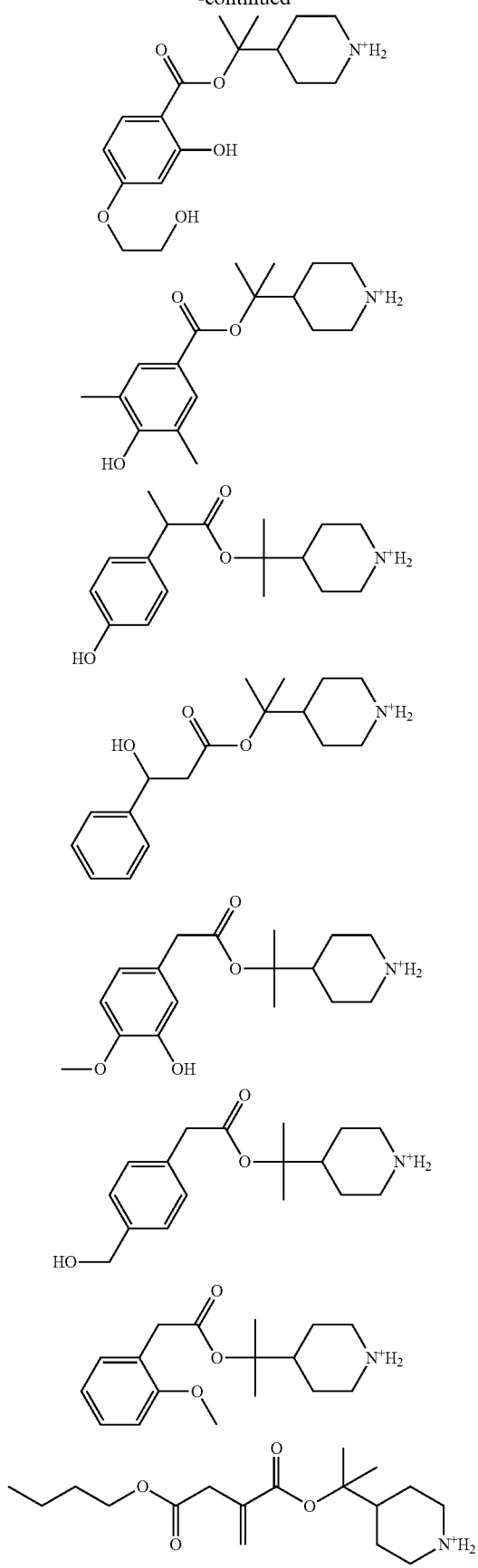

63
-continued
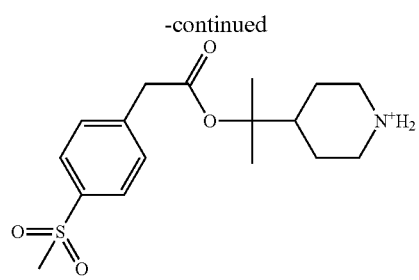
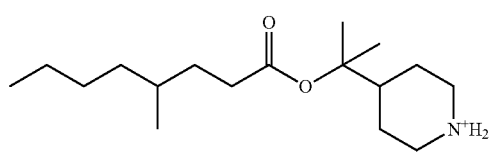
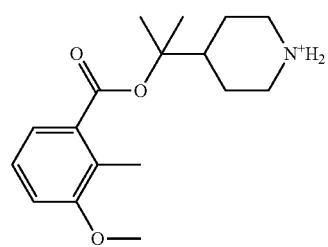
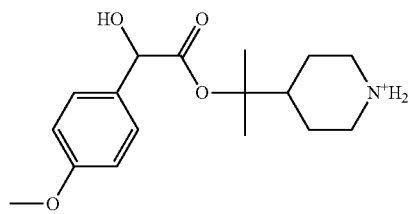
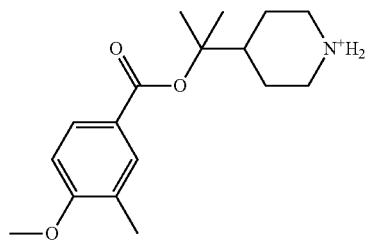
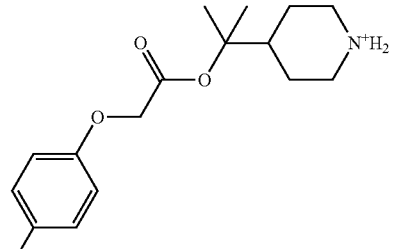
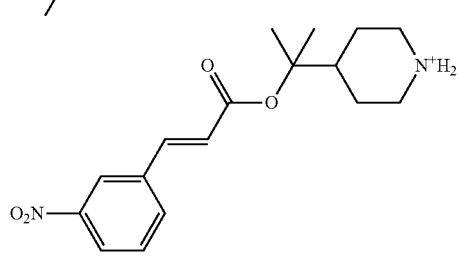
64
-continued
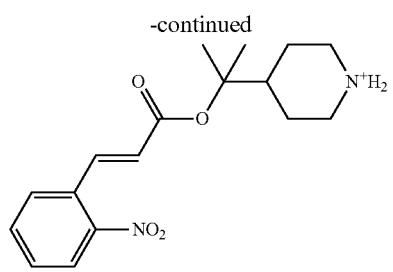
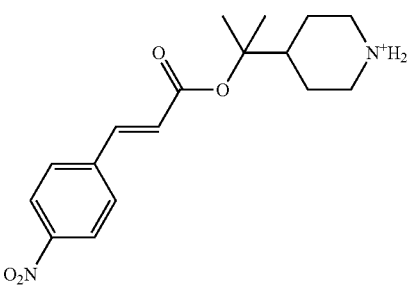
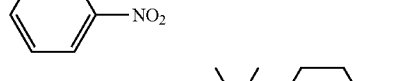
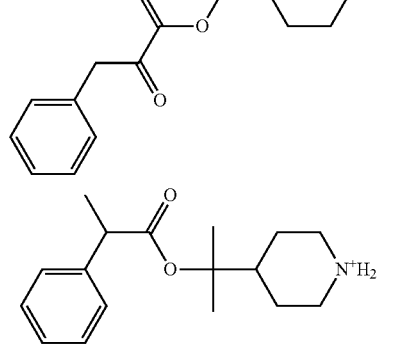

65
-continued
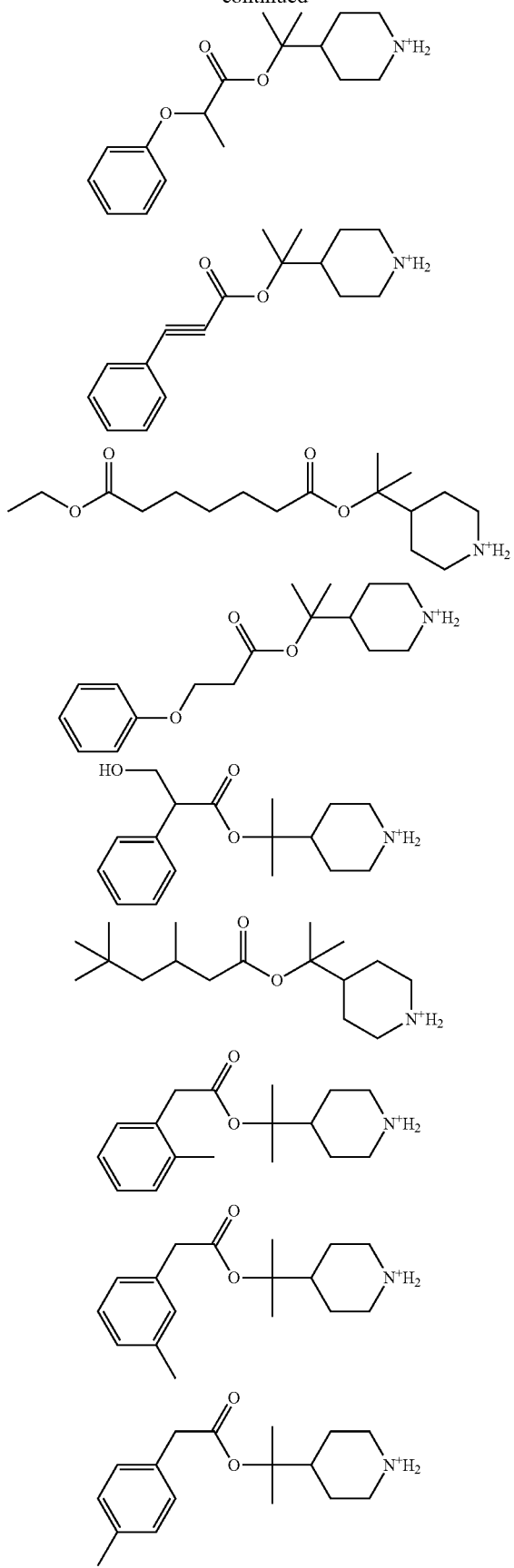
66
-continued
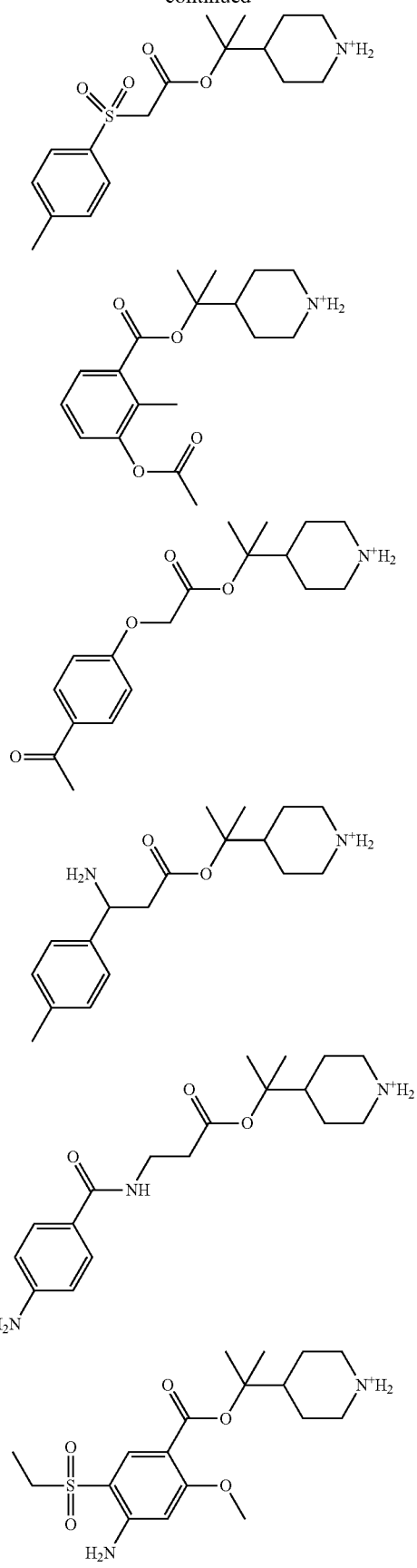

-continued
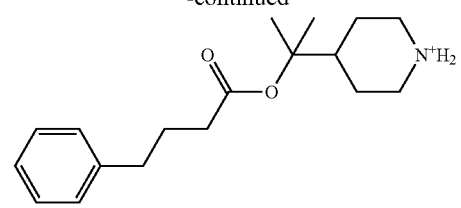
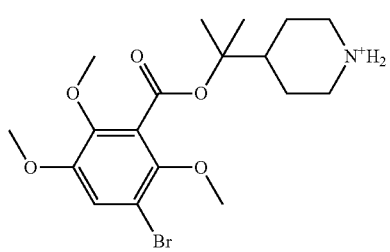
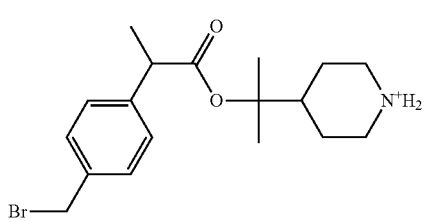
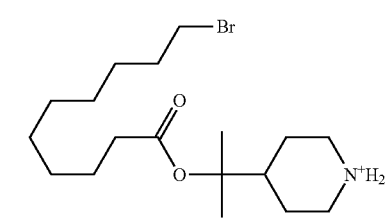
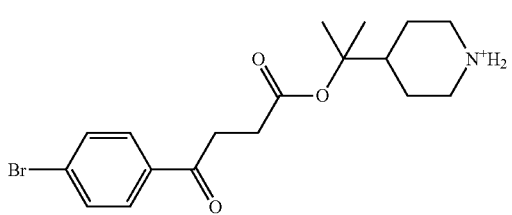
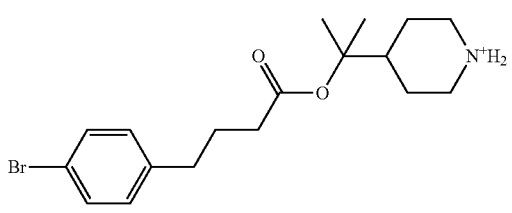
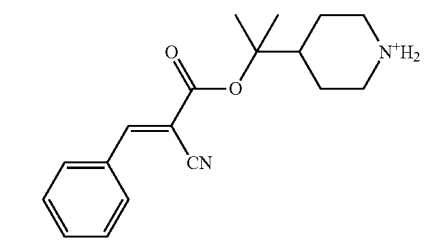
-continued
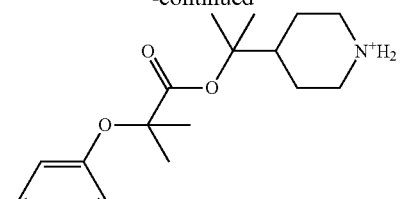
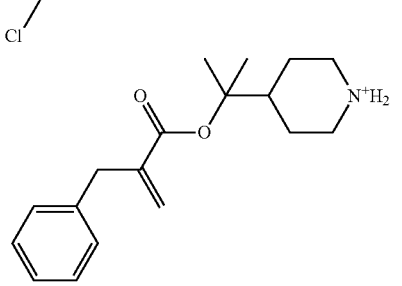
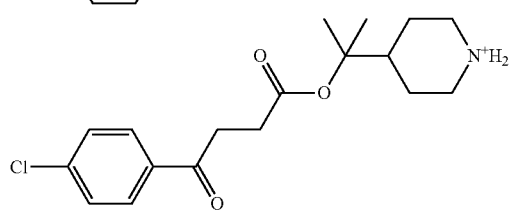
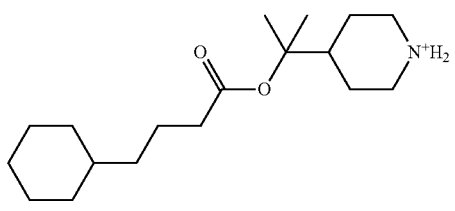
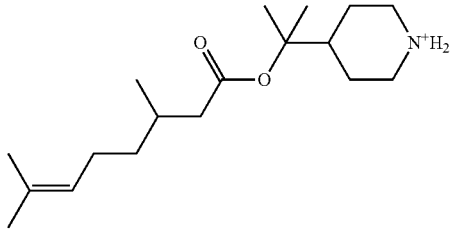

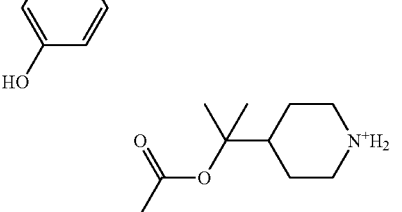
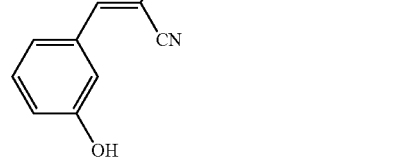

69
-continued
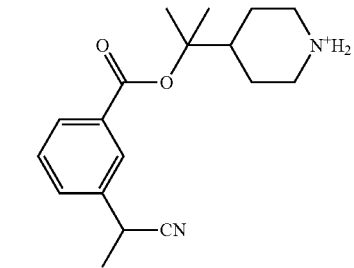
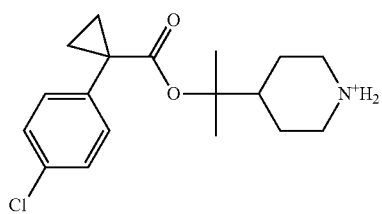
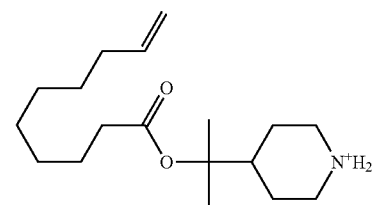
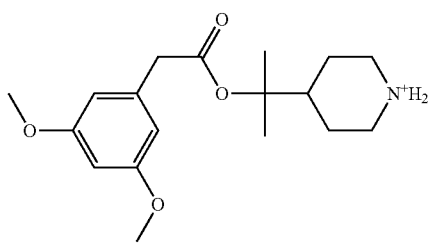
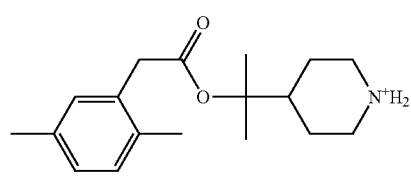
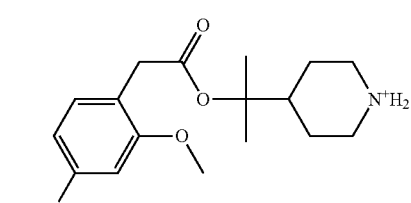
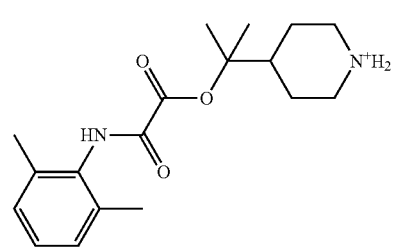
70
-continued
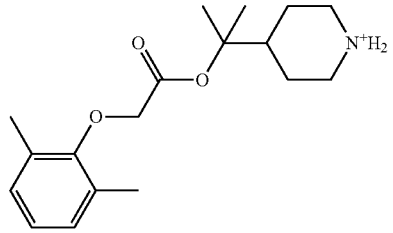
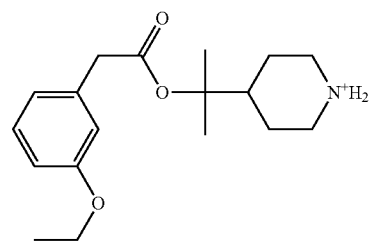
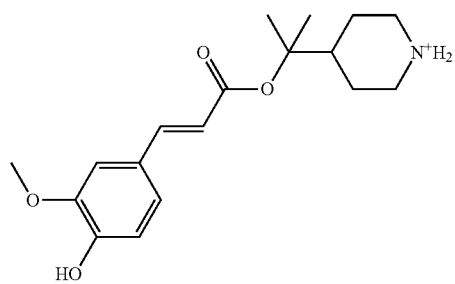
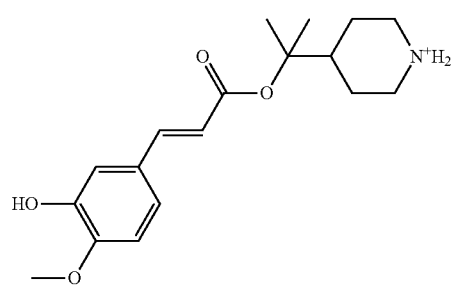
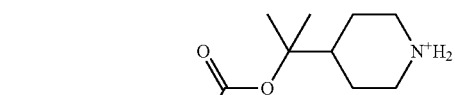
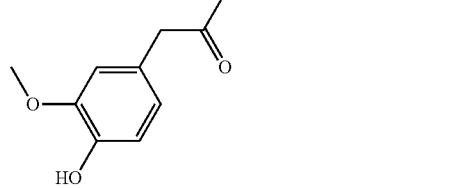
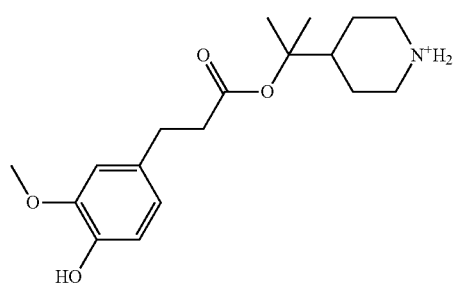

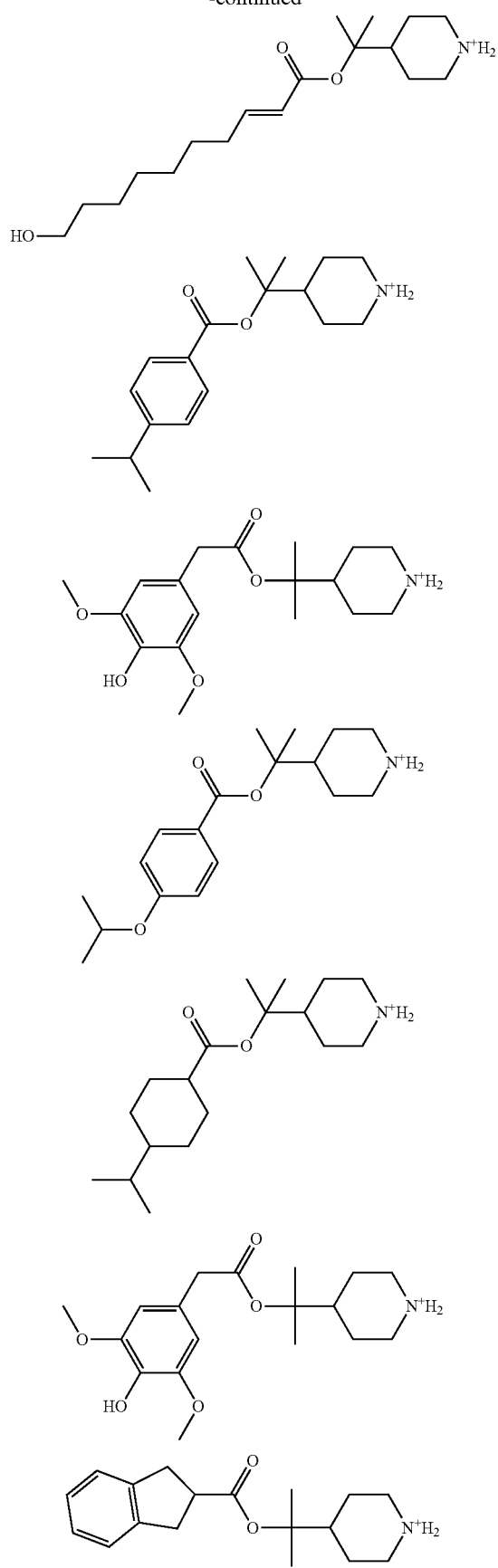
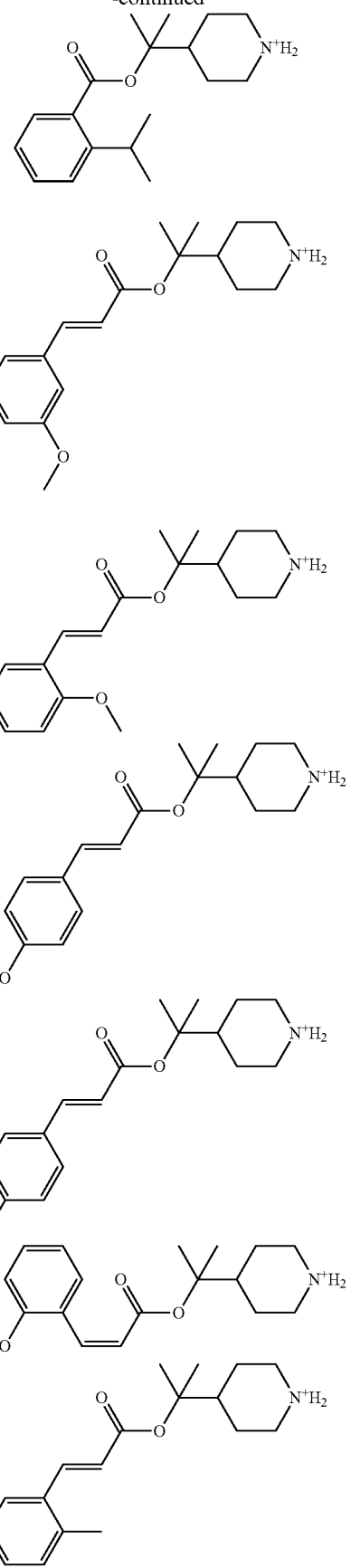

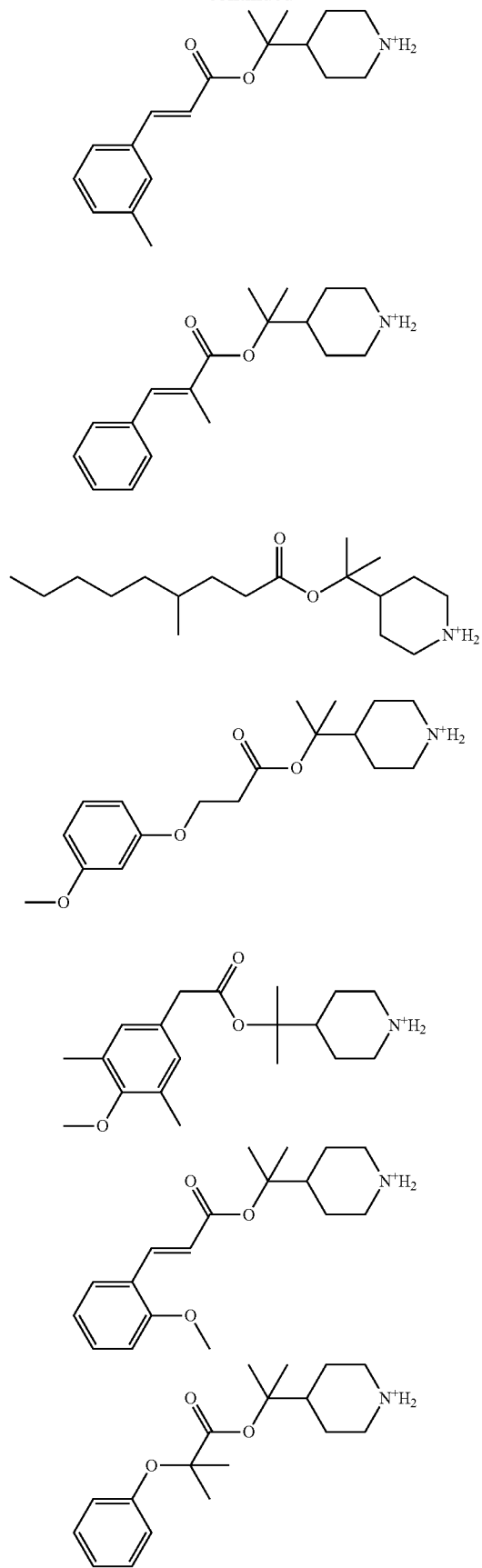
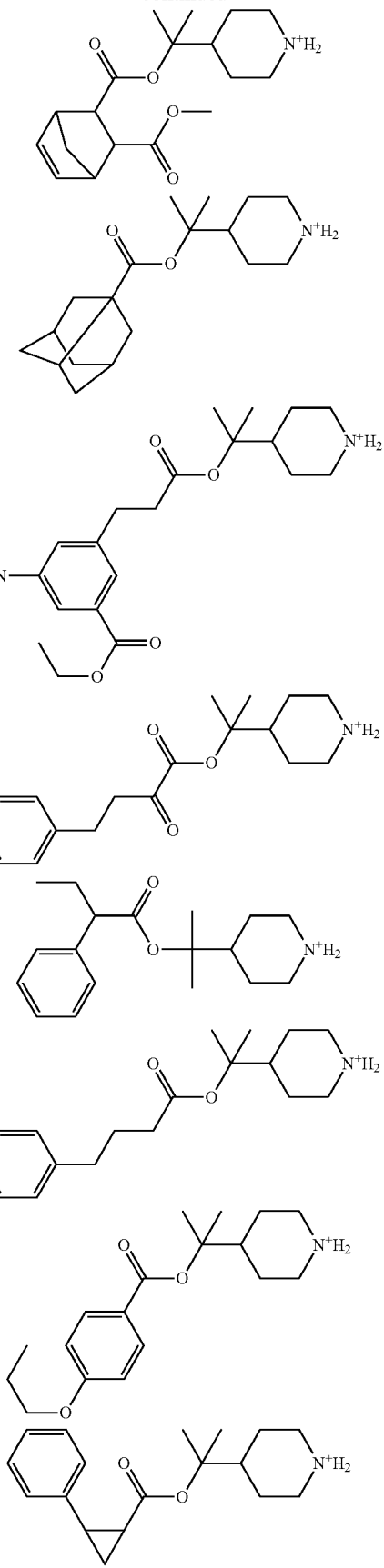

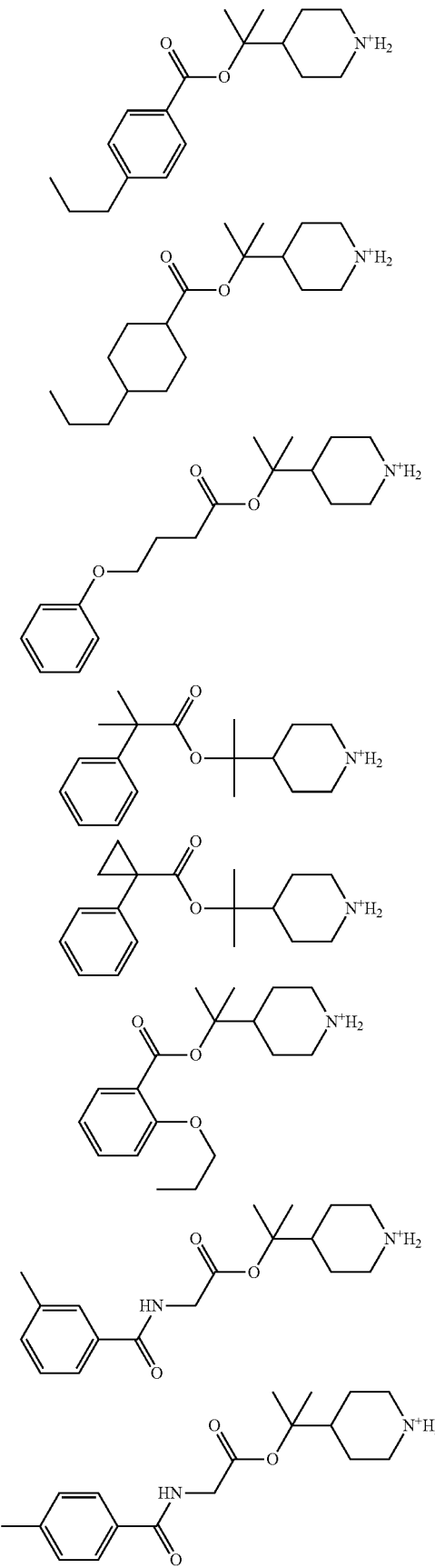
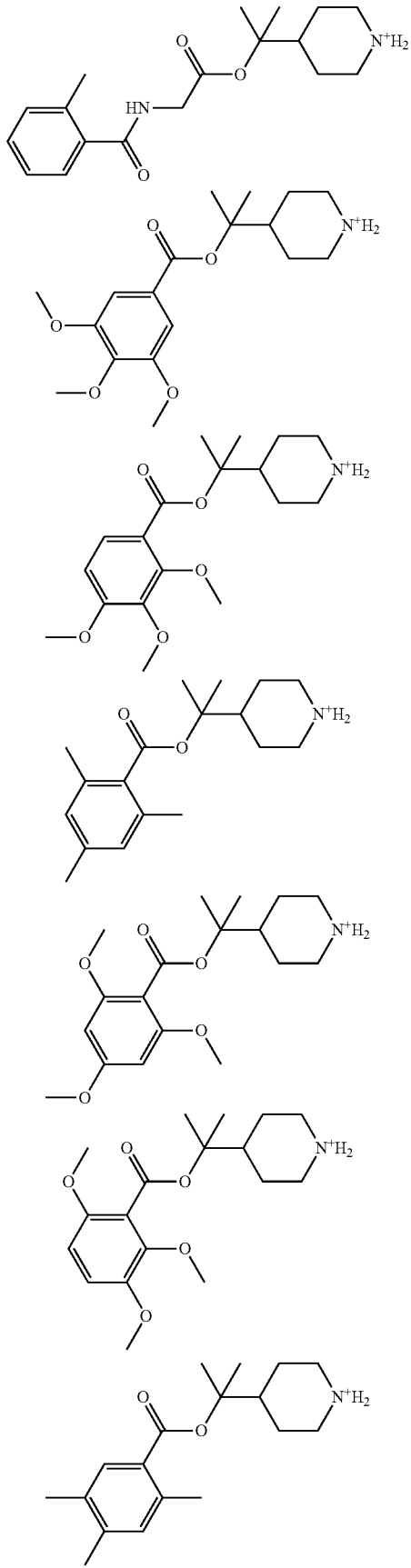

77
-continued
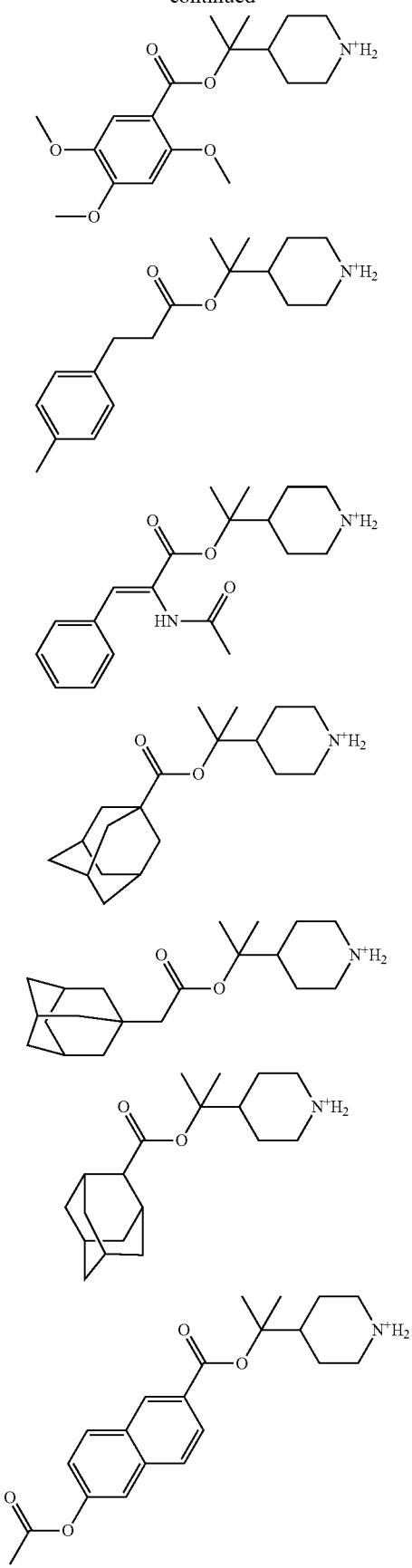
78
-continued
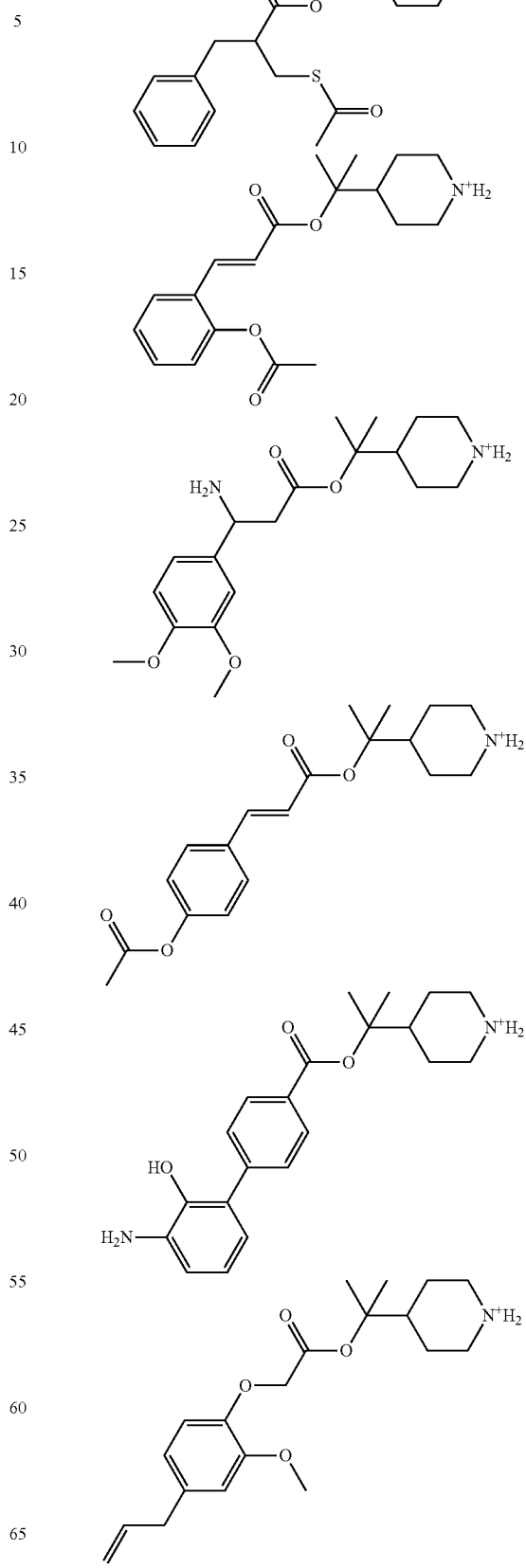

79
-continued
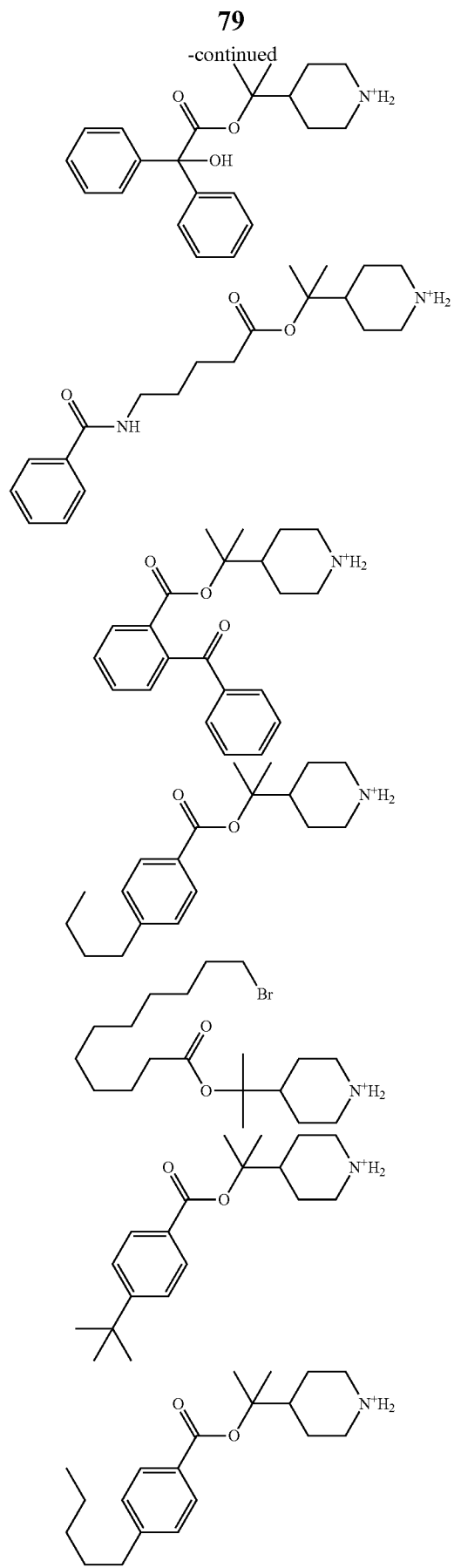
80
-continued
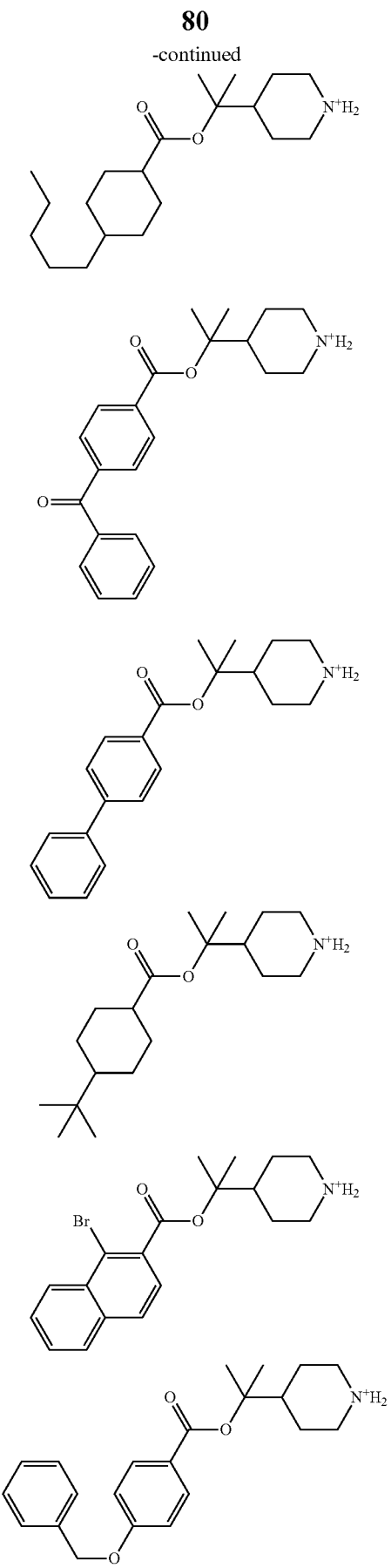

-continued
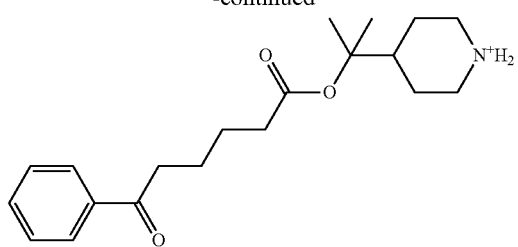
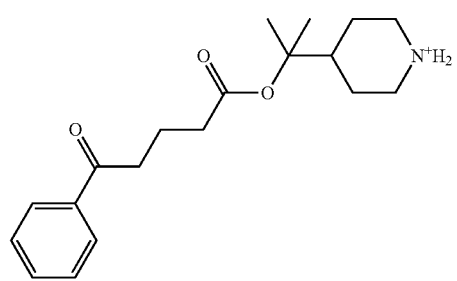
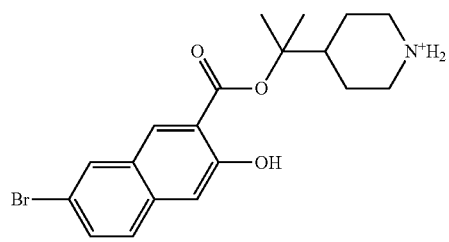
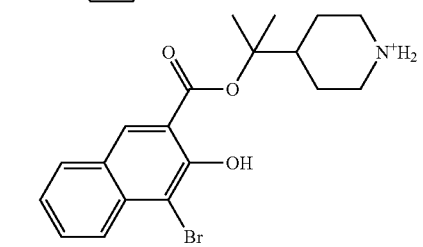
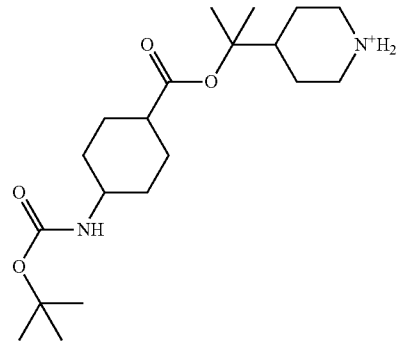
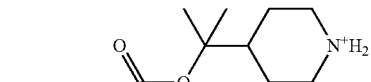
-continued
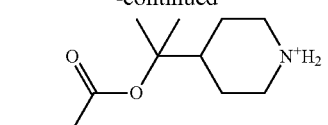
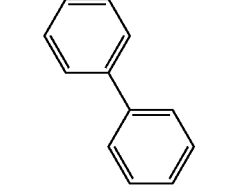
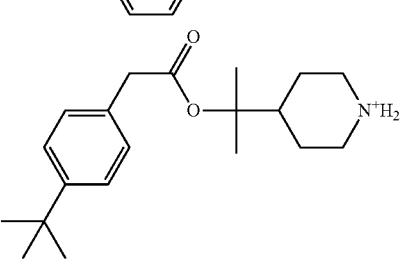
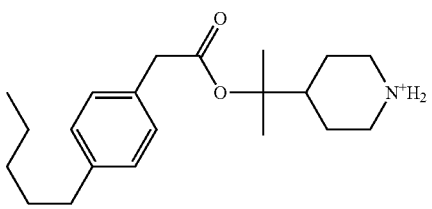
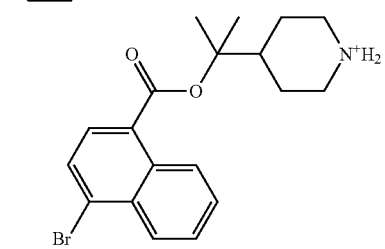
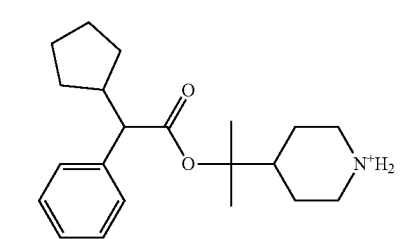
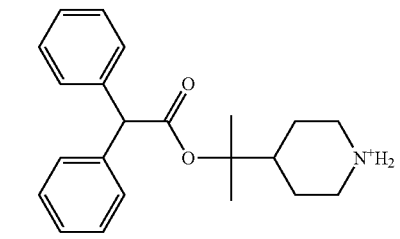
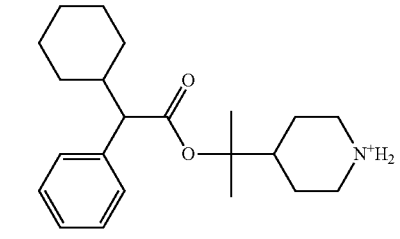

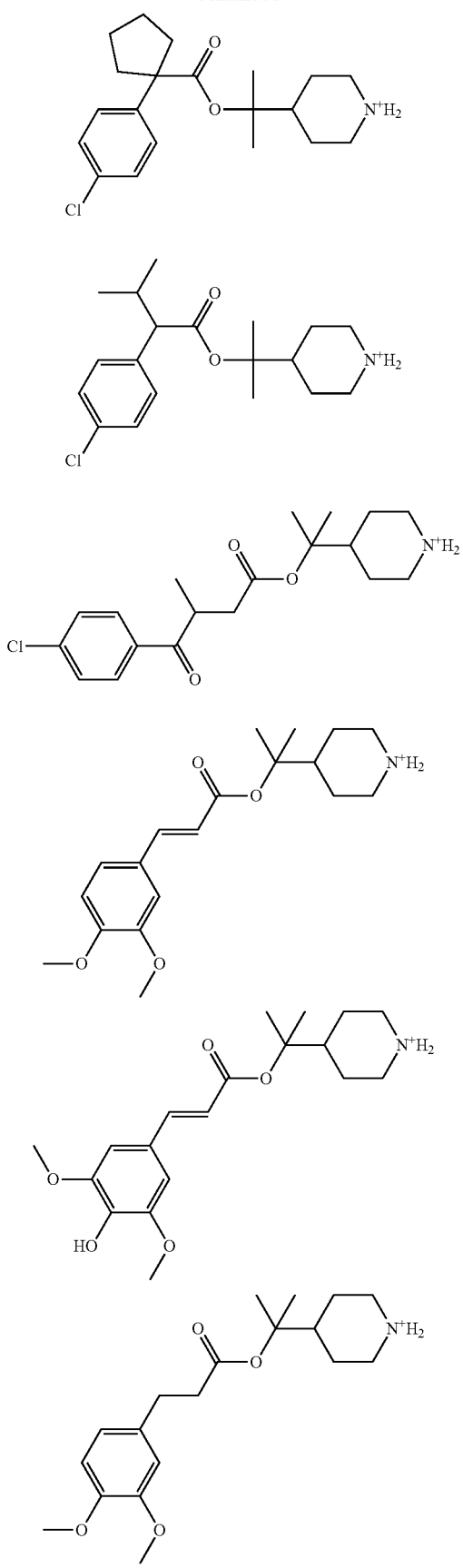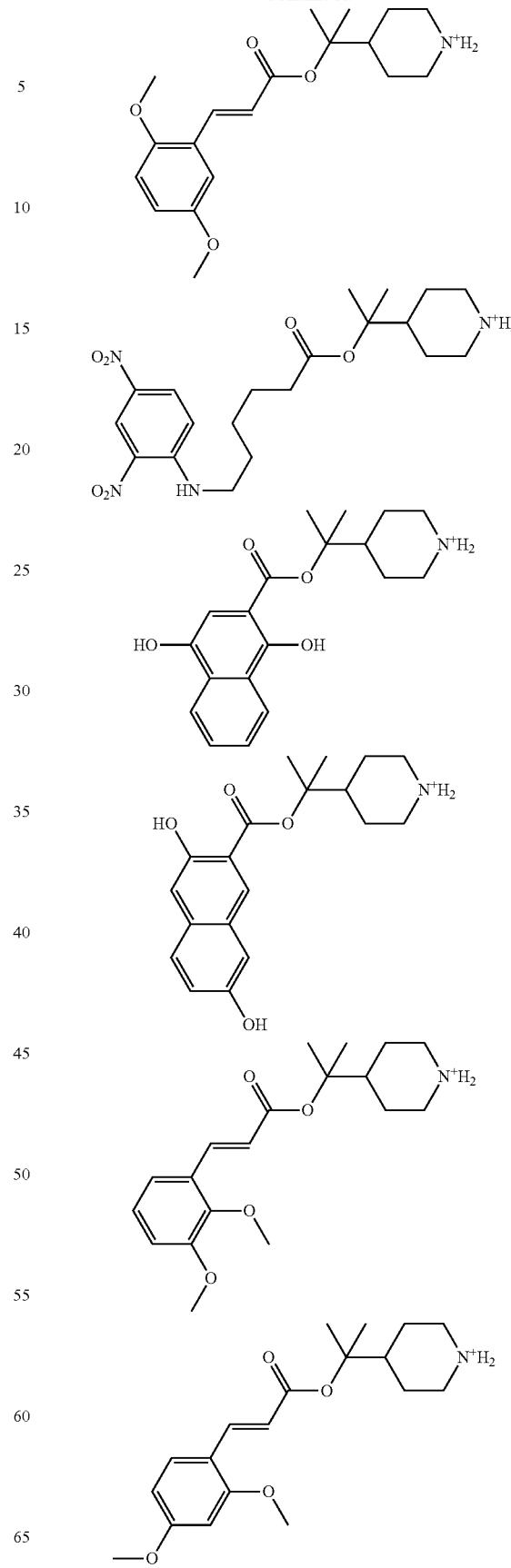

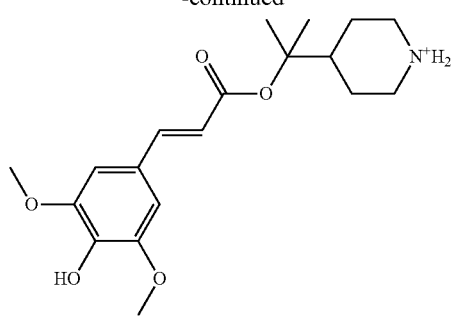
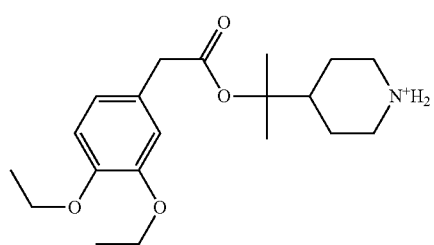
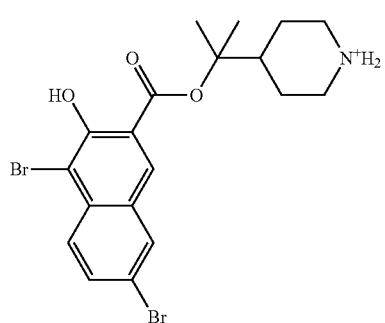
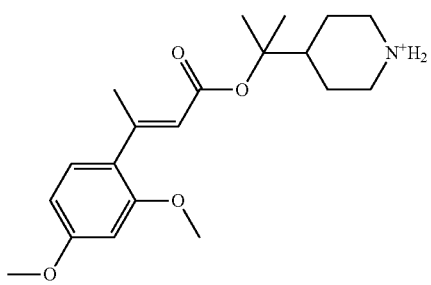
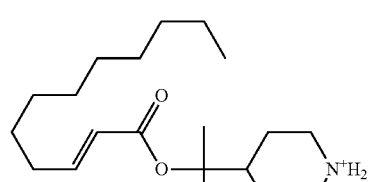
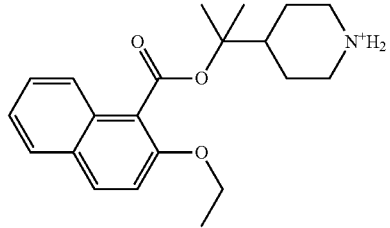
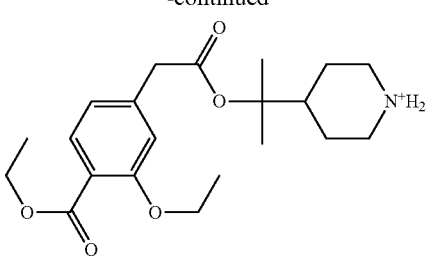
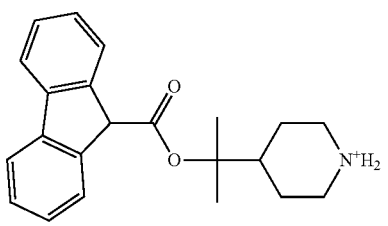
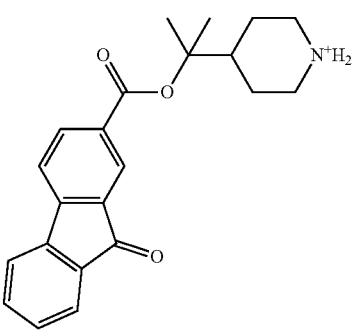
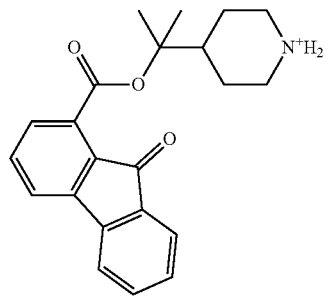
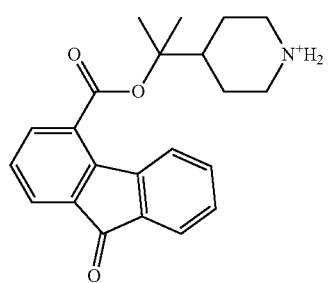
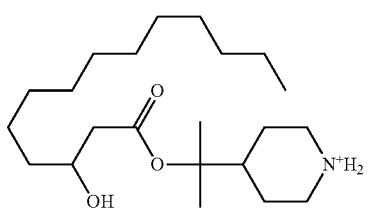

-continued
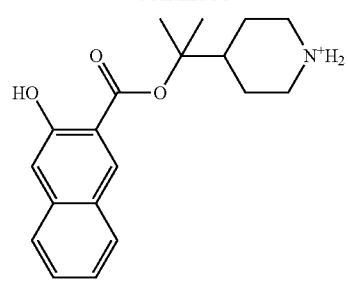
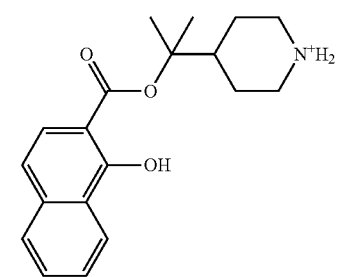
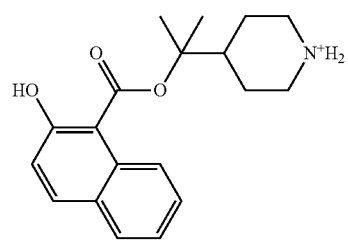
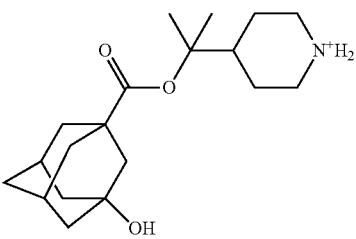
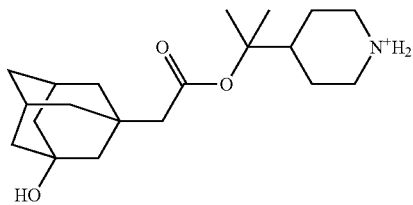
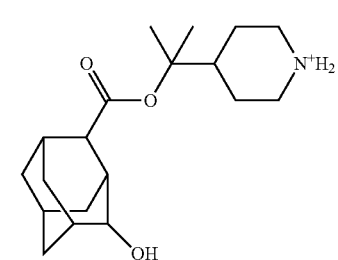
-continued
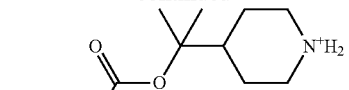
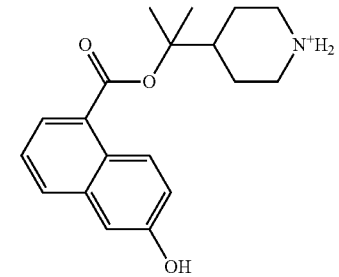
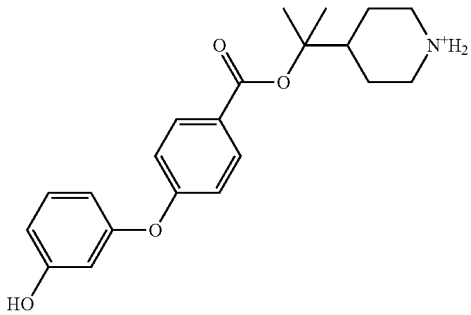
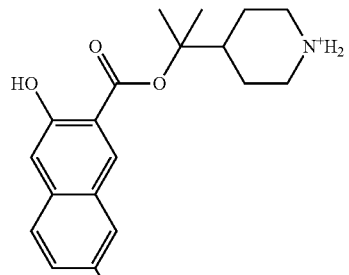
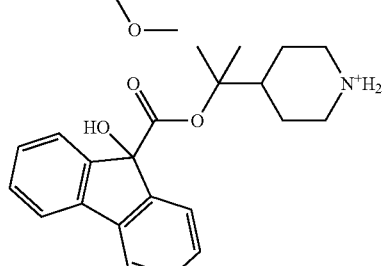
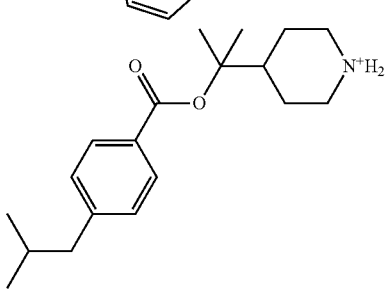

89
-continued
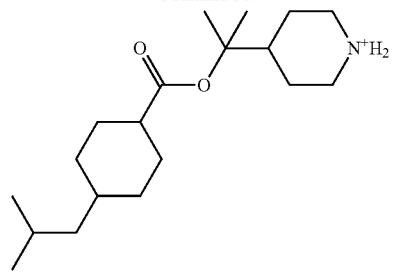
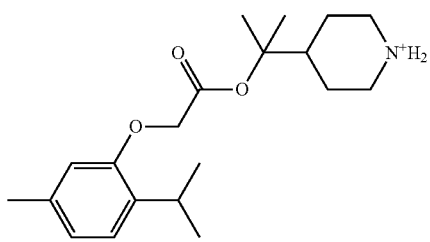
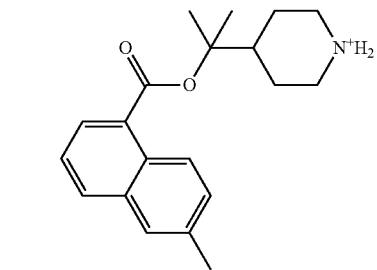
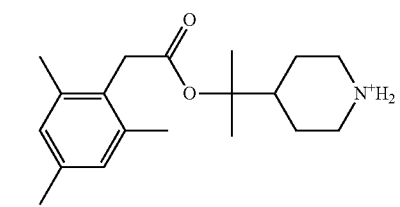
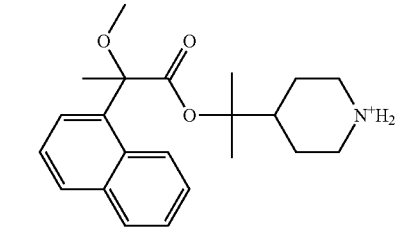
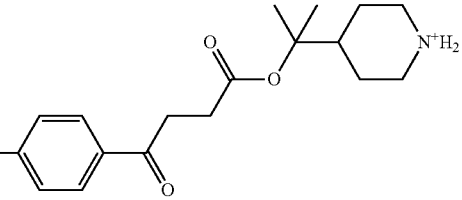
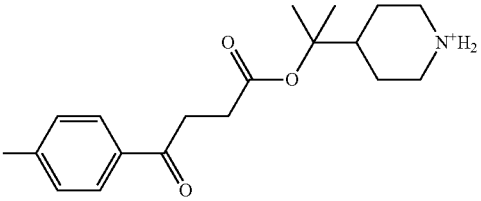
90
-continued
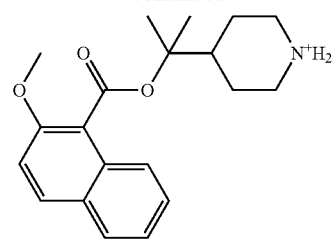
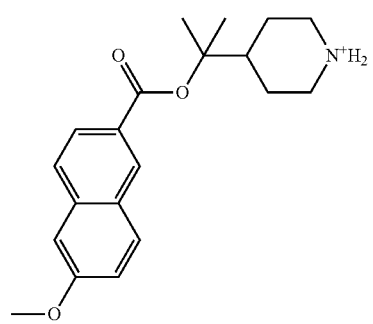
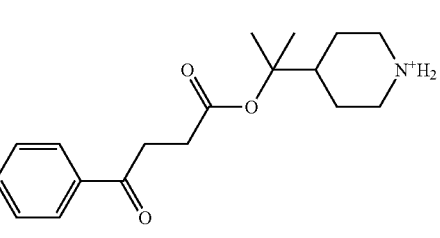
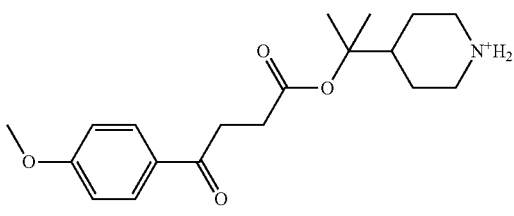
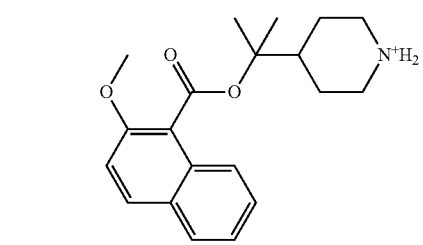
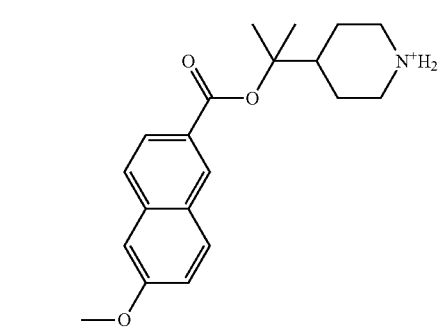

-continued
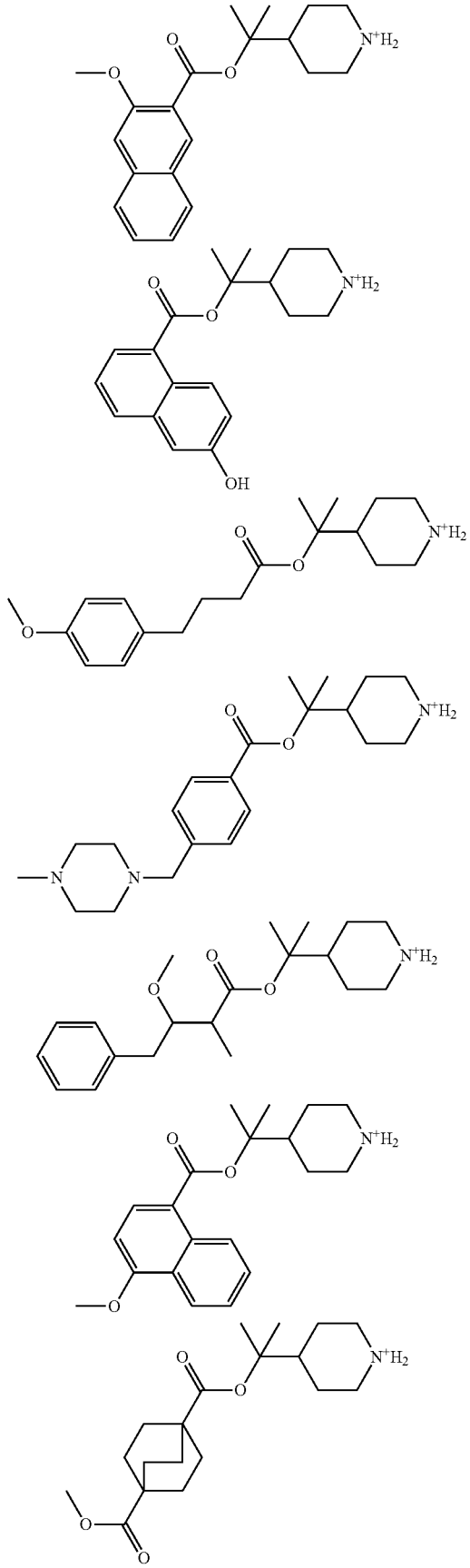
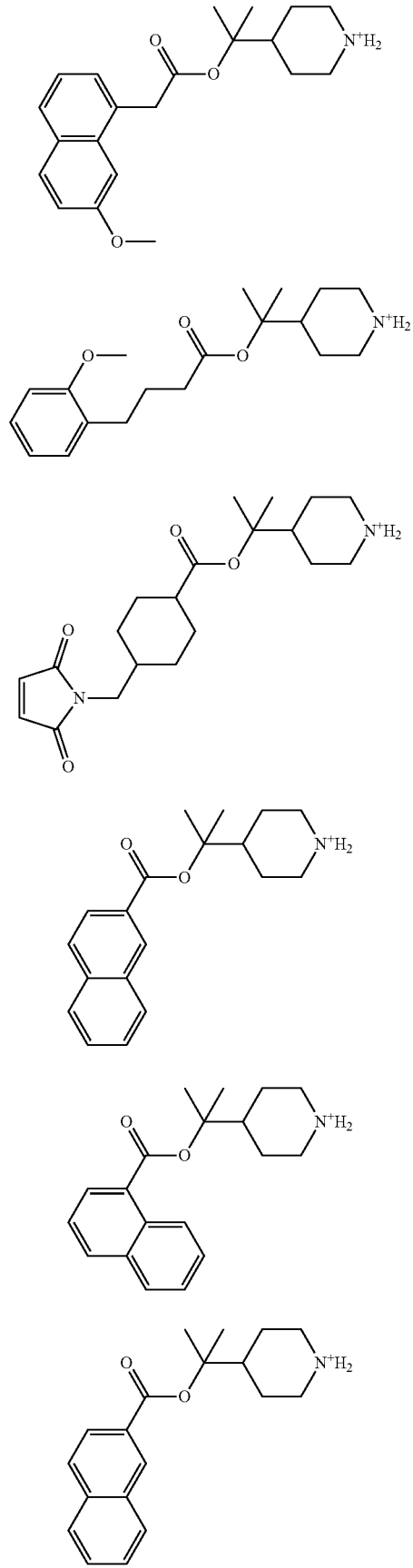

93
-continued
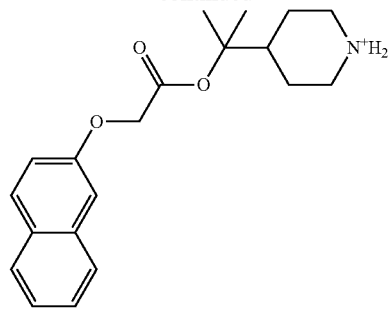
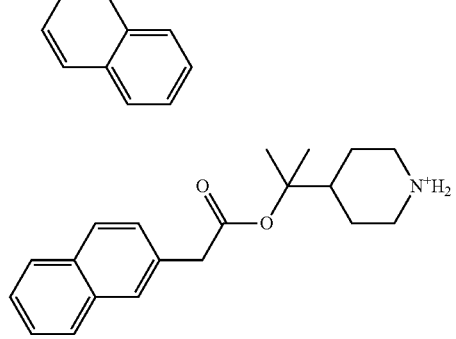
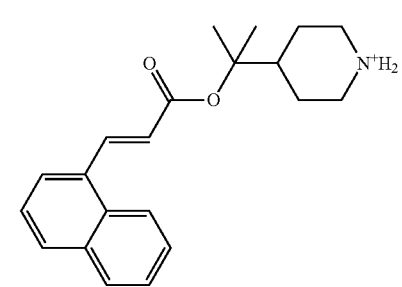
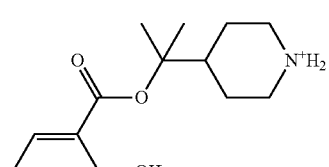
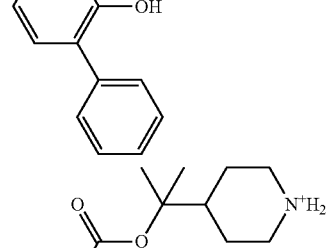
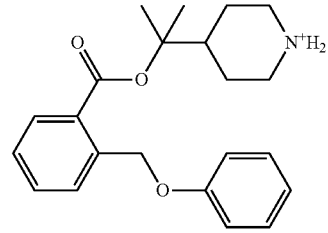
94
-continued
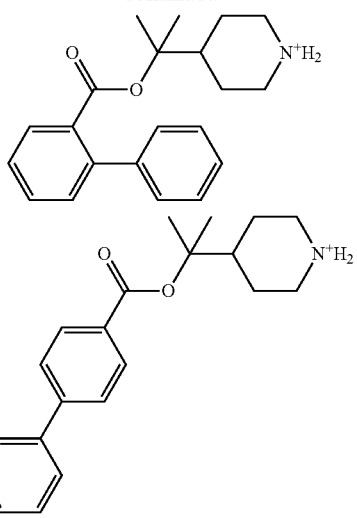
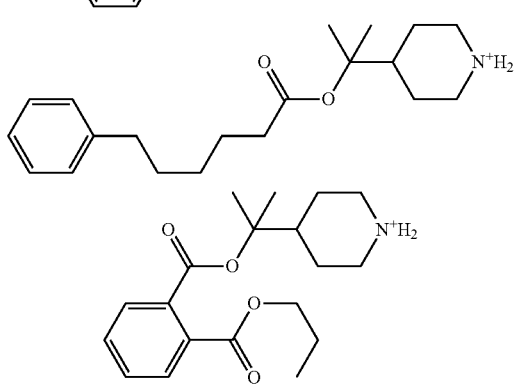
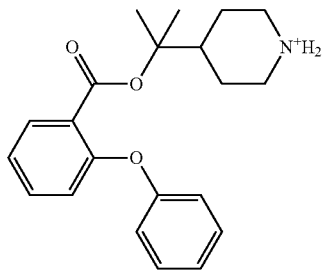
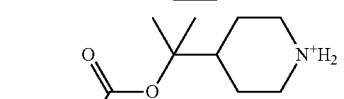
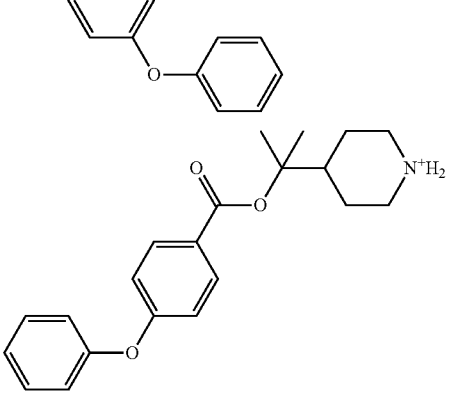

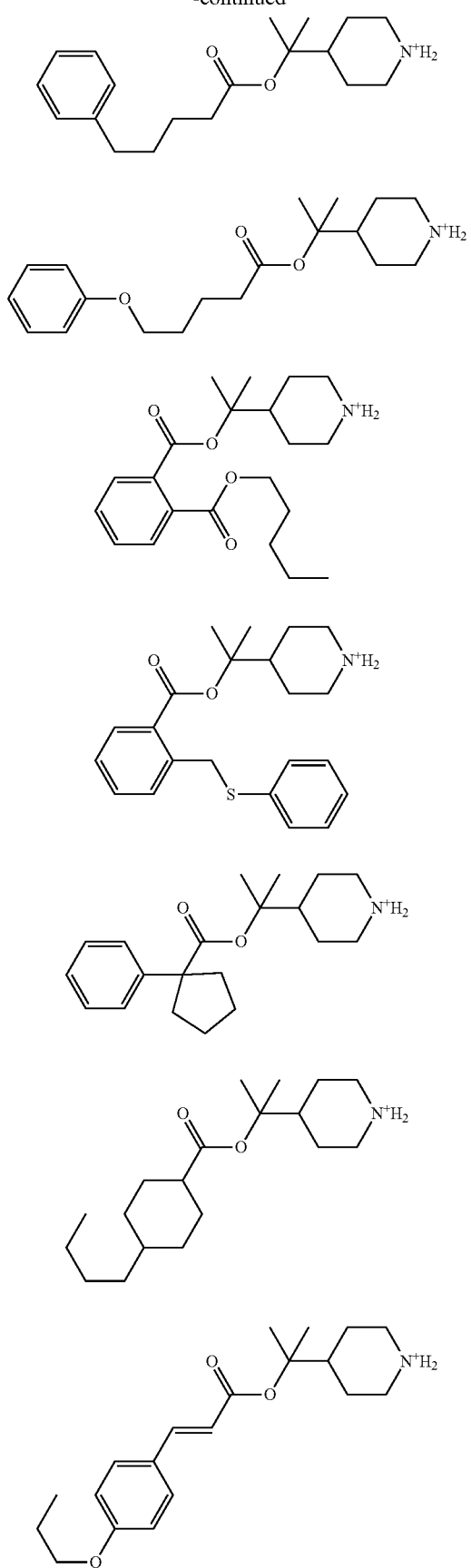
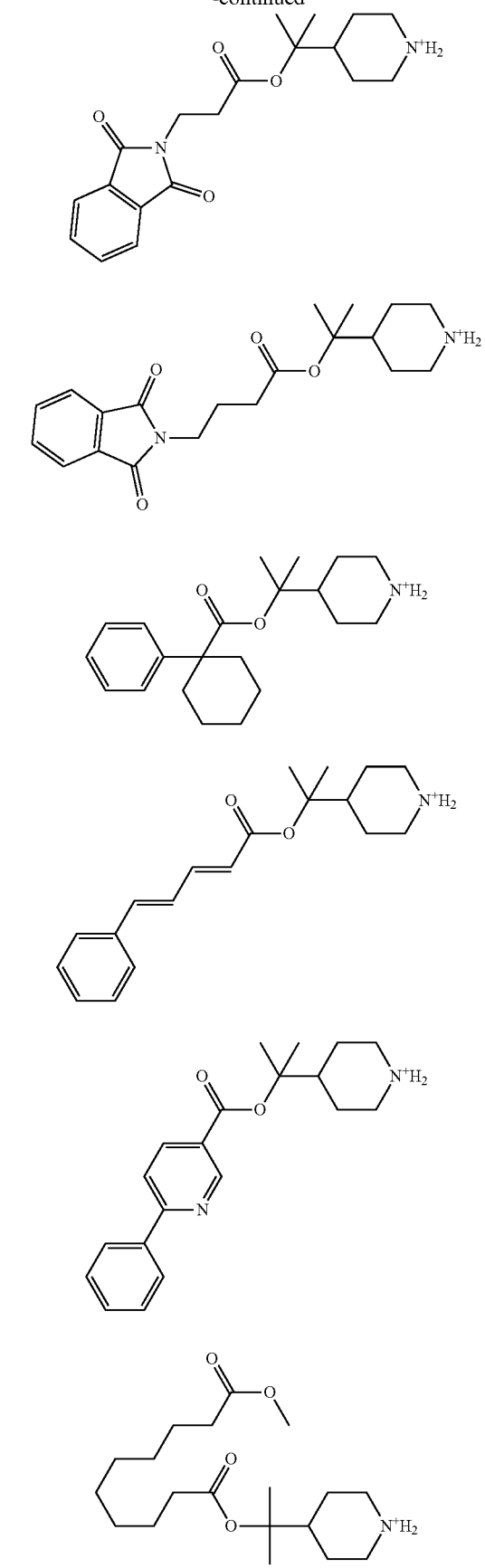

-continued
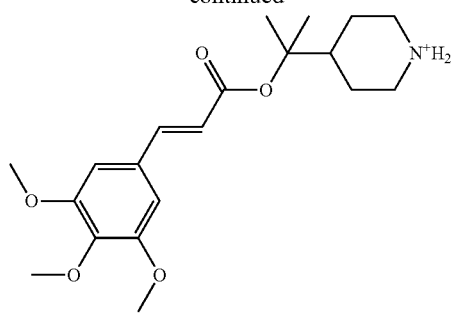
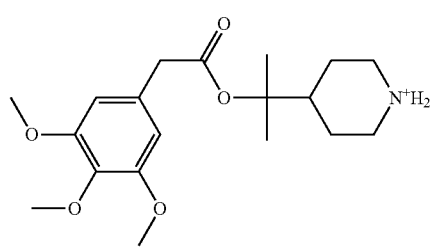
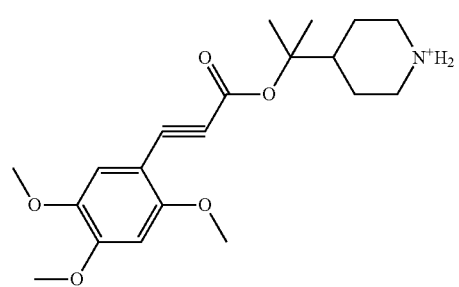
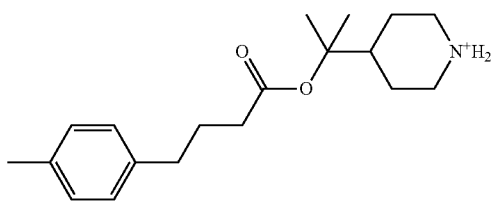
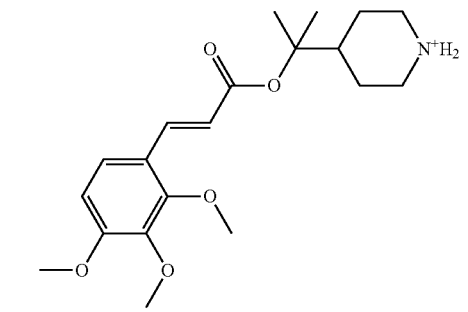
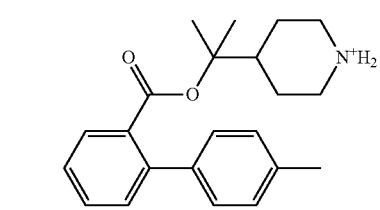
-continued
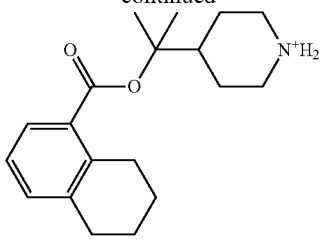
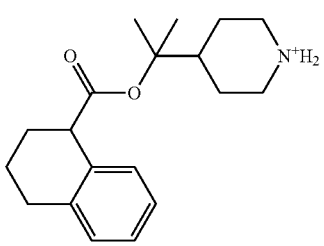
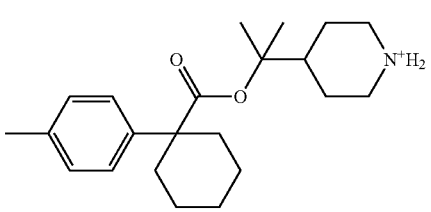
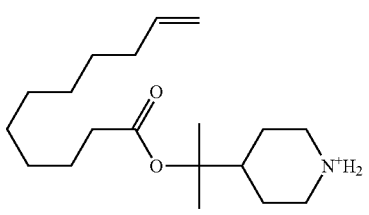
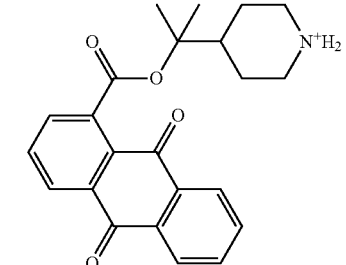
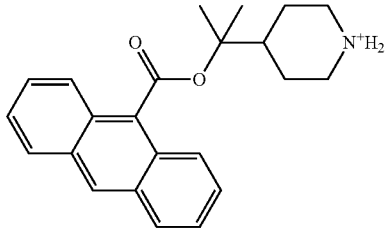

-continued
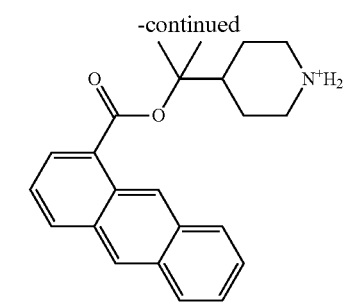
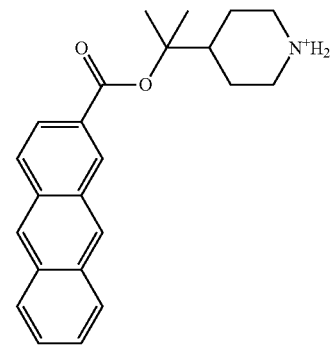
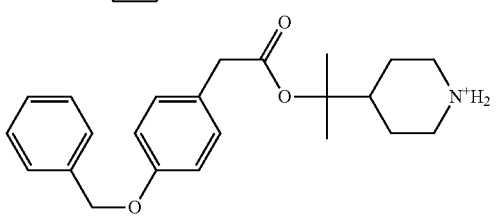
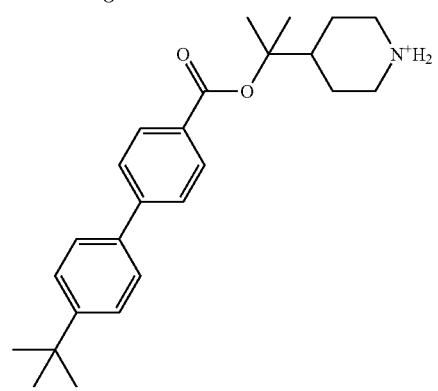
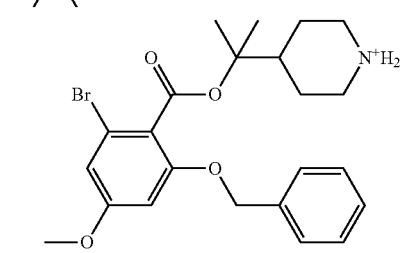
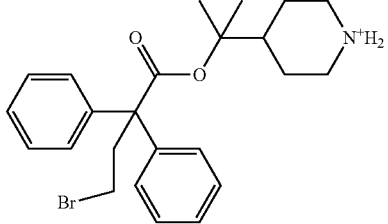
-continued
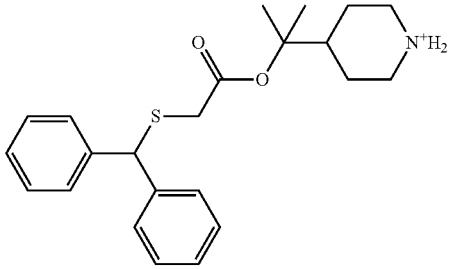
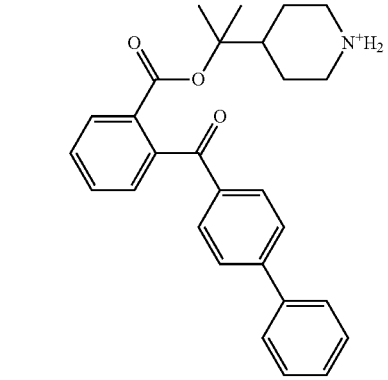
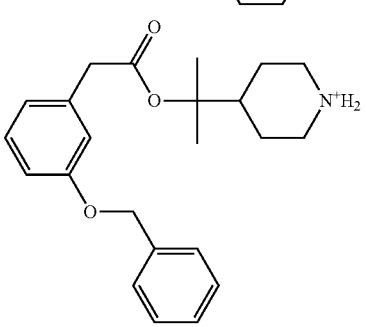
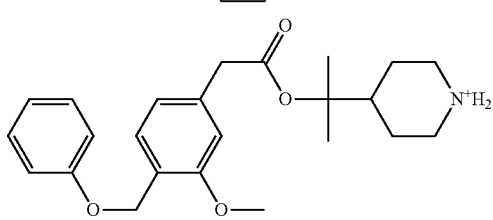
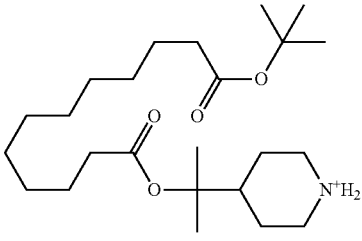
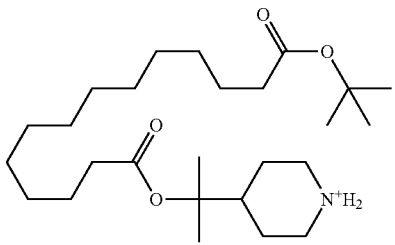

101
-continued

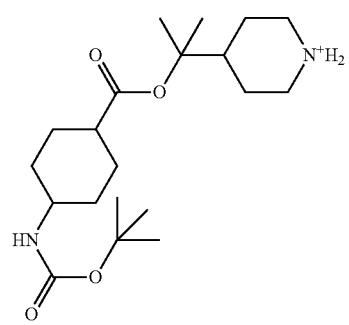
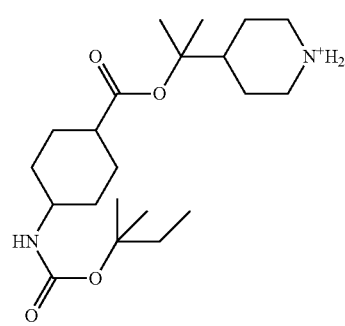
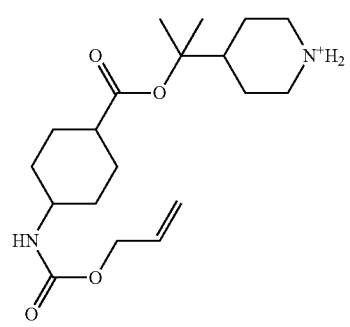
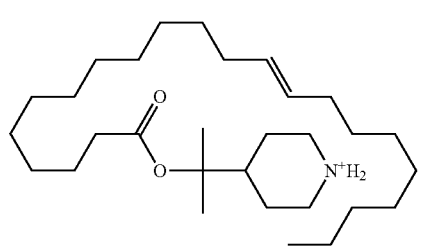
102
-continued
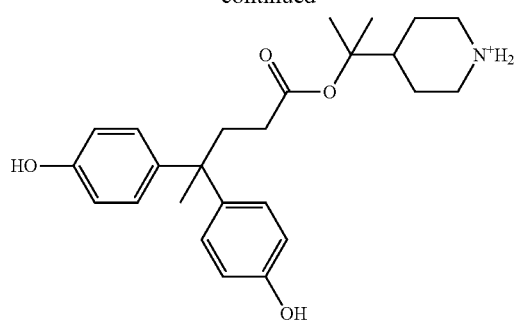
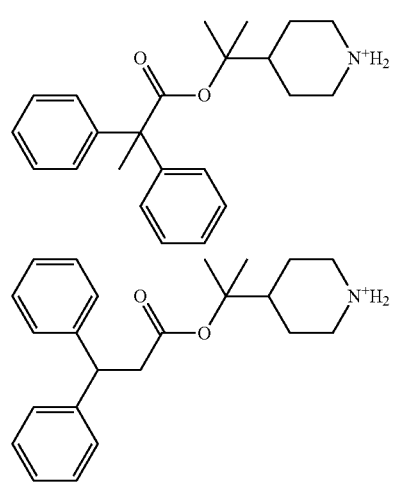
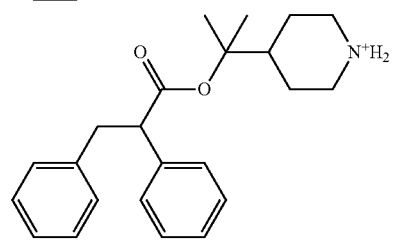
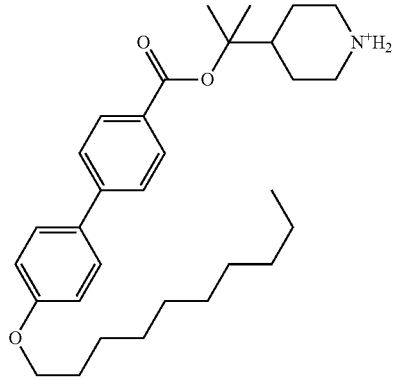
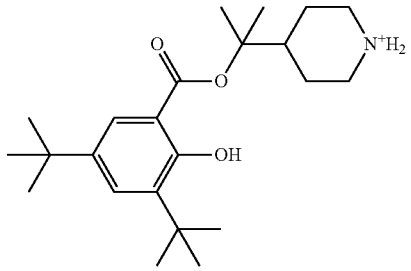

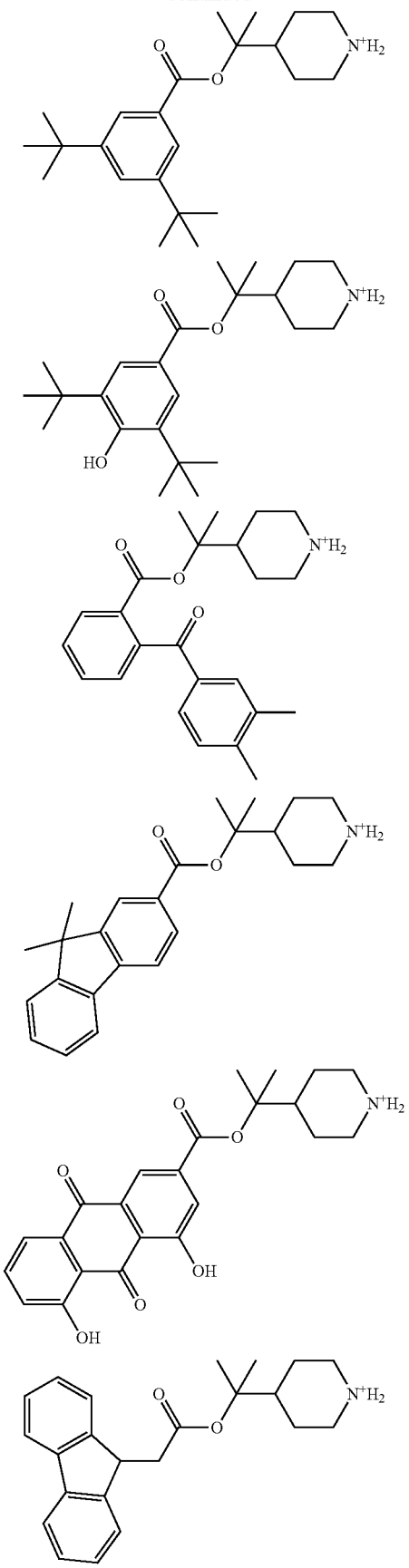
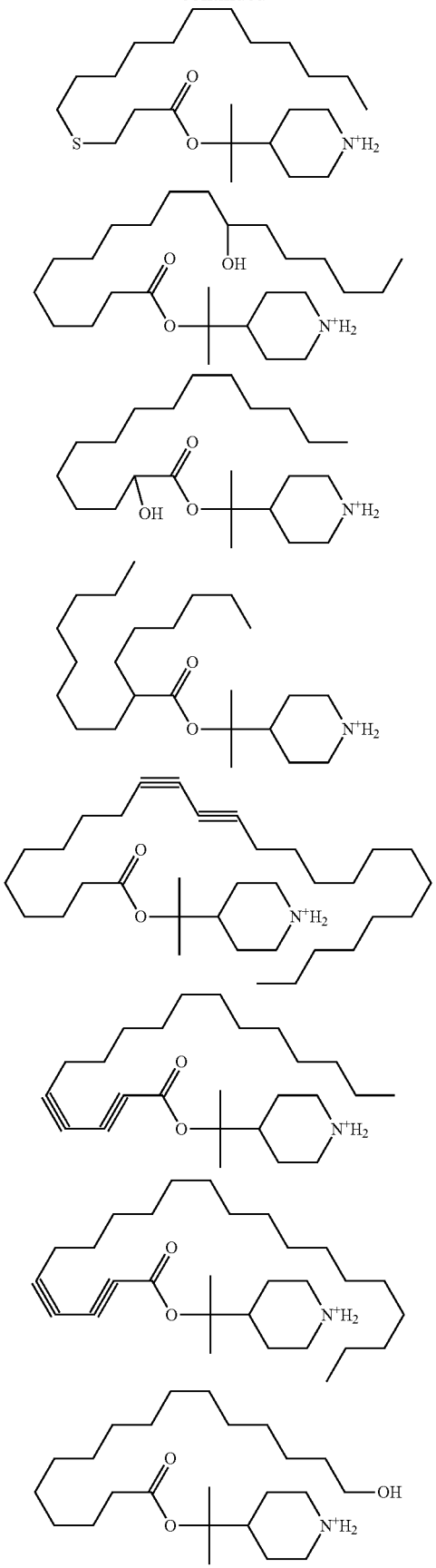

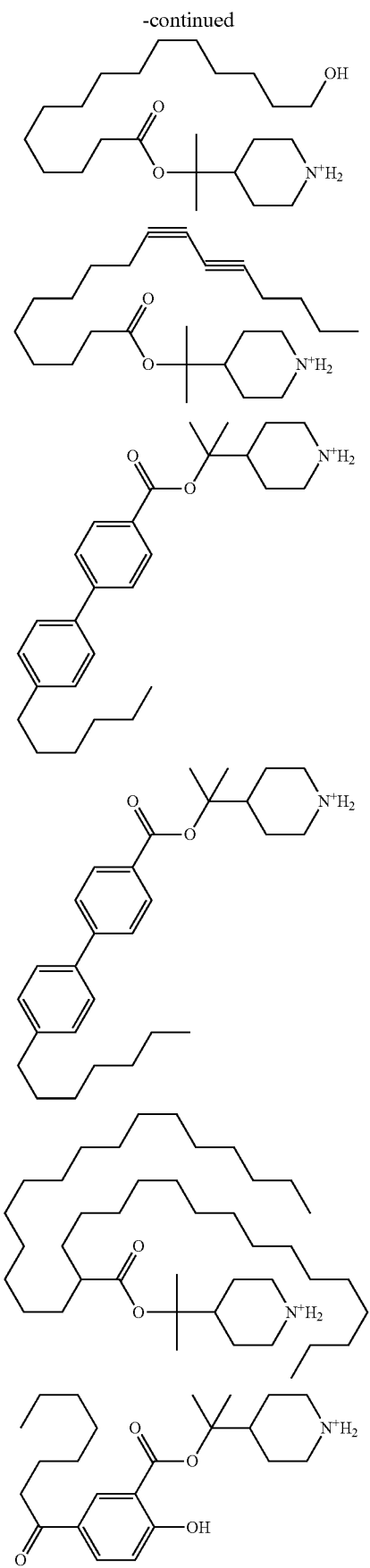
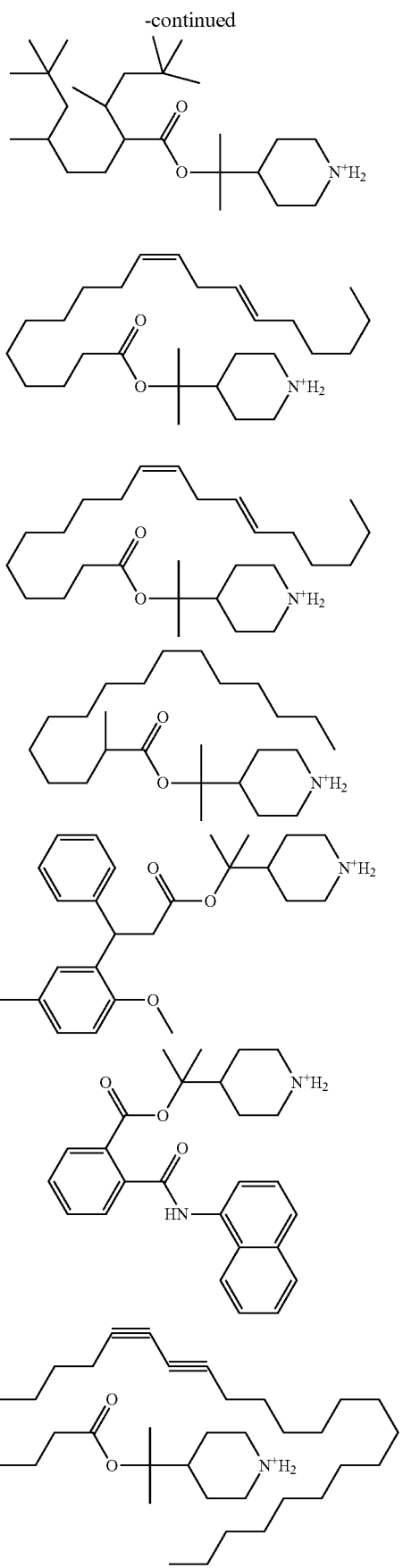

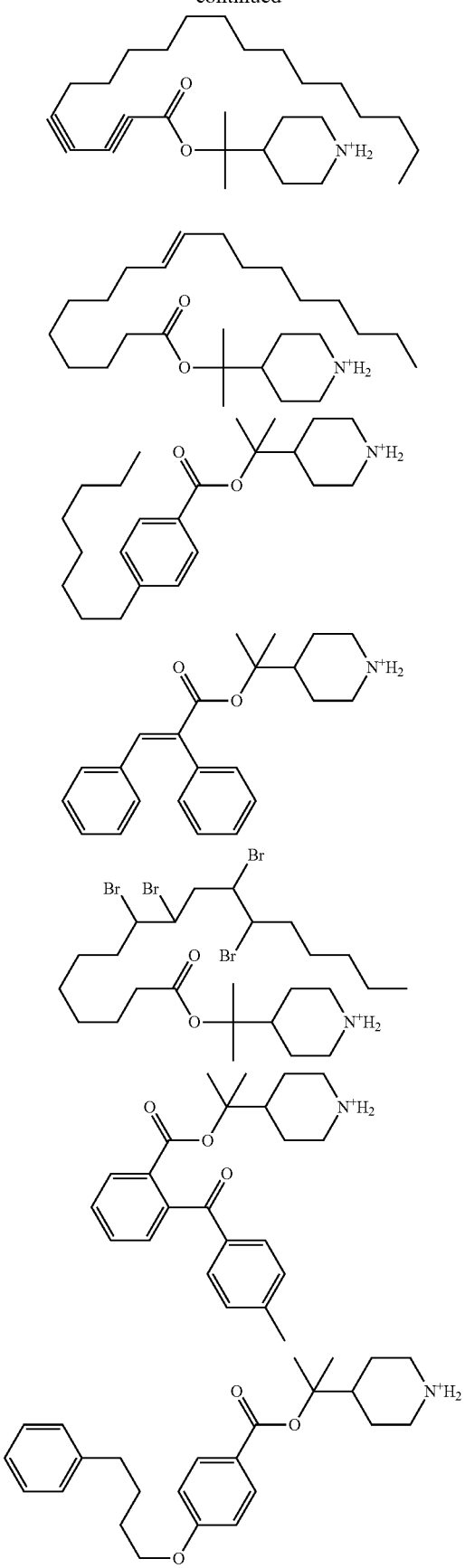
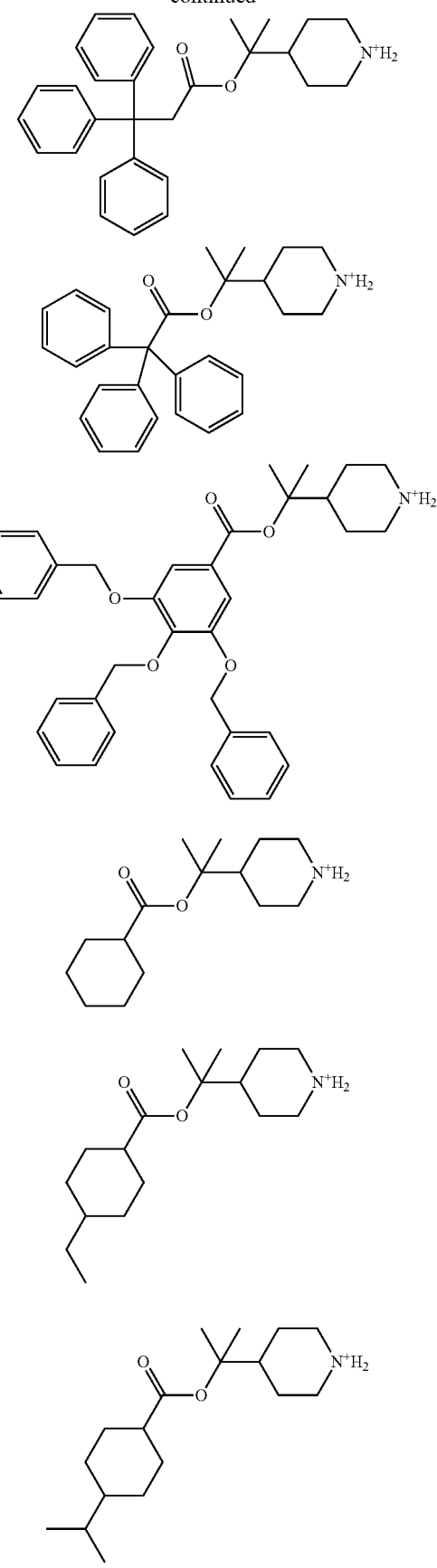

-continued
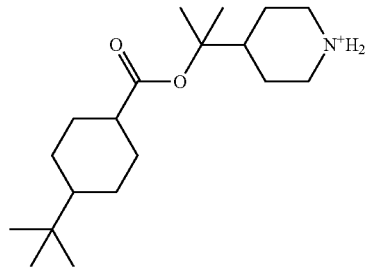
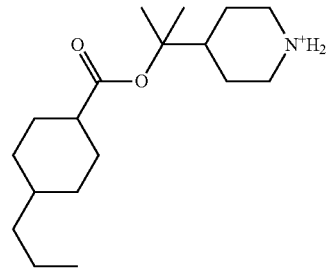
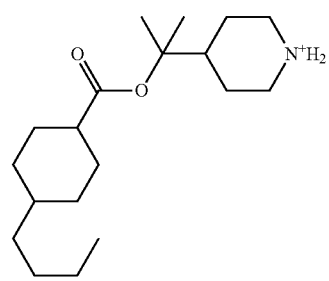
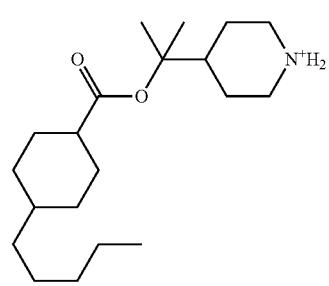
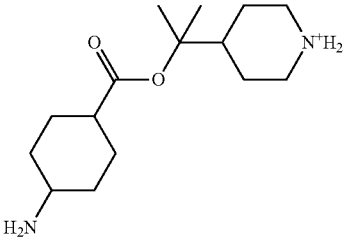
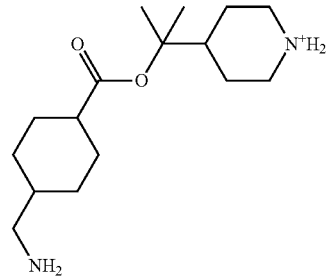
-continued
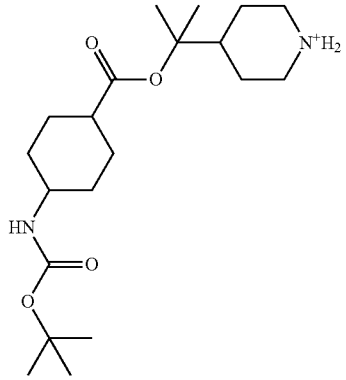
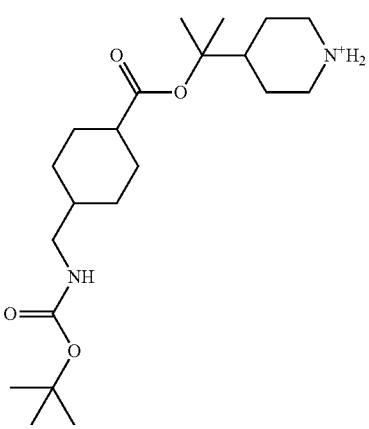
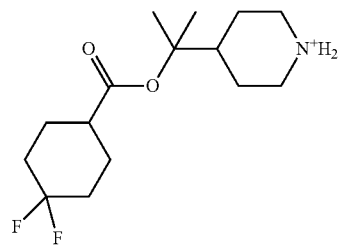
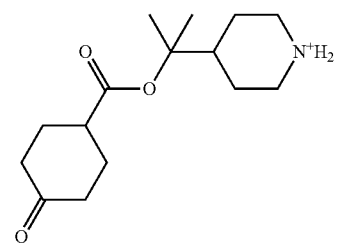
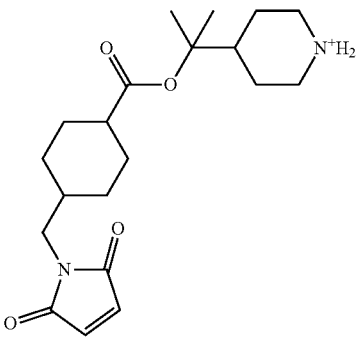

111
-continued
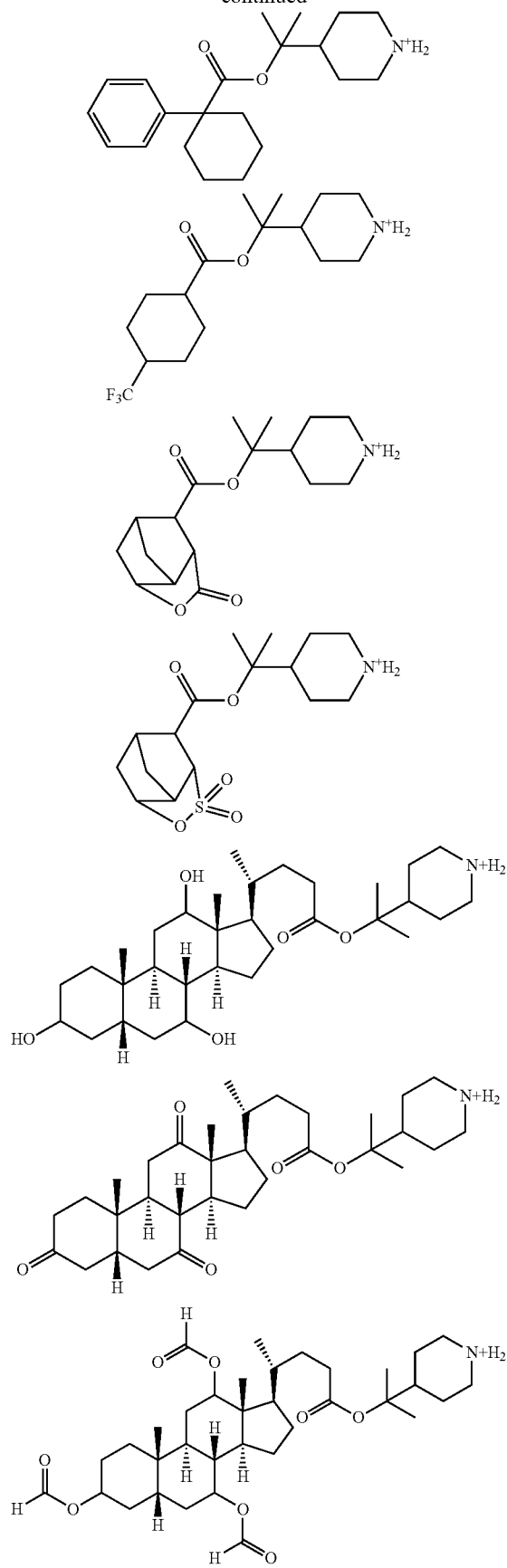
112
-continued
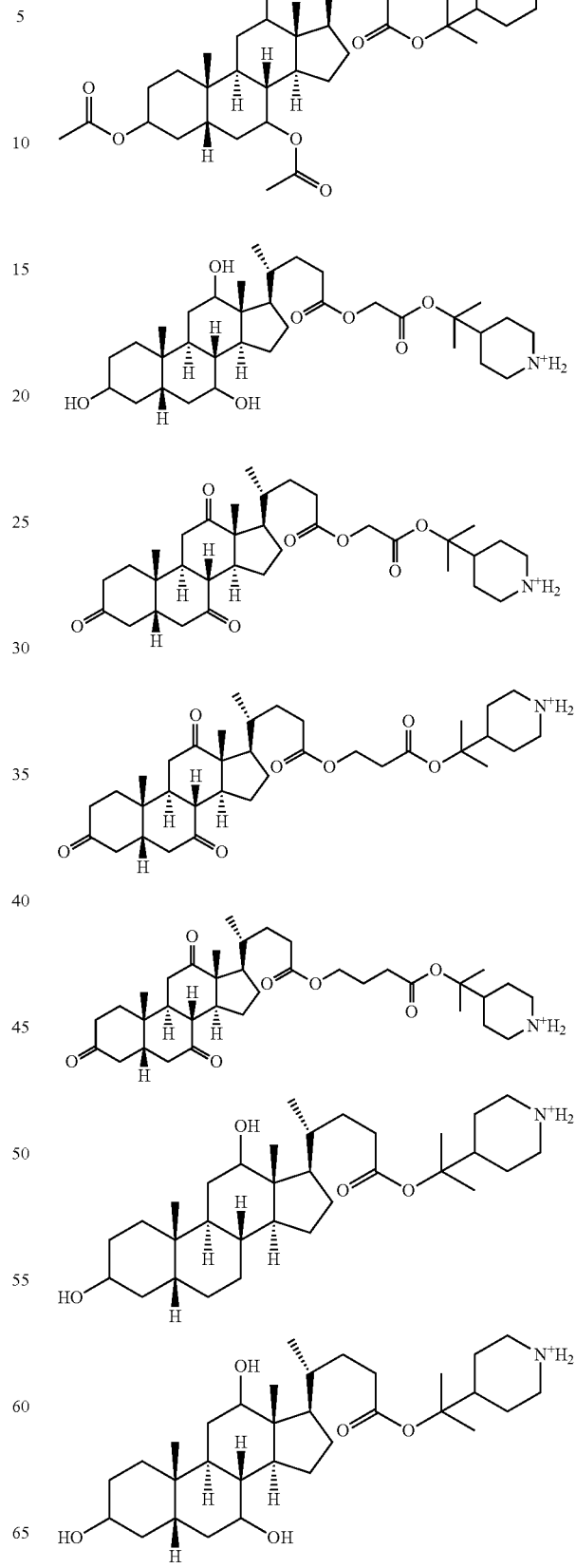

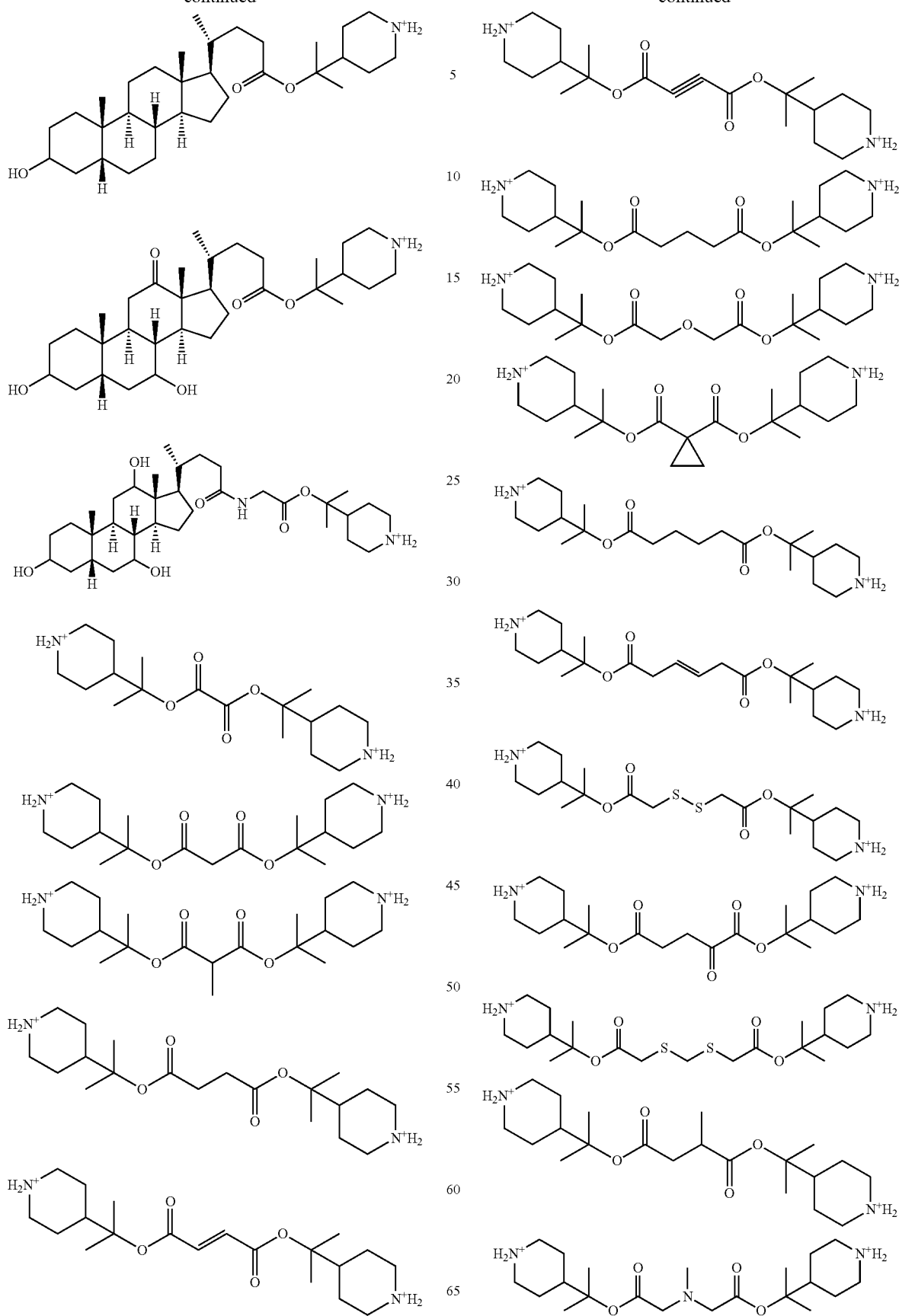

-continued
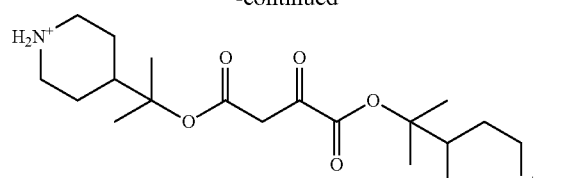
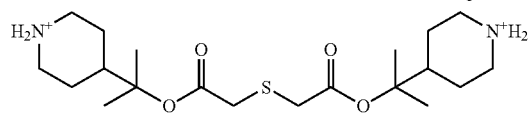
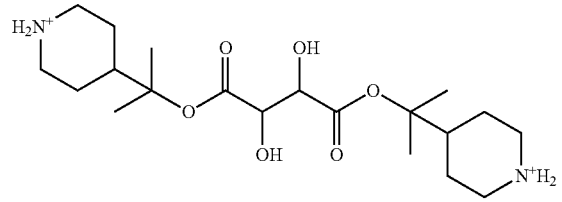
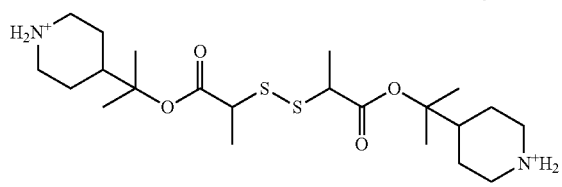
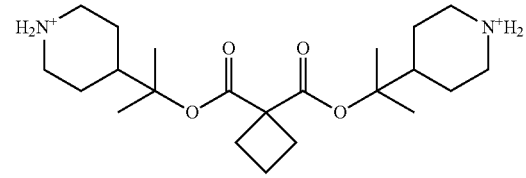
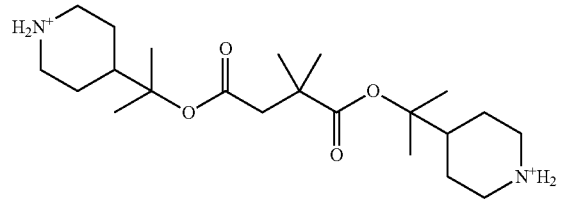
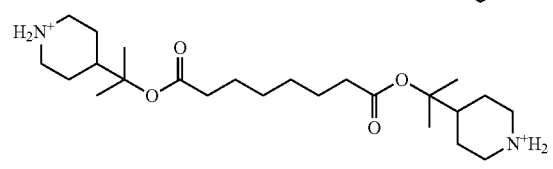
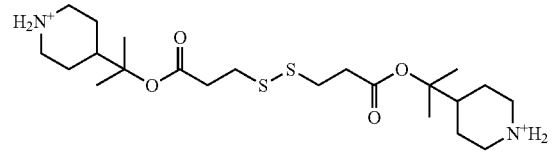
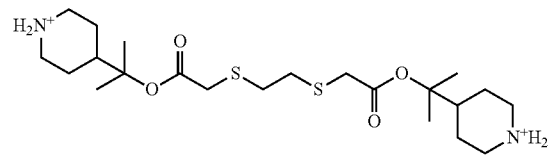
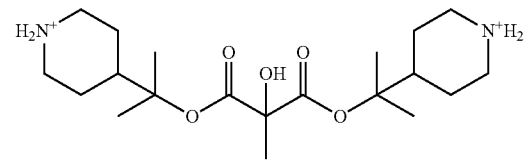
-continued
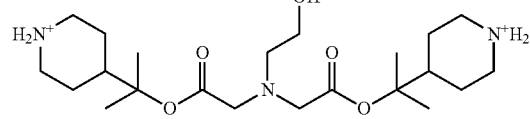
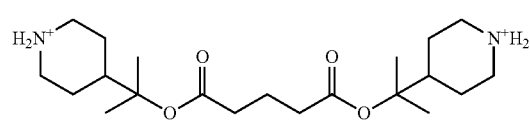
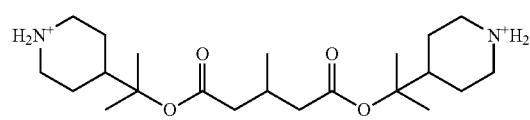
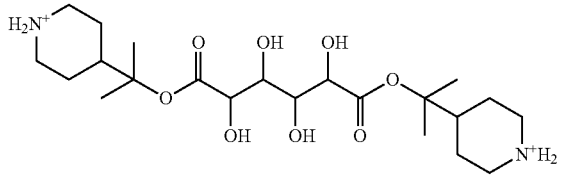
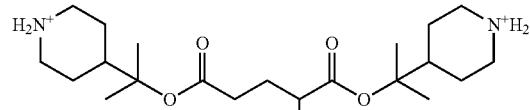
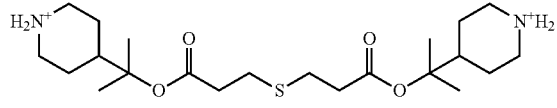
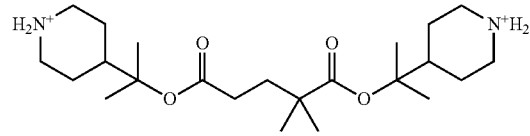
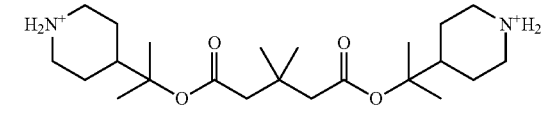
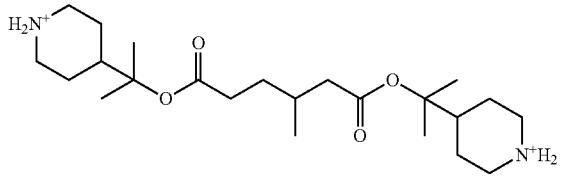

117
-continued
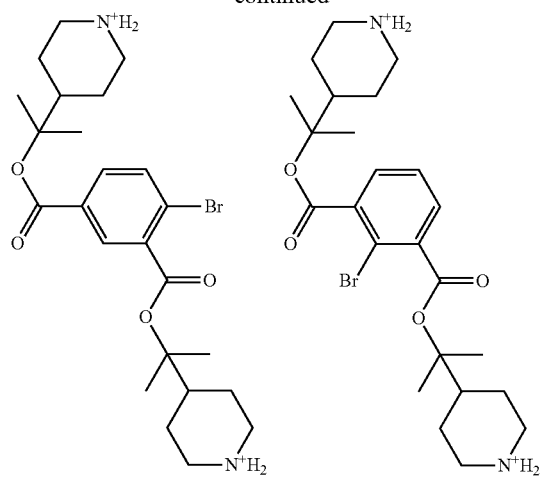
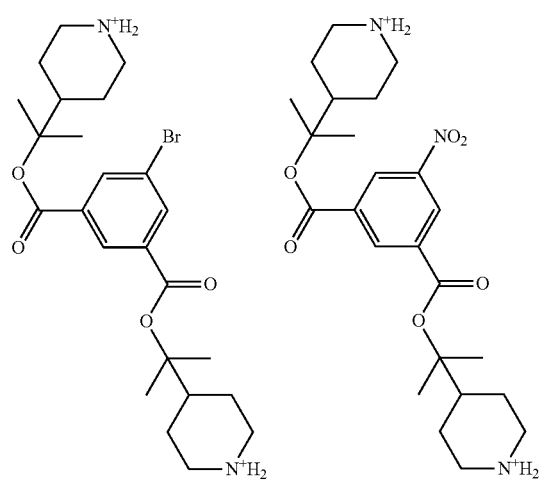
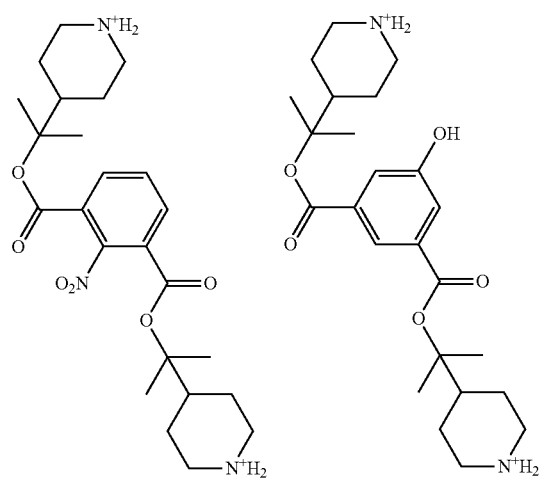
118
-continued
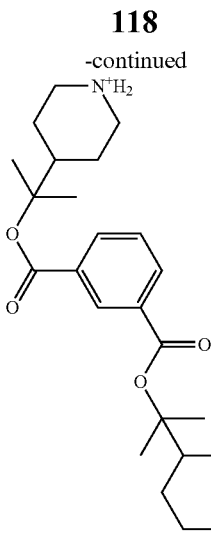
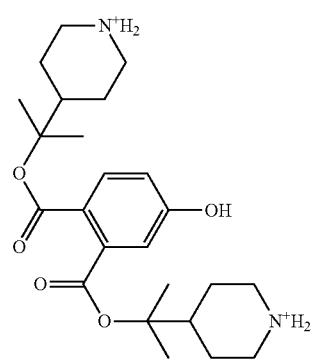
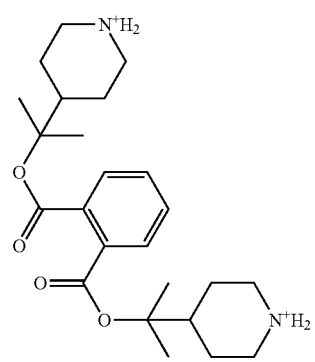
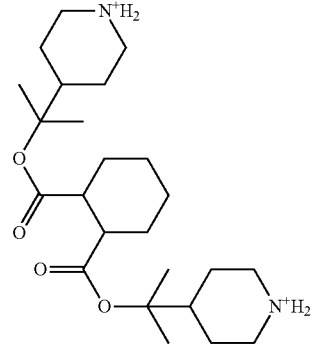

119
-continued
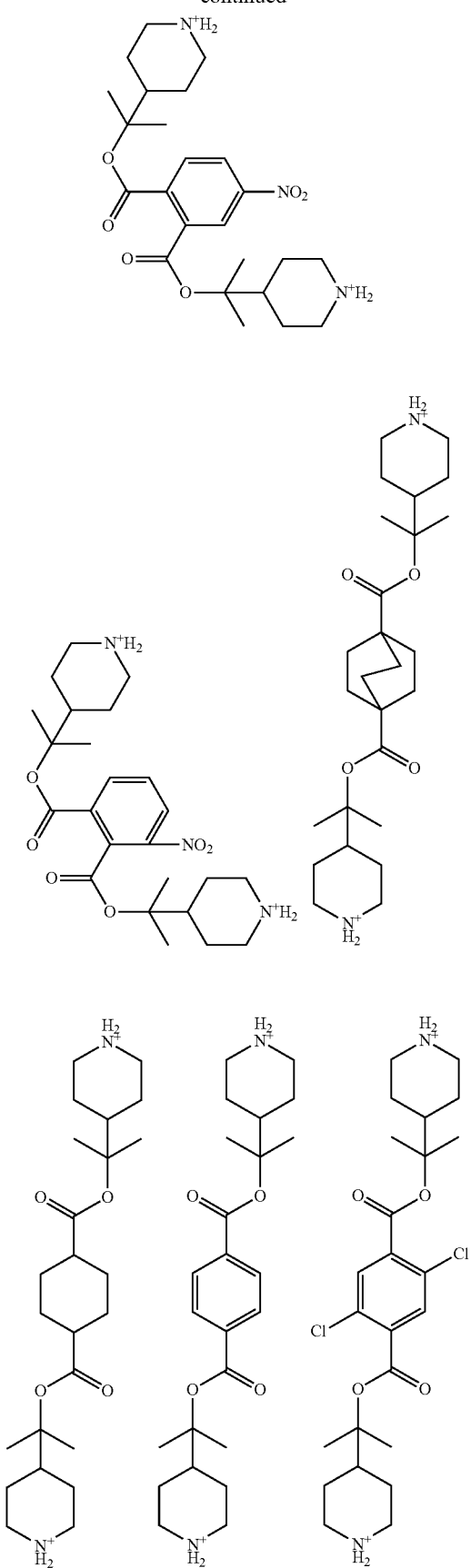
120
-continued
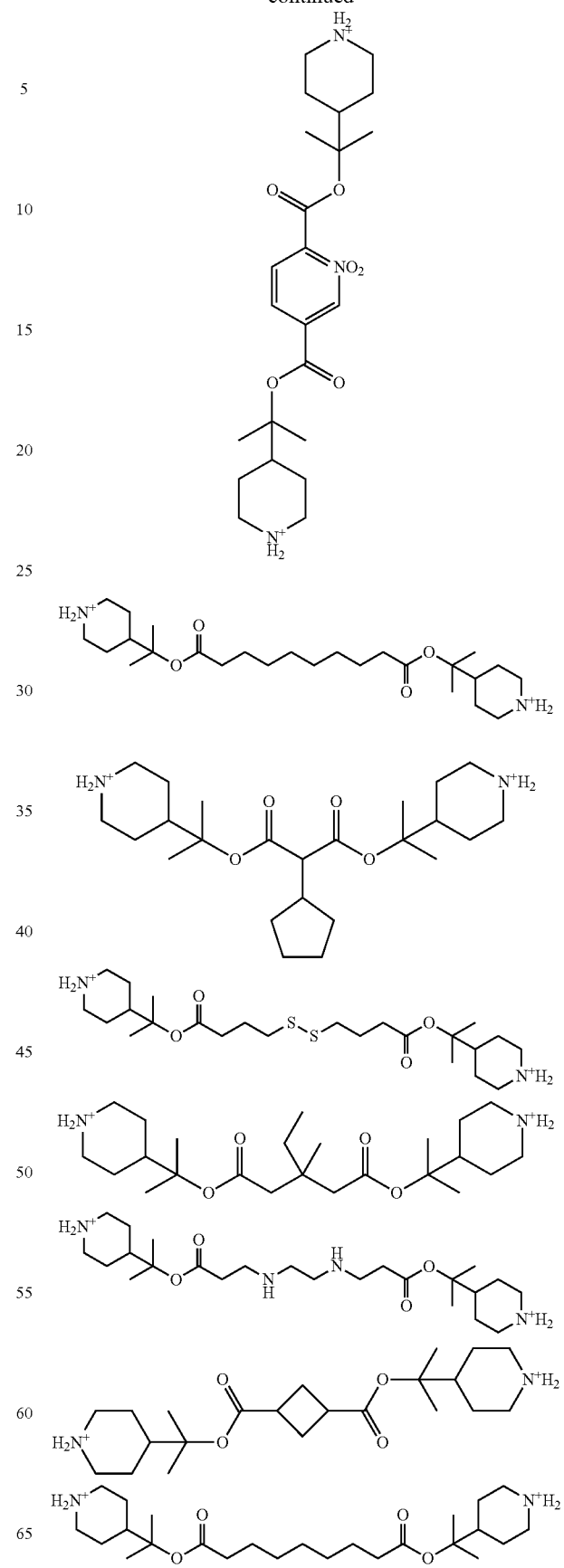

121
-continued
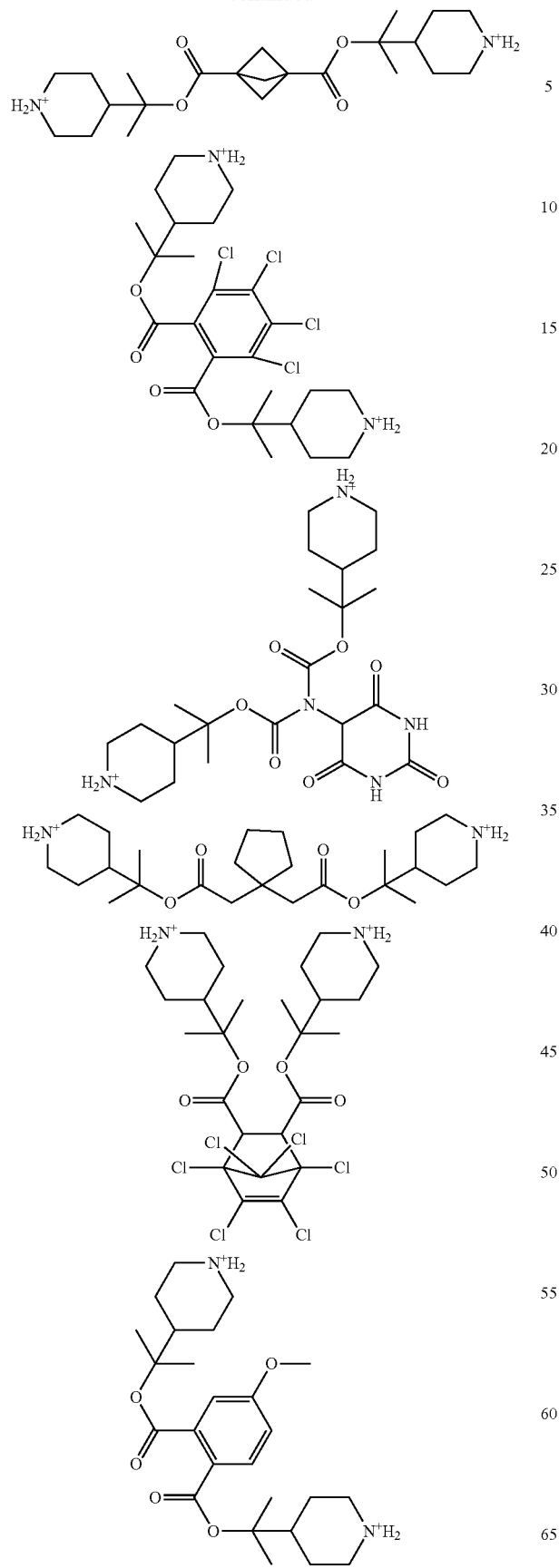
122
-continued
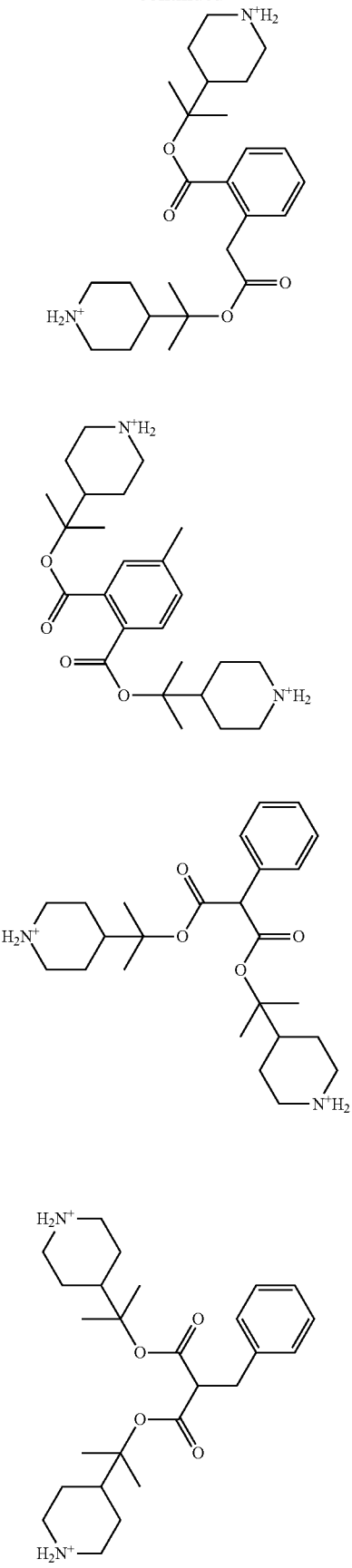

123
-continued
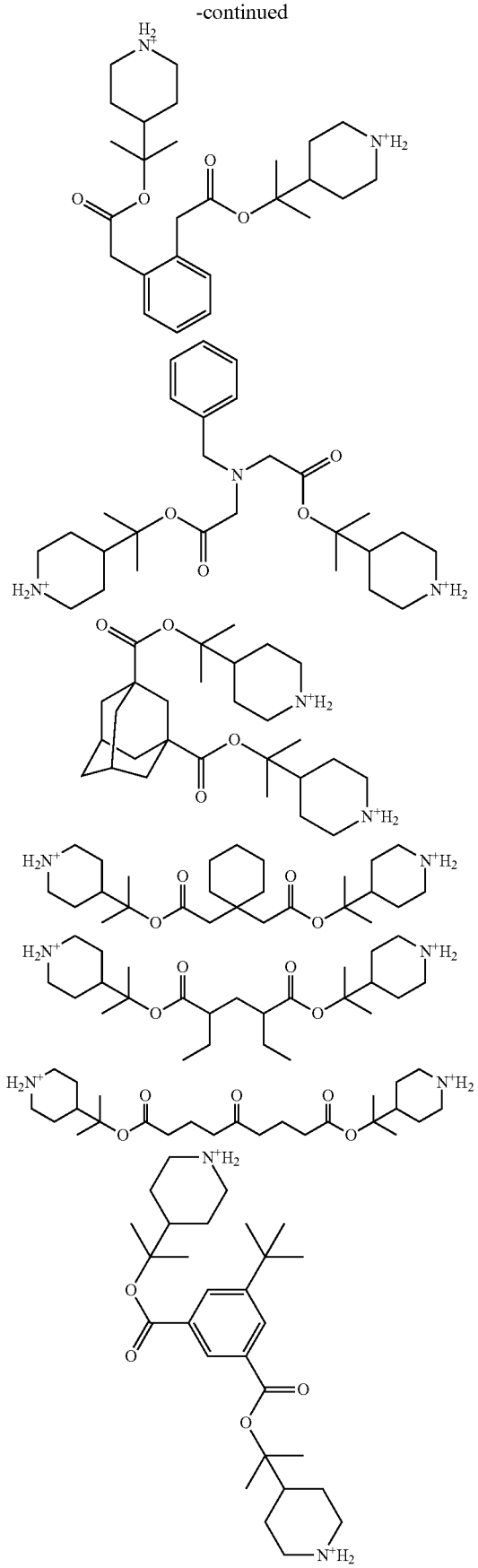
124
-continued
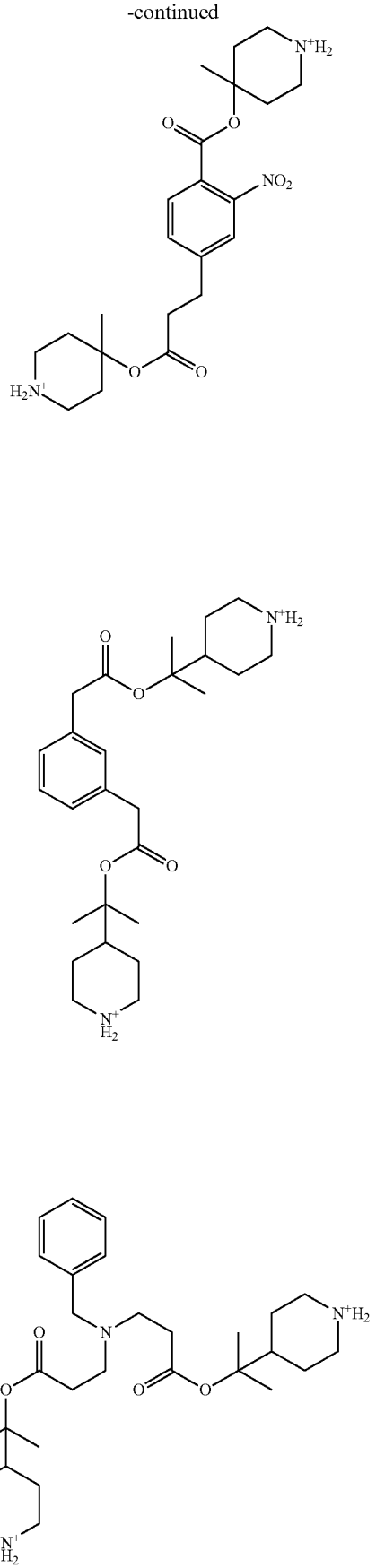

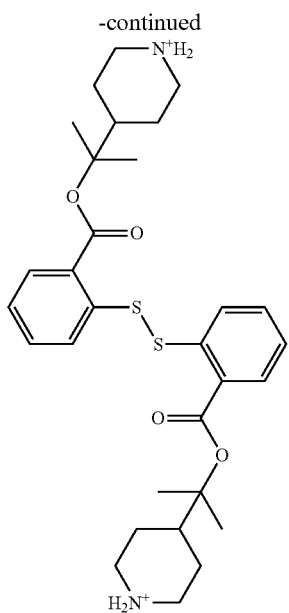
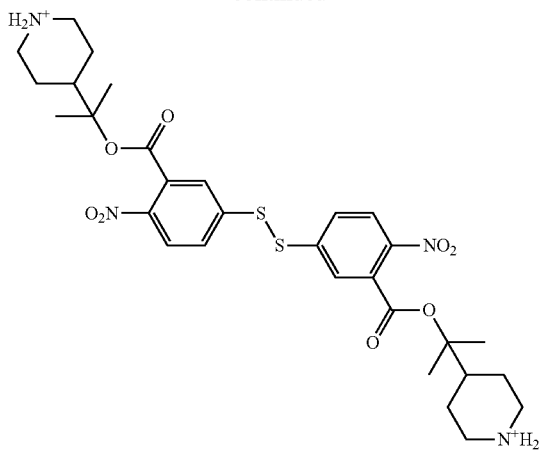
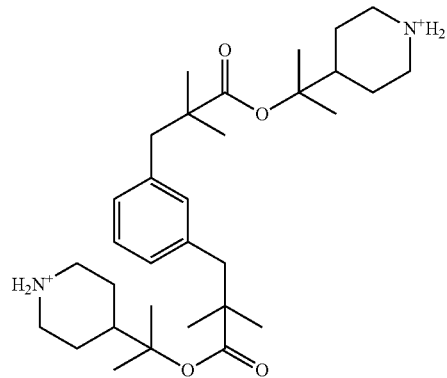
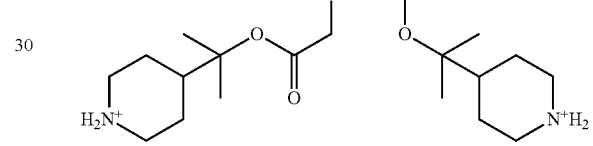
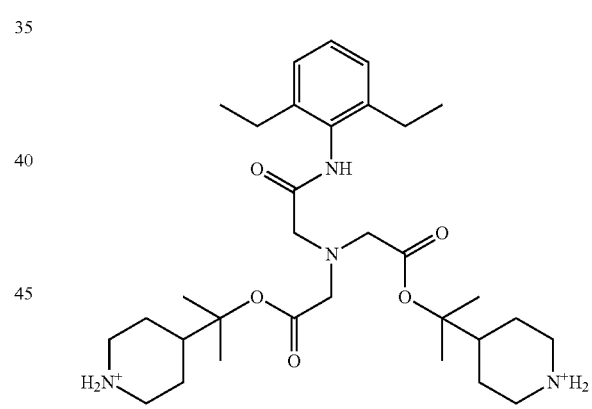
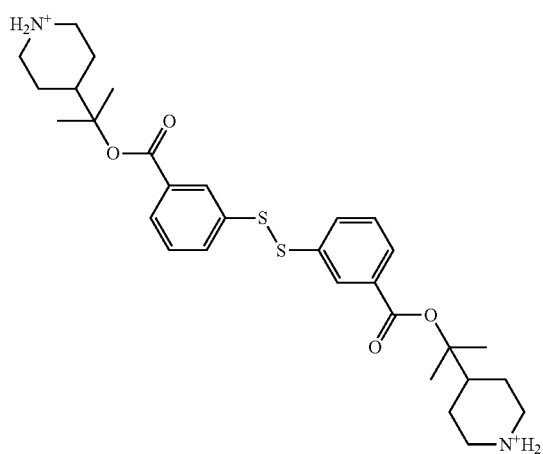
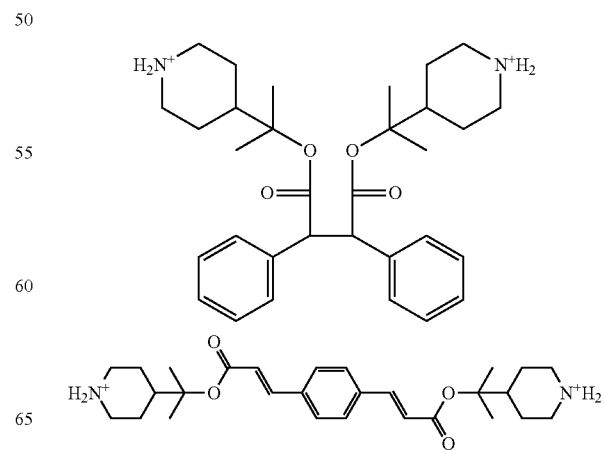

127
-continued
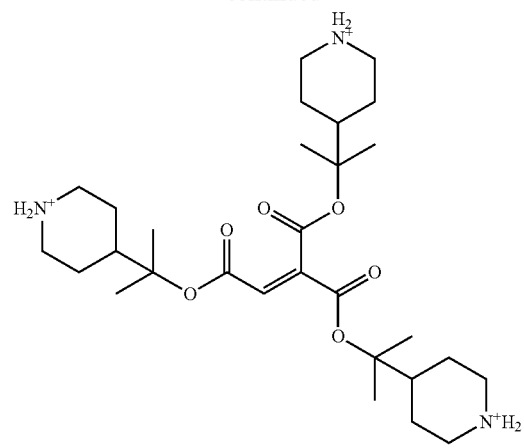
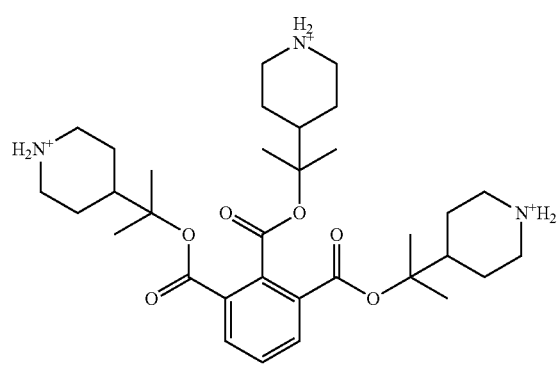
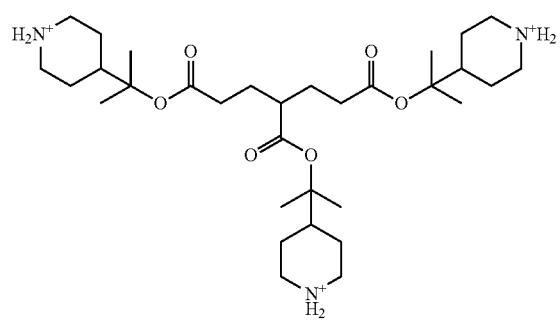
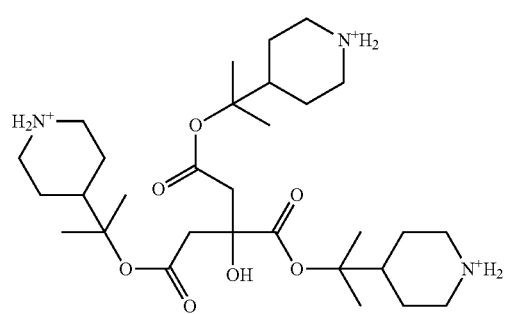
128
-continued
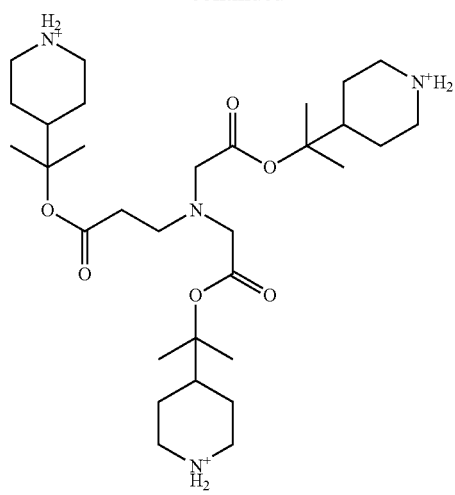
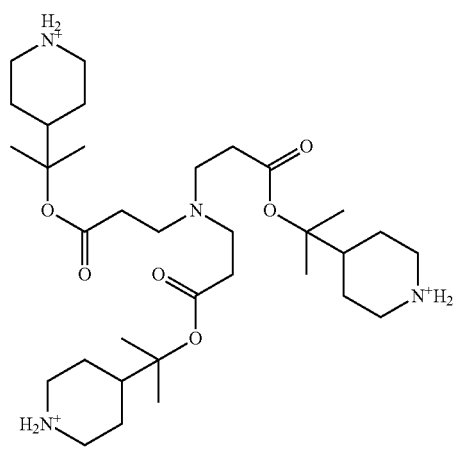
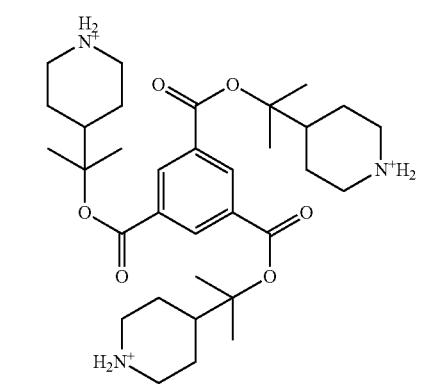
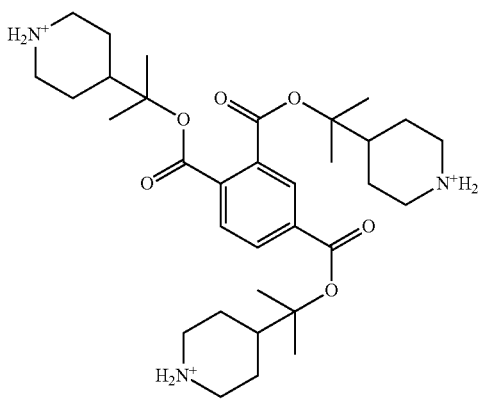

129
-continued
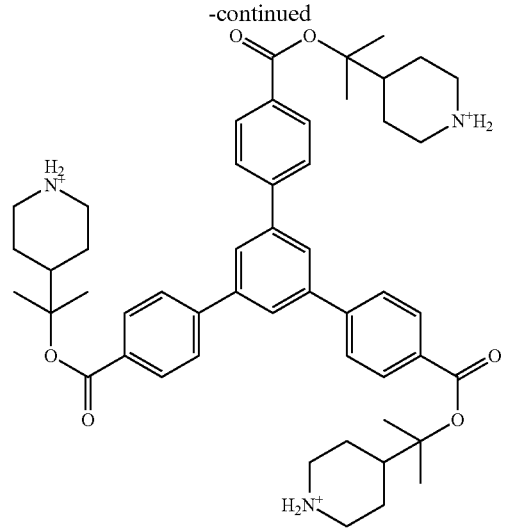
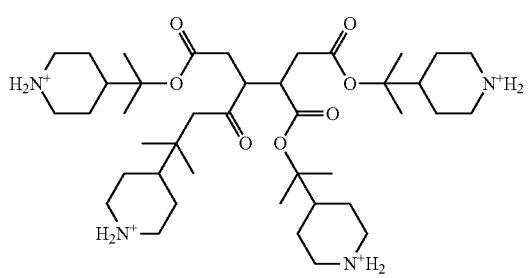
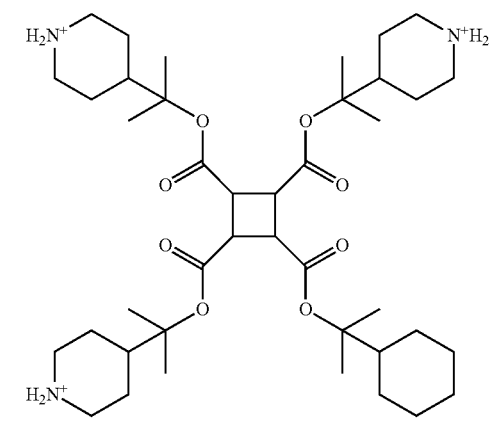
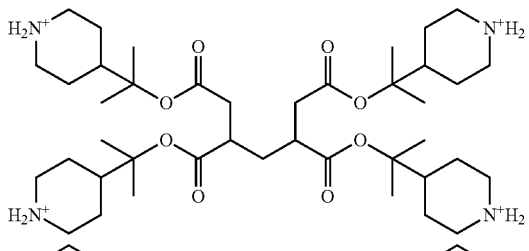
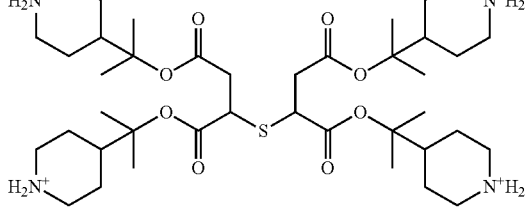
130
-continued
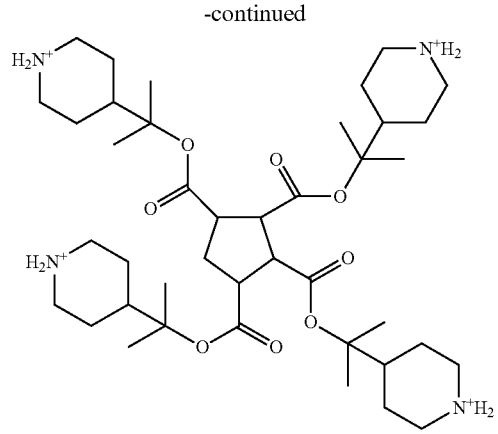
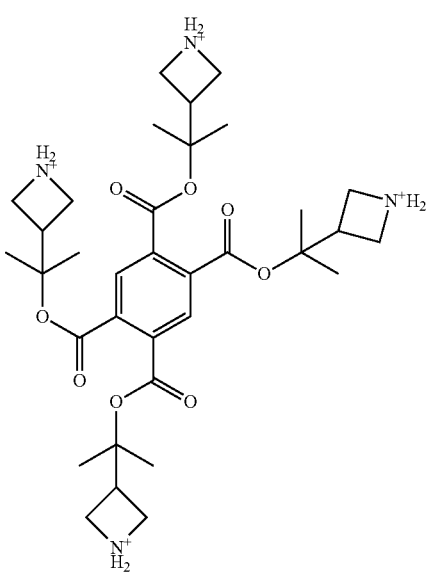
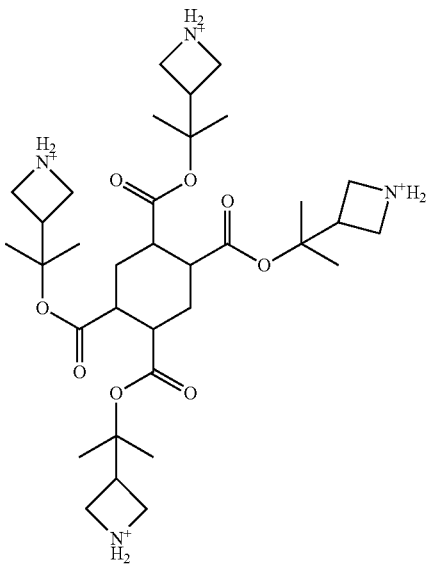

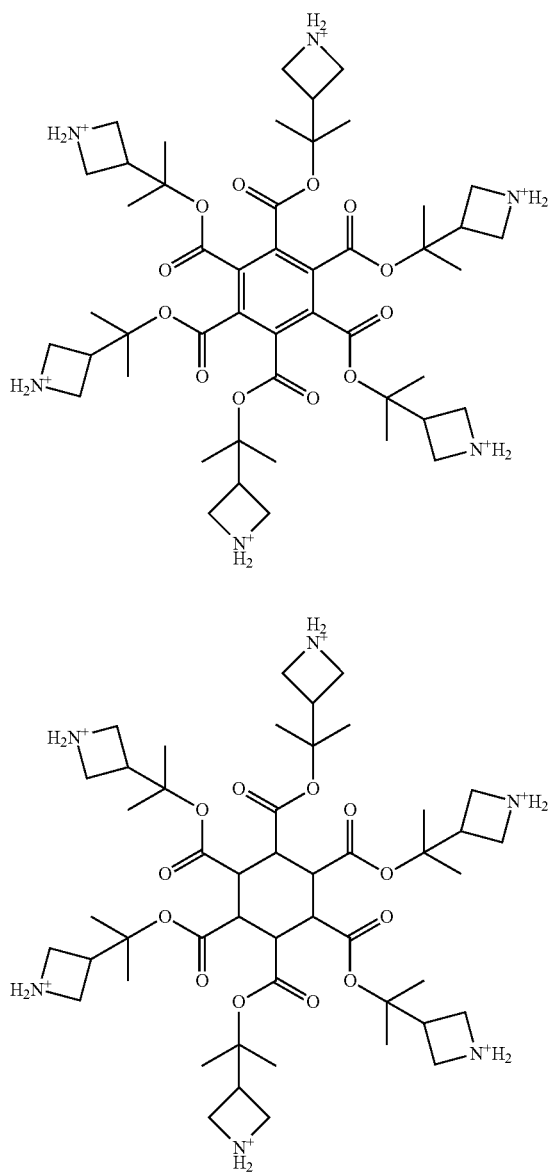
Examples of the cation having formula (A-2) are shown below, but not limited thereto.
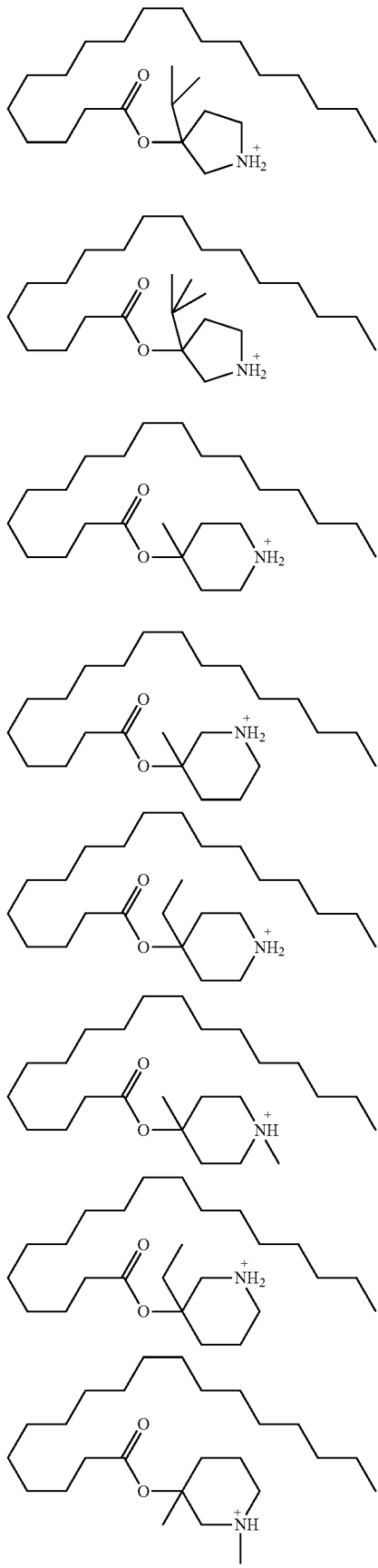

133
-continued
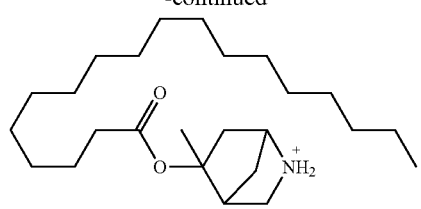
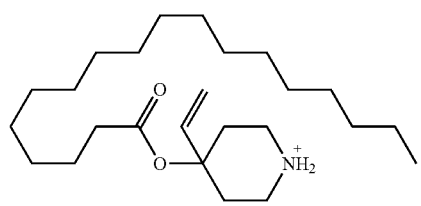
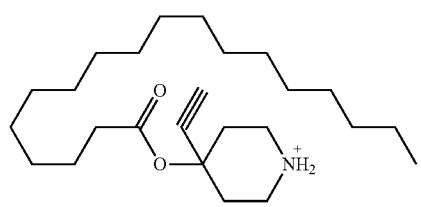
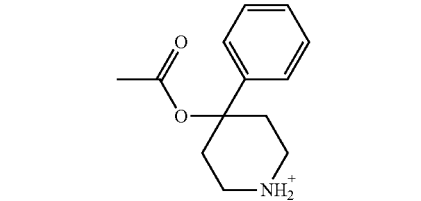
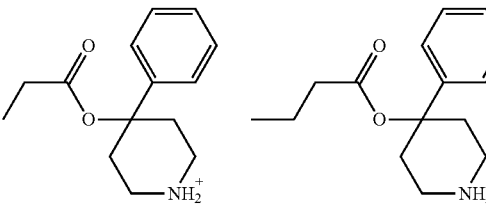
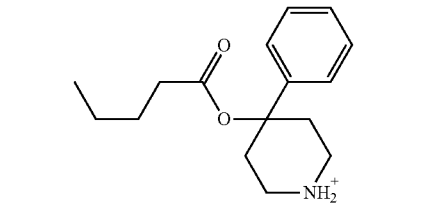
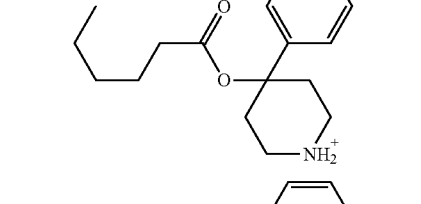
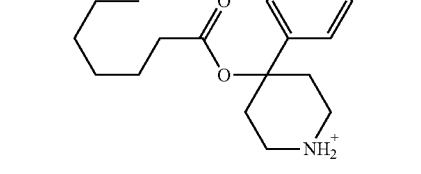
134
-continued
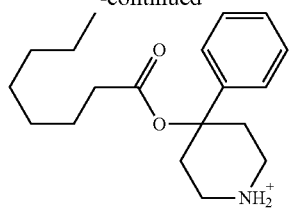
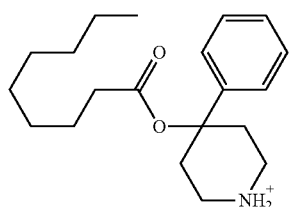
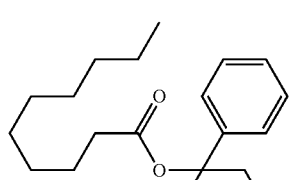
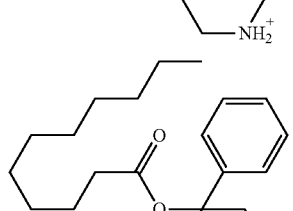
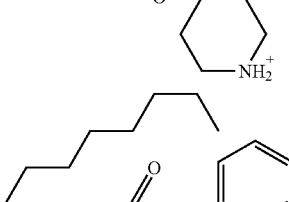
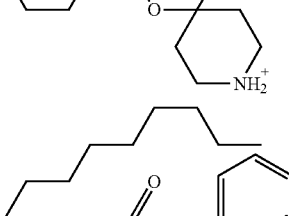
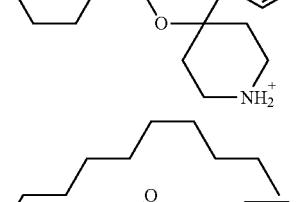
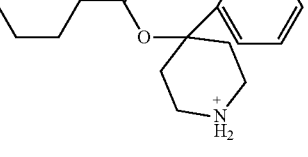

135
-continued
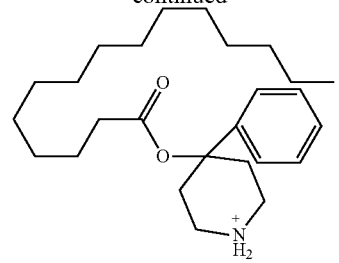
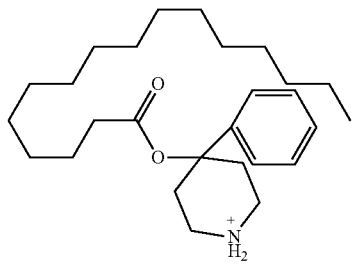
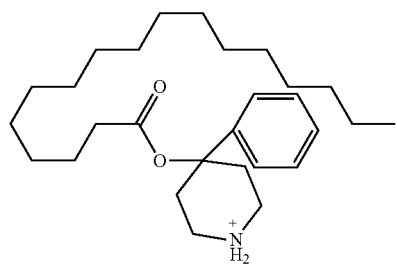
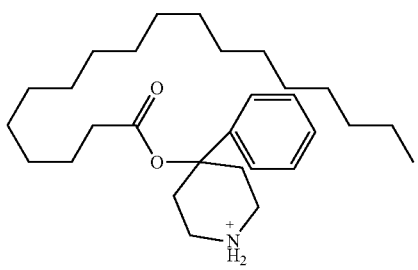
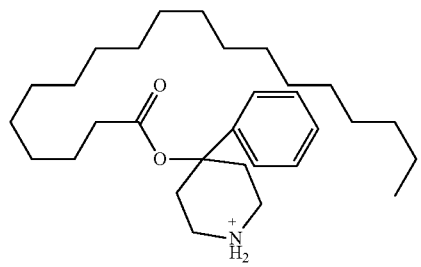
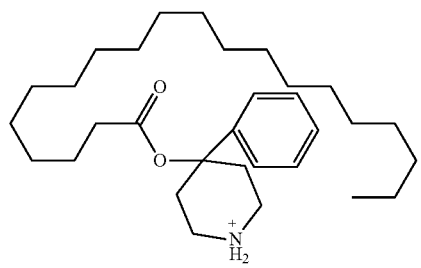
136
-continued
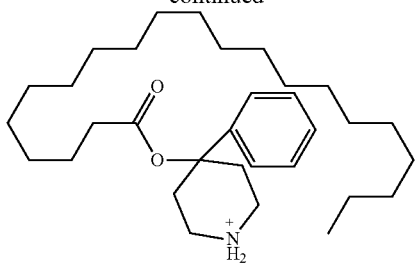
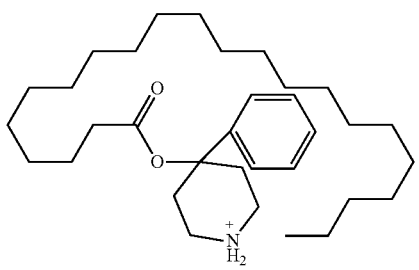
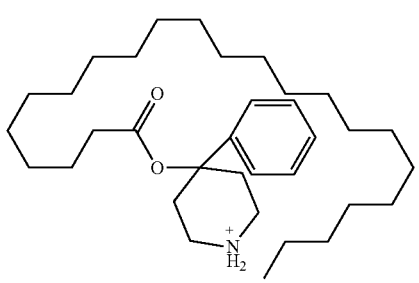
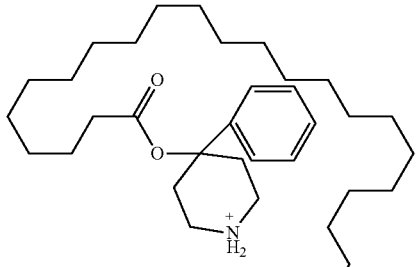
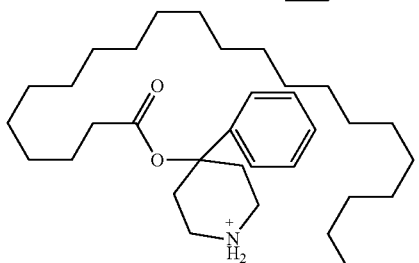
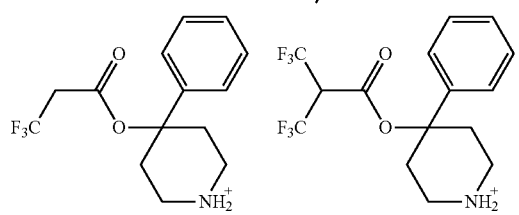

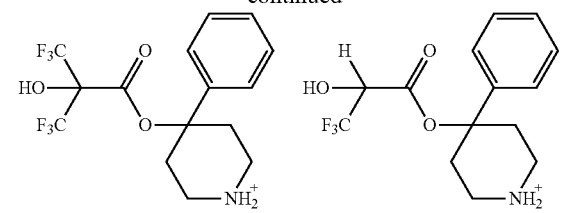
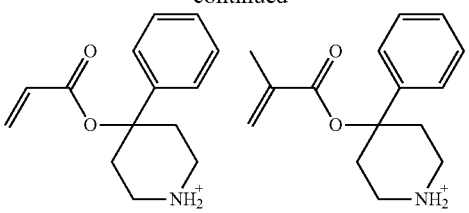
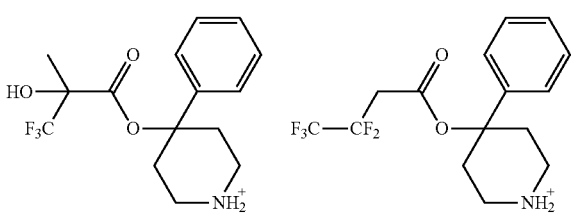
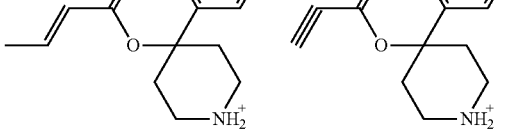
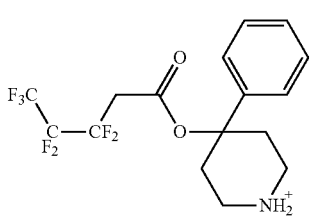
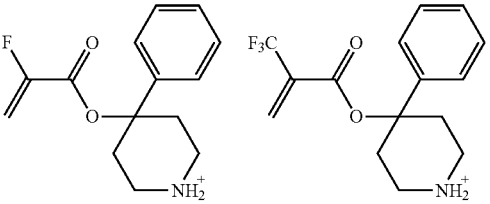
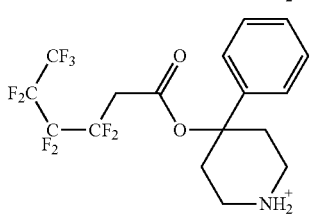
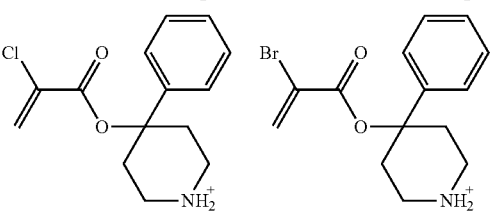
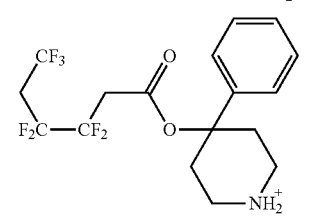
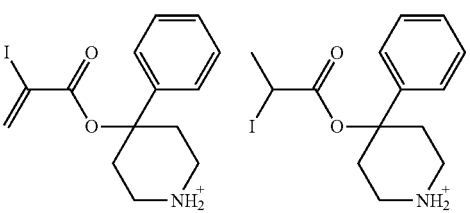
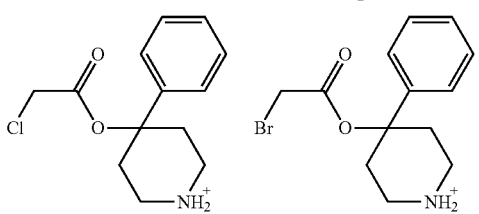
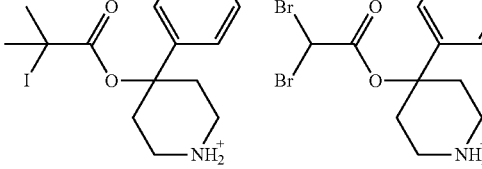
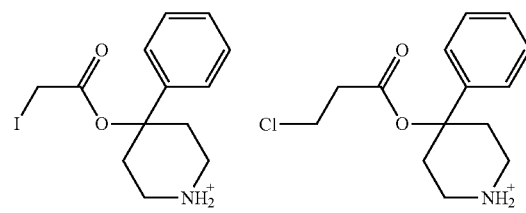
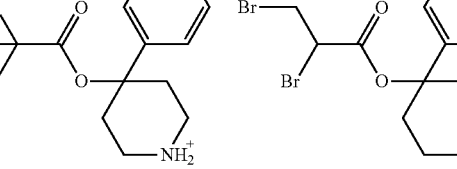
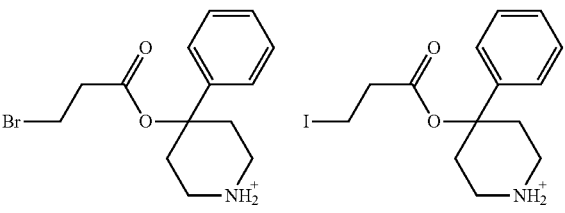
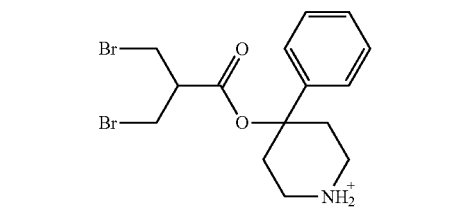

-continued
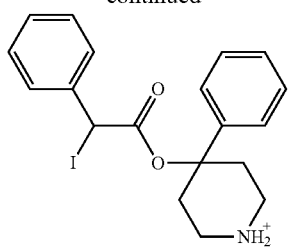
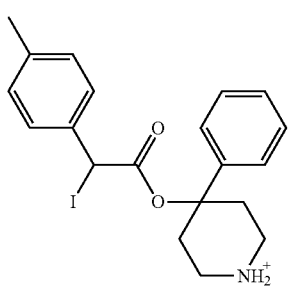
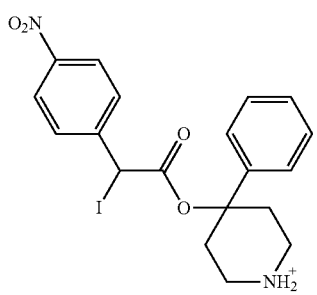
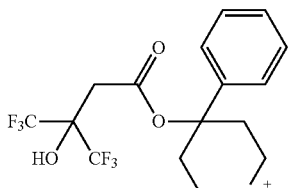
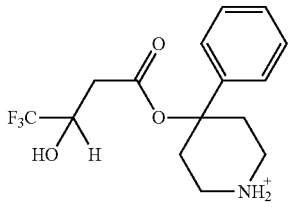
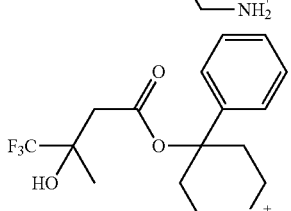
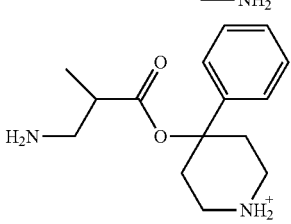
-continued
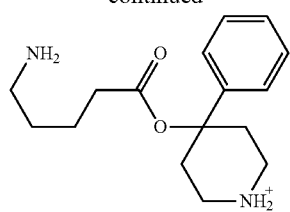
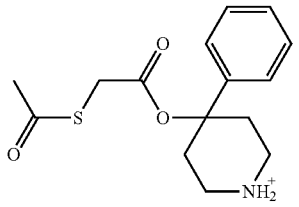
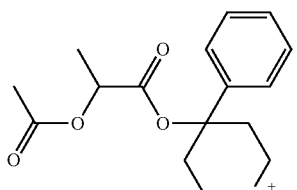

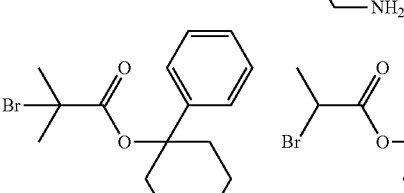

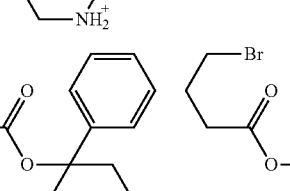
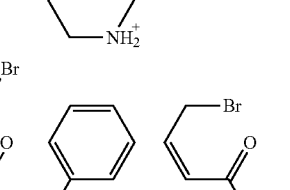

-continued
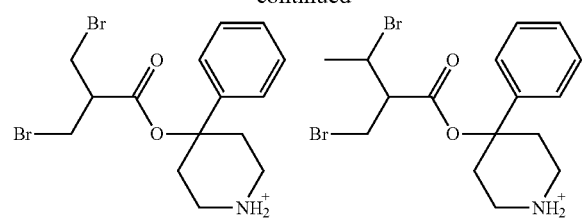
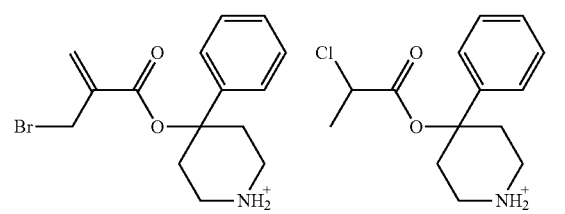
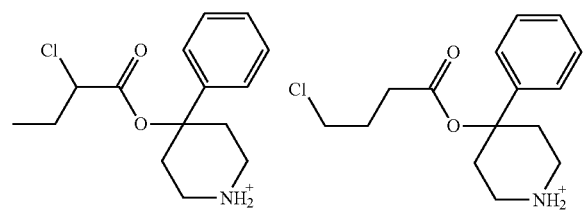
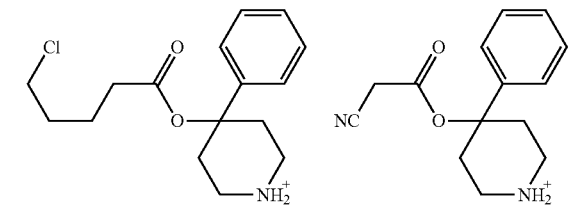
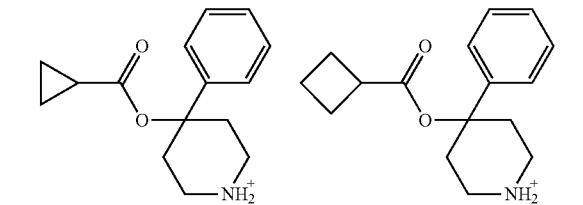
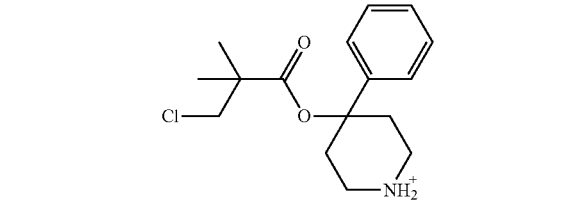
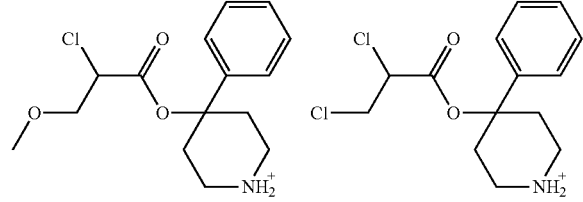
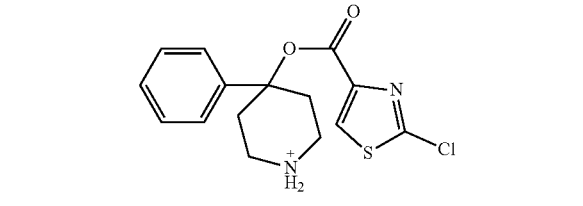
-continued
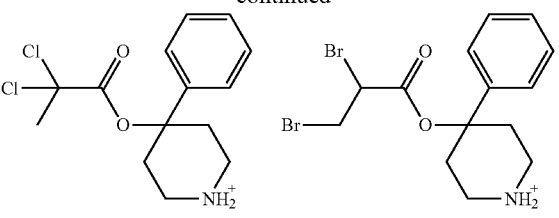
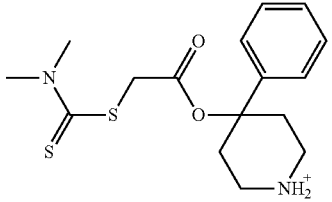
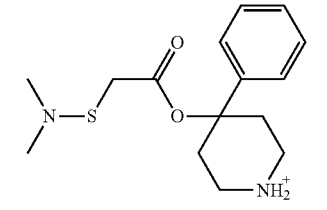
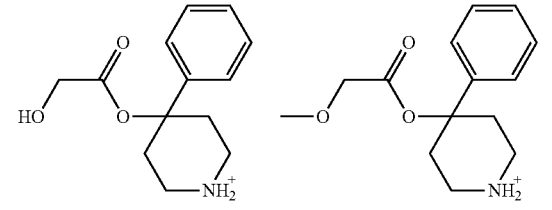
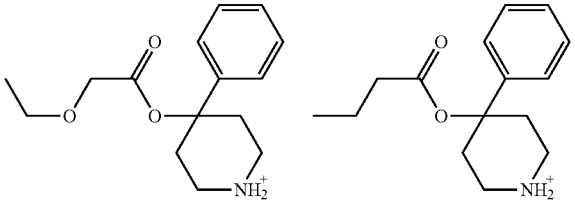
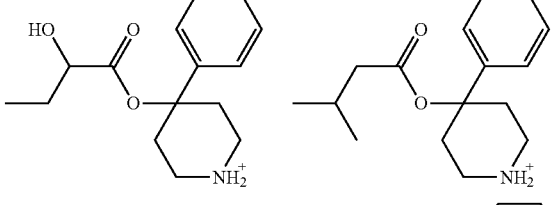
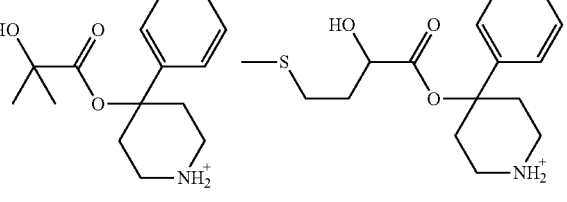
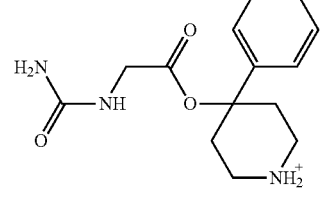

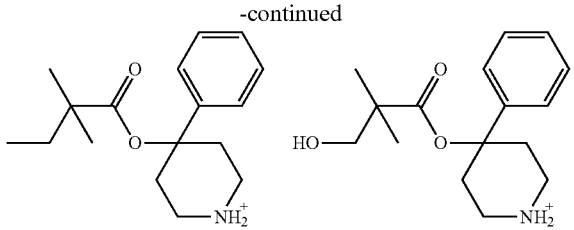
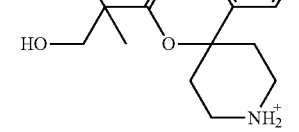
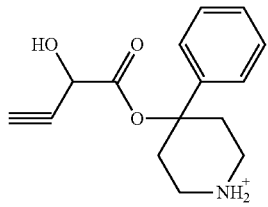
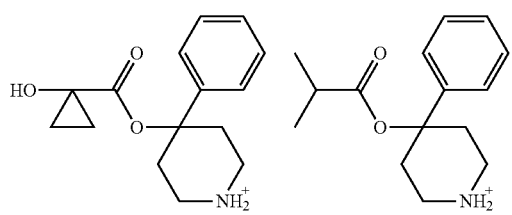
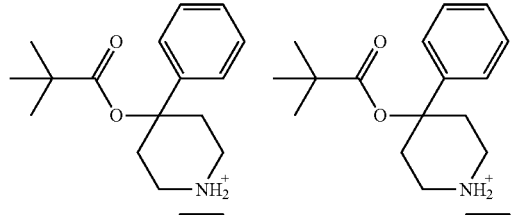
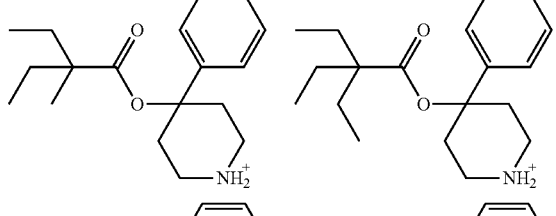
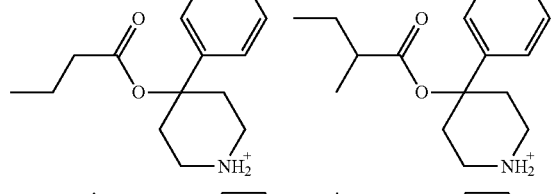
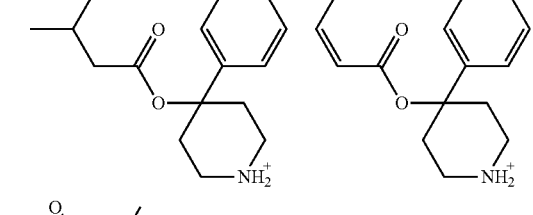
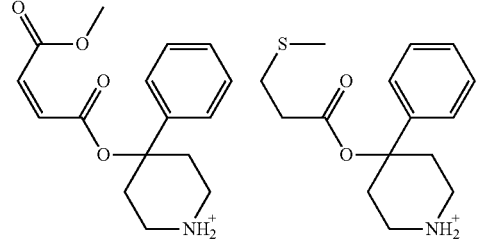
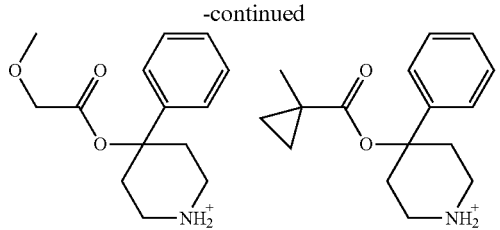
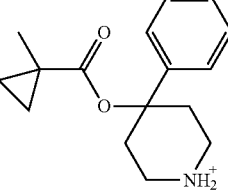
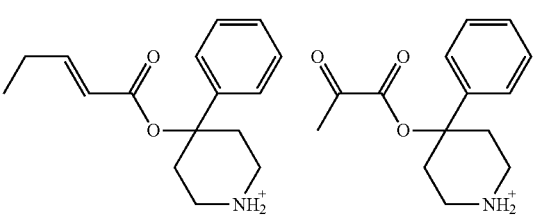
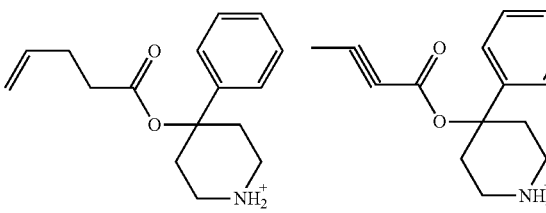
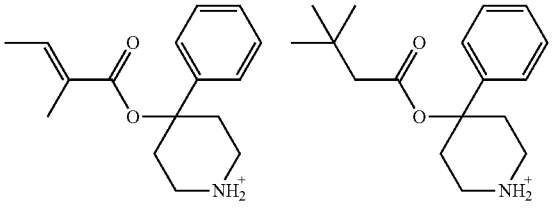
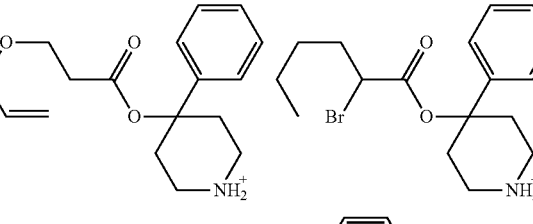
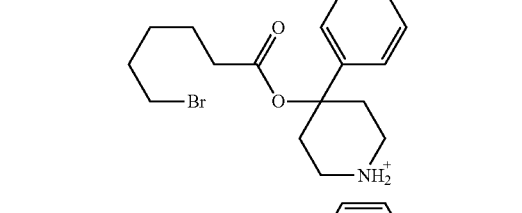
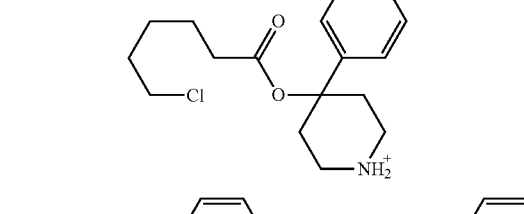
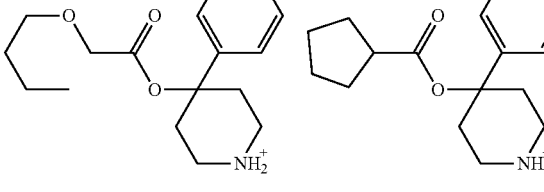

145
-continued
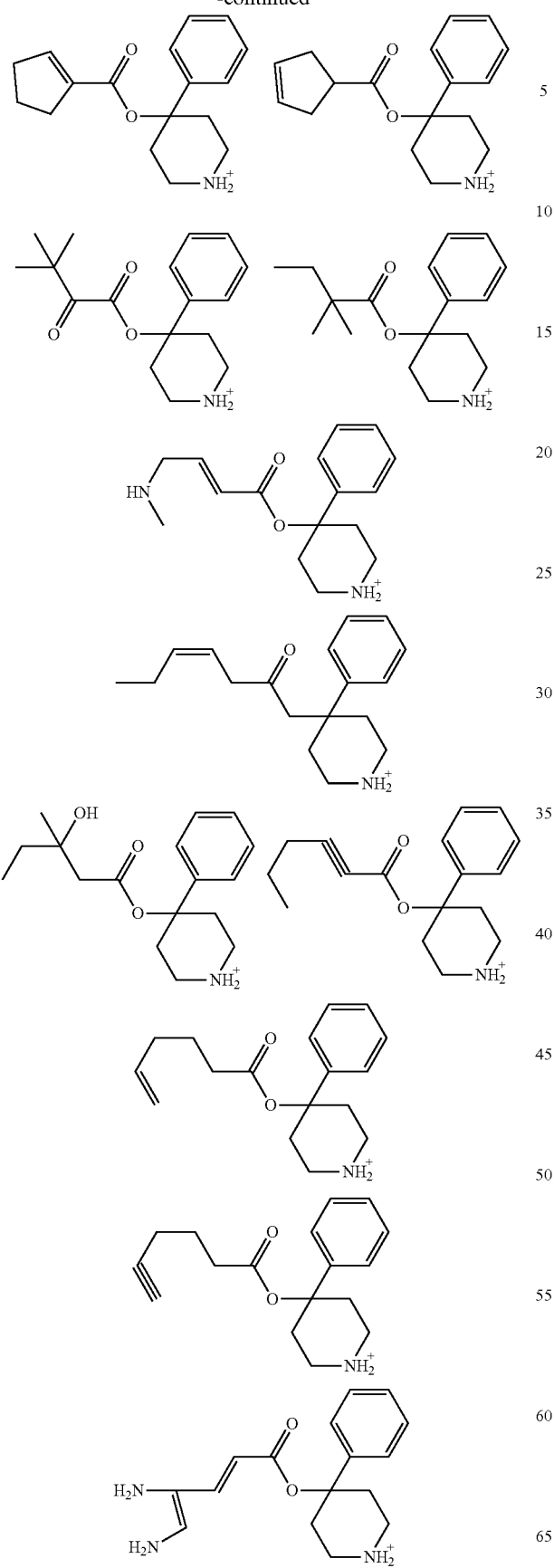
146
-continued
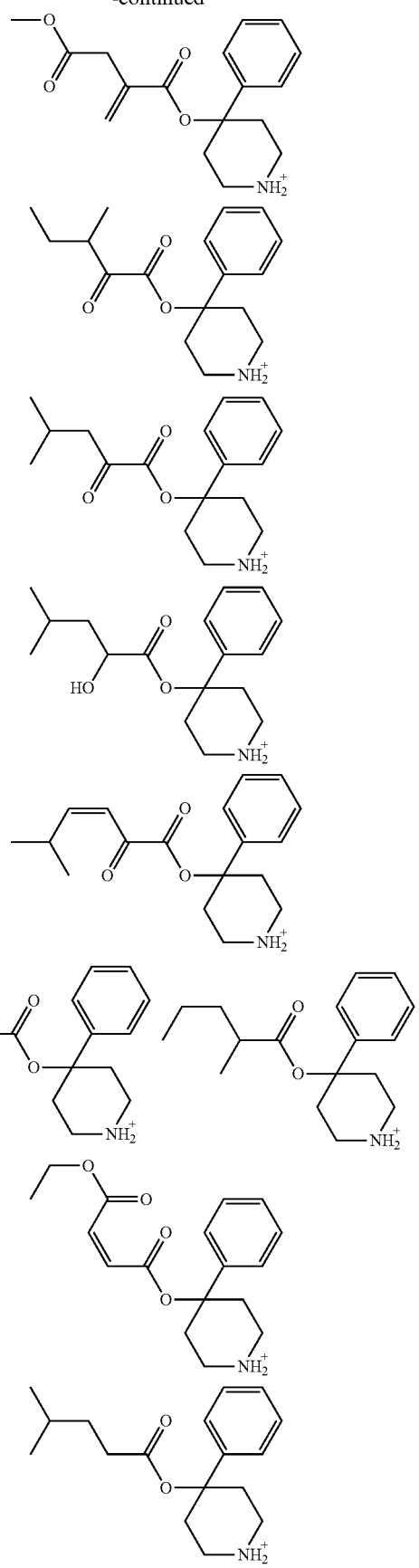

-continued

-continued
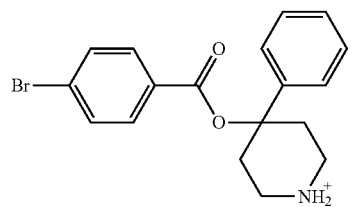
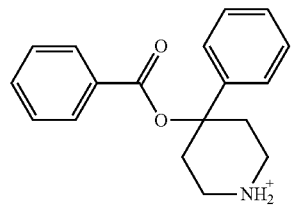
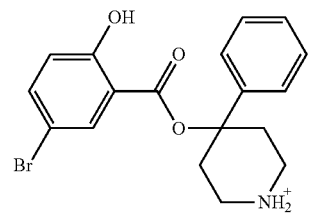
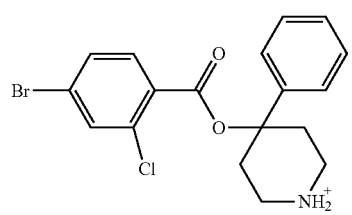
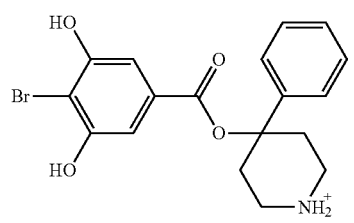
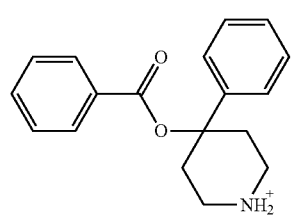
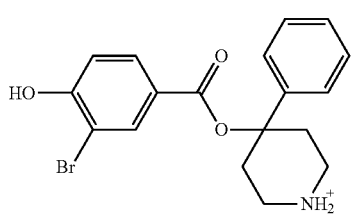
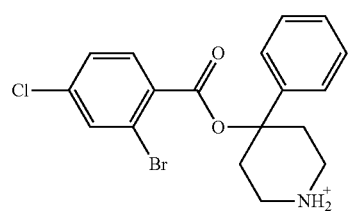
-continued
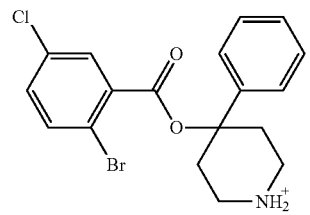
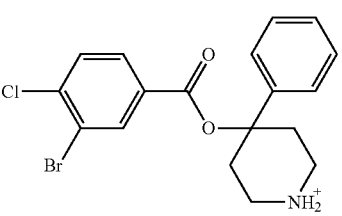
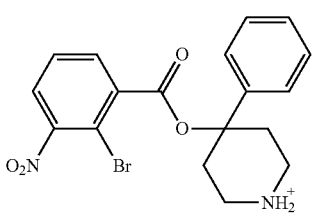
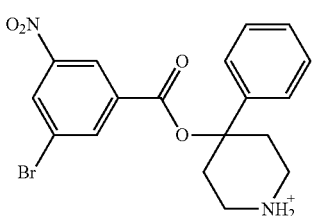
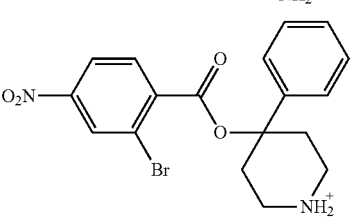
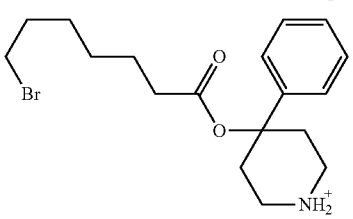
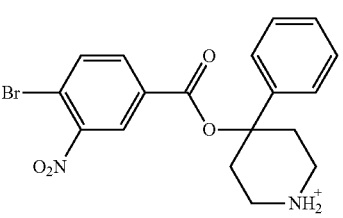
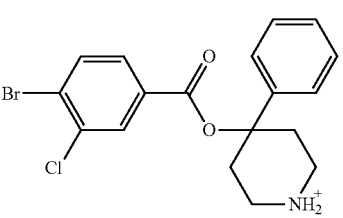

-continued
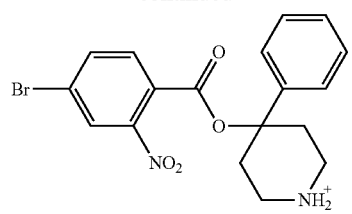
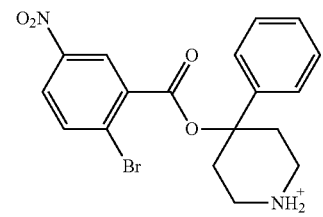
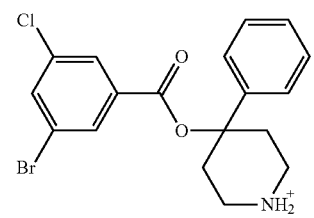
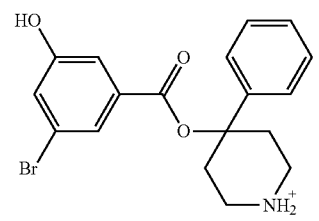
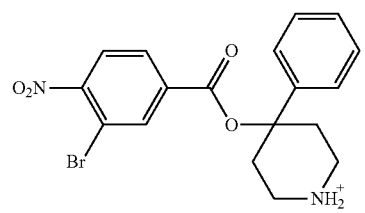
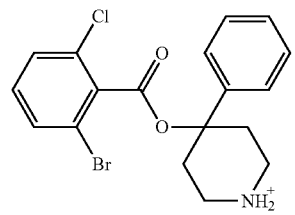
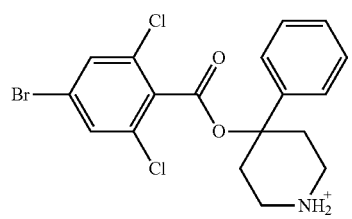
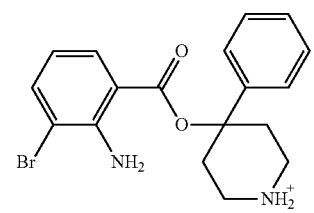
-continued
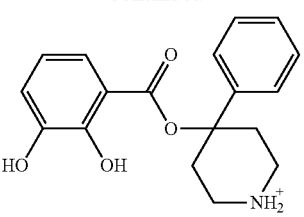
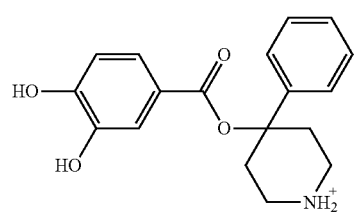
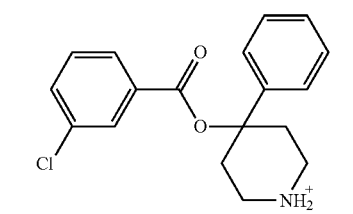
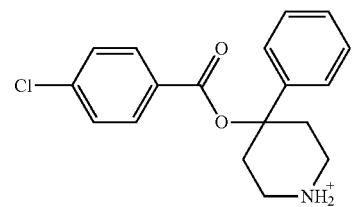
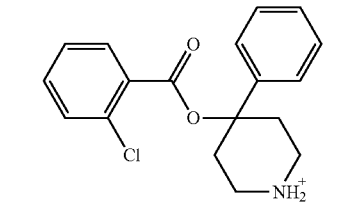
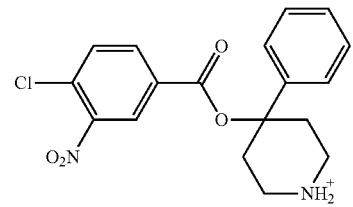
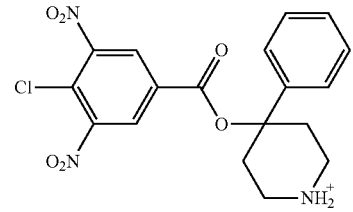
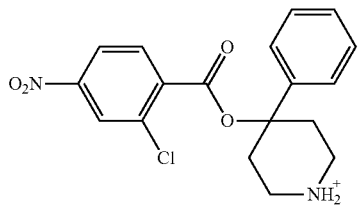

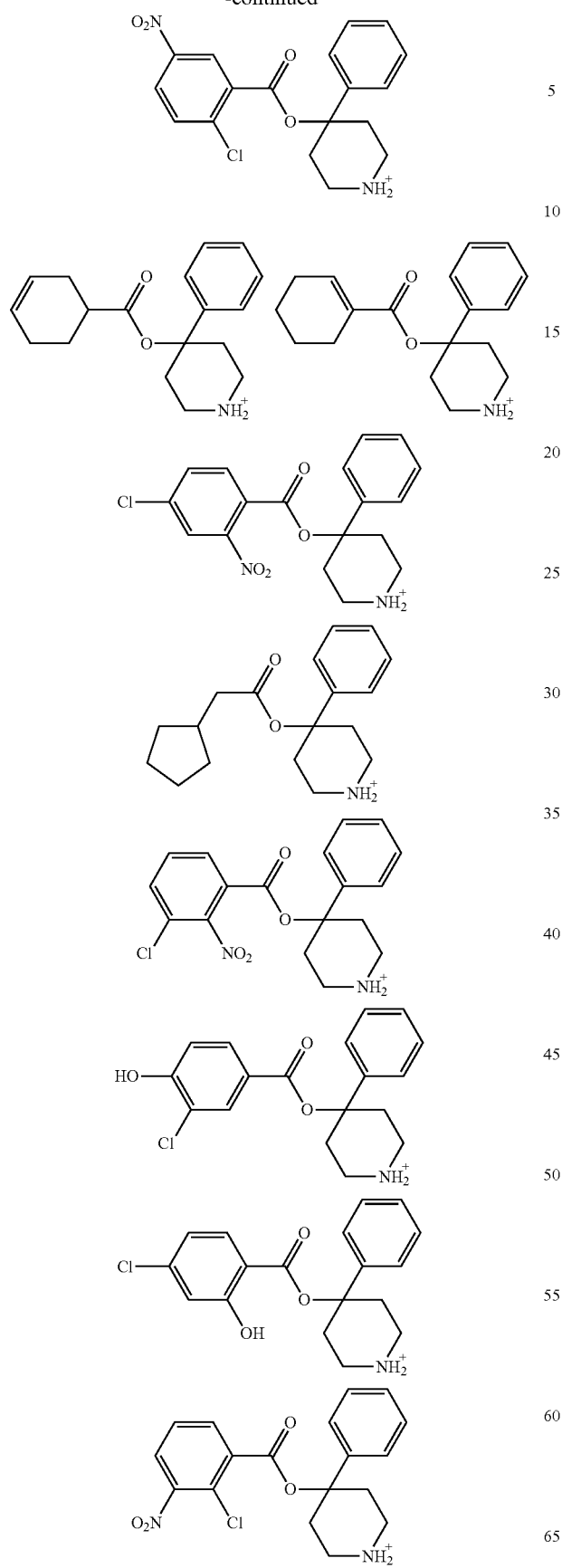
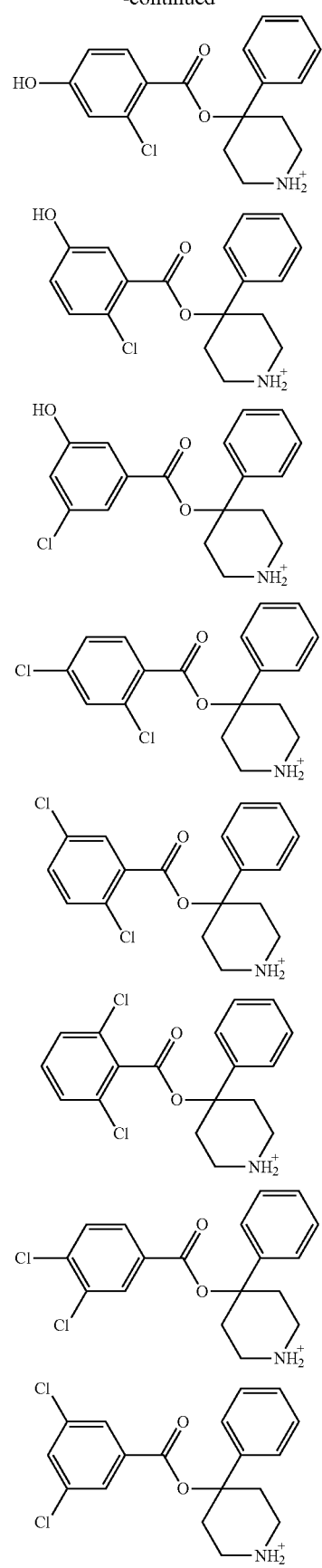

-continued
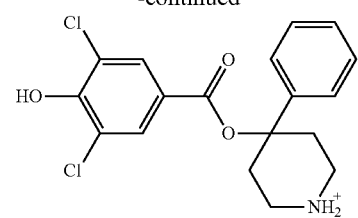
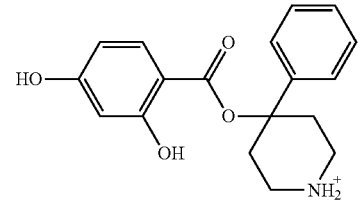
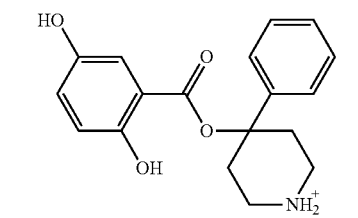
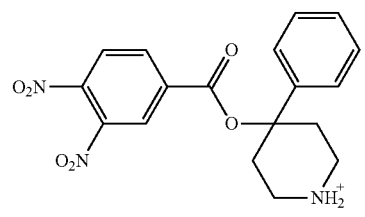
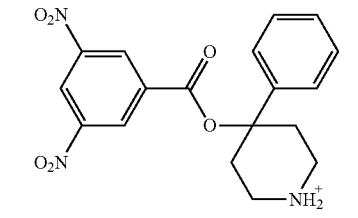
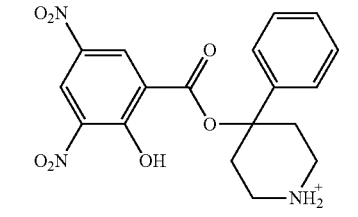
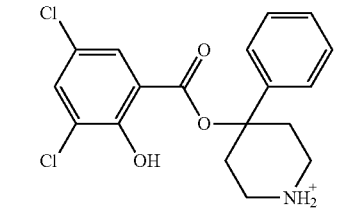
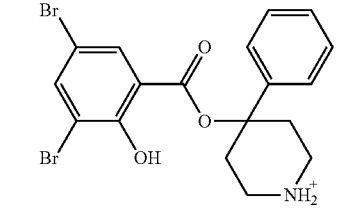
-continued
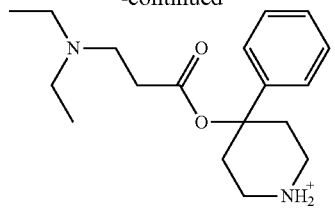
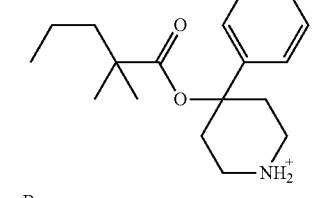
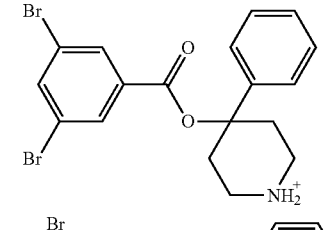
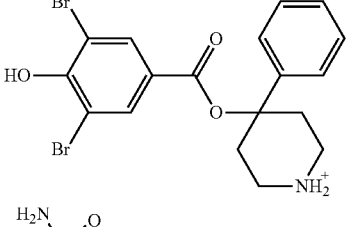
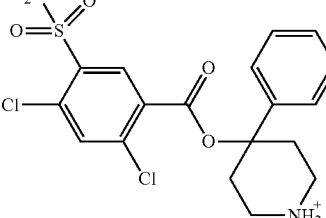
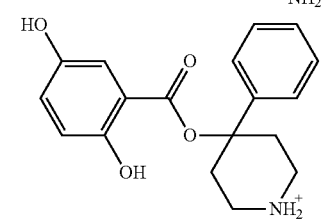
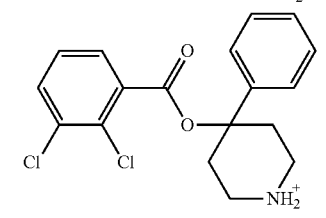
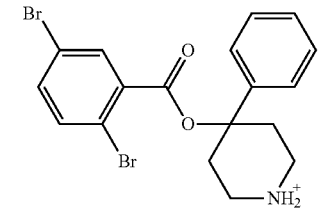

157
-continued
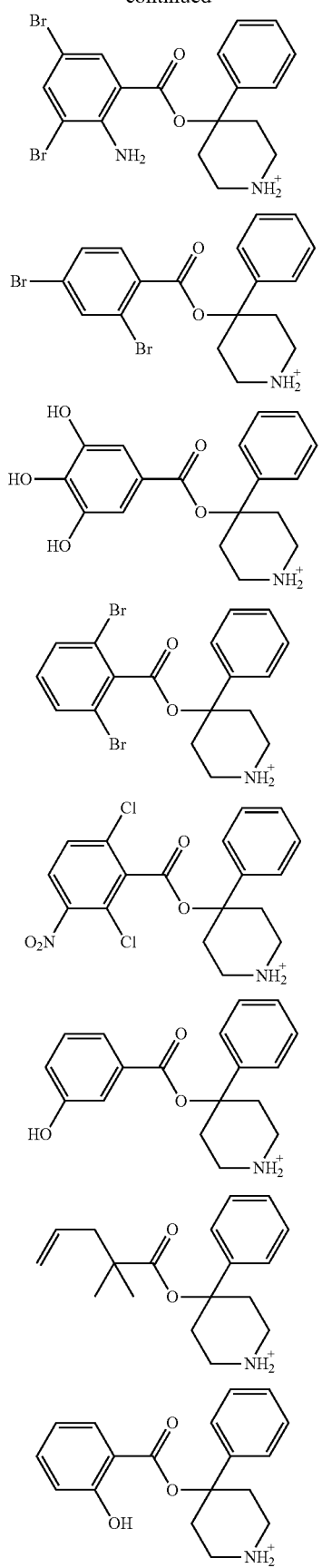
158
-continued
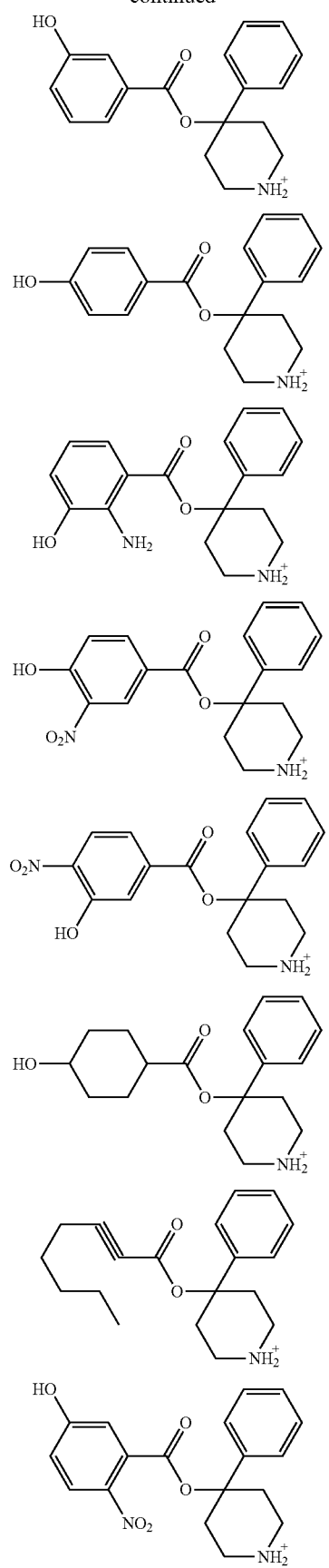

-continued
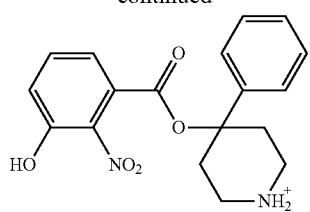
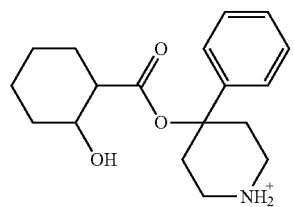
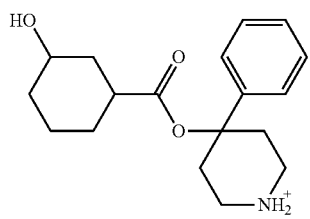
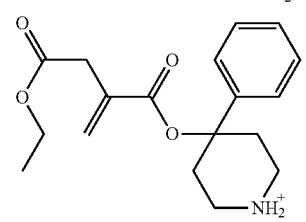
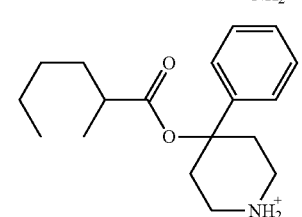
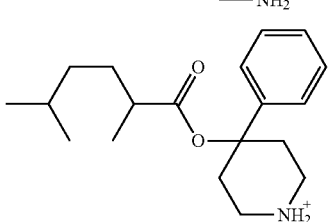
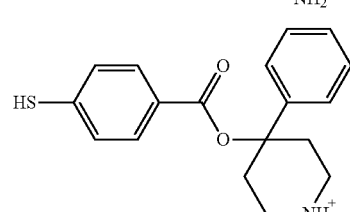
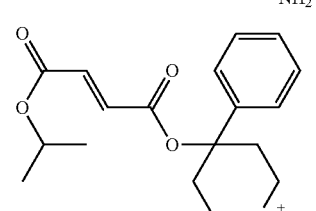
-continued
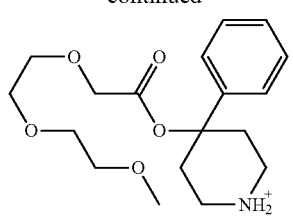
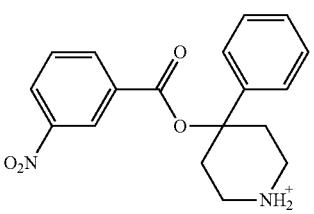
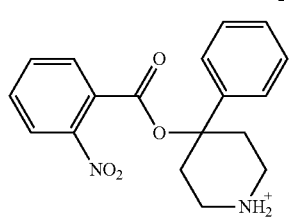
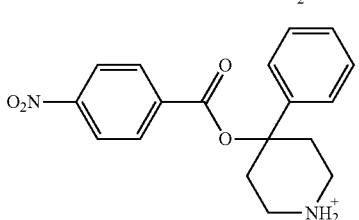
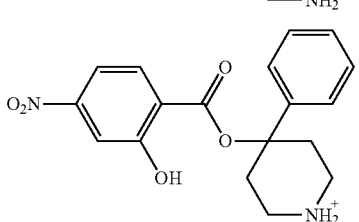
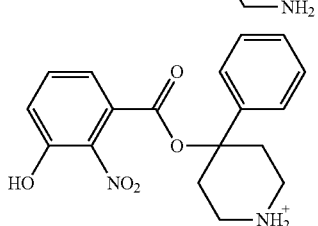
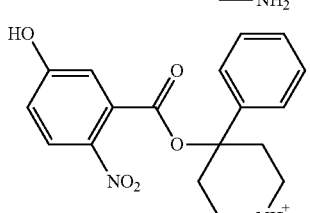
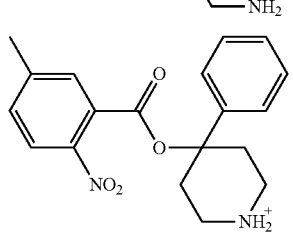

-continued
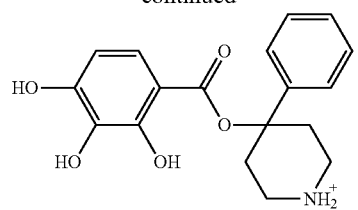
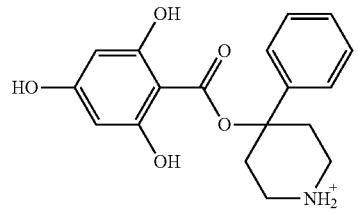
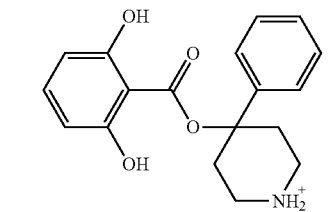
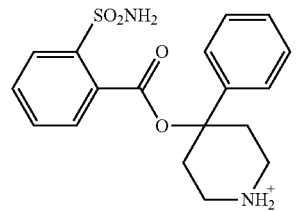
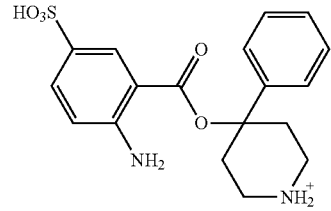
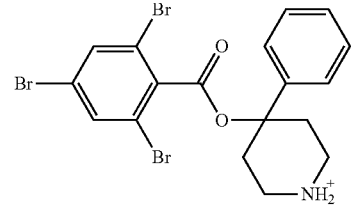
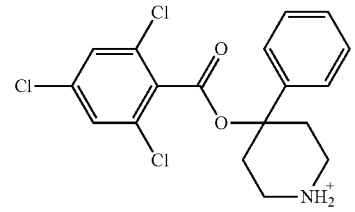
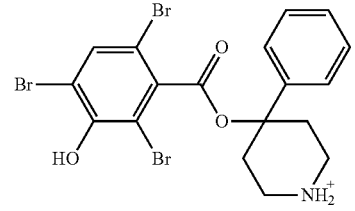
-continued
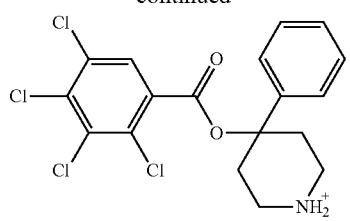
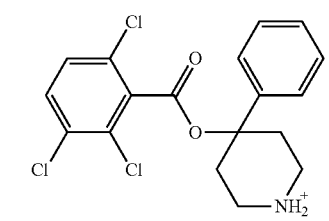
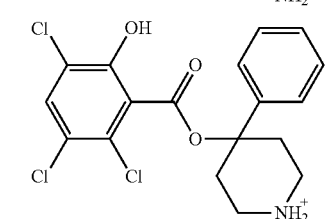
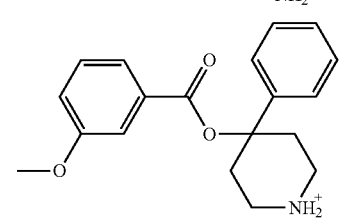
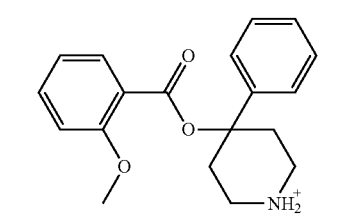
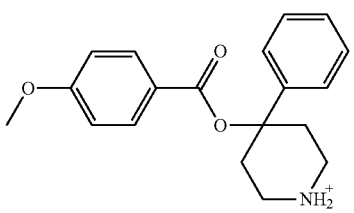
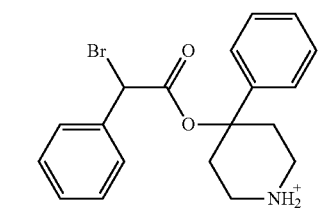
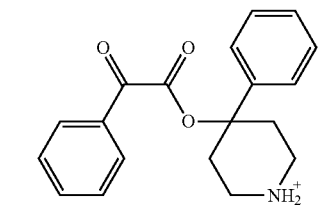

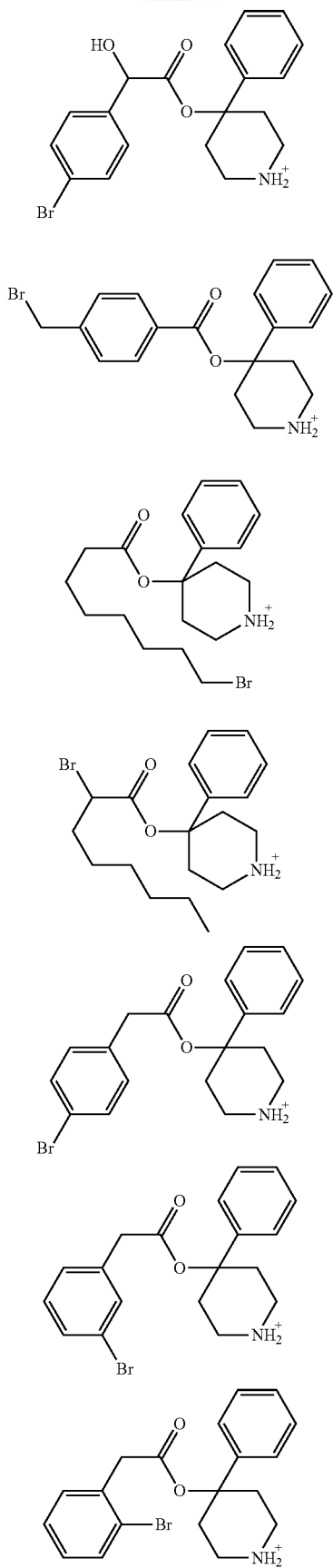
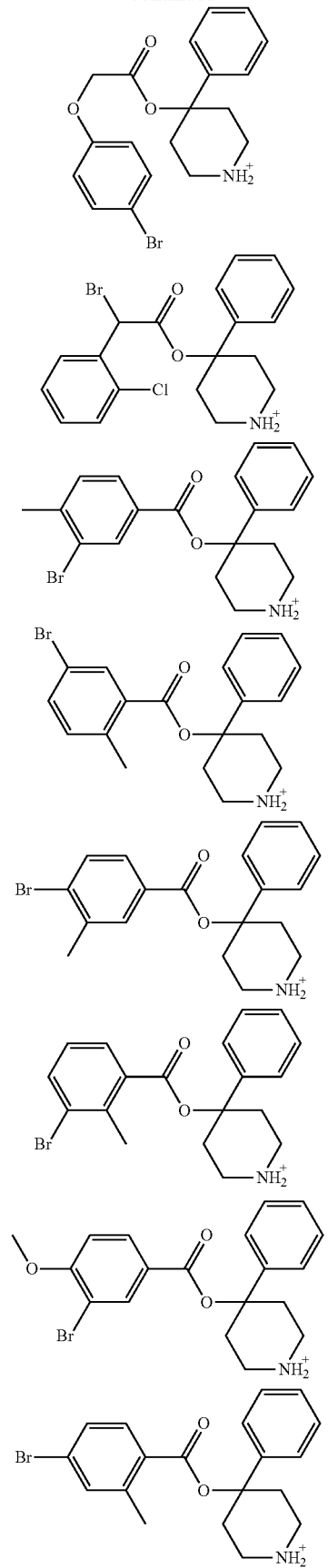

-continued
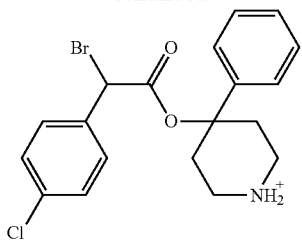
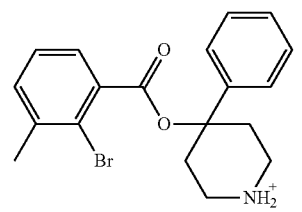
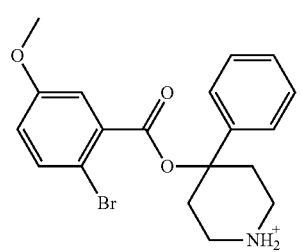
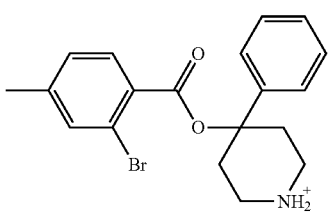
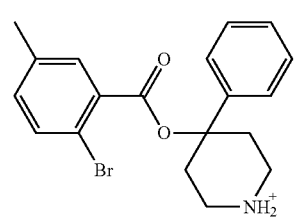
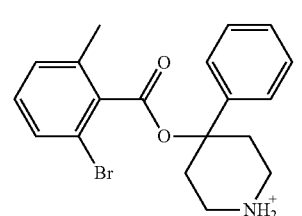
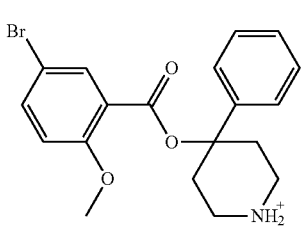
-continued
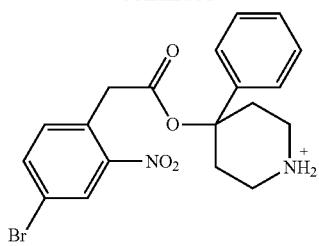
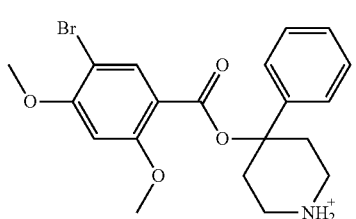
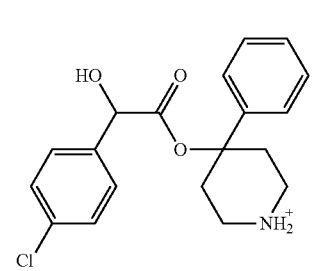
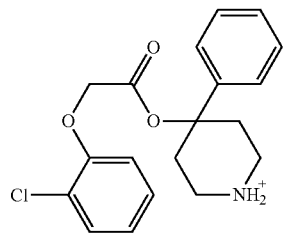
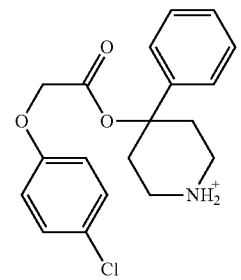
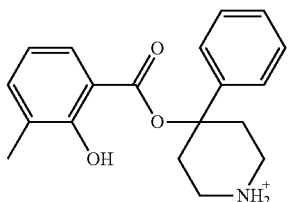
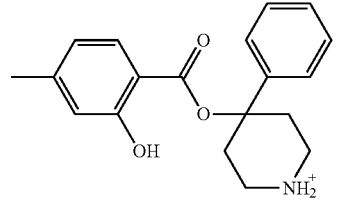

167
-continued
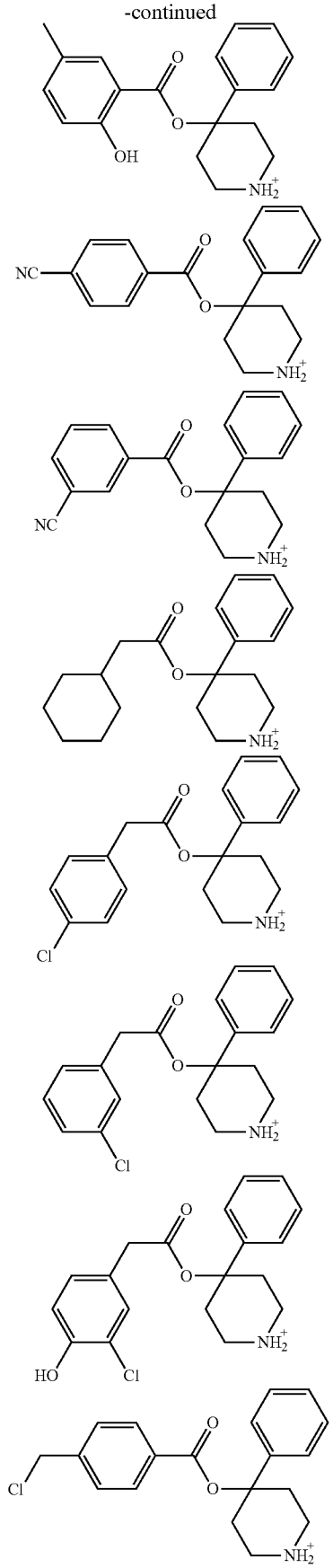
168
-continued
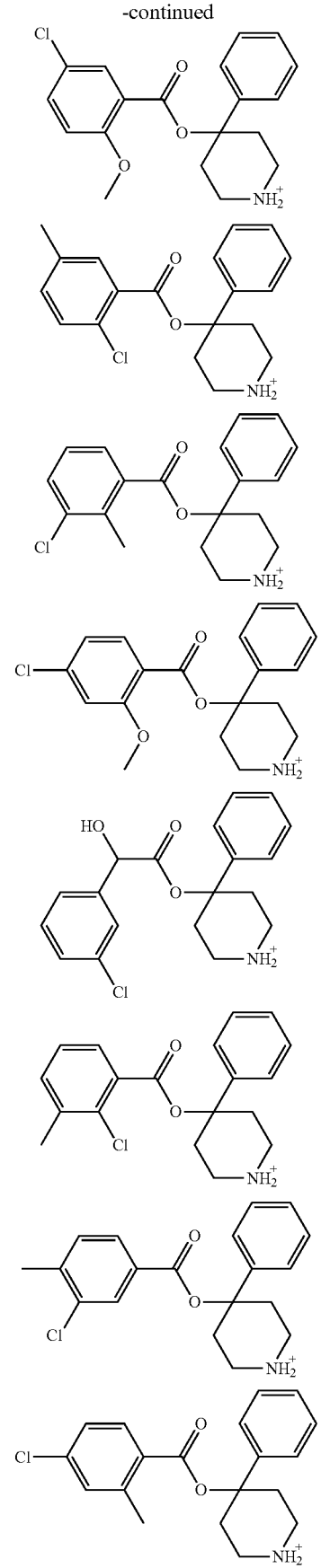

-continued
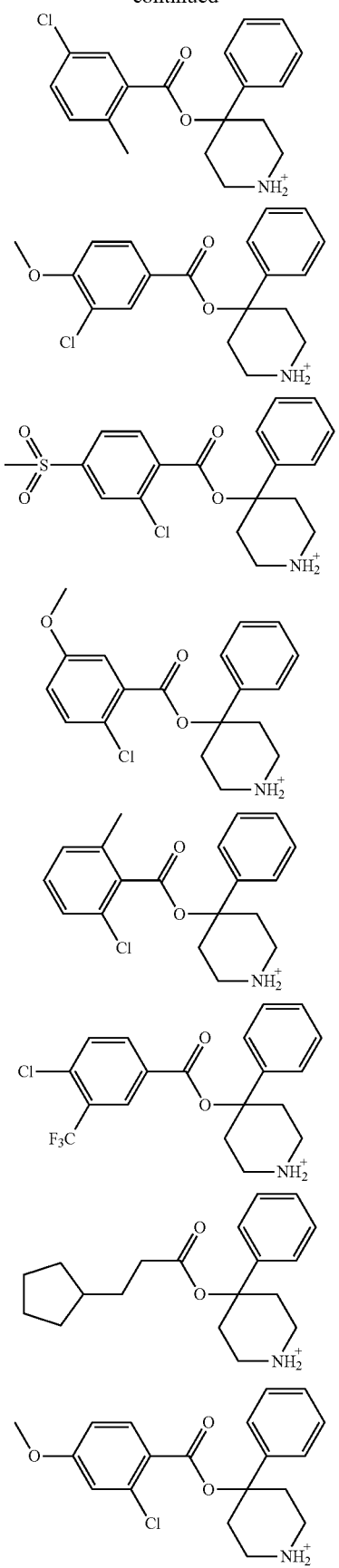
-continued
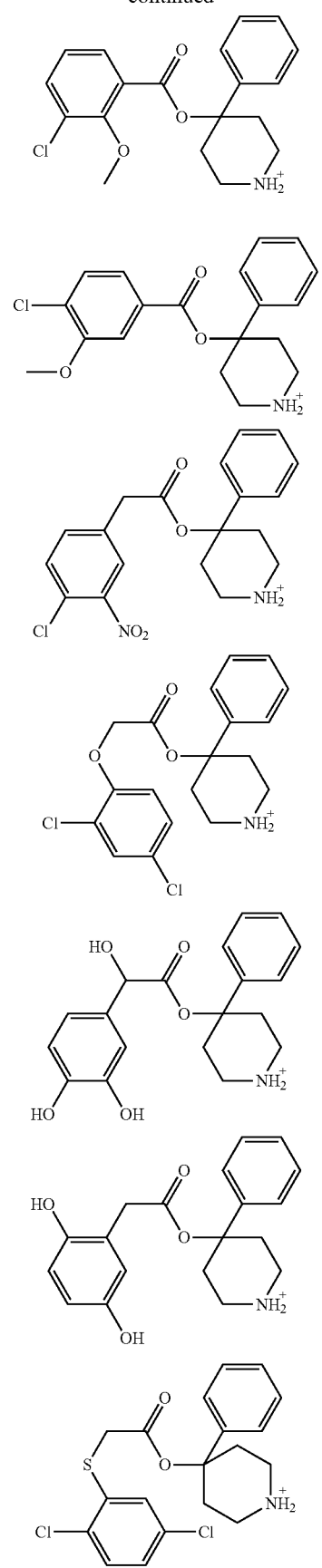

171                                          172
-continued                                   -continued

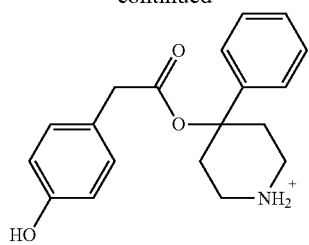
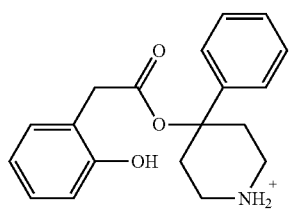
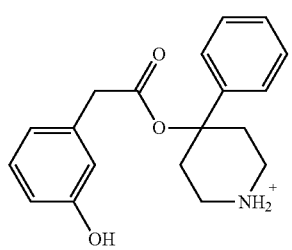
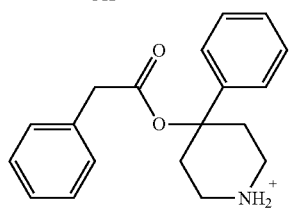
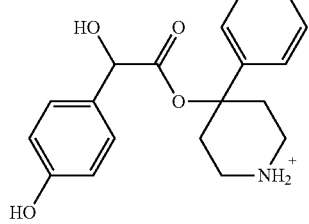
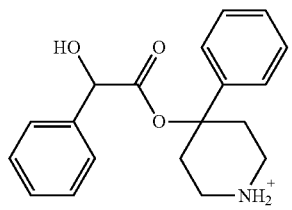
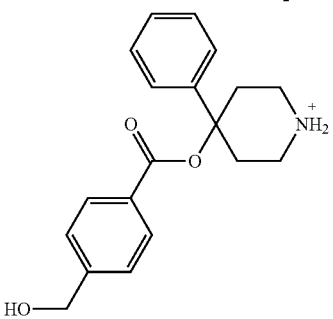
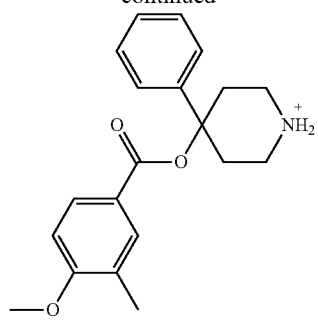
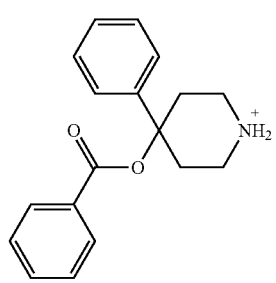
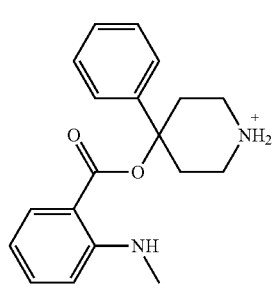
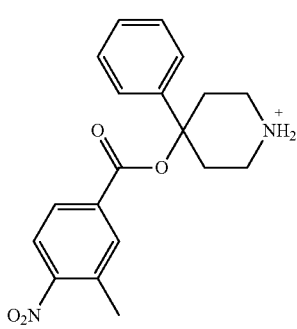
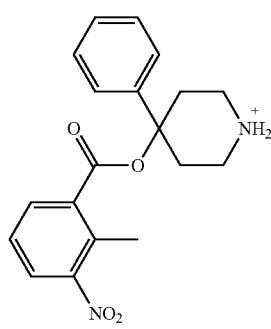

-continued
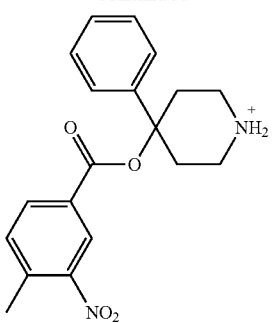
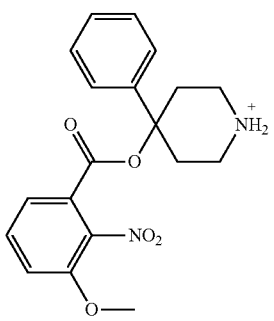
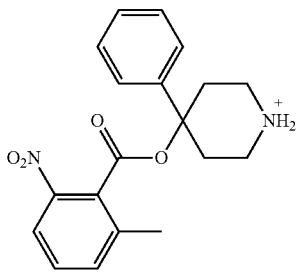
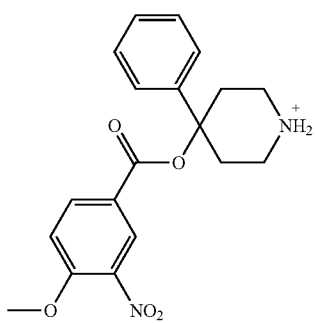
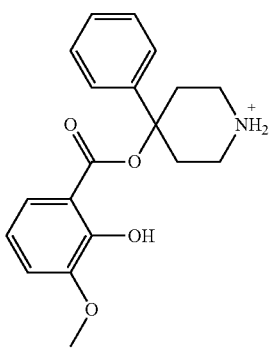
-continued
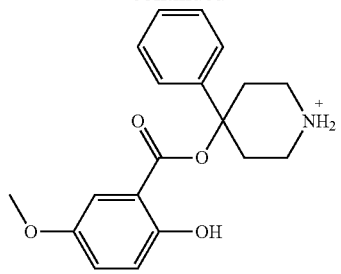
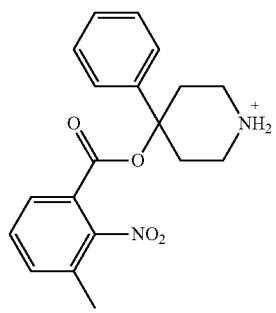
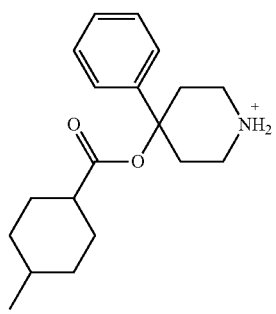
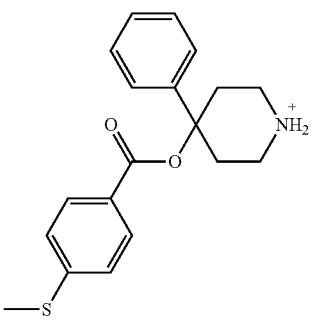
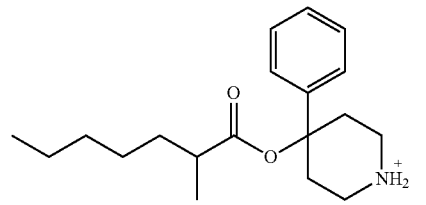
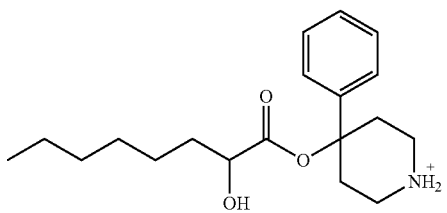

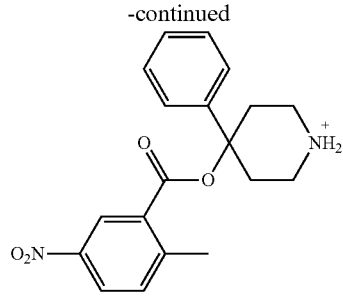
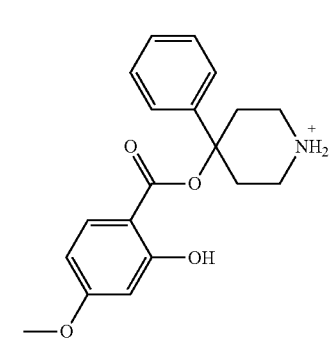
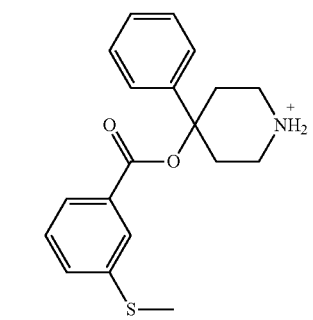
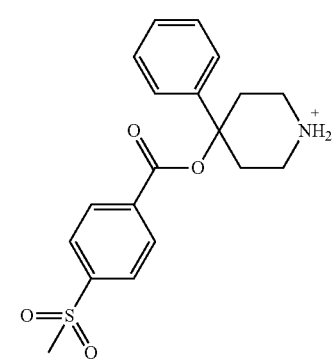
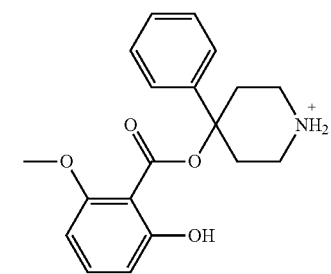
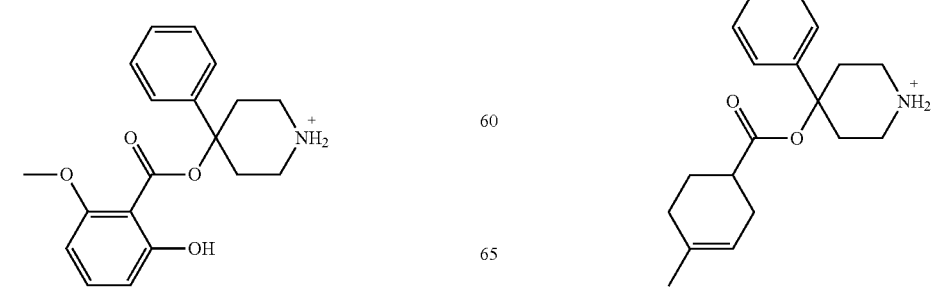
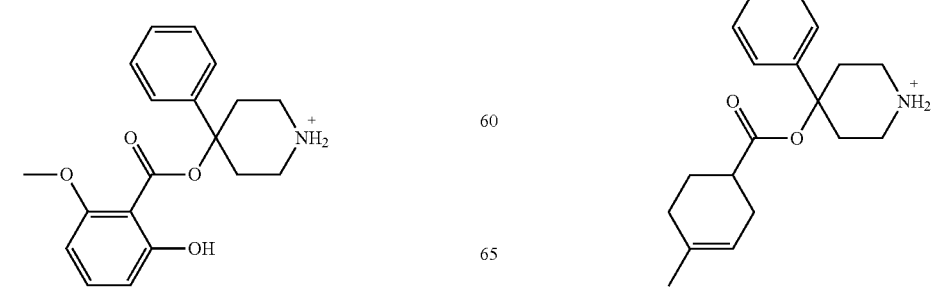

179
-continued
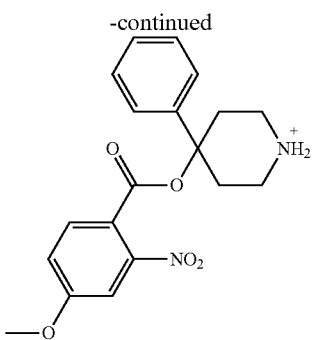
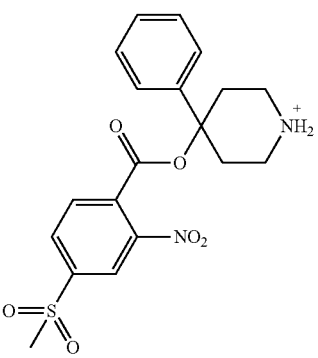
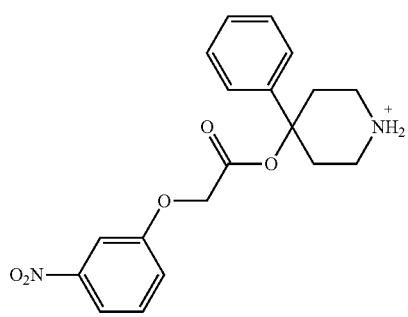
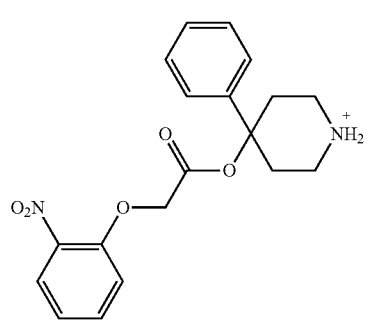
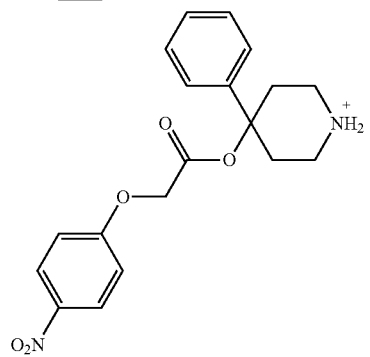
180
-continued
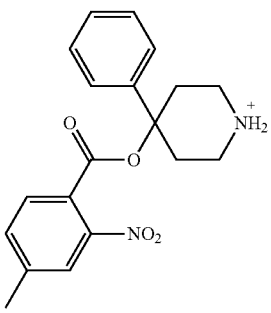
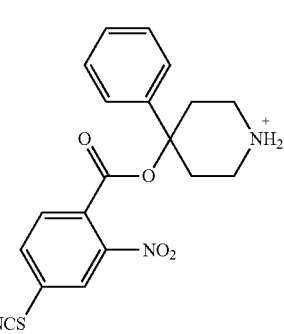
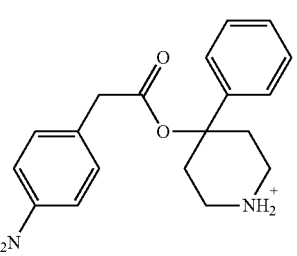
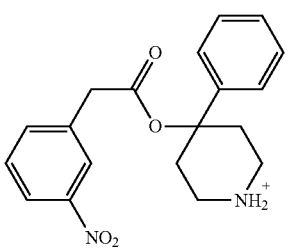
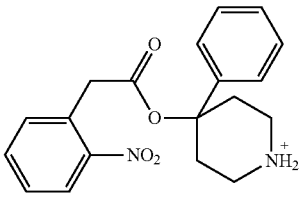
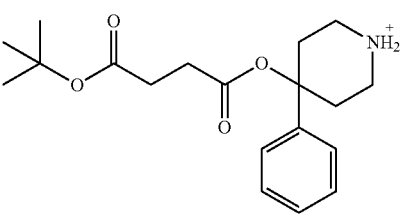

181
-continued
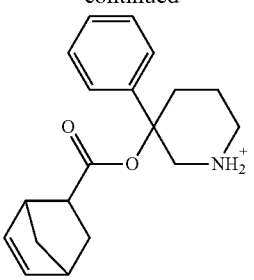
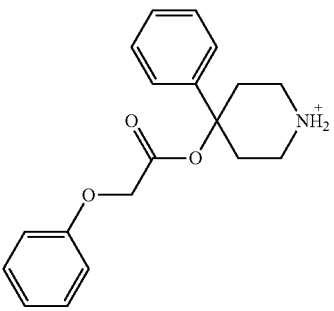
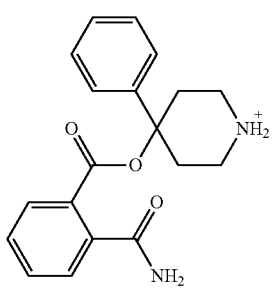
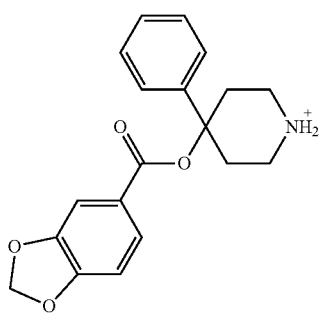
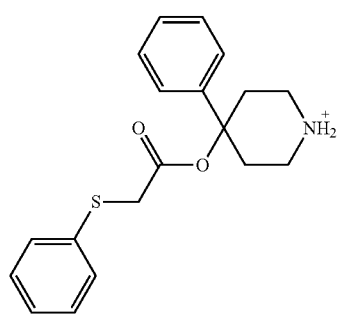
182
-continued
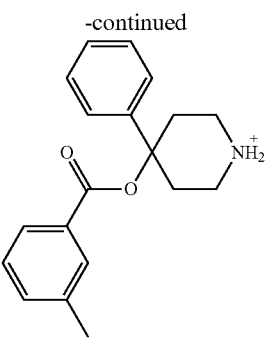
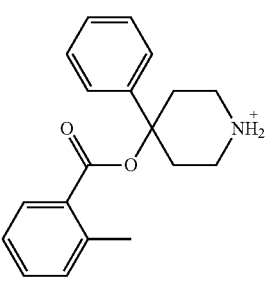
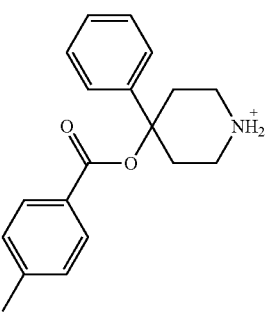
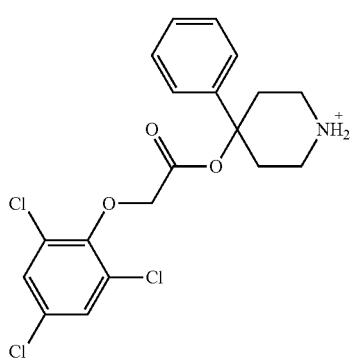
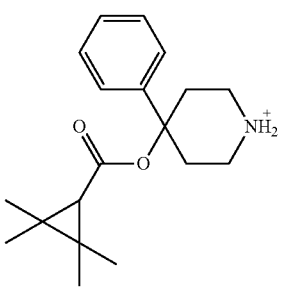

-continued
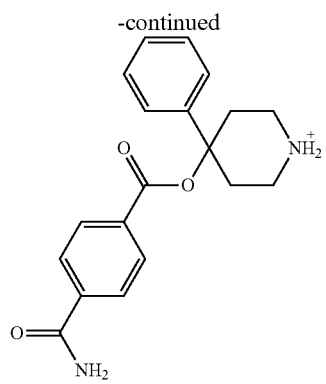
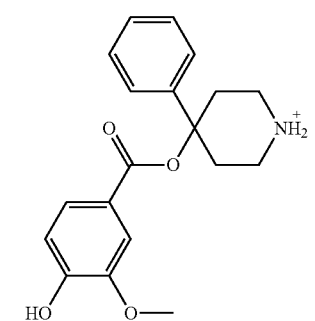
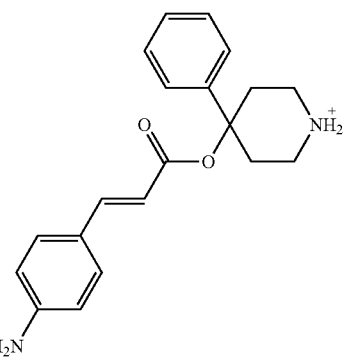
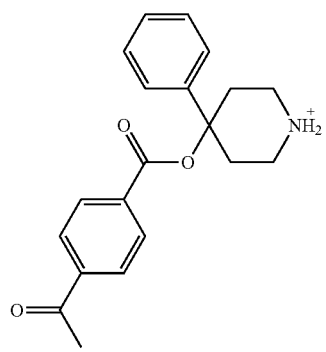
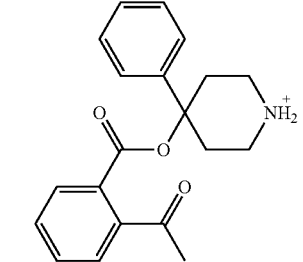
-continued
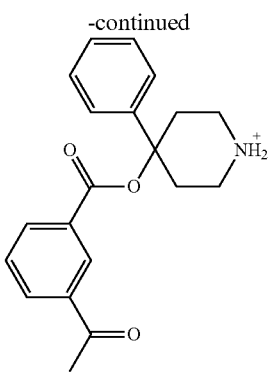
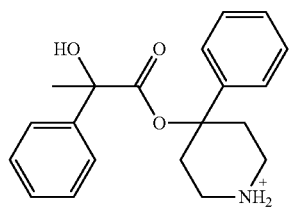
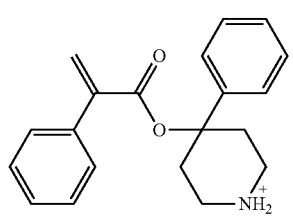
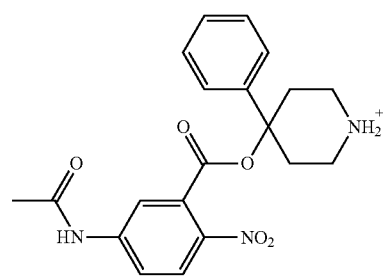
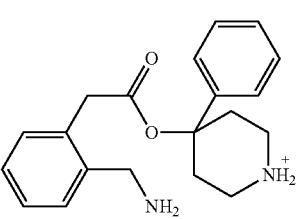
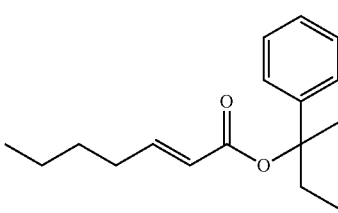

-continued
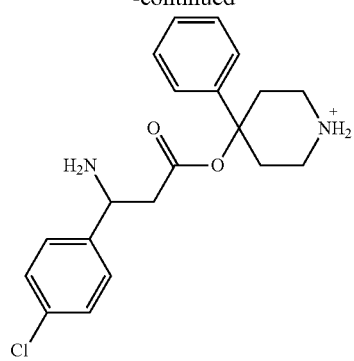
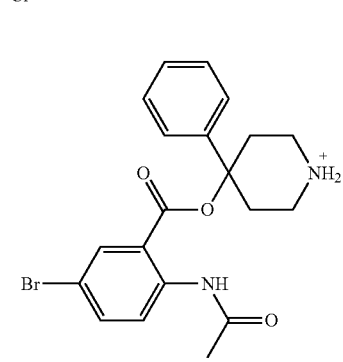
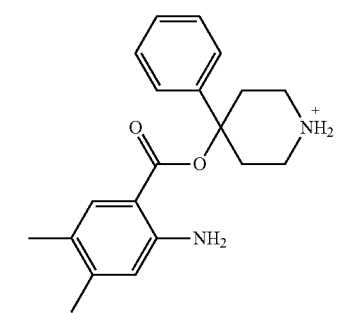
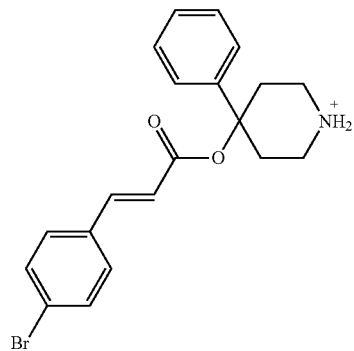
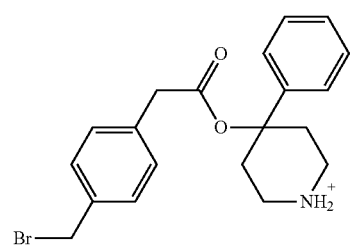
-continued
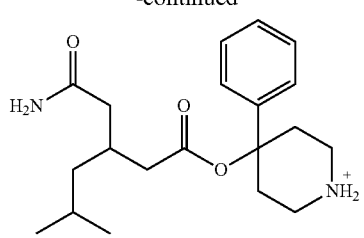
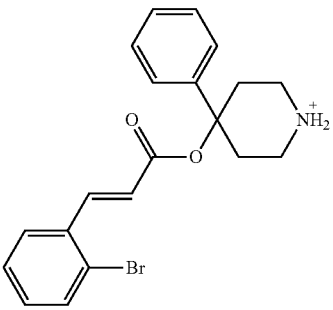
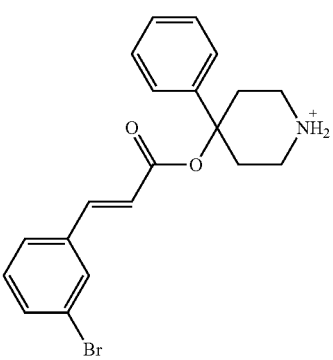
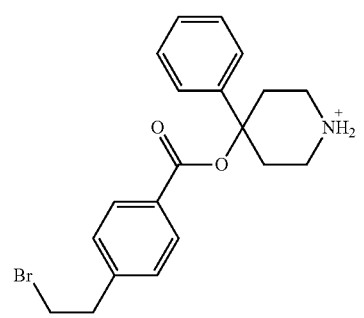
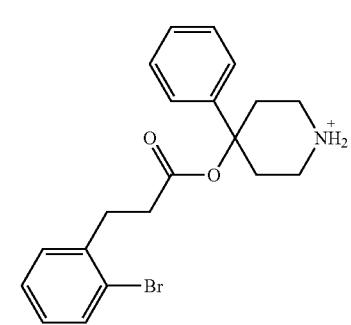

187
-continued
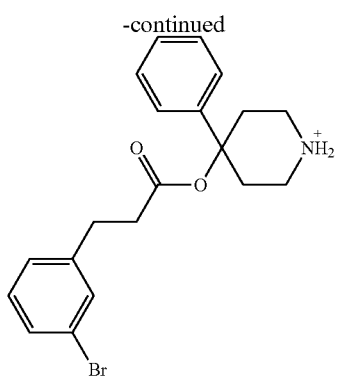
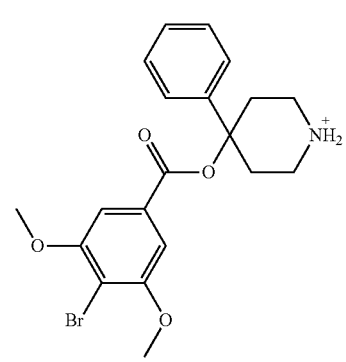
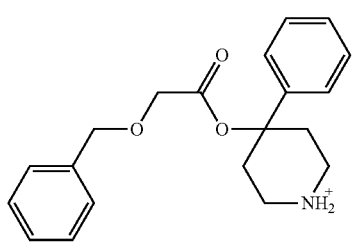
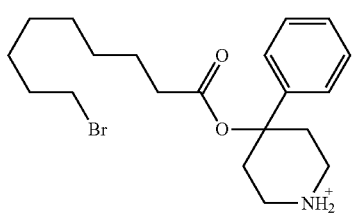
188
-continued
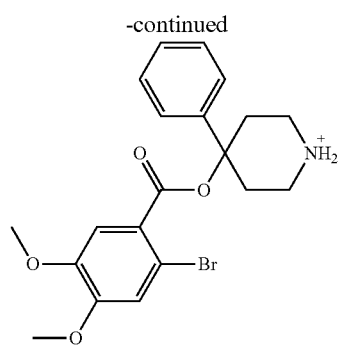
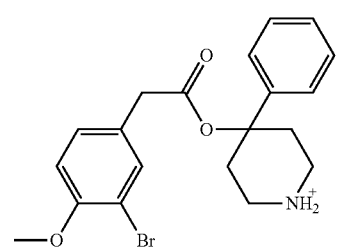
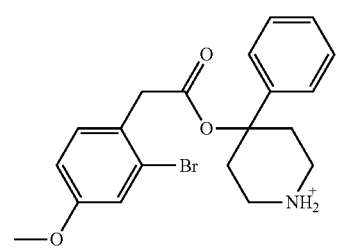
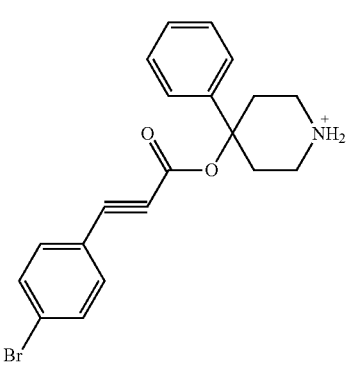
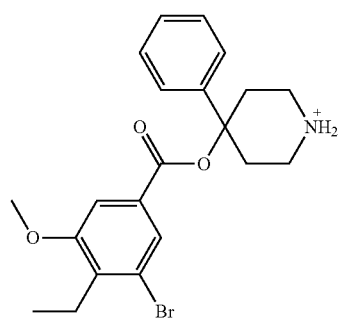

189
-continued
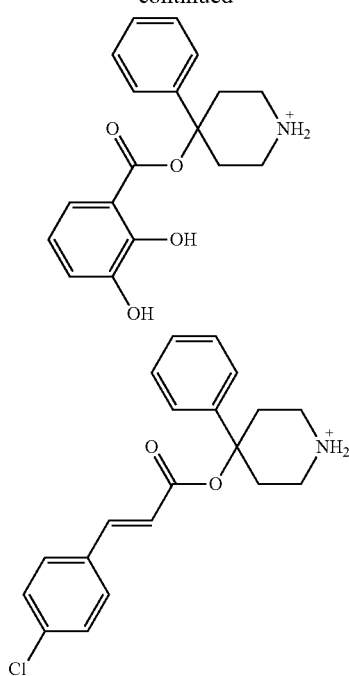
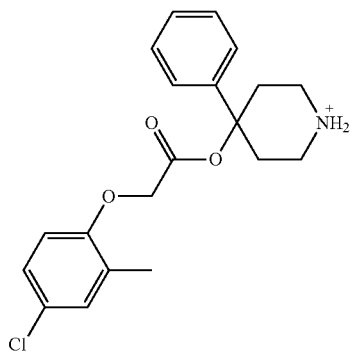
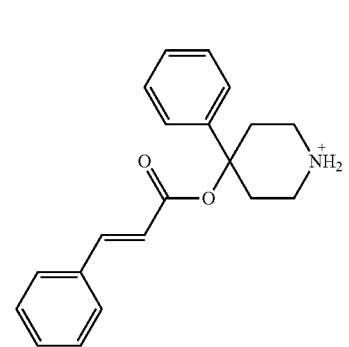
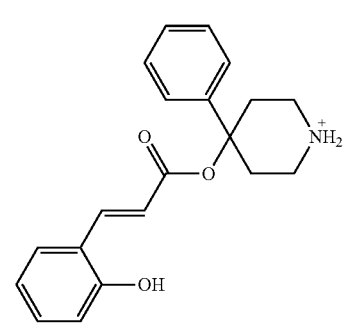
190
-continued
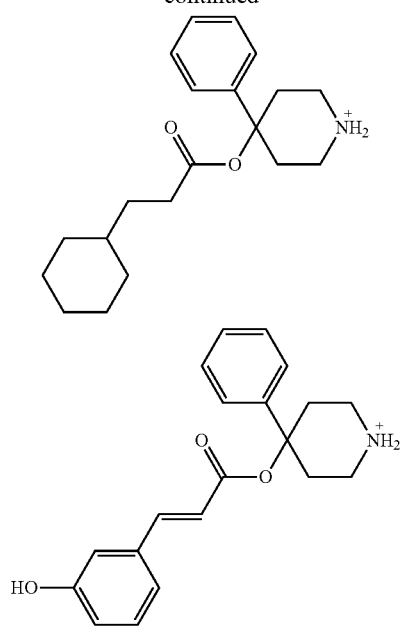
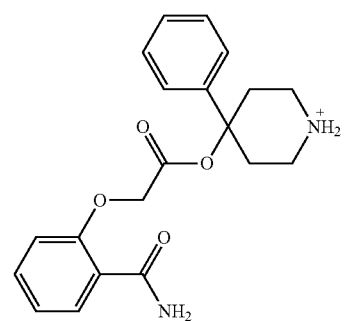
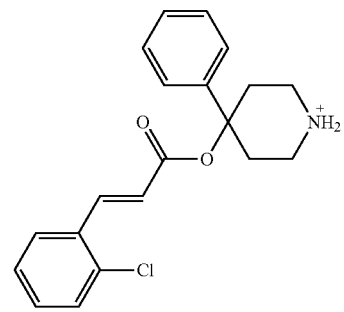
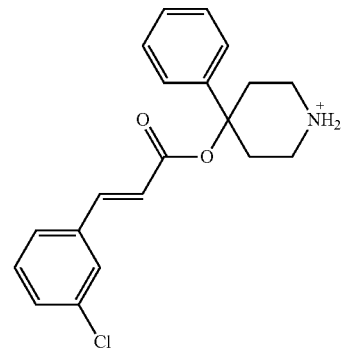

191
-continued
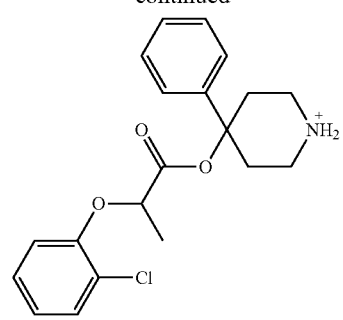
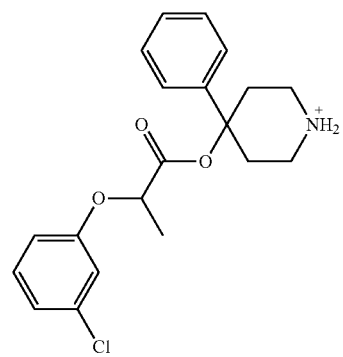
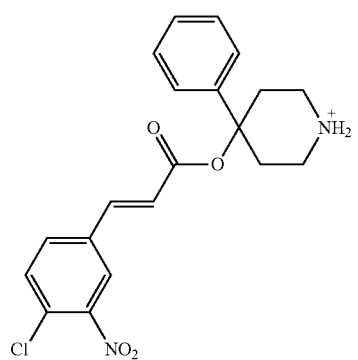
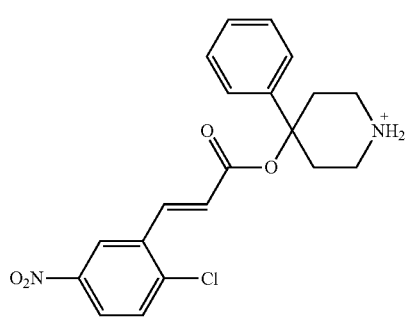
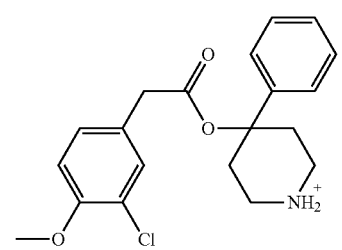
192
-continued
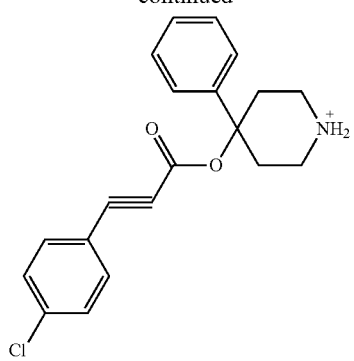
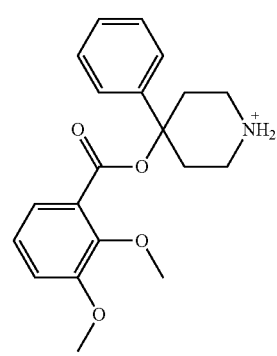
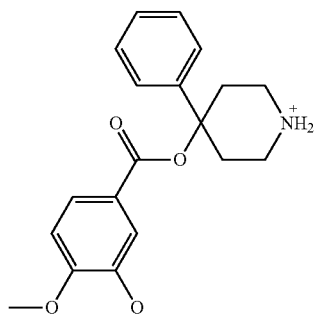
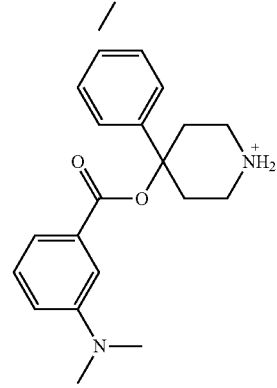
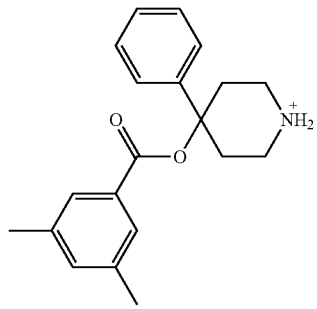

-continued
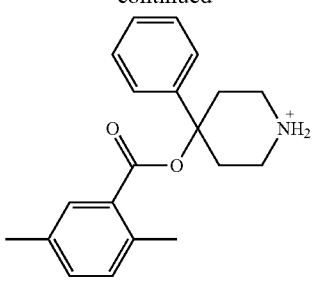
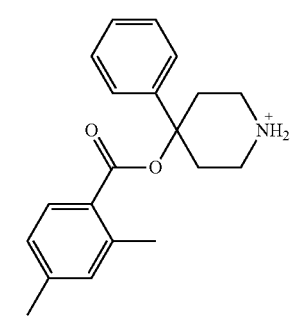
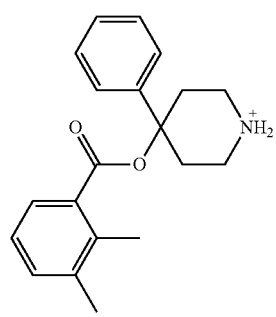
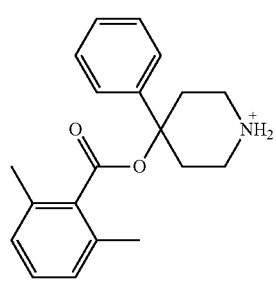
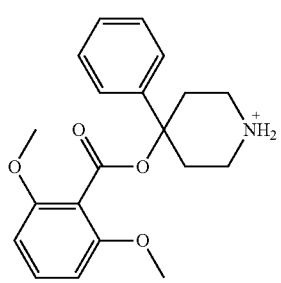
-continued
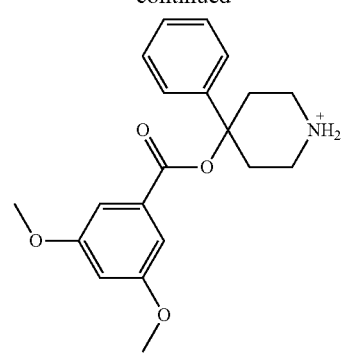
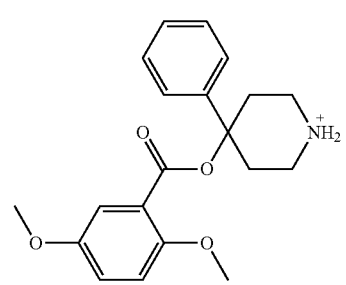
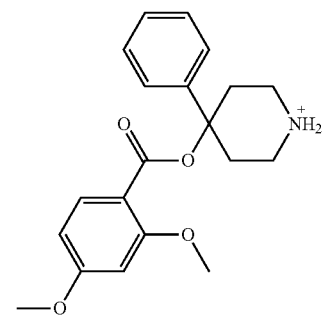
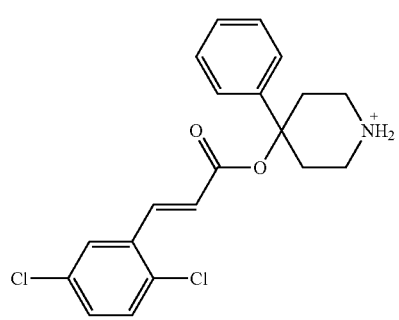
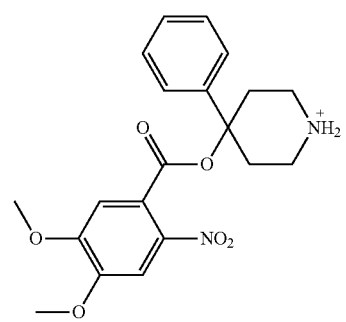

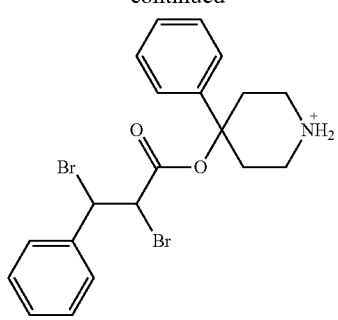
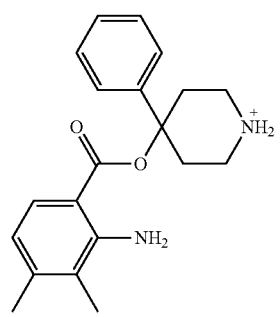
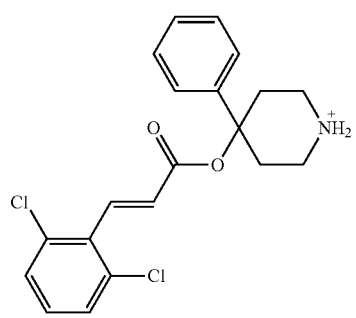
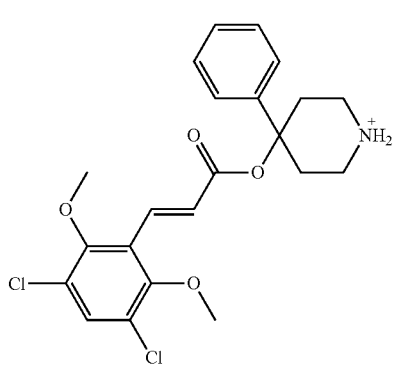
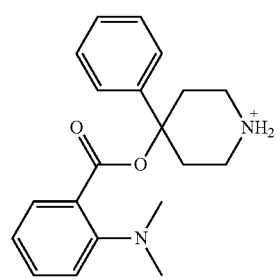
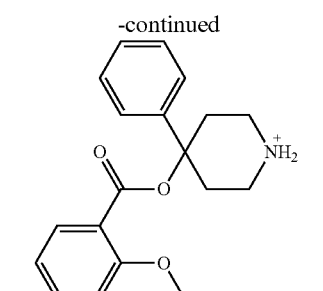
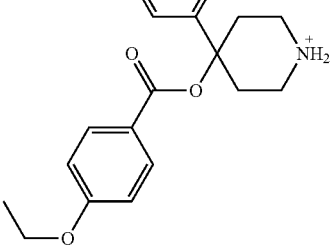
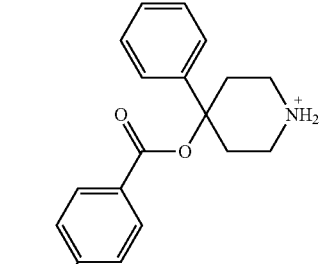
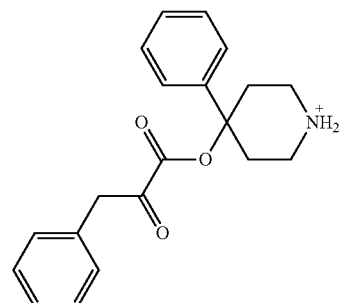
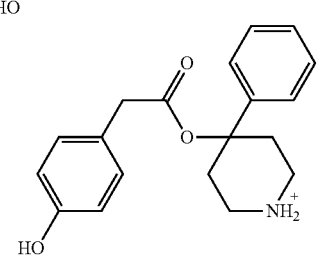
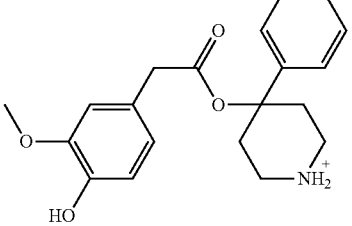

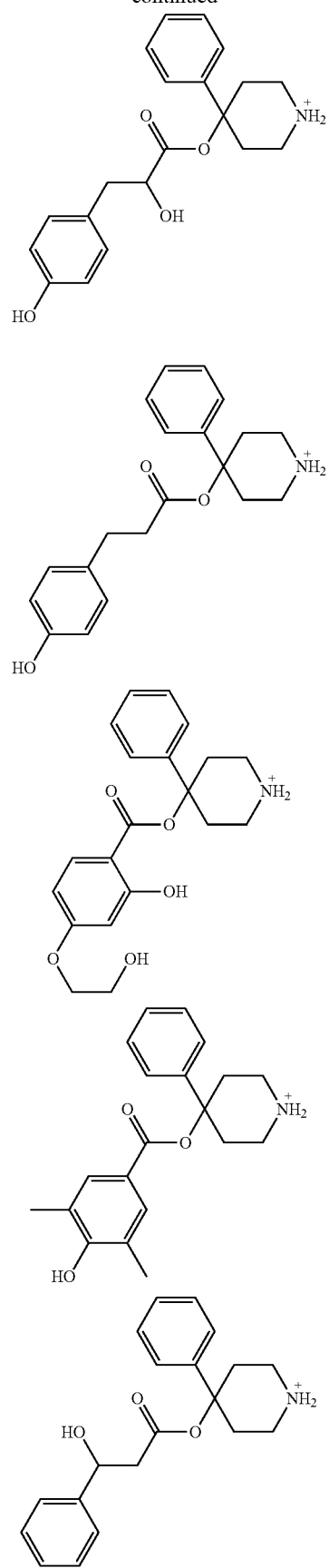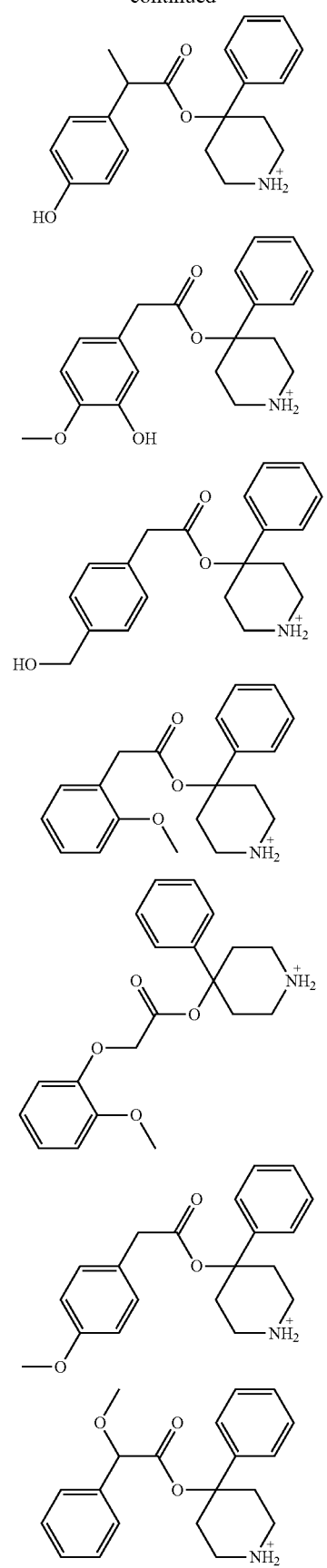

199
-continued
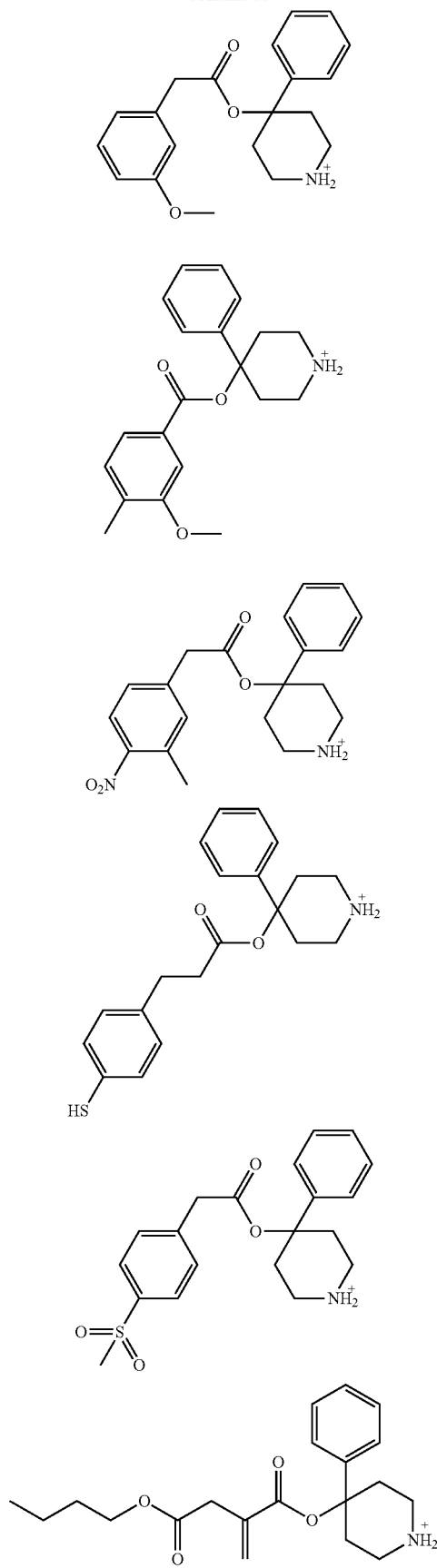
200
-continued
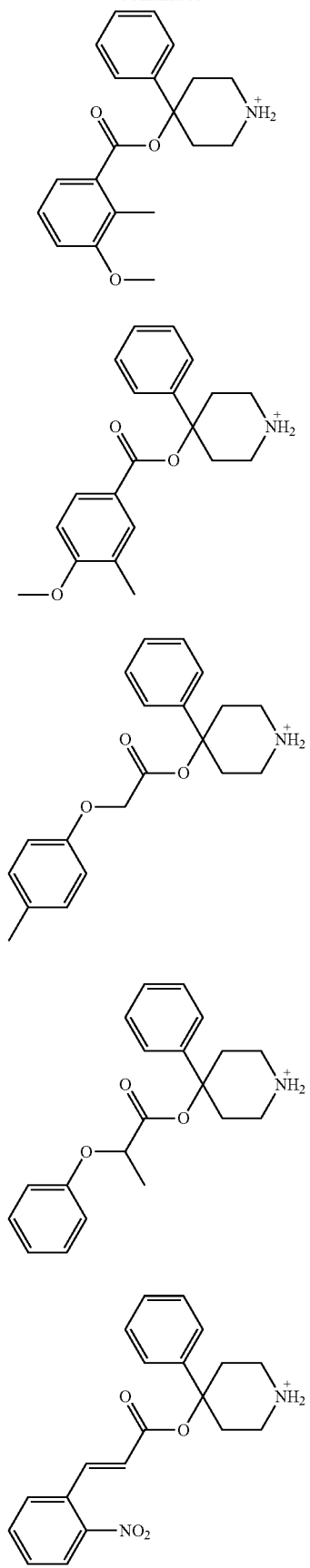

201
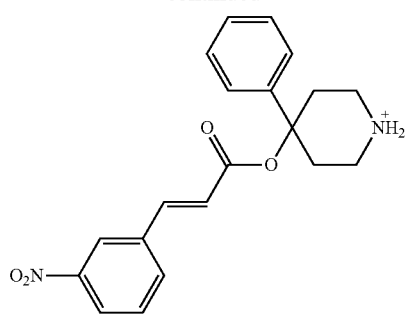
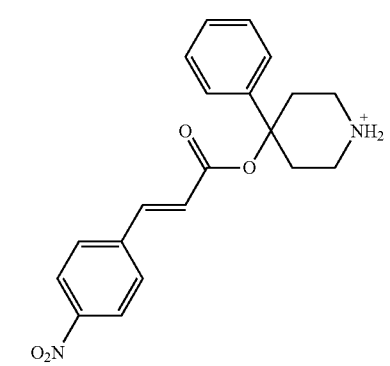
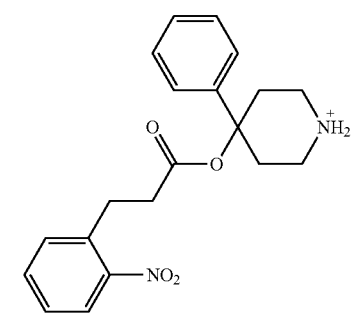
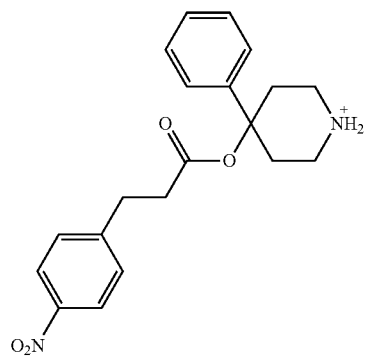
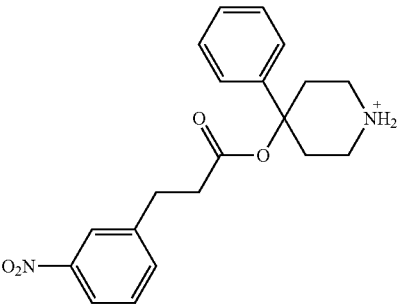
202
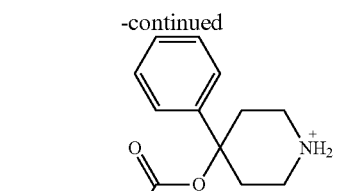
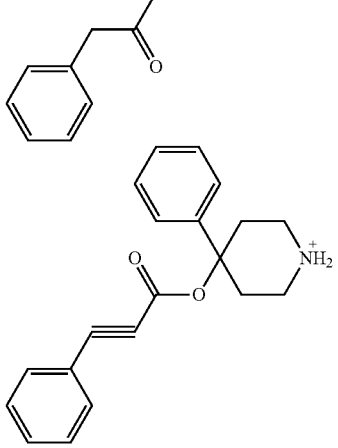
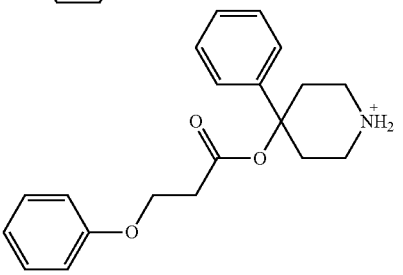
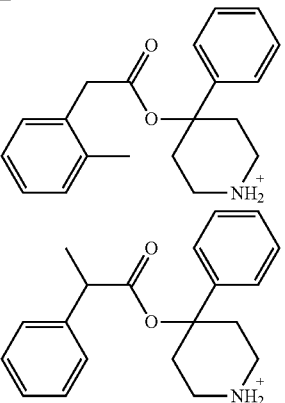
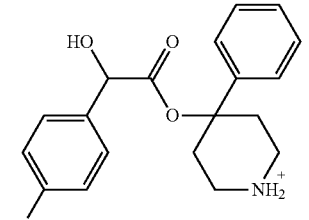
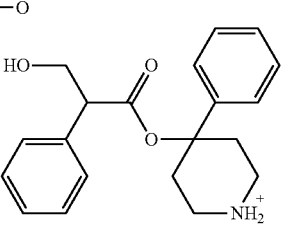

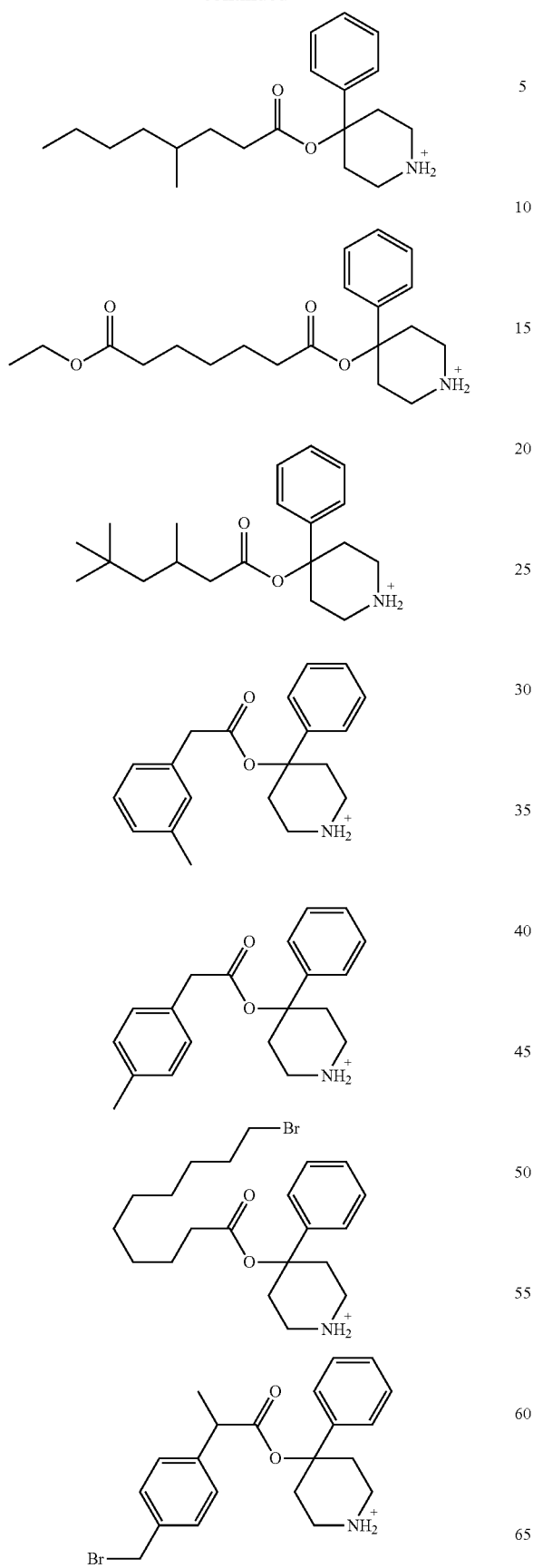
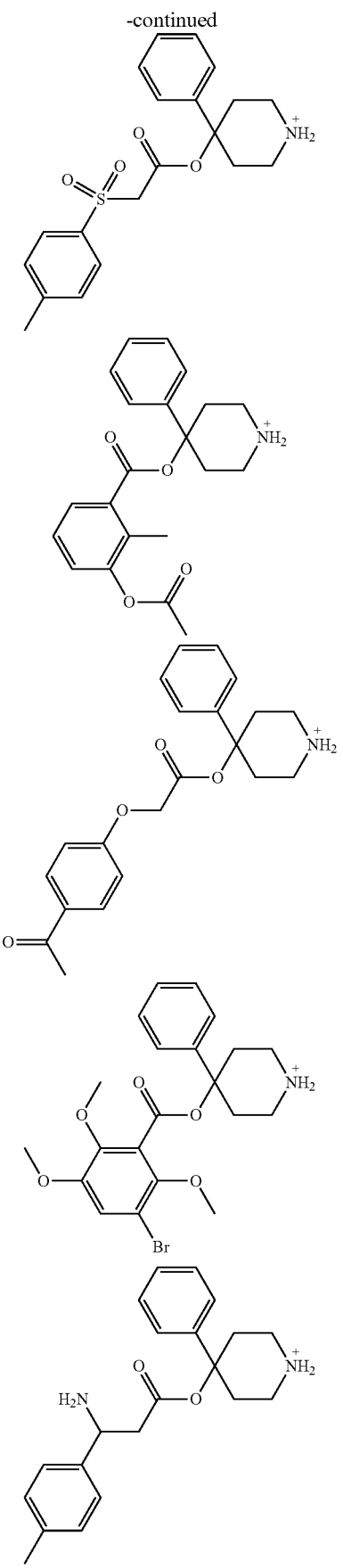

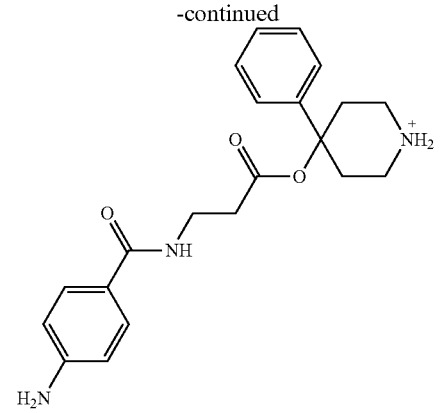
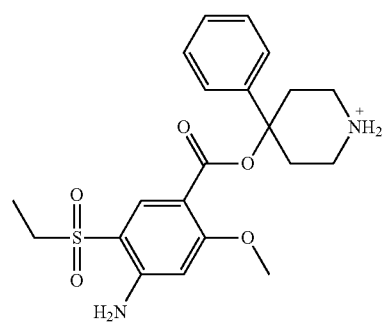
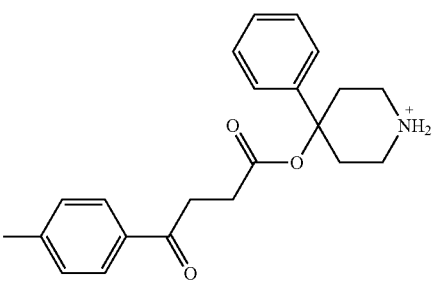
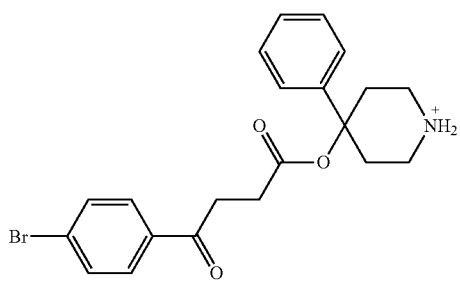
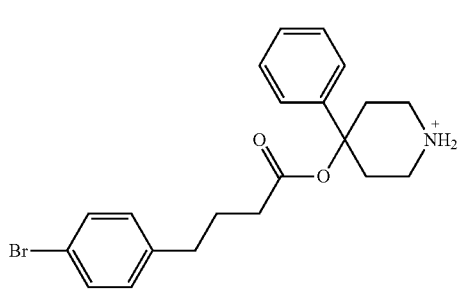
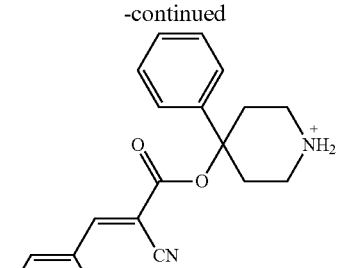
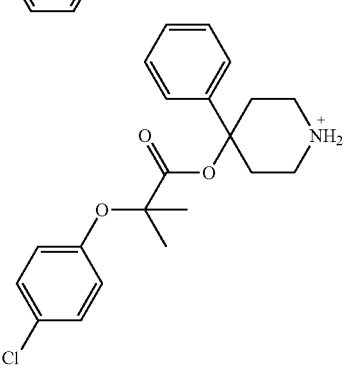
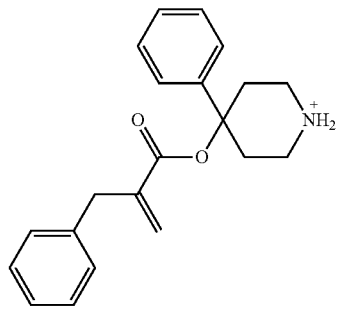
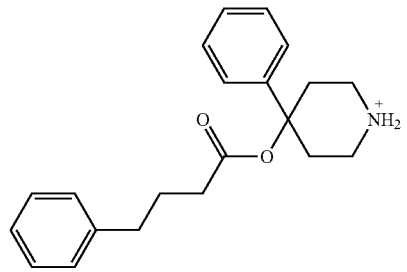
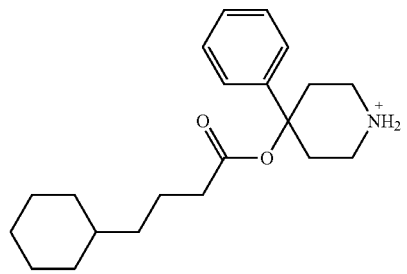
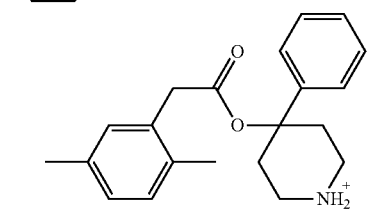

207
-continued
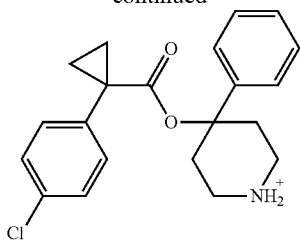
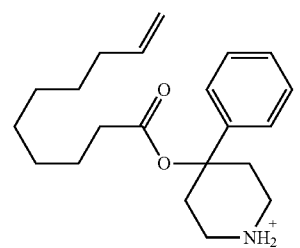
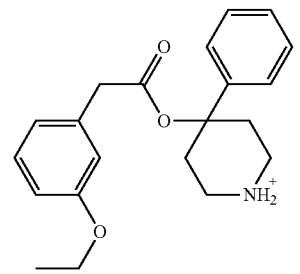
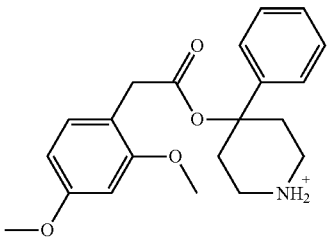
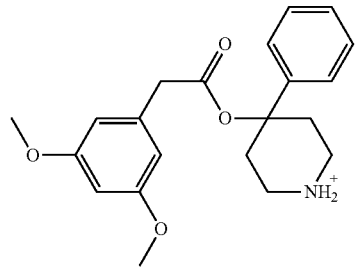
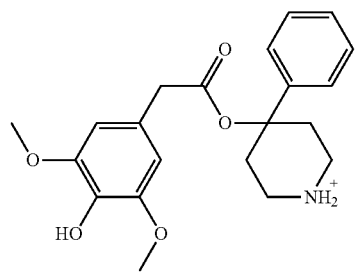
208
-continued
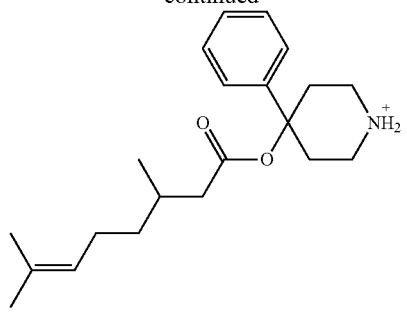
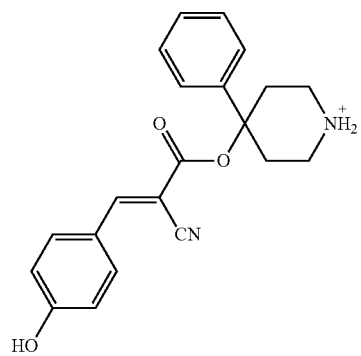
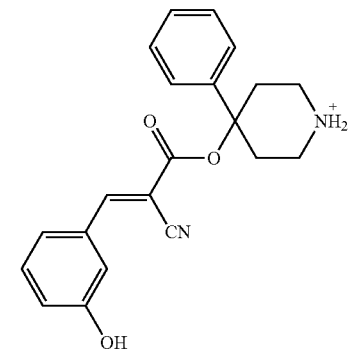
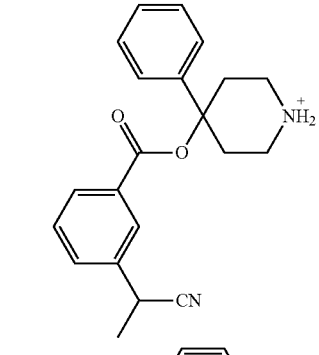
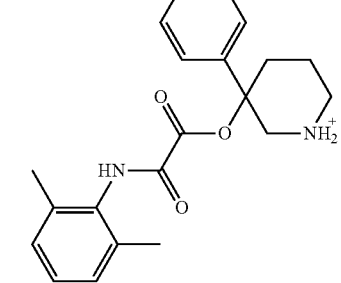

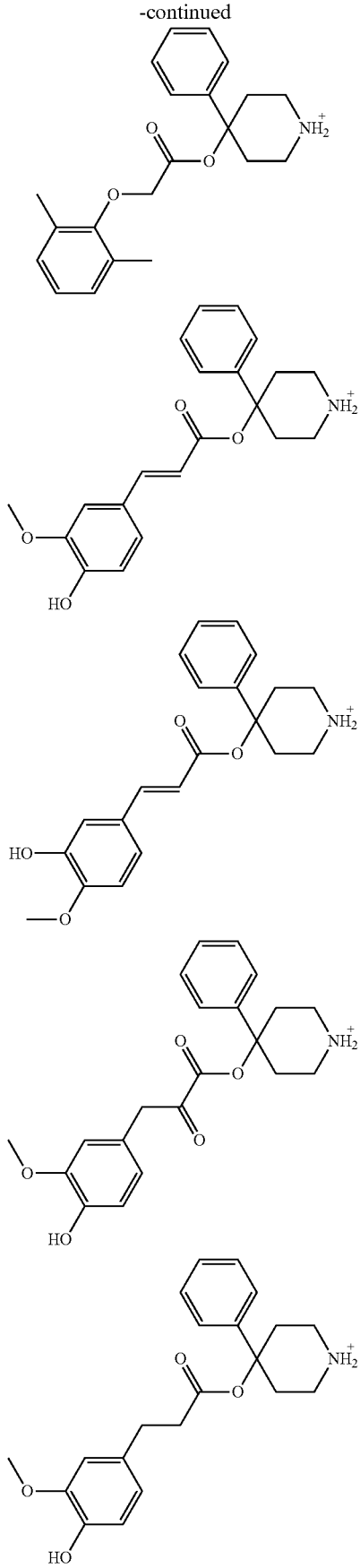

211
-continued
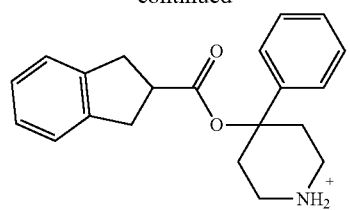
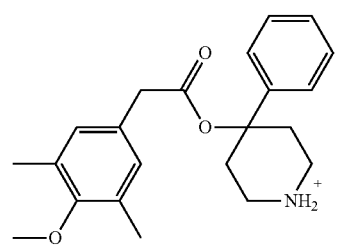
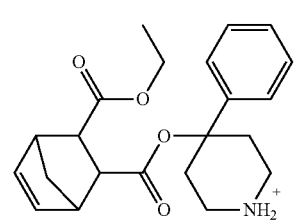
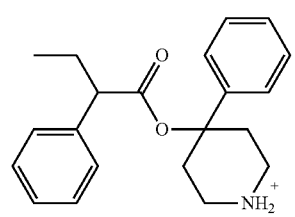
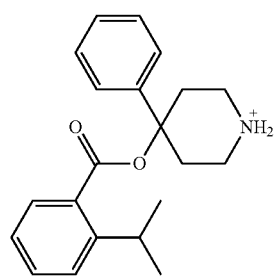
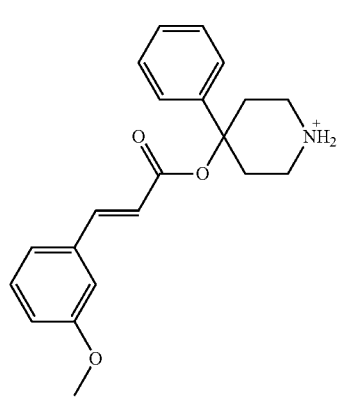
212
-continued
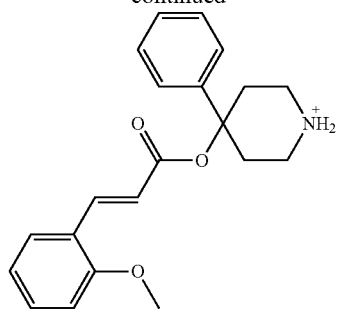
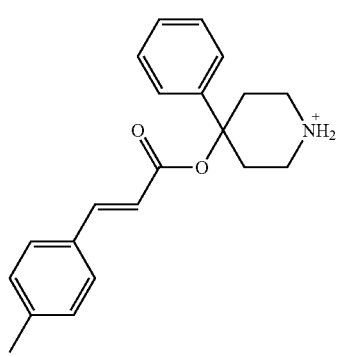
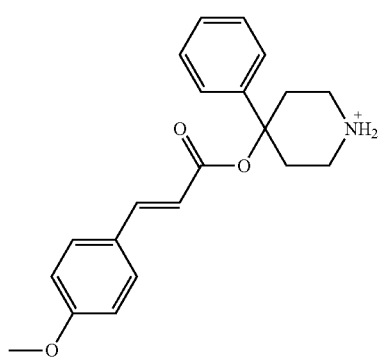
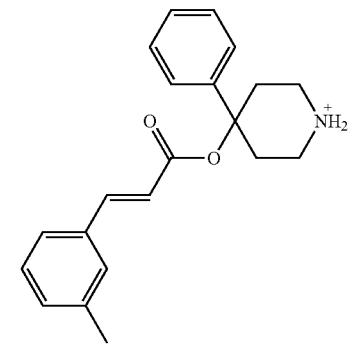
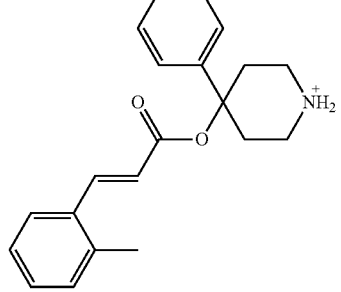

213
-continued
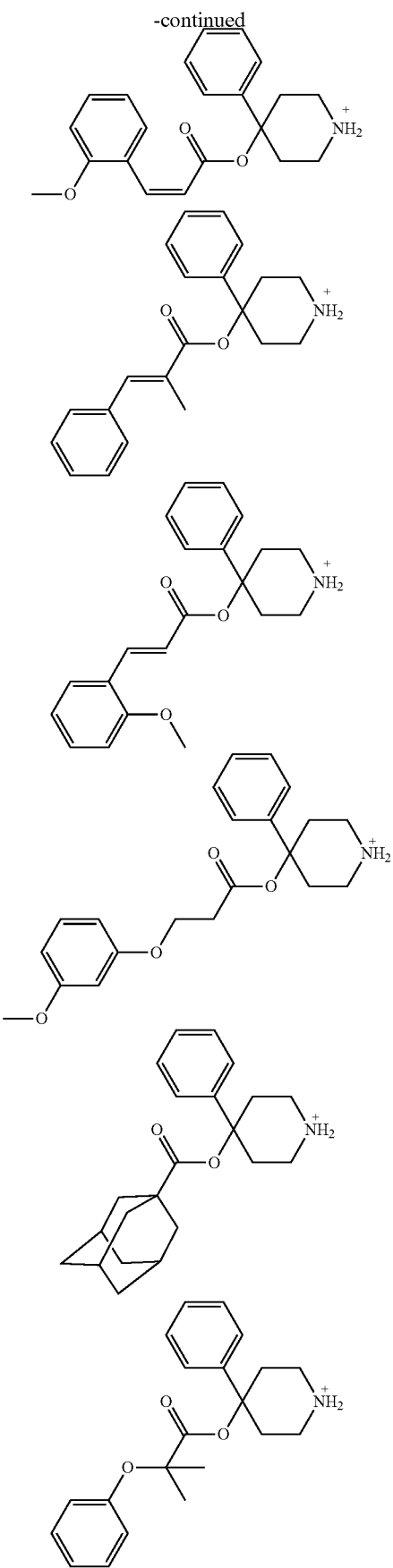
214
-continued
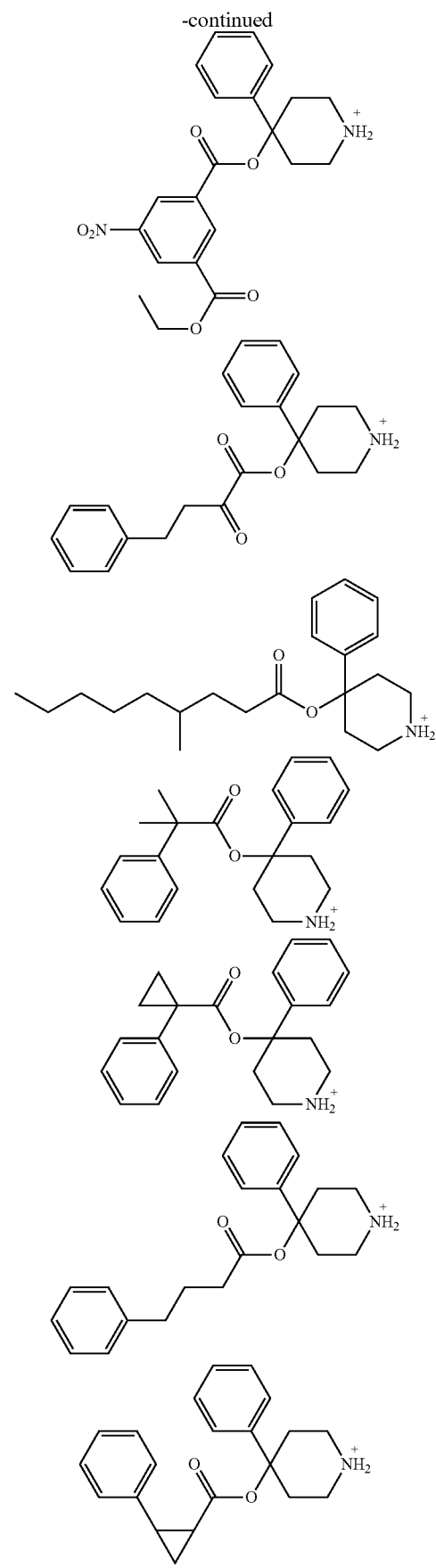

-continued
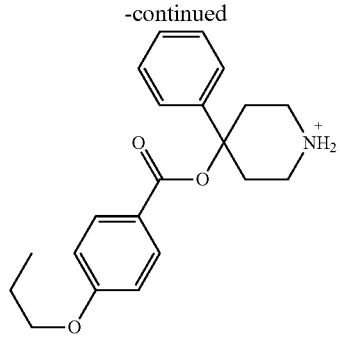
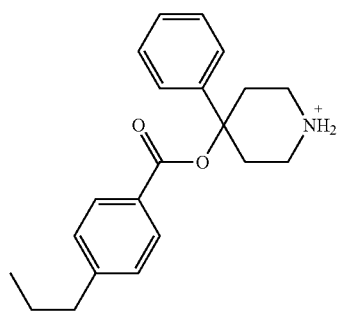
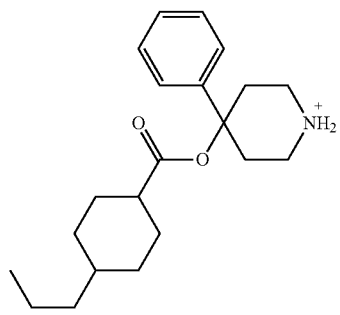
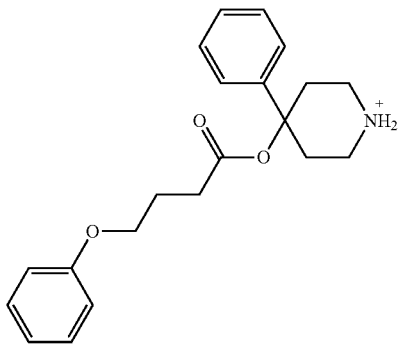
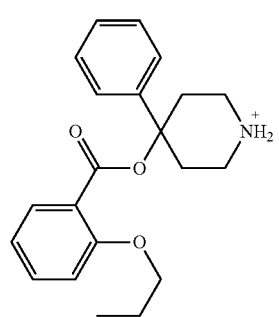
-continued
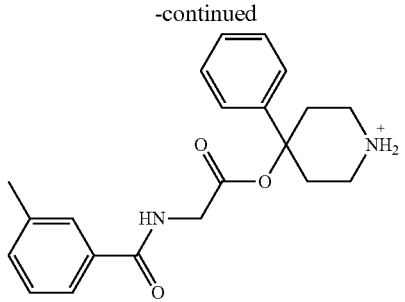
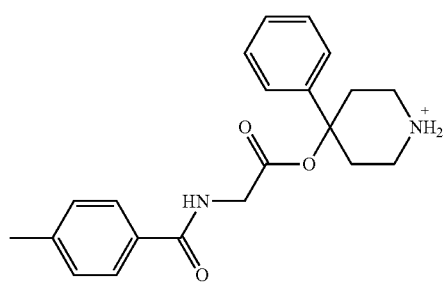
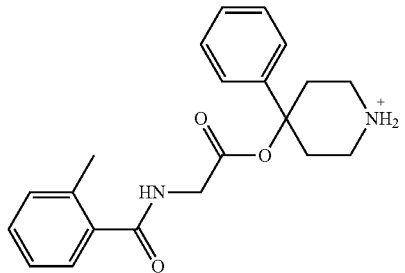
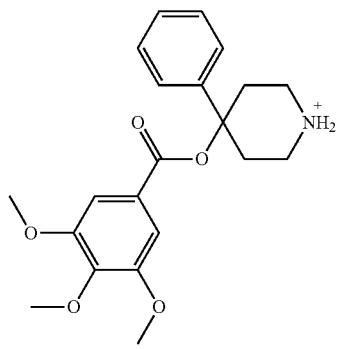
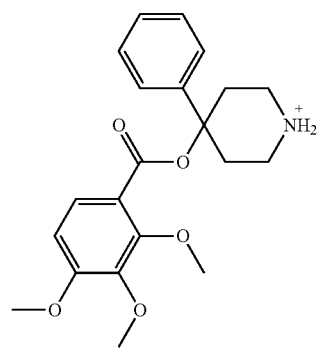

217
-continued
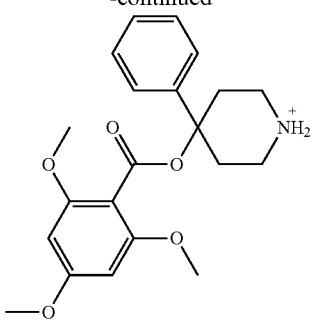
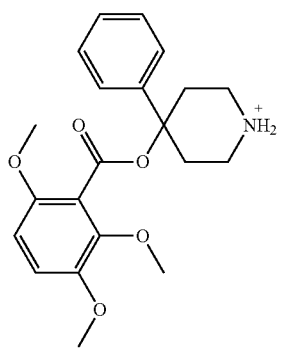
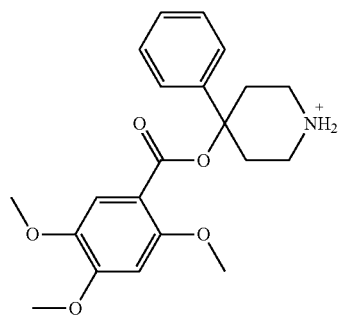
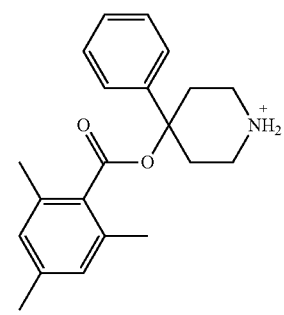
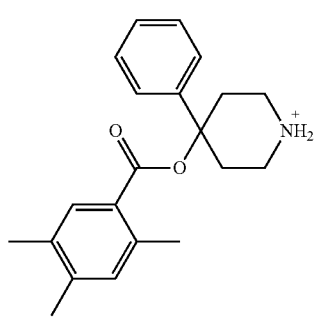
218
-continued
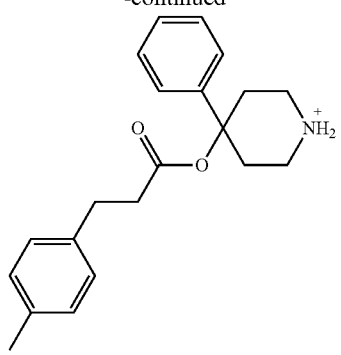
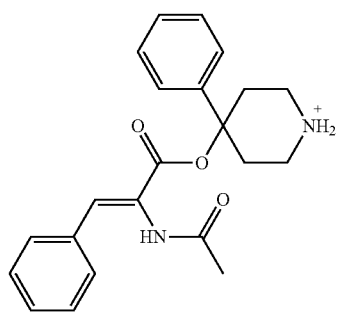
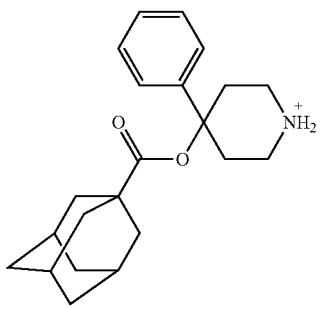
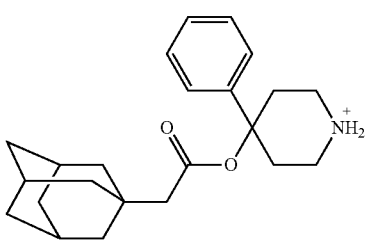
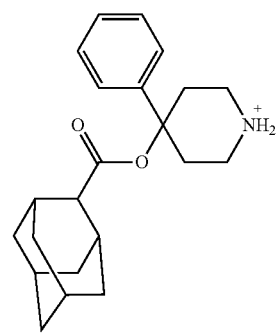

219
-continued
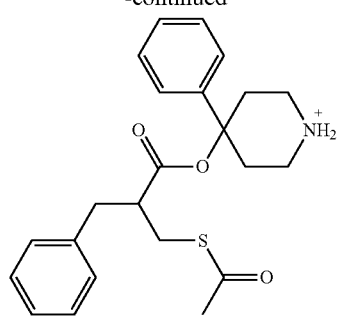
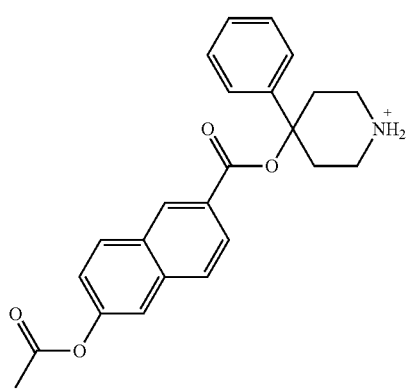
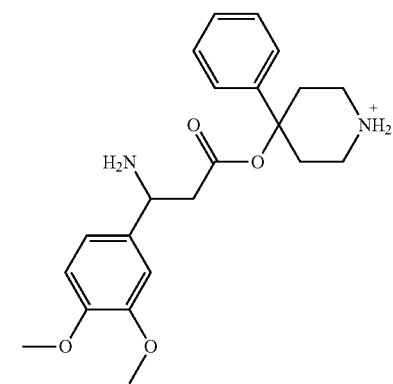
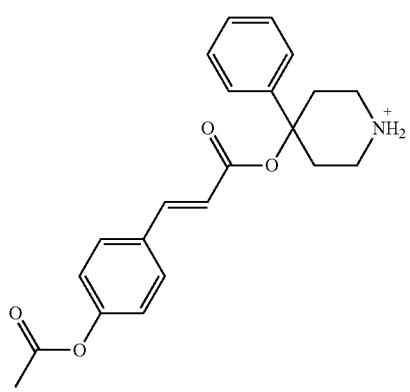
220
-continued
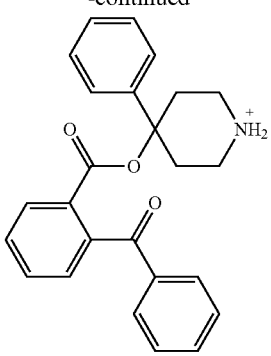
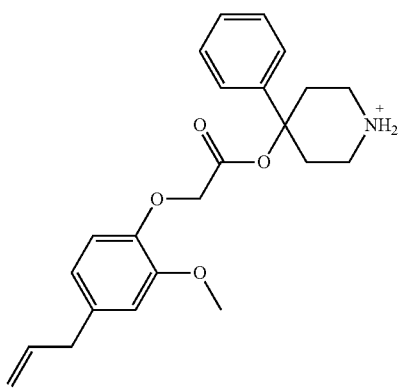
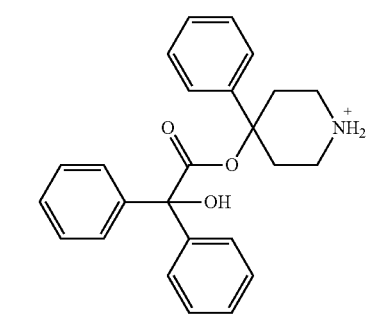
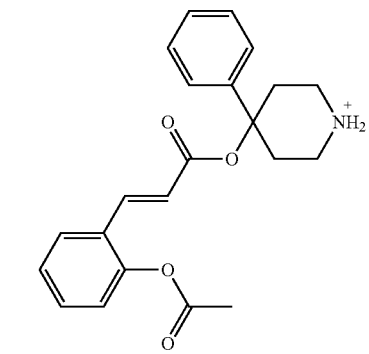

221
-continued
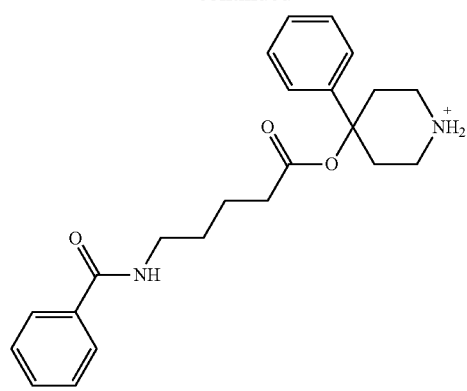
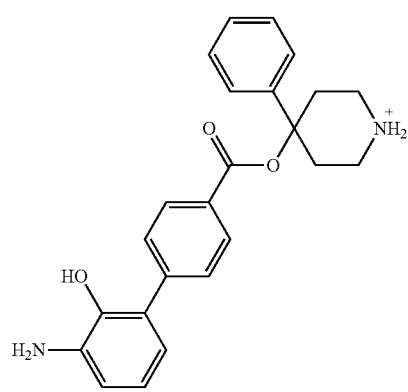
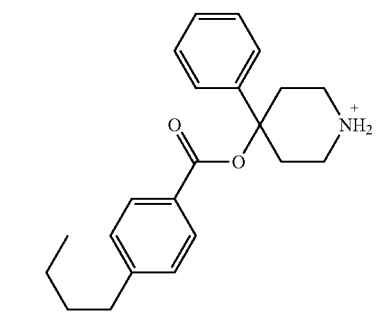
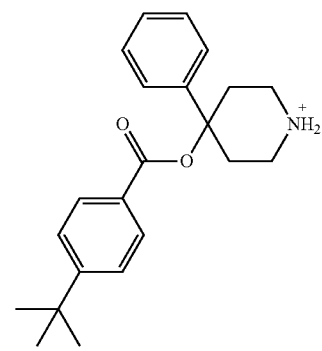
222
-continued
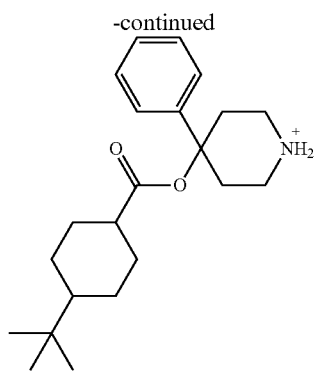
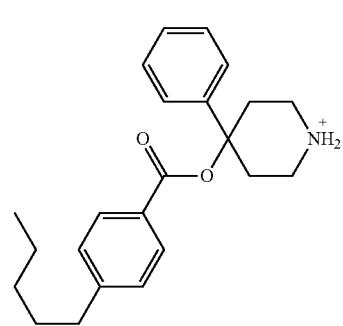
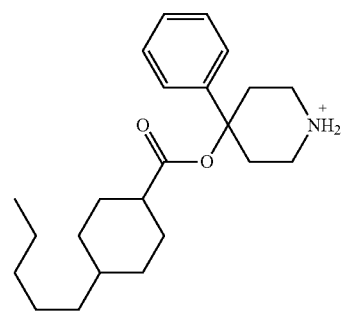
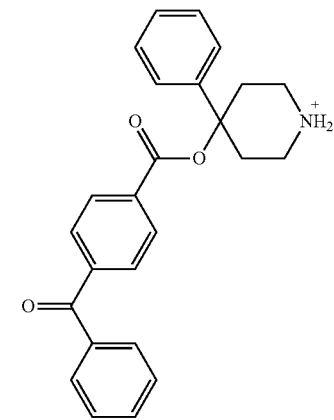

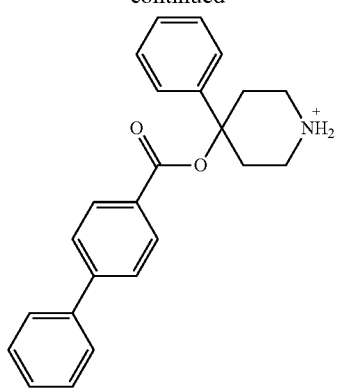
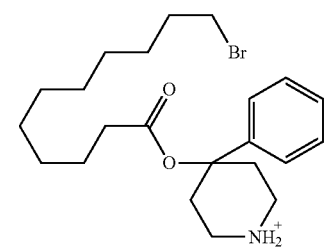
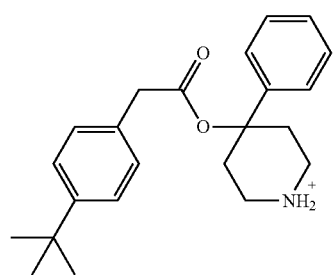
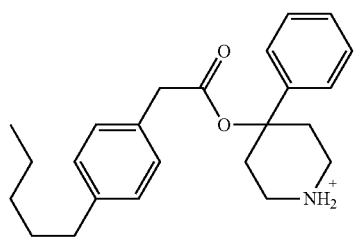
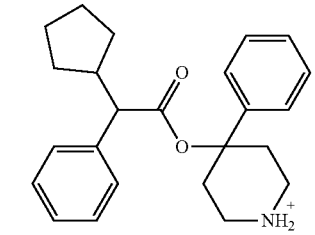
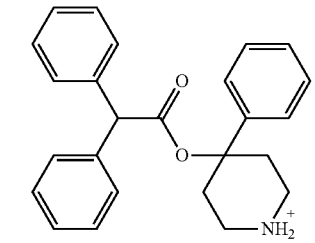
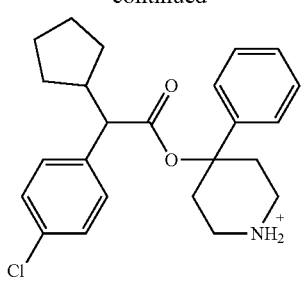
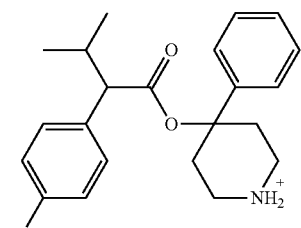
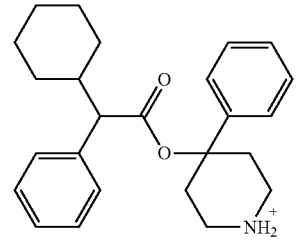
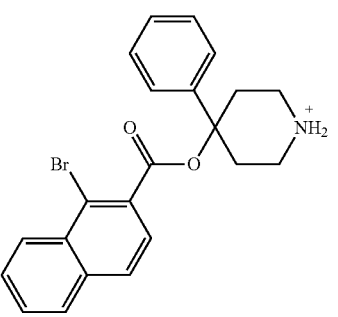
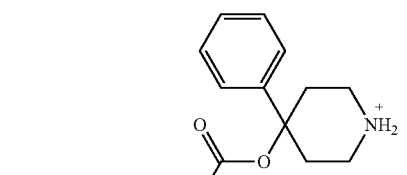
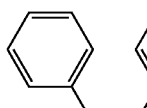
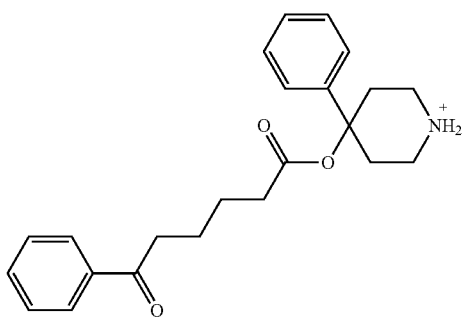

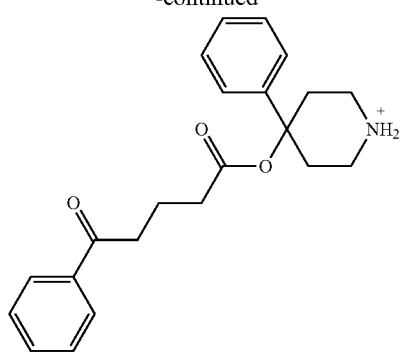
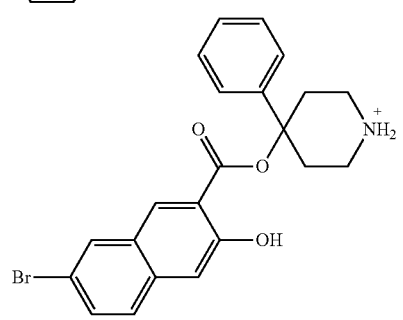
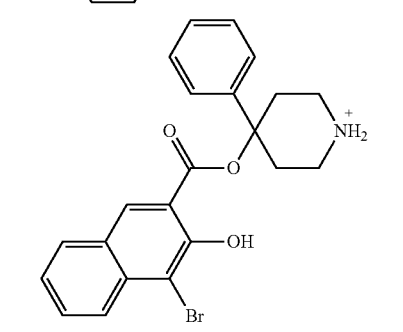
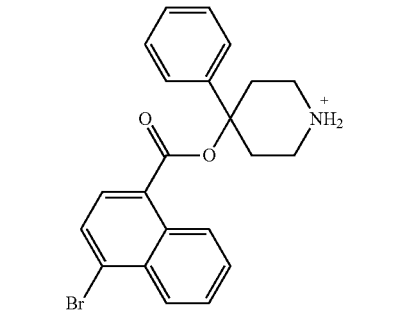
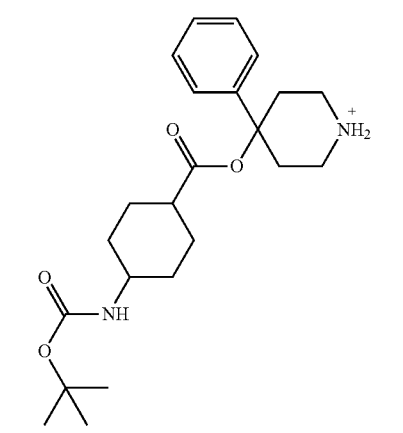
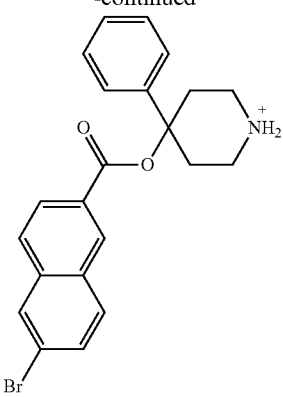
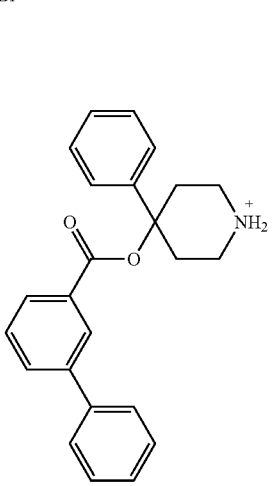
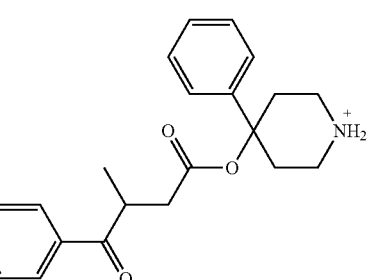
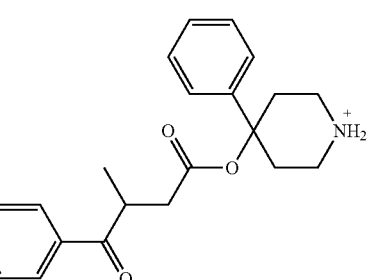
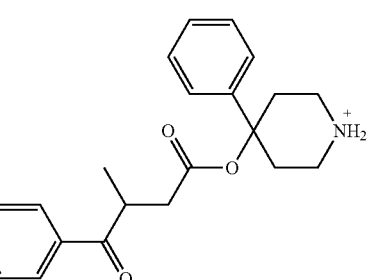

227
-continued
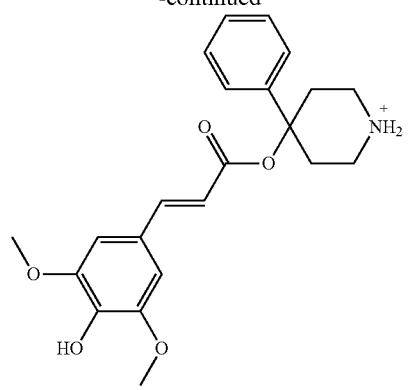
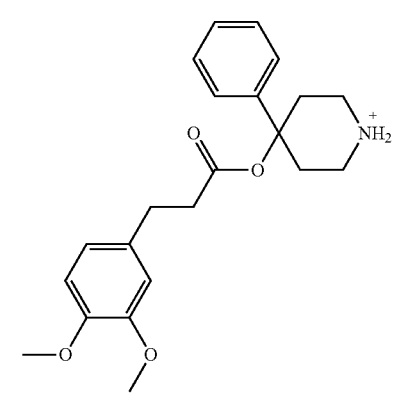
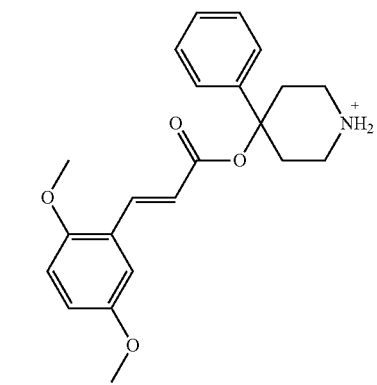
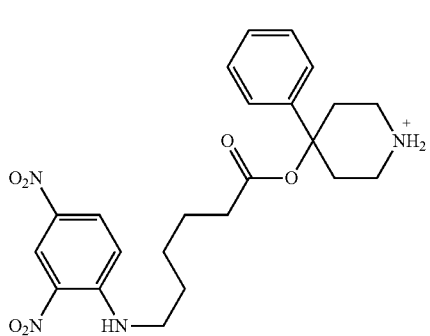
228
-continued
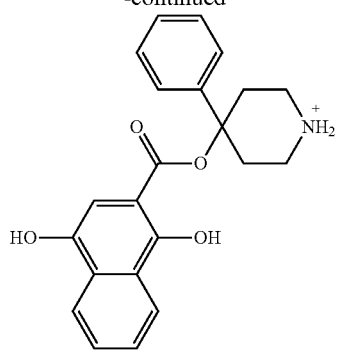
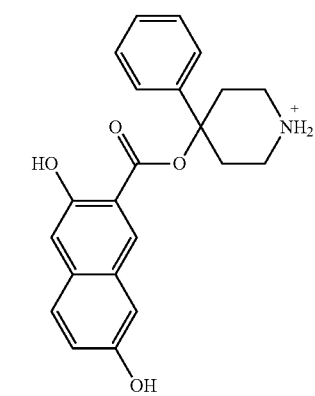
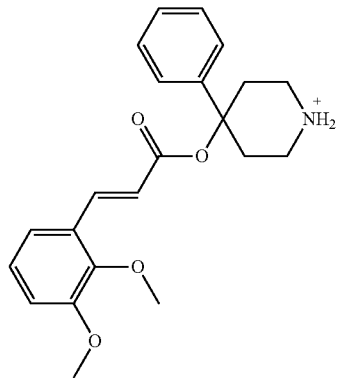
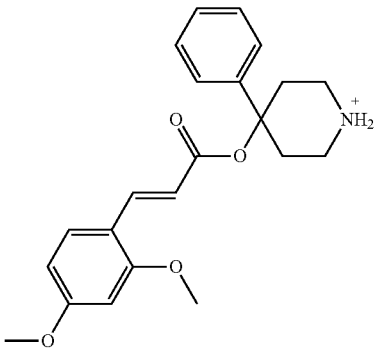

229
-continued
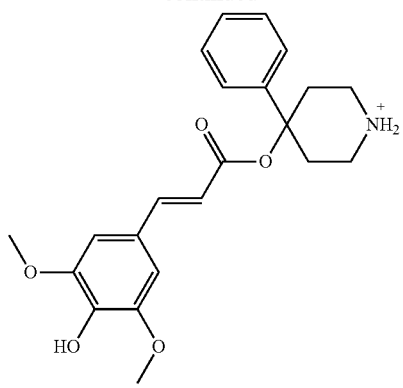
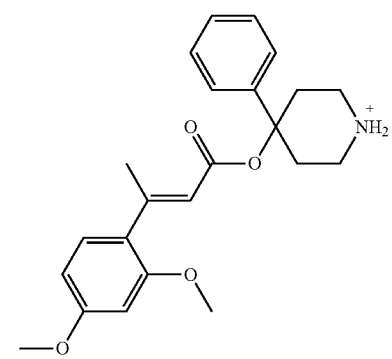
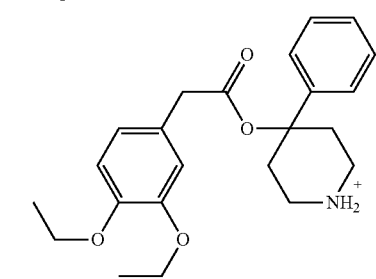
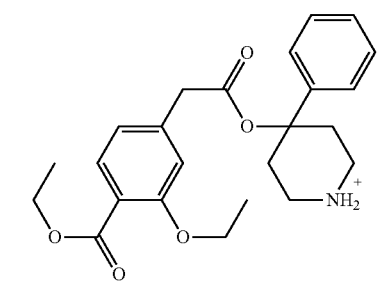
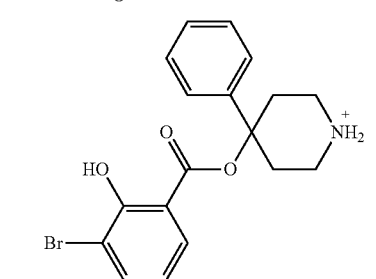
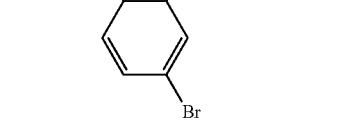
230
-continued
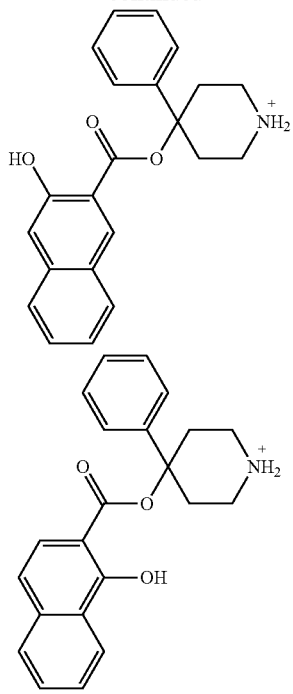
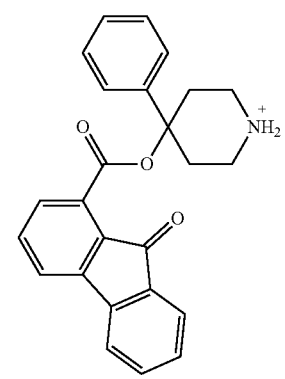
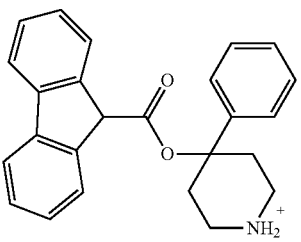
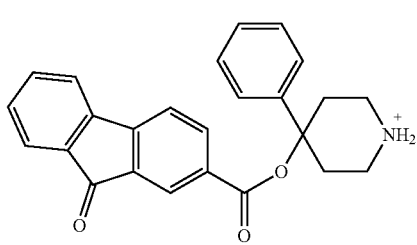

231
-continued
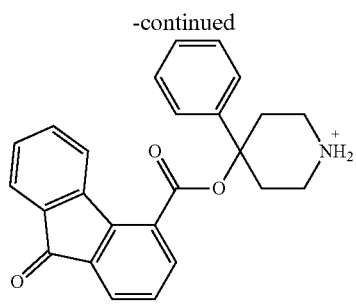
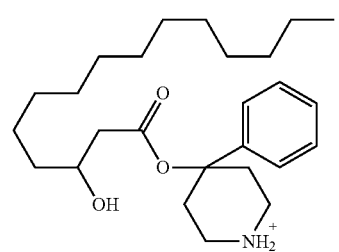
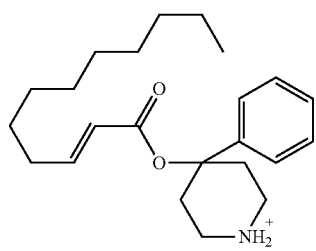
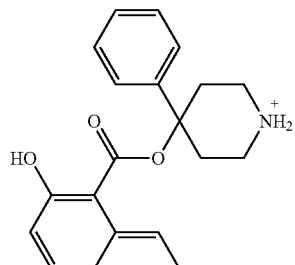
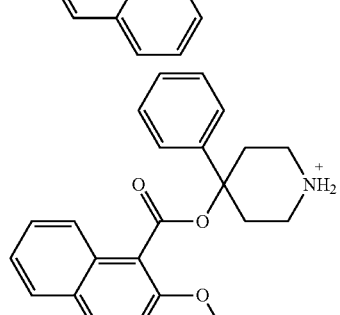
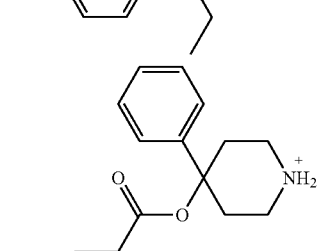
232
-continued
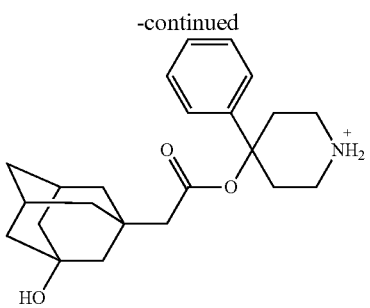
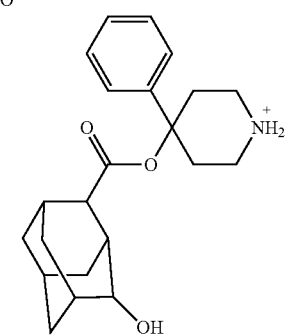
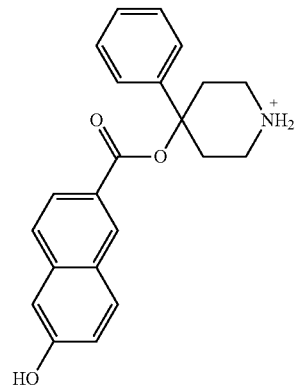
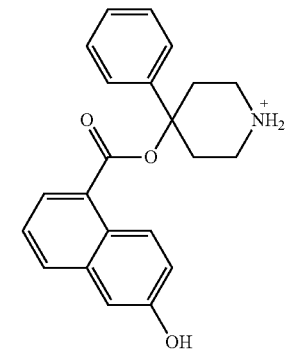
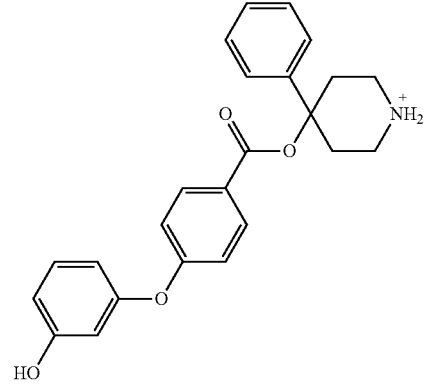

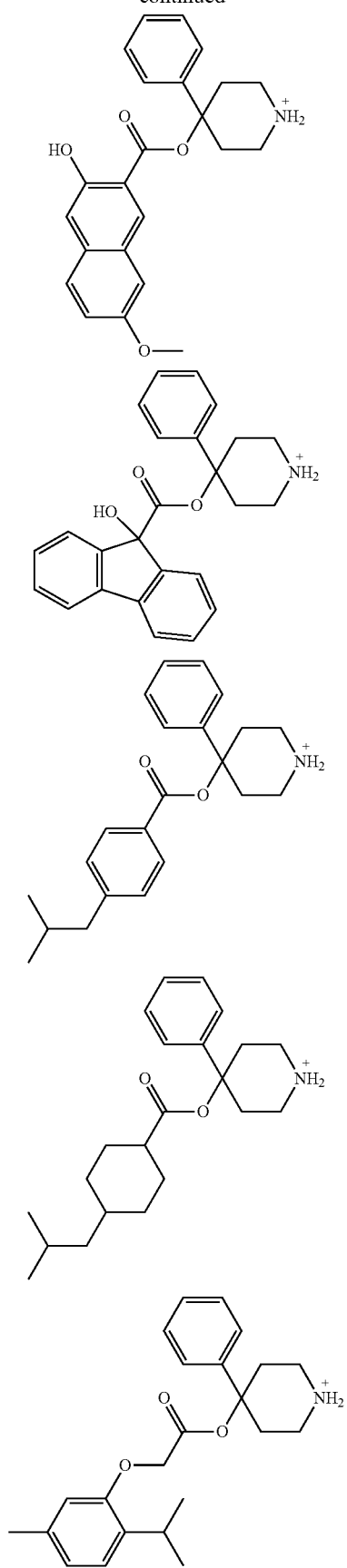
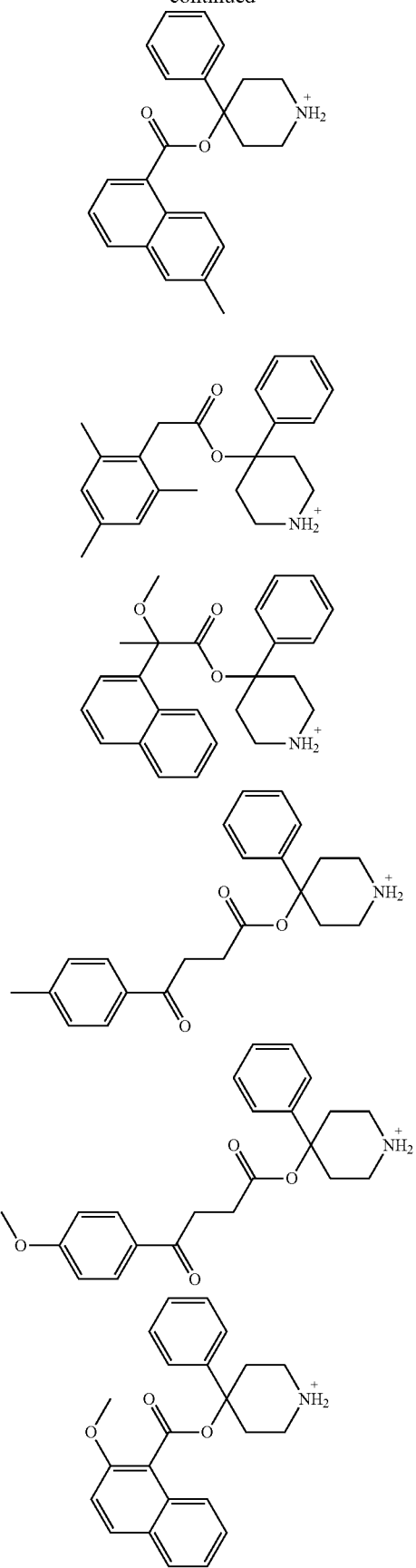

-continued
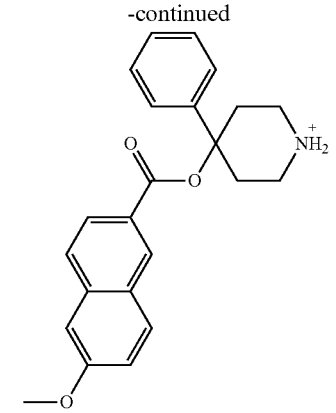
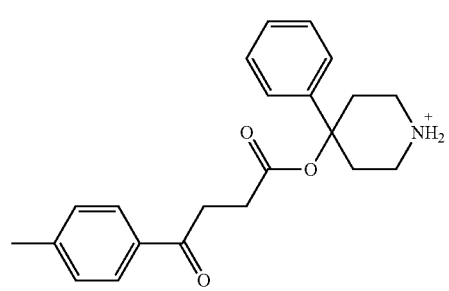
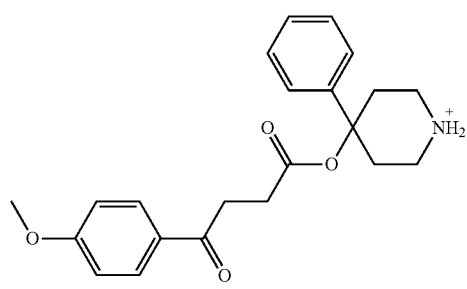
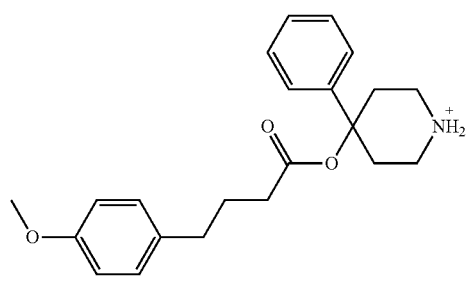
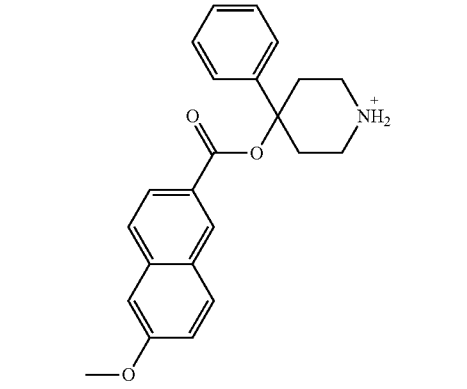
-continued
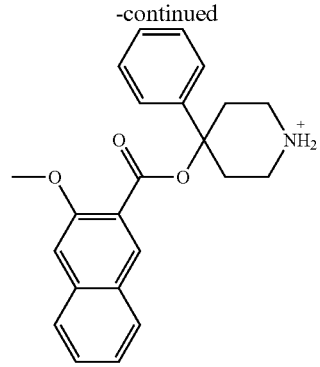
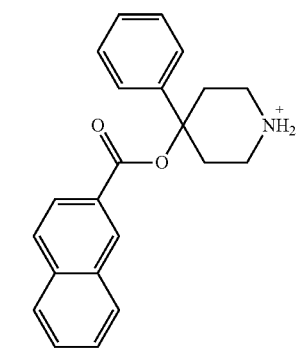
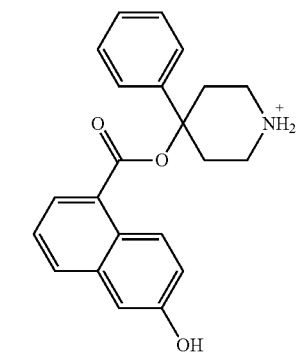
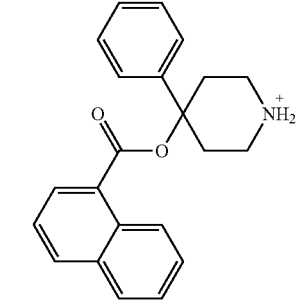
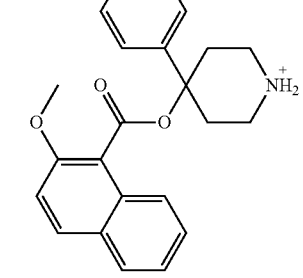

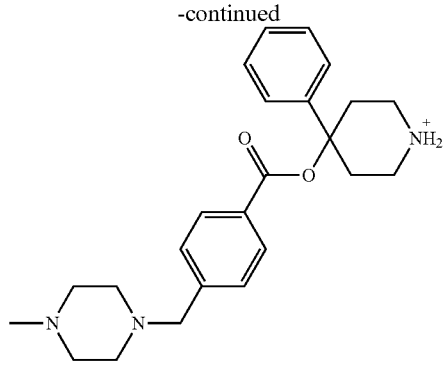
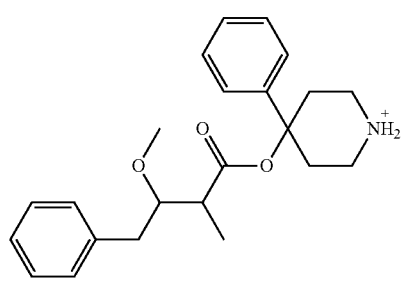
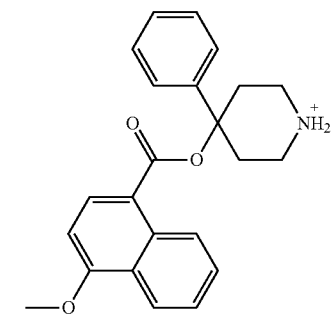
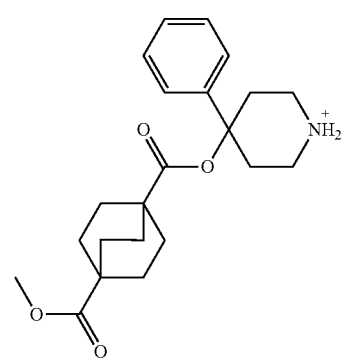
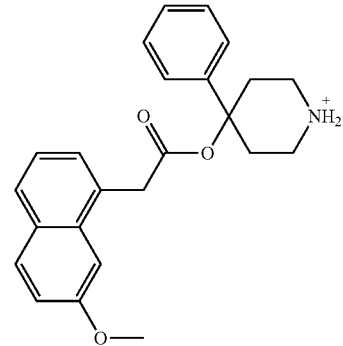
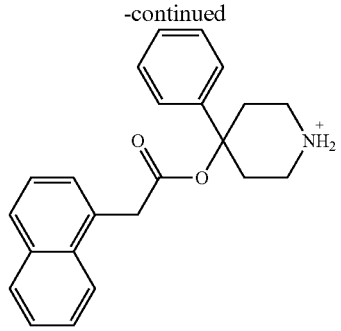
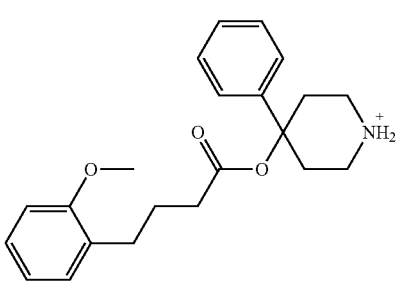
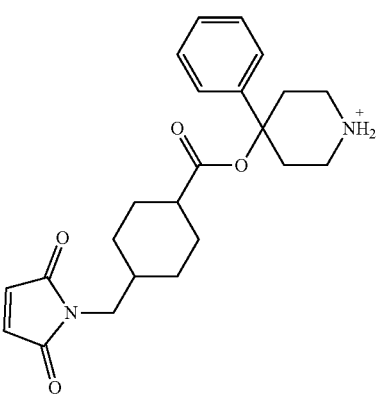
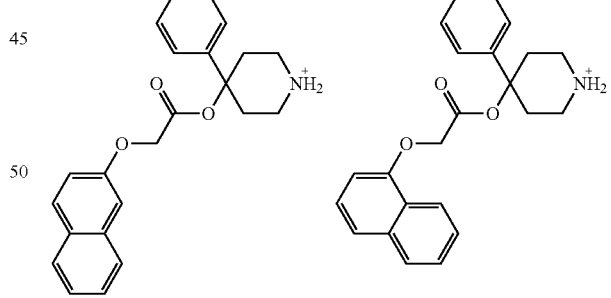
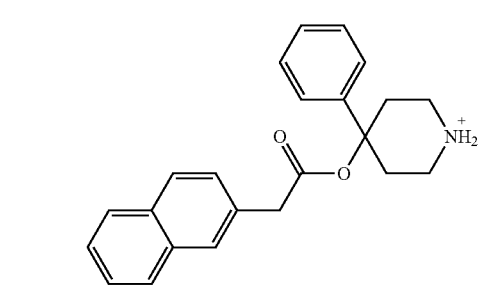

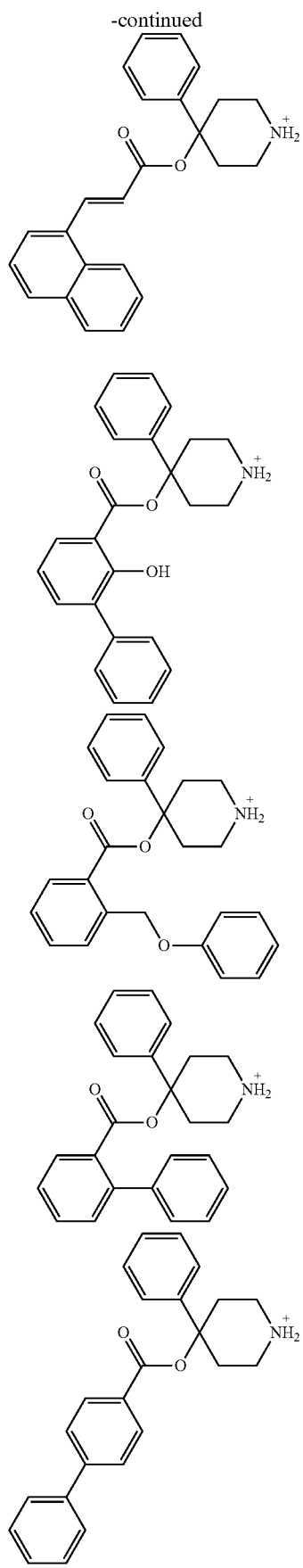

-continued
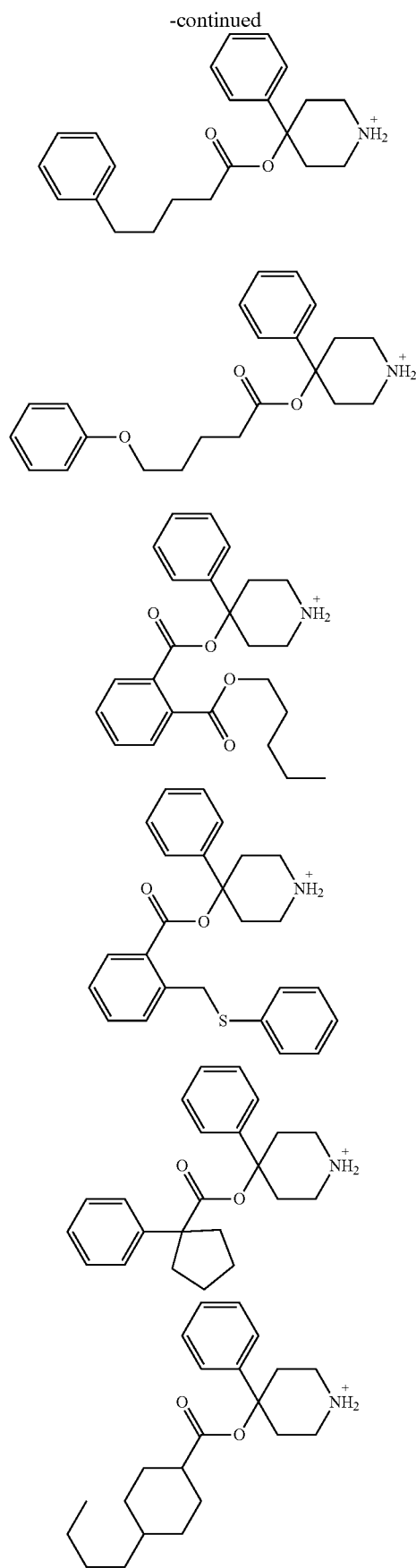
-continued
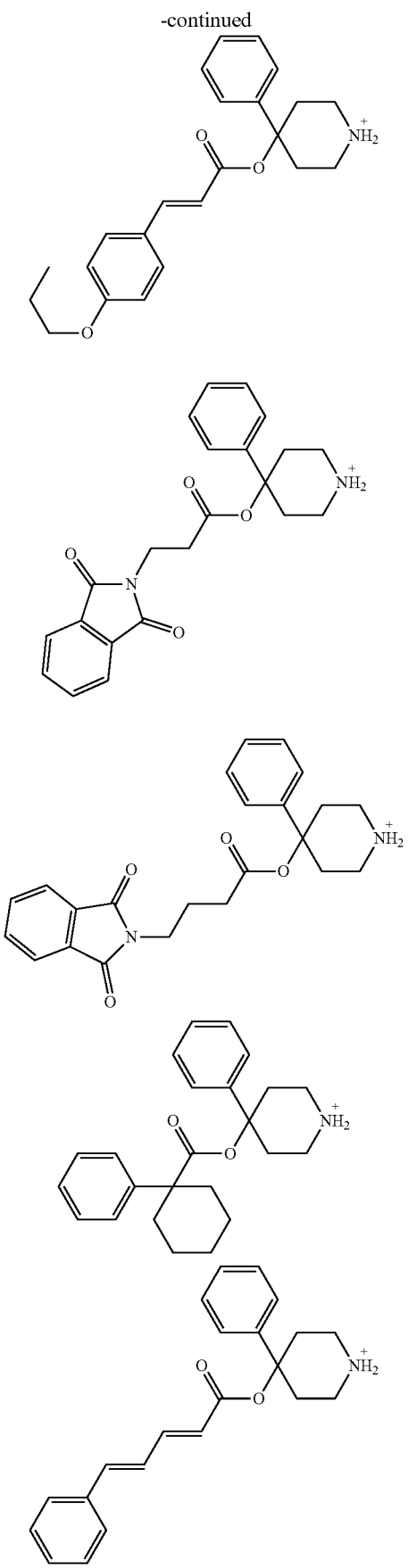

-continued
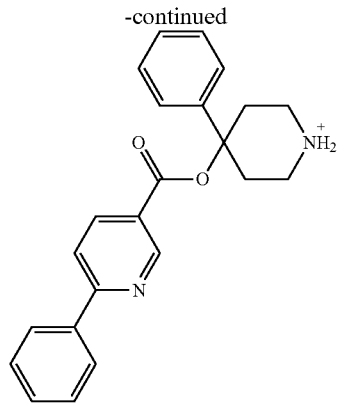
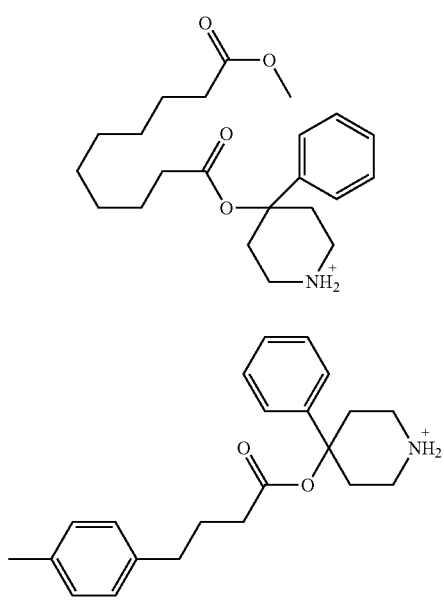
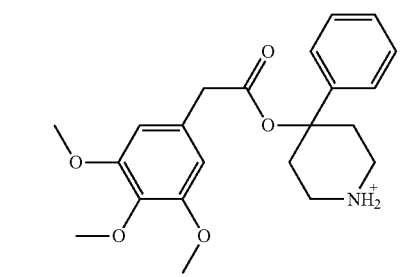
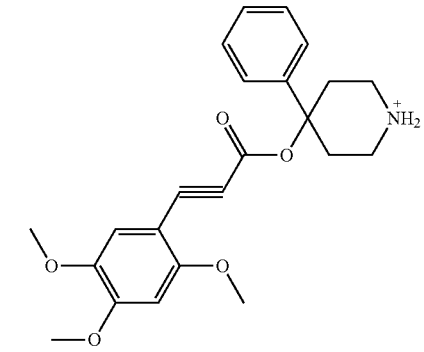
-continued
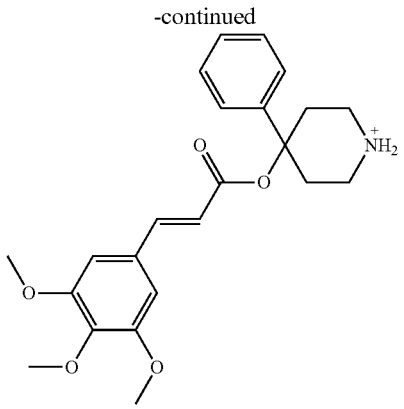
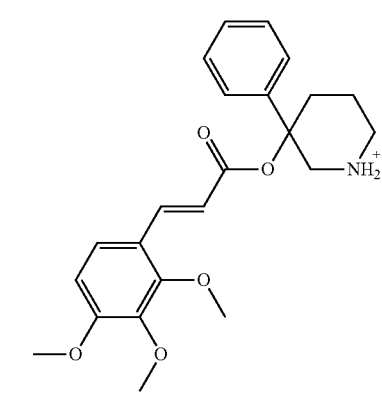
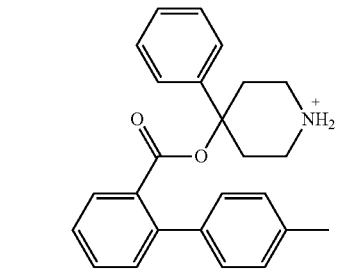
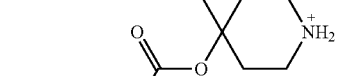
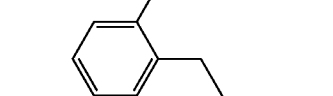
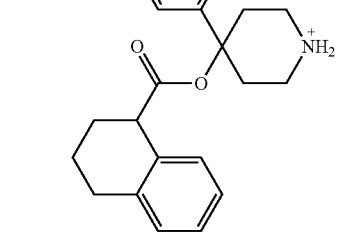

245
-continued
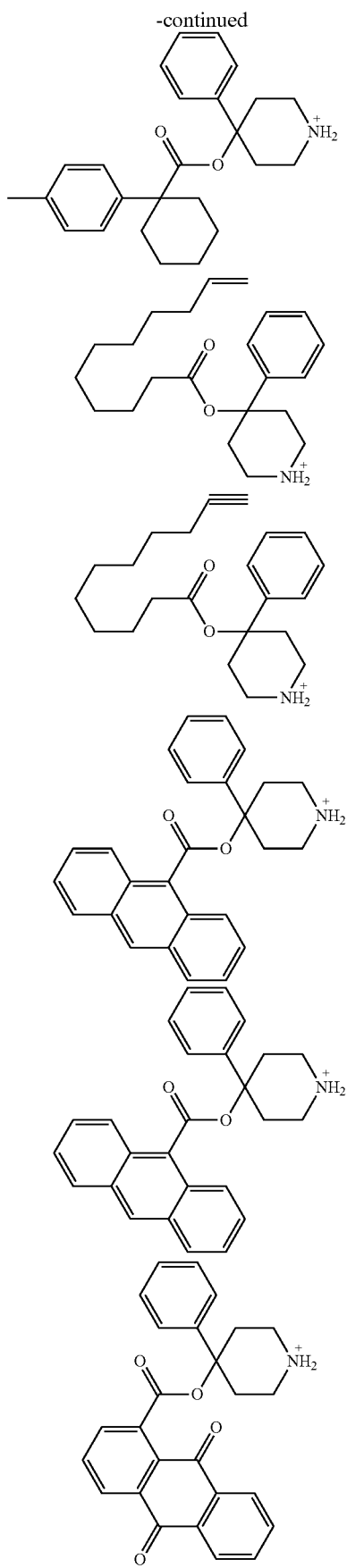
246
-continued
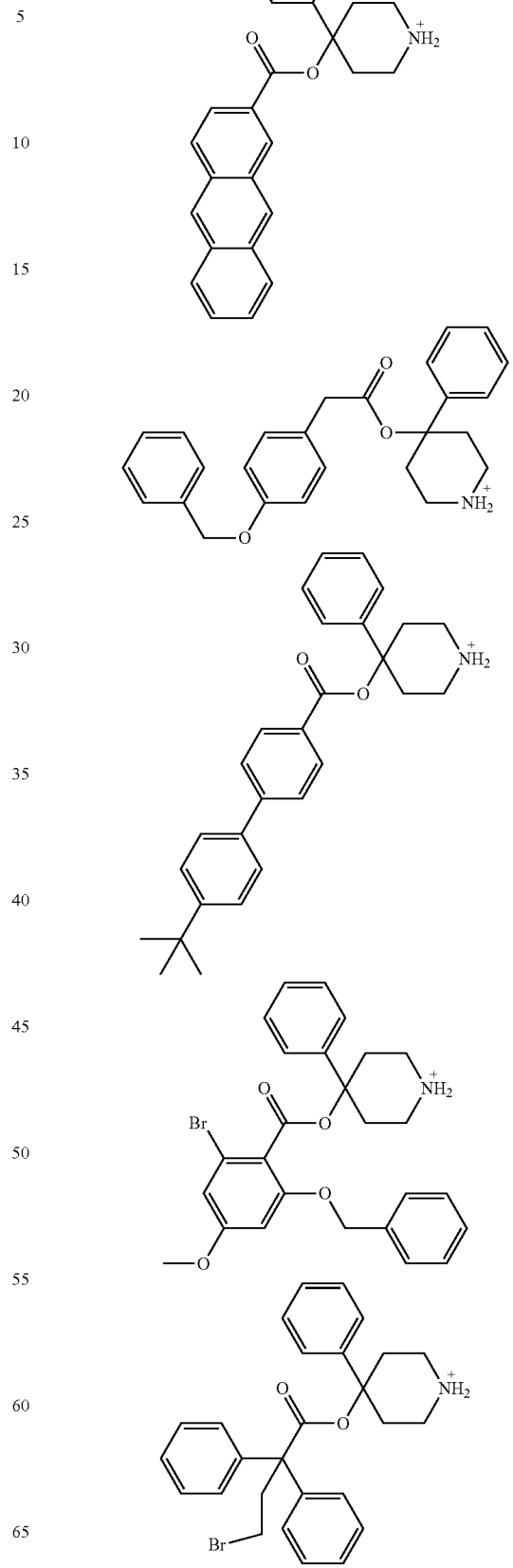

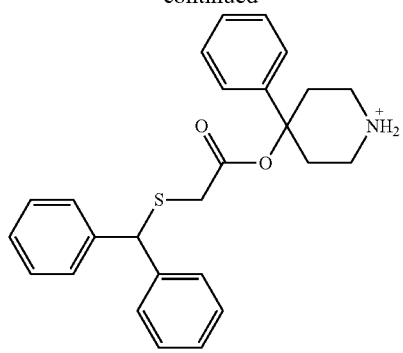
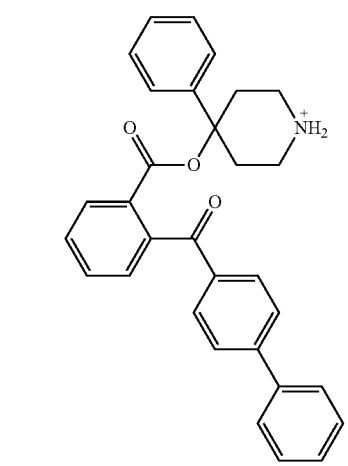
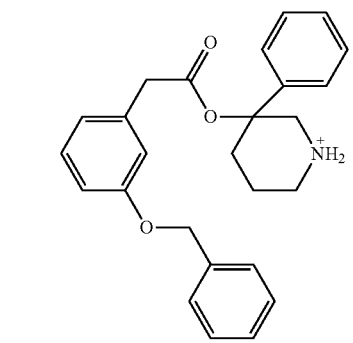
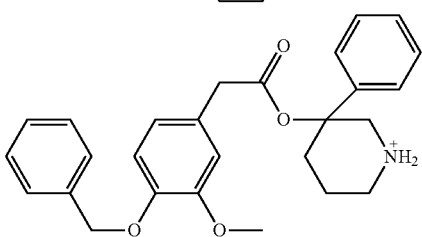
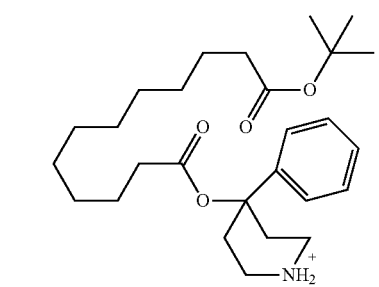
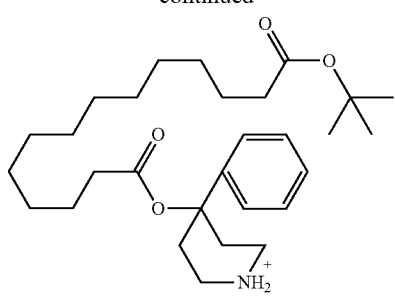
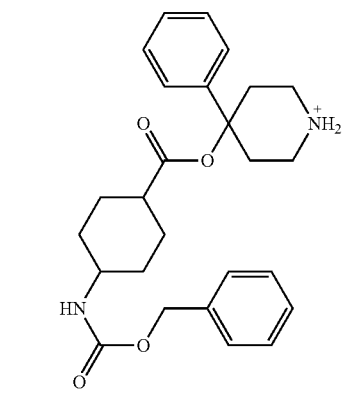
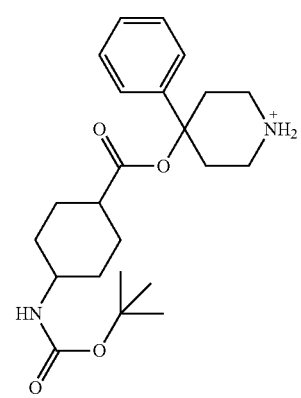
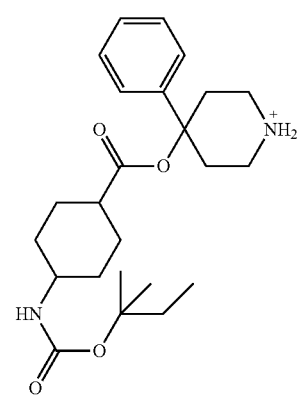

249
-continued
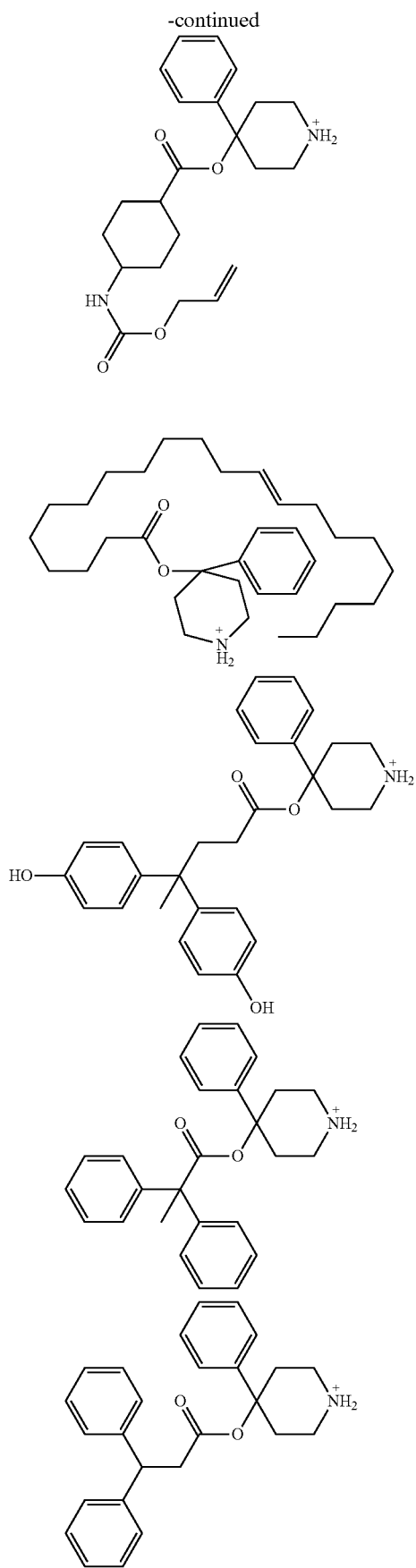
250
-continued
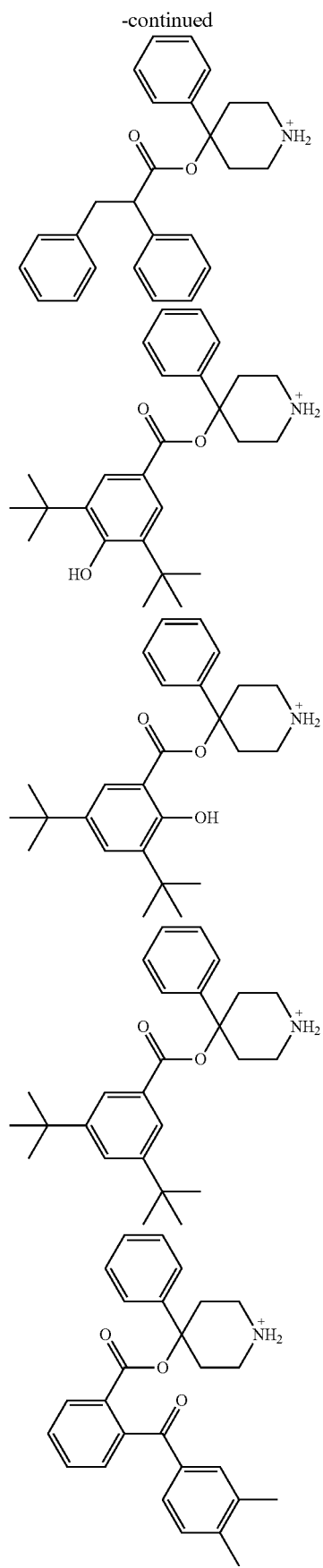

251
-continued
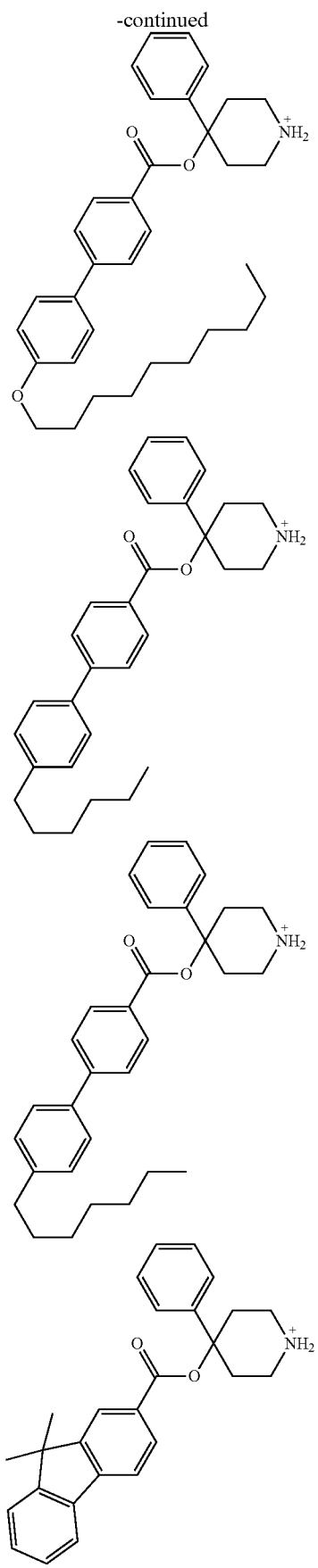
252
-continued
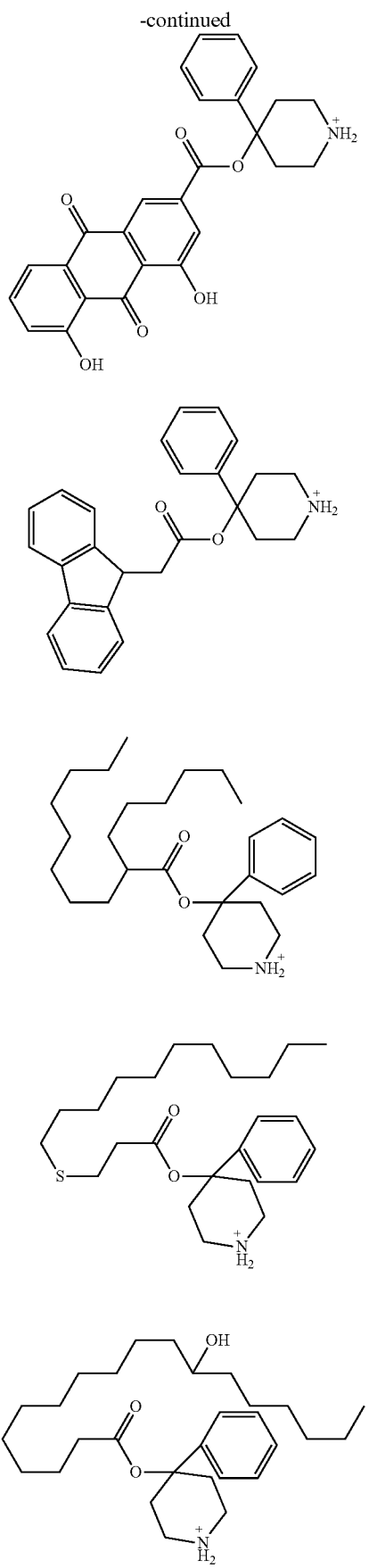

253
-continued
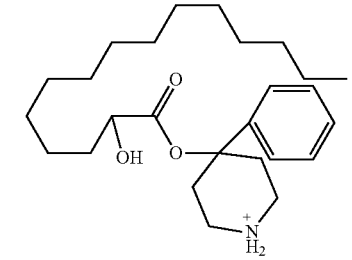
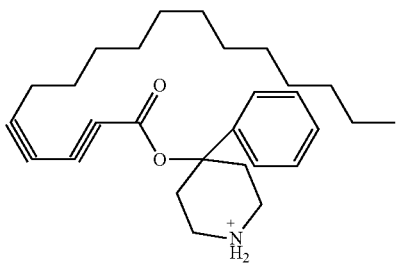
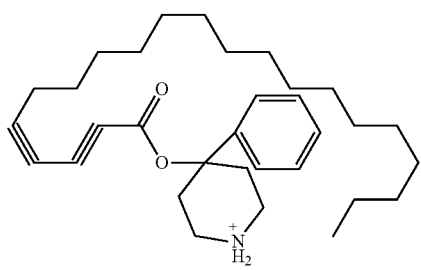
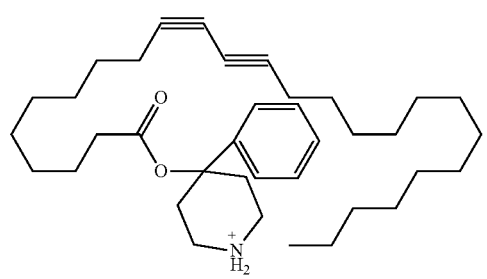
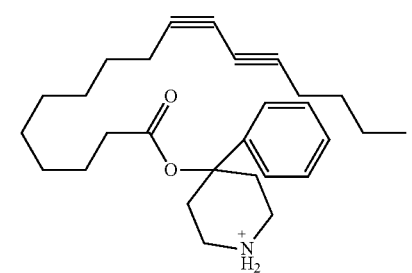
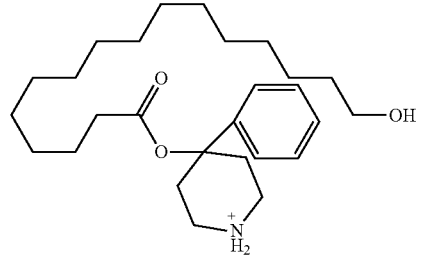
254
-continued
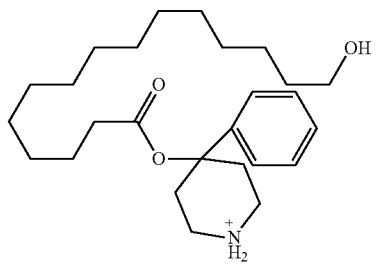
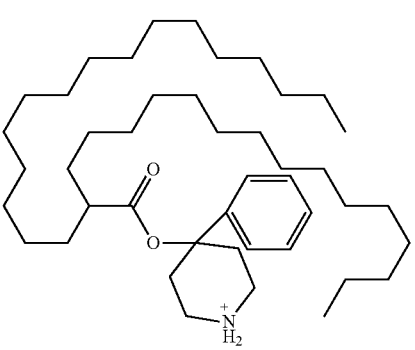
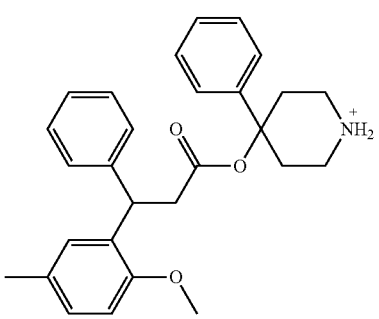
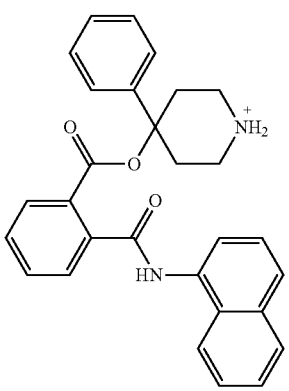
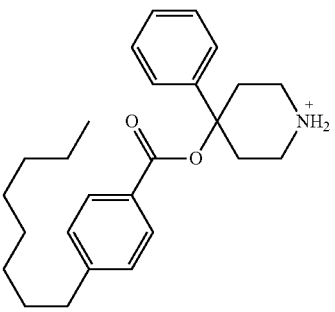

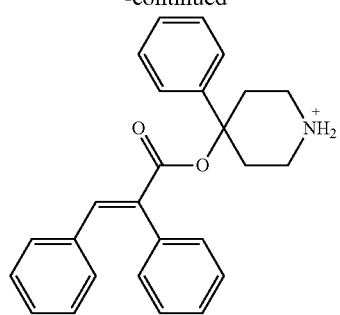
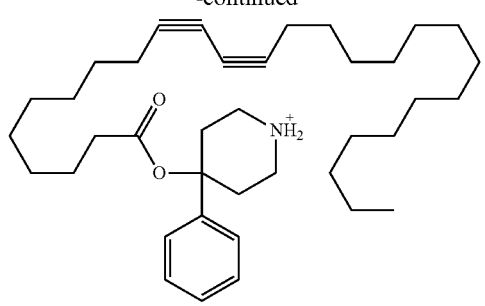
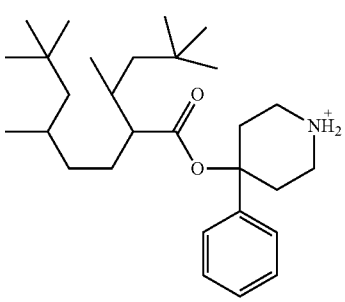
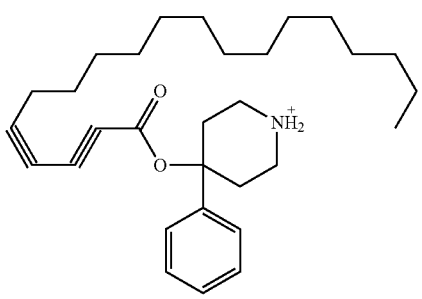
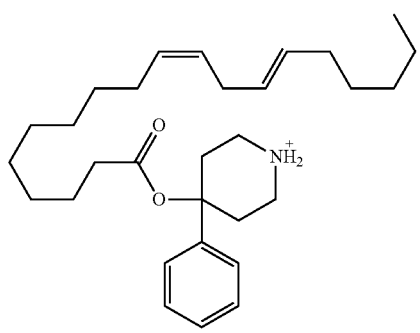
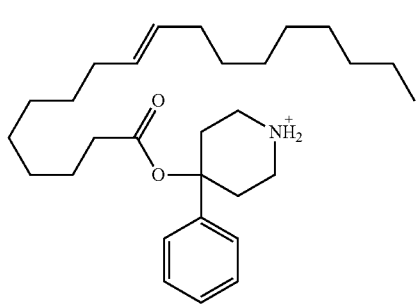
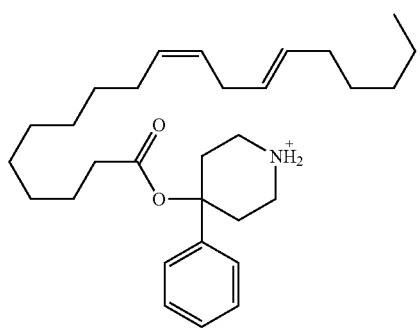
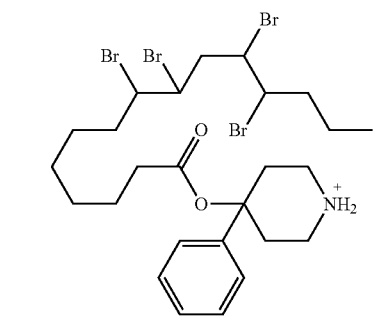
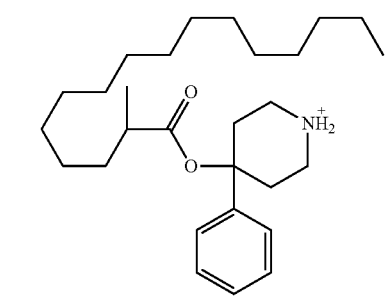
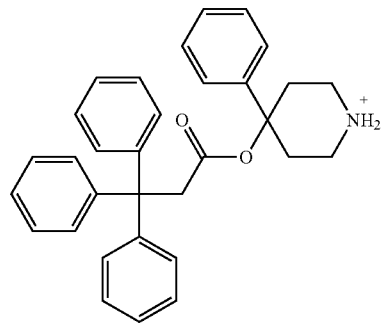

257
-continued
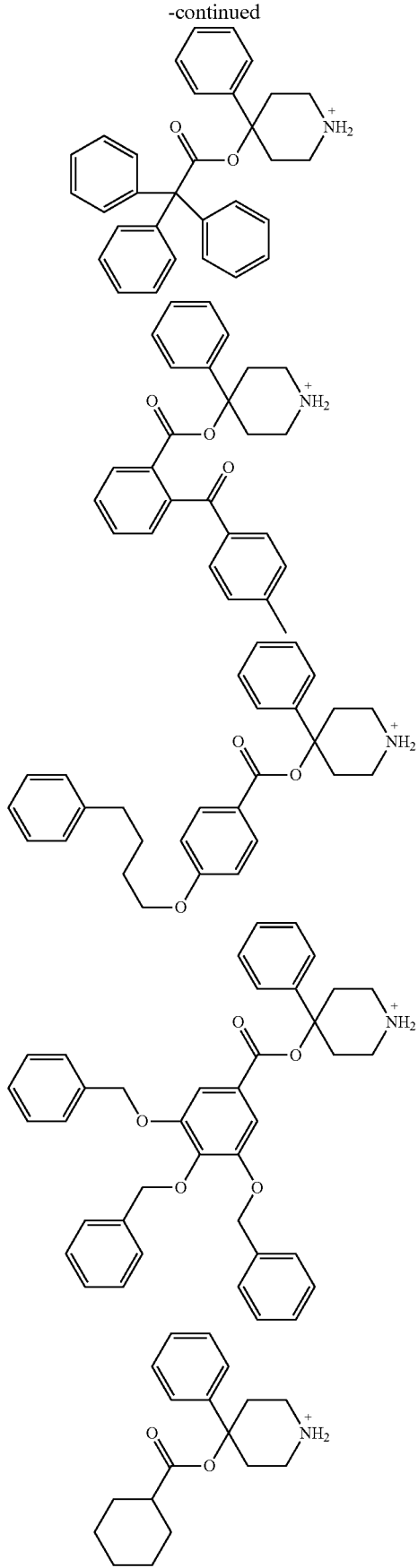
258
-continued
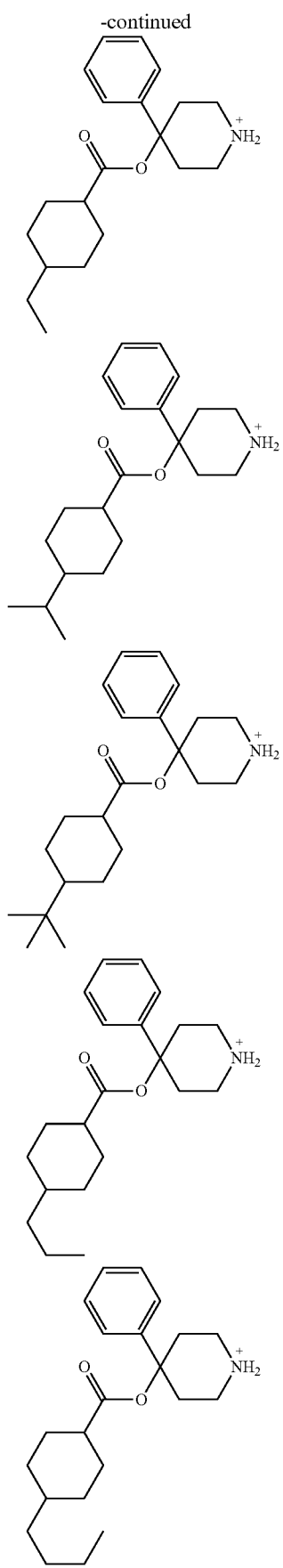

259
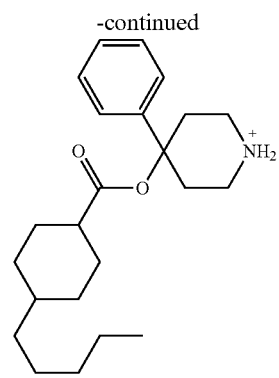
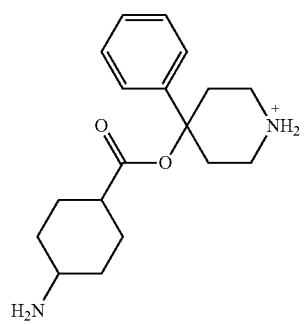
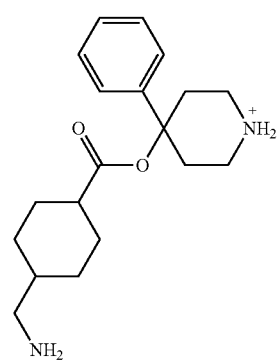
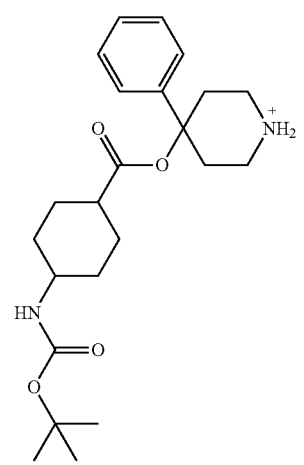
260
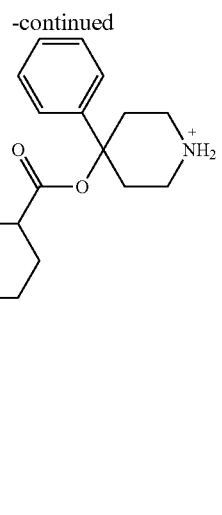
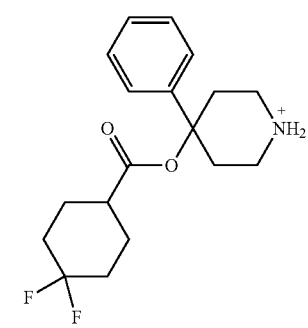
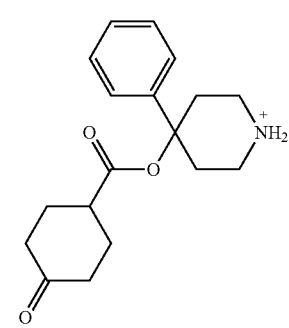
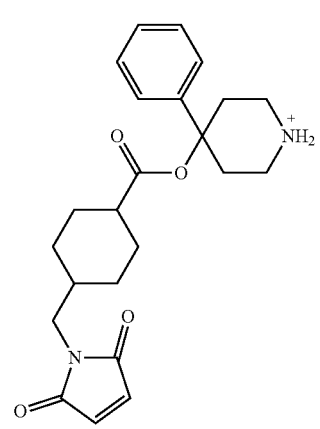

261
-continued
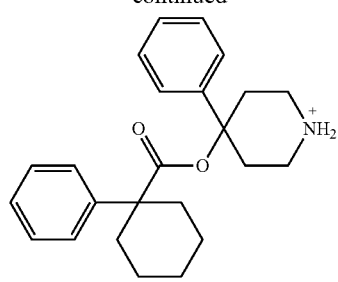
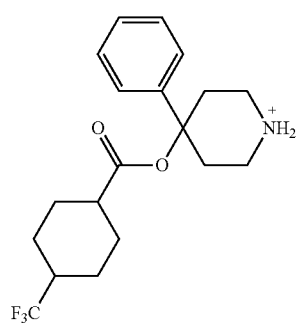
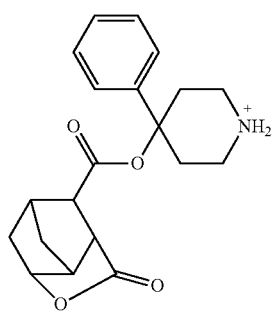
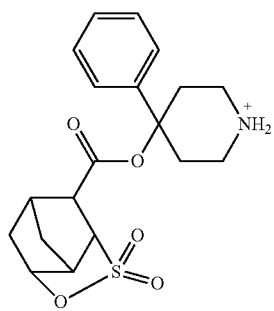
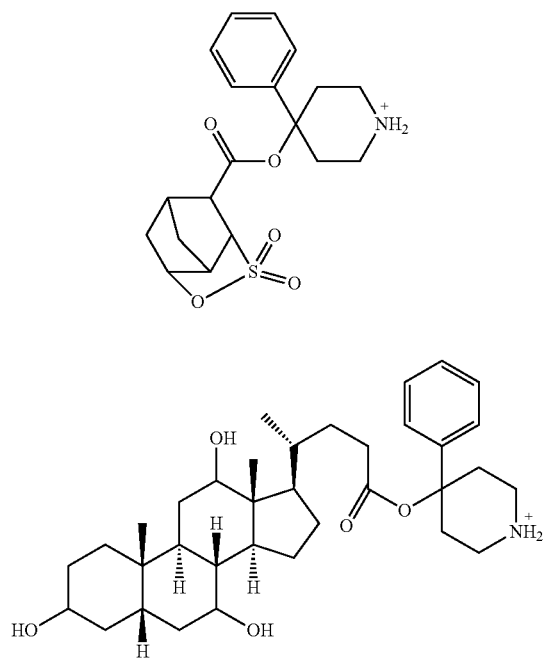
262
-continued
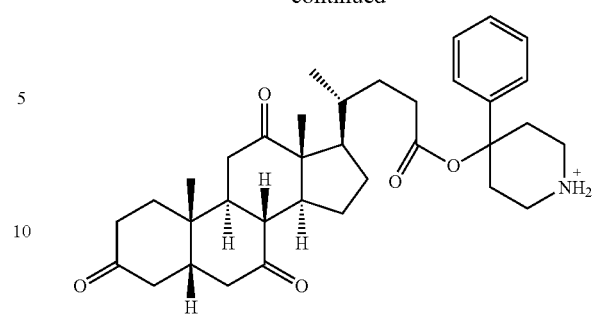
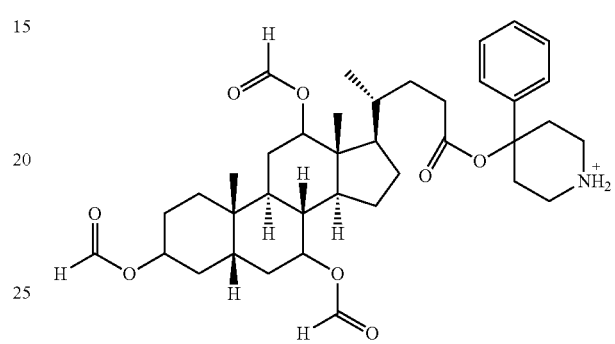
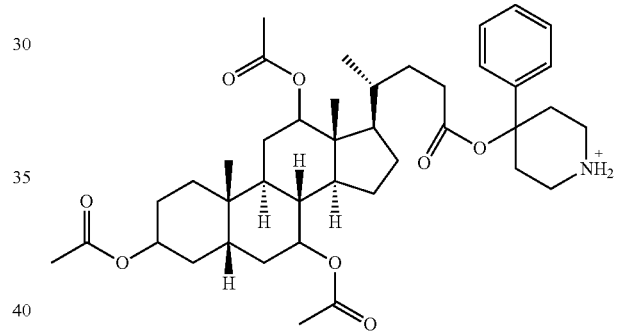
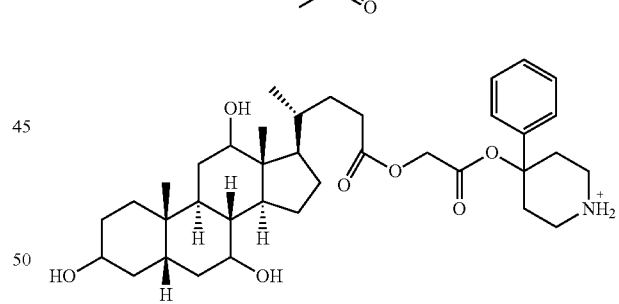
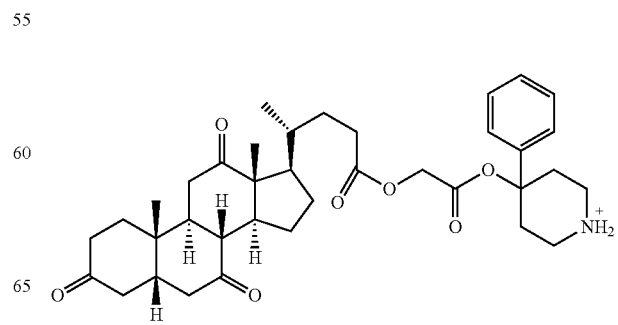

263
-continued
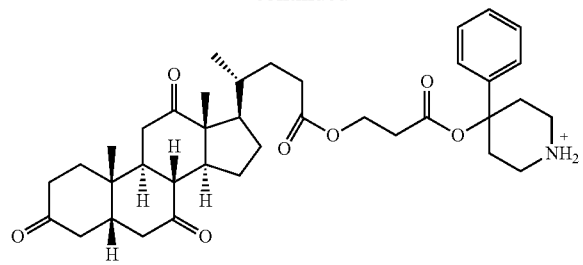
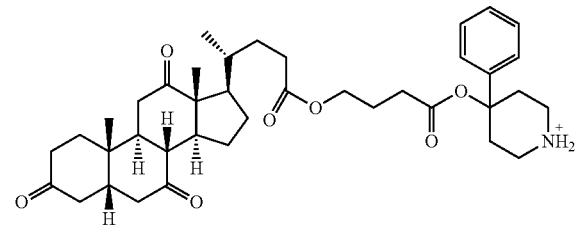
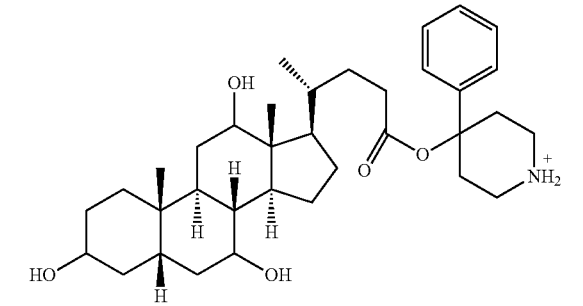
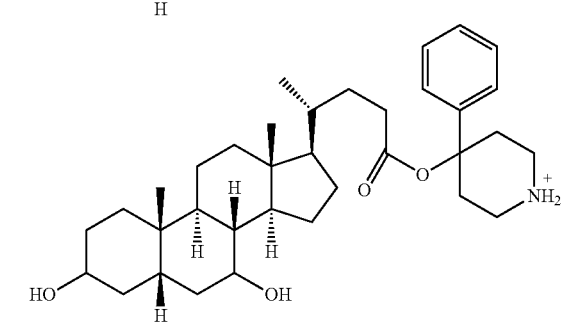
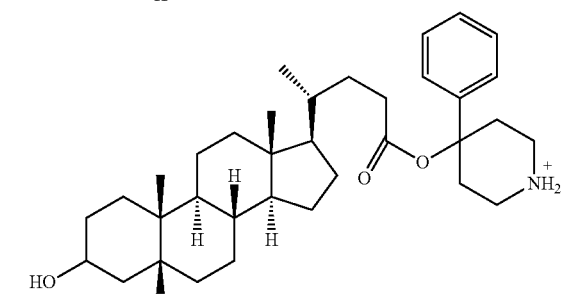
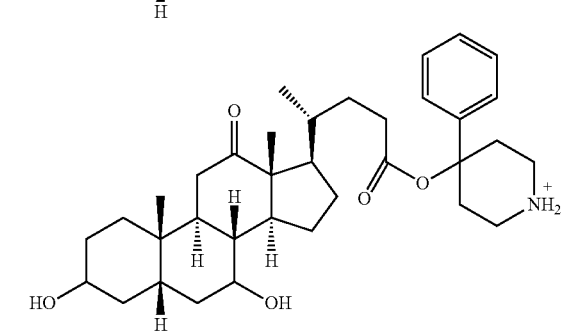
264
-continued
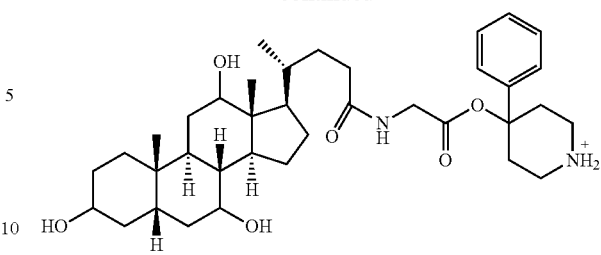
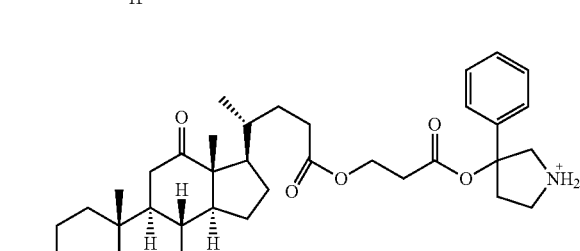
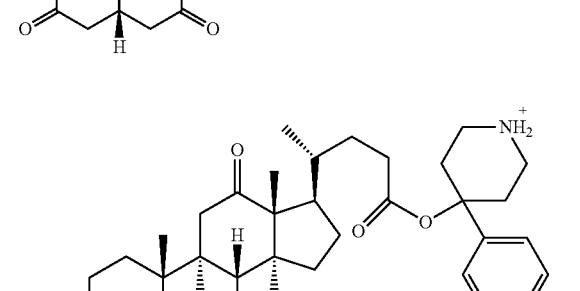
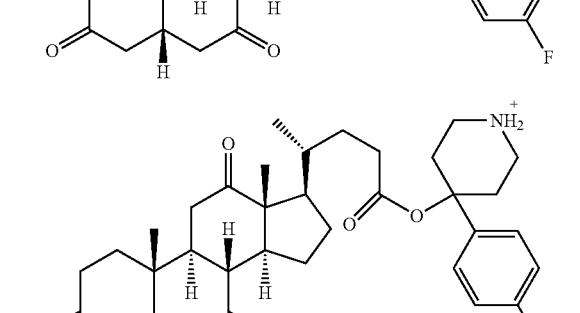
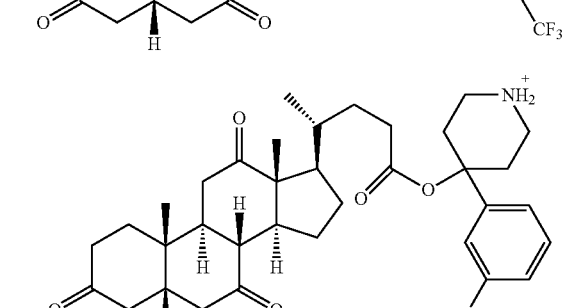
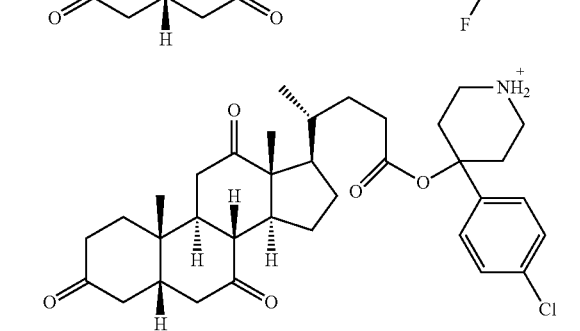

265
-continued
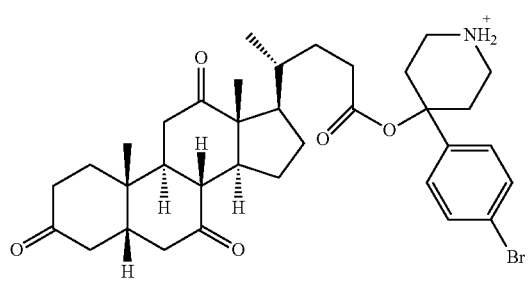
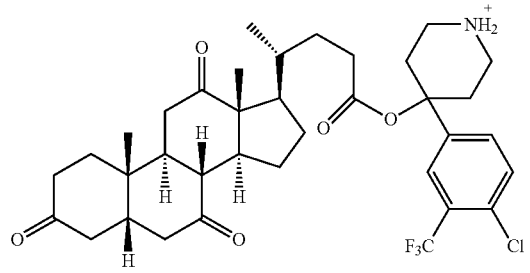
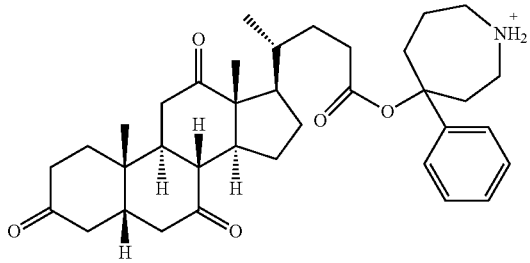
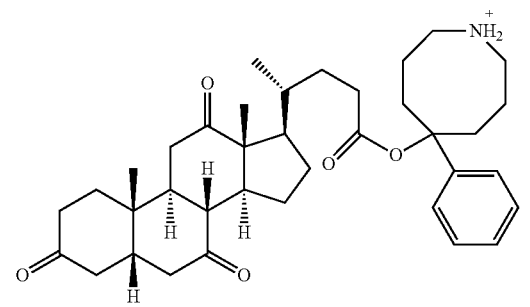
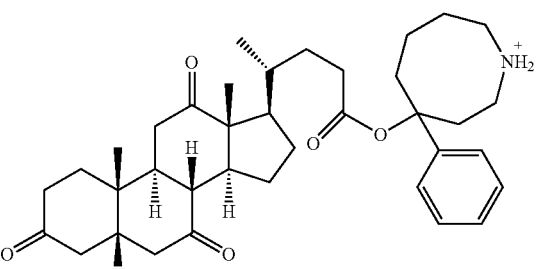
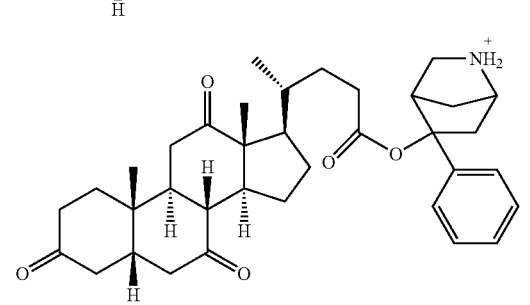
266
-continued
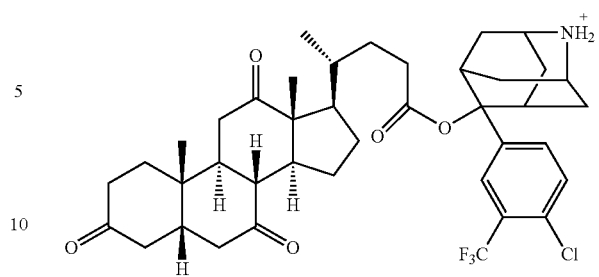
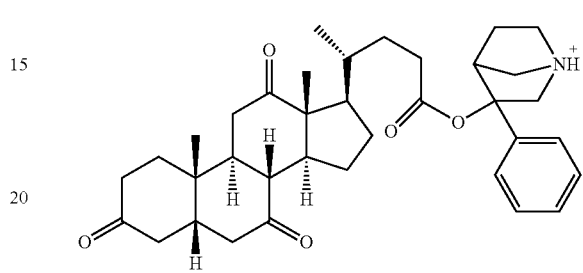
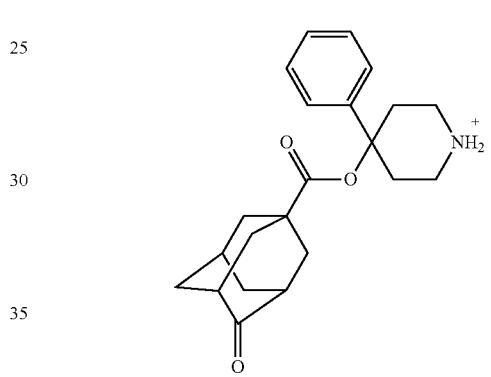
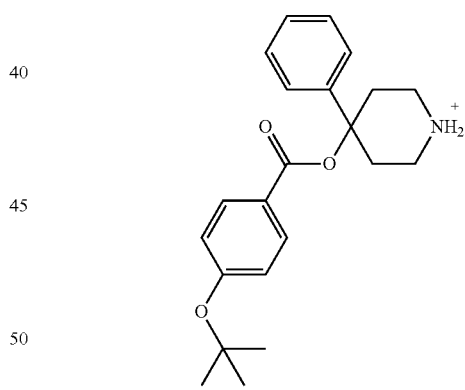
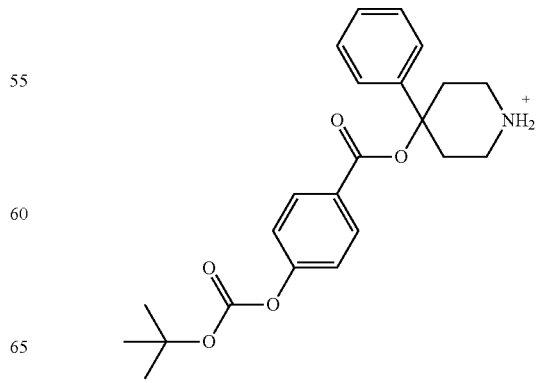

267
-continued
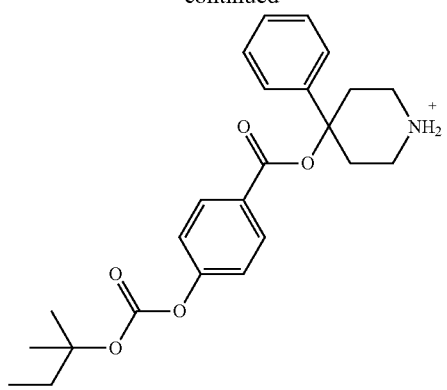
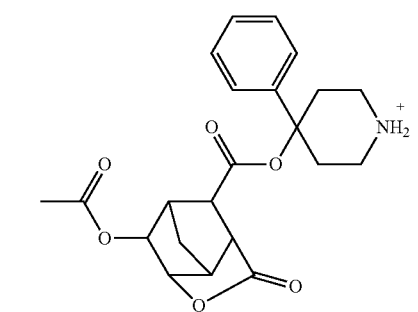
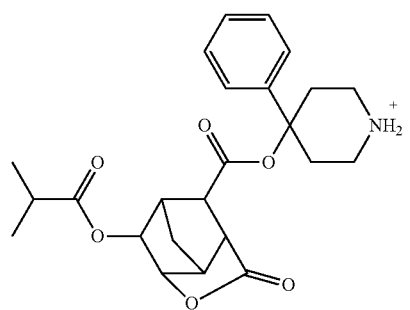
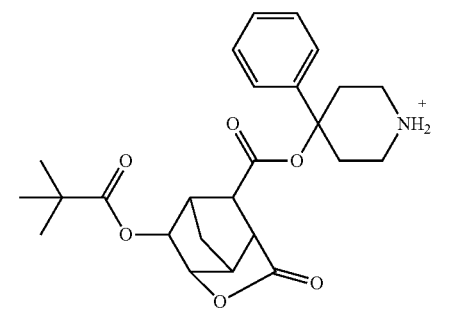
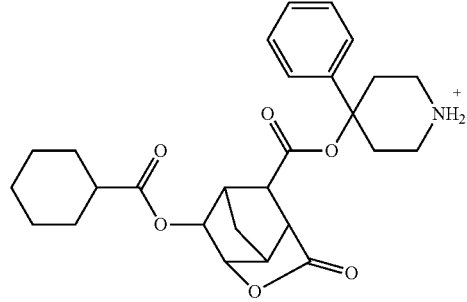
268
-continued
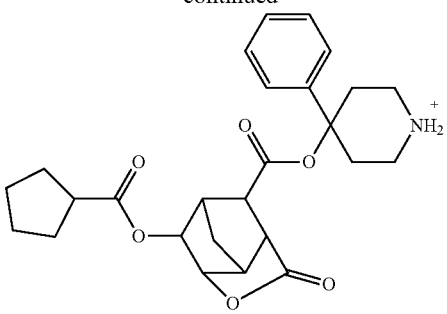
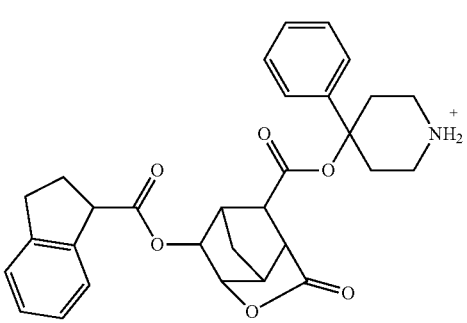
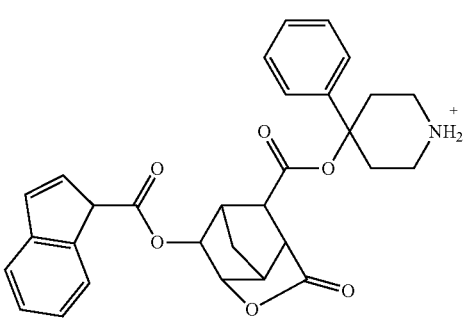
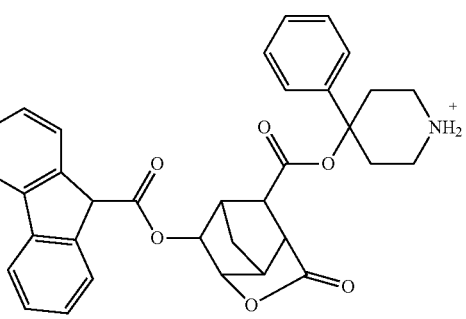
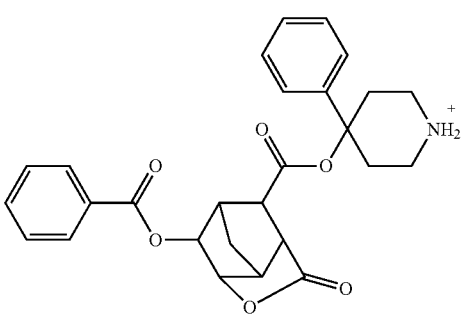

269
-continued
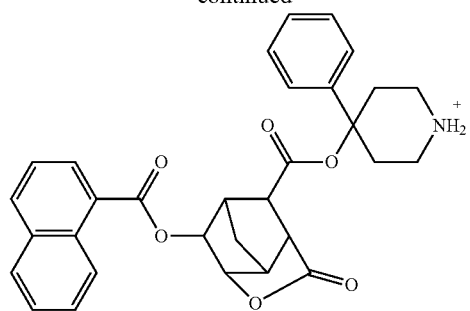
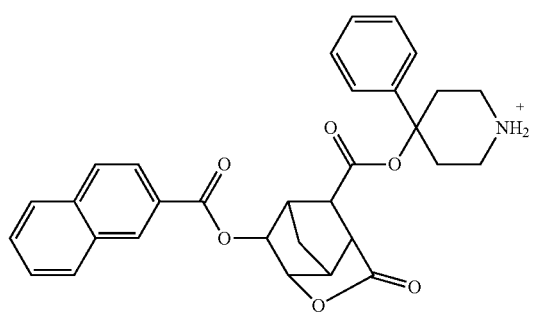
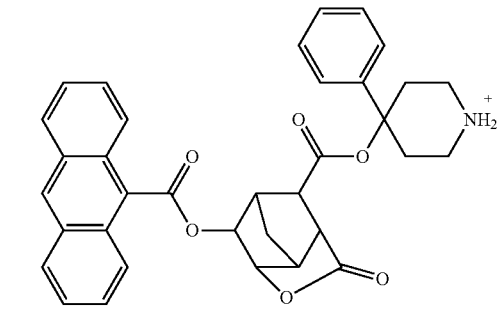
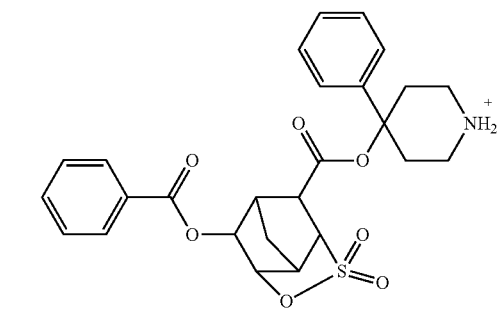
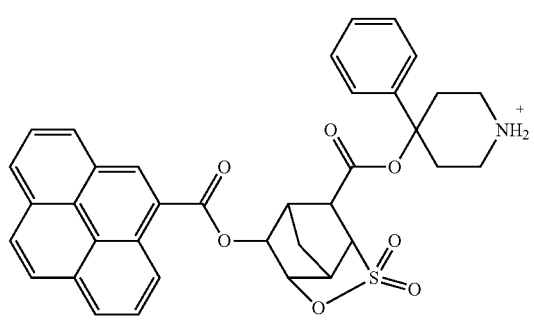
270
-continued
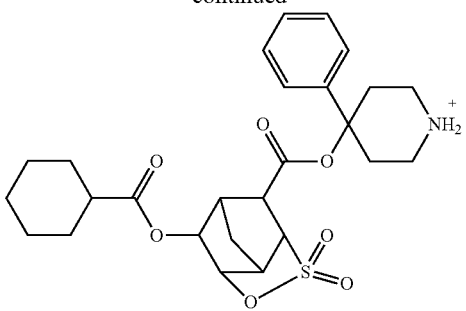
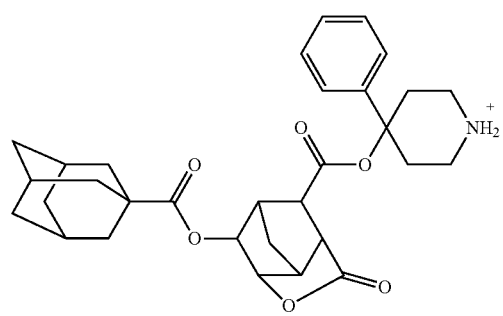
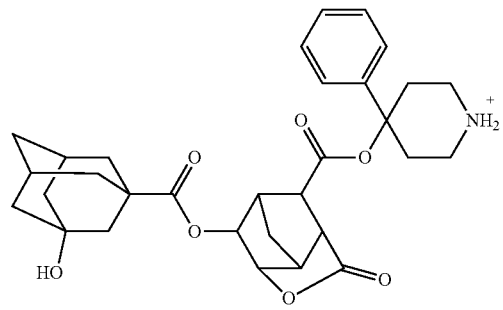
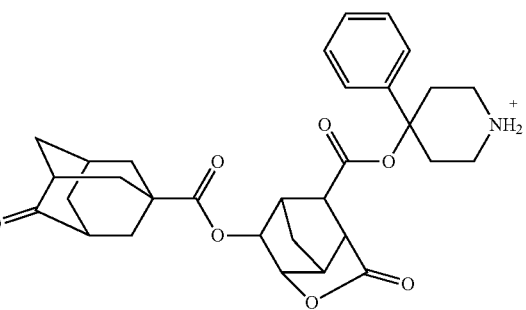
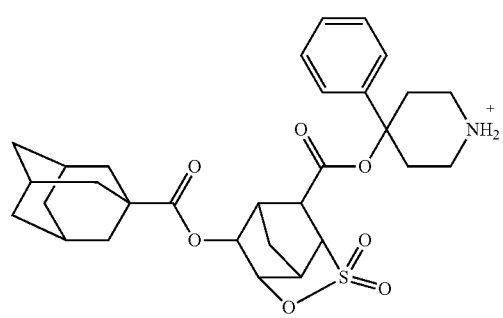

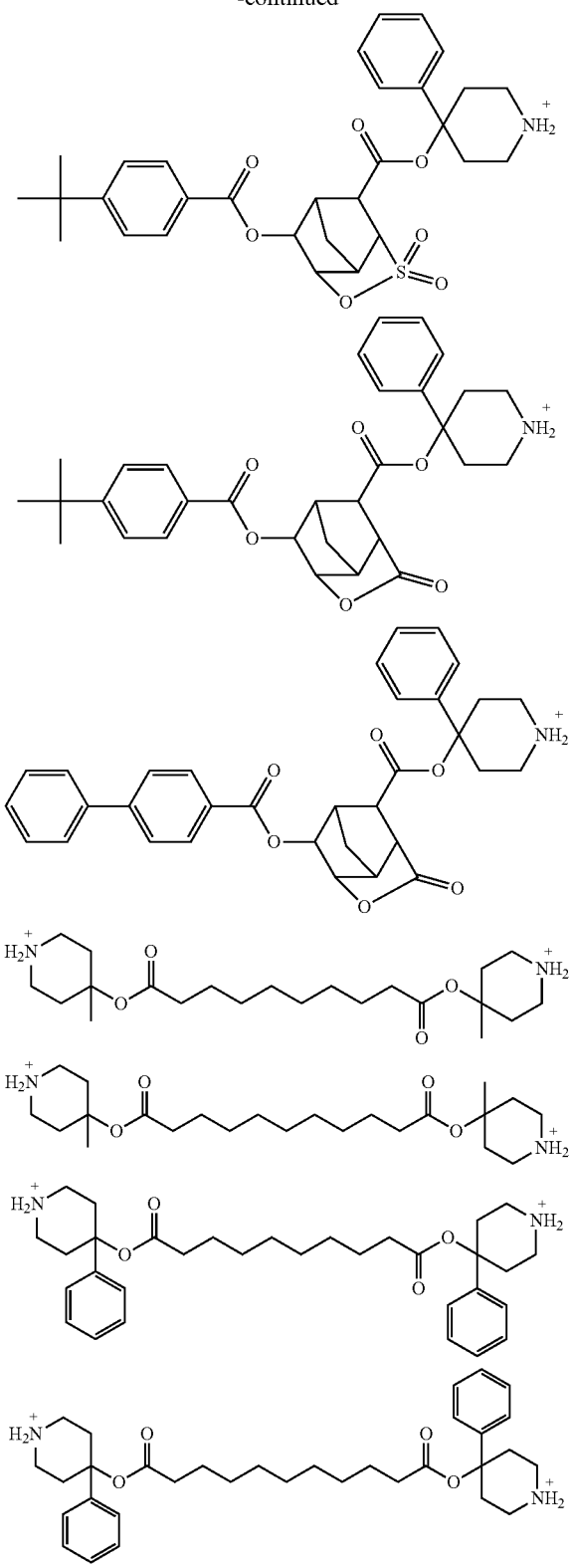

The cyclic ammonium salt compound contains a 1,1,1,3,3,3-hexafluoro-2-propoxide anion having bonded thereto a group selected from trifluoromethyl, hydrocarbylcarbonyl and hydrocarbyloxycarbonyl. Preferably the anion has the formula (B).

$$R^7 \!-\! \underset{CF_3}{\overset{CF_3}{\underset{|}{\overset{|}{C}}}} \!-\! O^-  \quad (B)$$

In formula (B), $R^7$ is a trifluoromethyl group, $C_1$-$C_{20}$ hydrocarbyloxy group or $C_2$-$C_{21}$ hydrocarbyloxycarbonyl group. The hydrocarbyl moiety in the hydrocarbyloxy group or hydrocarbyloxycarbonyl group may contain at least one moiety selected from ether bond, ester bond, thiol, cyano, nitro, hydroxyl, sultone, sulfonate bond, amide bond, and halogen.

The hydrocarbyl moiety in the hydrocarbyloxy group or hydrocarbyloxycarbonyl group represented by $R^7$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, isopentyl, sec-pentyl, 3-pentyl, tert-pentyl, neopentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclobutyl, cyclopentyl, cyclohexyl, adamantyl, norbornyl, cyclpropylmethyl, cyclopropylethyl, cyclobutylmethyl, cyclobutylethyl, cyclopentylmethyl, cyclopentylethyl, cyclohexylmethyl, cyclohexylethyl, methylcyclopropyl, methylcyclobutyl, methylcyclopentyl, methylcyclohexyl, ethylcyclopropyl, ethylcyclobutyl, ethylcyclopentyl and ethylcyclohexyl; $C_2$-$C_{20}$ alkenyl groups such as vinyl, 1-propenyl, 2-propenyl, butenyl, pentenyl, hexenyl, heptenyl, nonenyl, decenyl, undecenyl, dodecenyl, tridecenyl, tetradecenyl pentadecenyl, hexadecenyl, heptadecenyl, octadecenyl, nonadecenyl and icosenyl; $C_2$-$C_{20}$ alkynyl groups such as ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl and icosynyl; $C_3$-$C_{20}$ cyclic unsaturated aliphatic hydrocarbyl groups such as cyclopentenyl, cyclohexenyl, methylcyclopentenyl, methylcyclohexenyl, ethylcyclopentenyl, ethylcyclohexenyl and norbomenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutyhnaphthyl, sec-butylnaphthyl and tert-butylnaphthyl; $C_7$-$C_{20}$ aralkyl groups such as benzyl, phenethyl, phenylpropyl, phenylbutyl, 1-naphthylmethyl, 2-naphthylmethyl, 9-fluorenylmethyl, I-naphthylethyl, 2-naphthylethyl and 9-fluorenylethyl; and combinations thereof.

Examples of the anion are shown below, but not limited thereto.

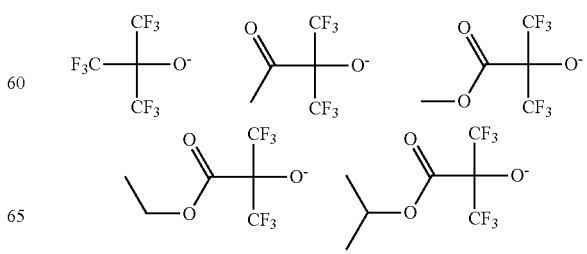

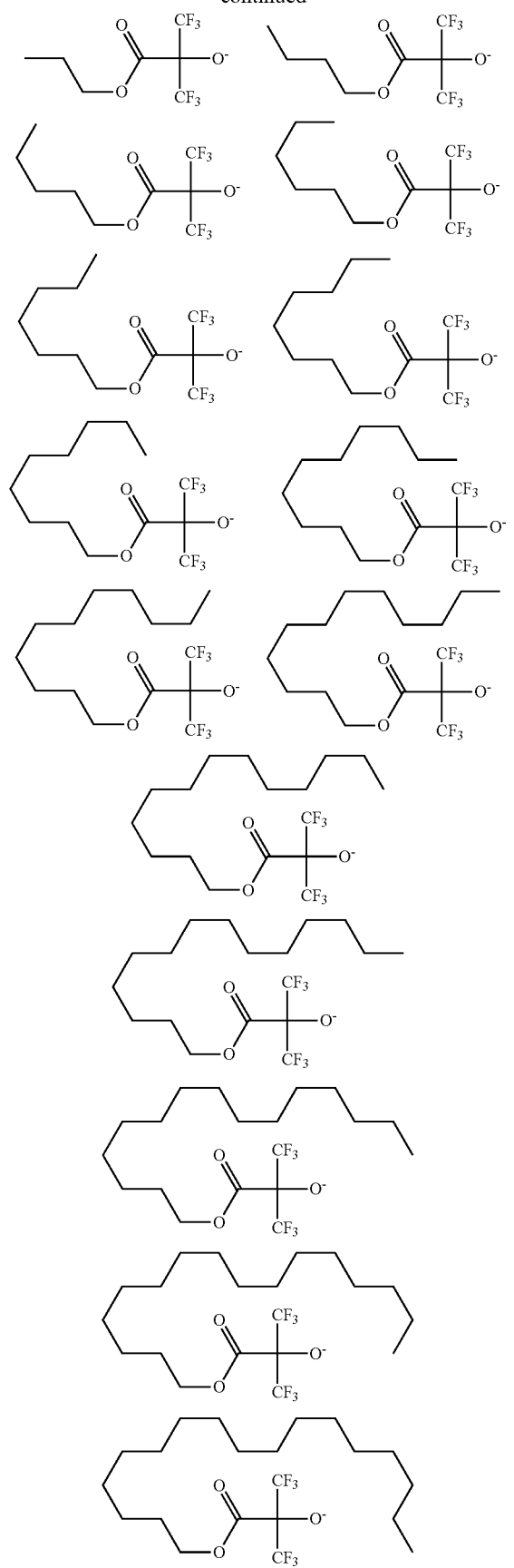
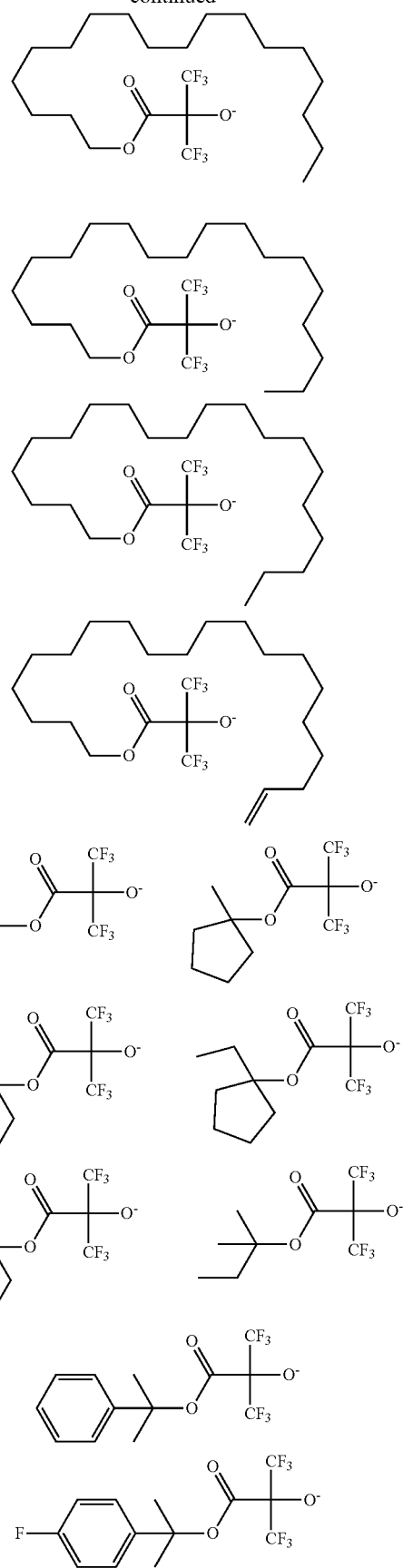

275
-continued
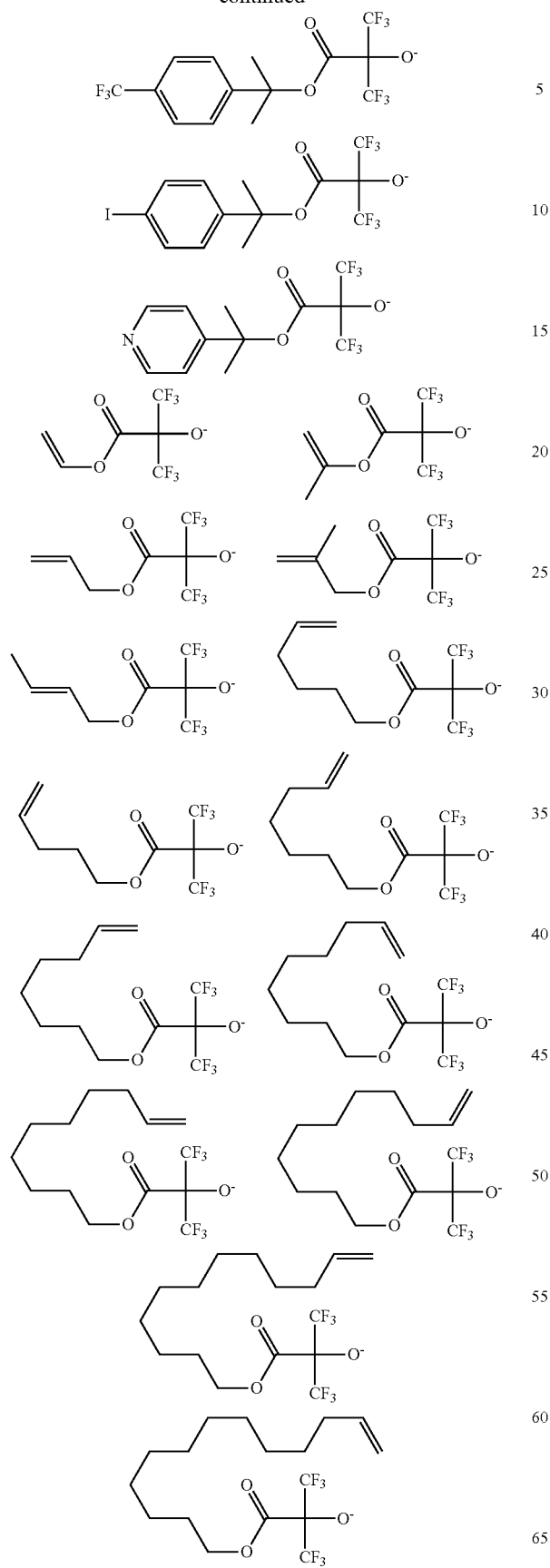
276
-continued
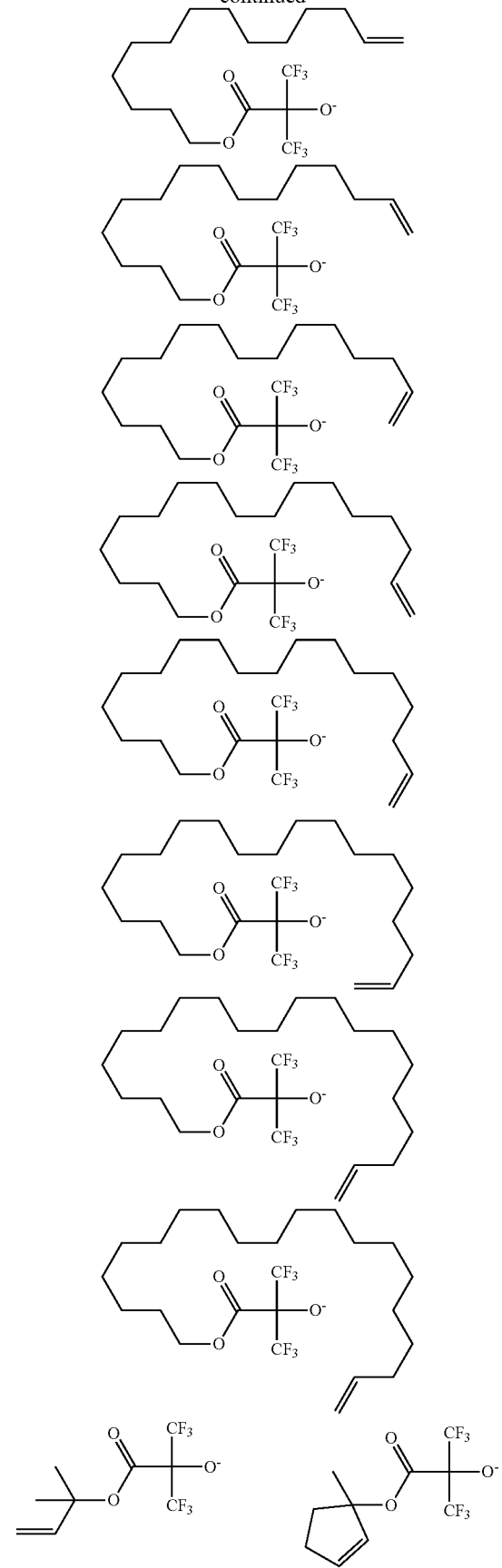

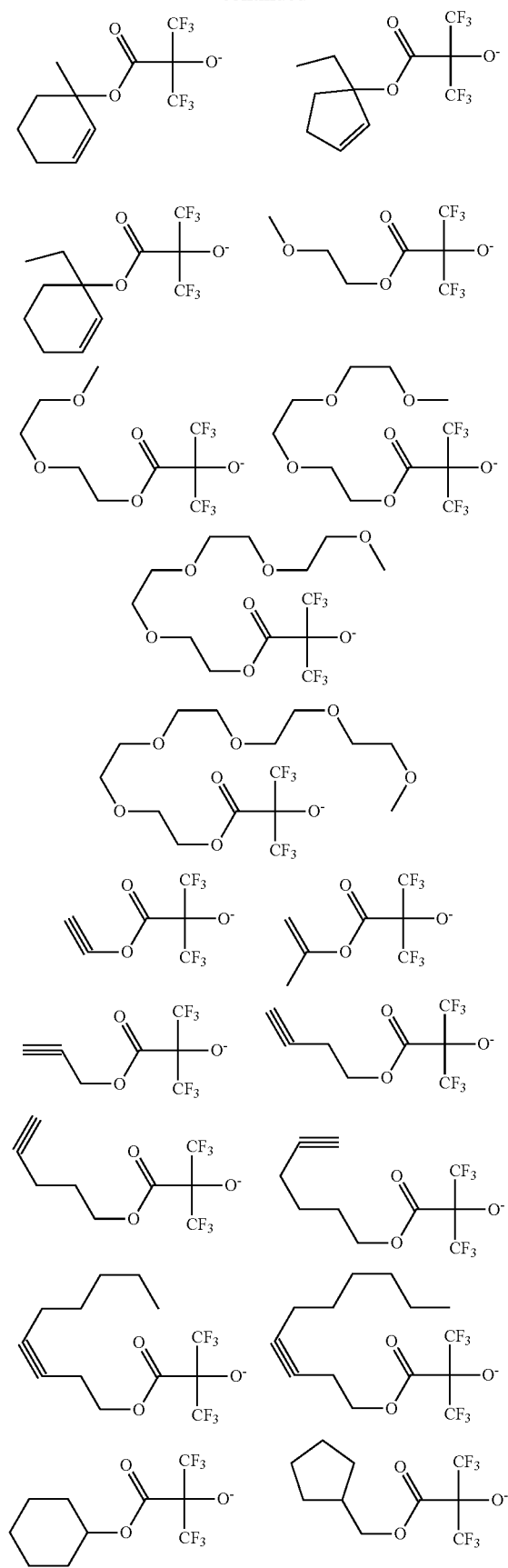
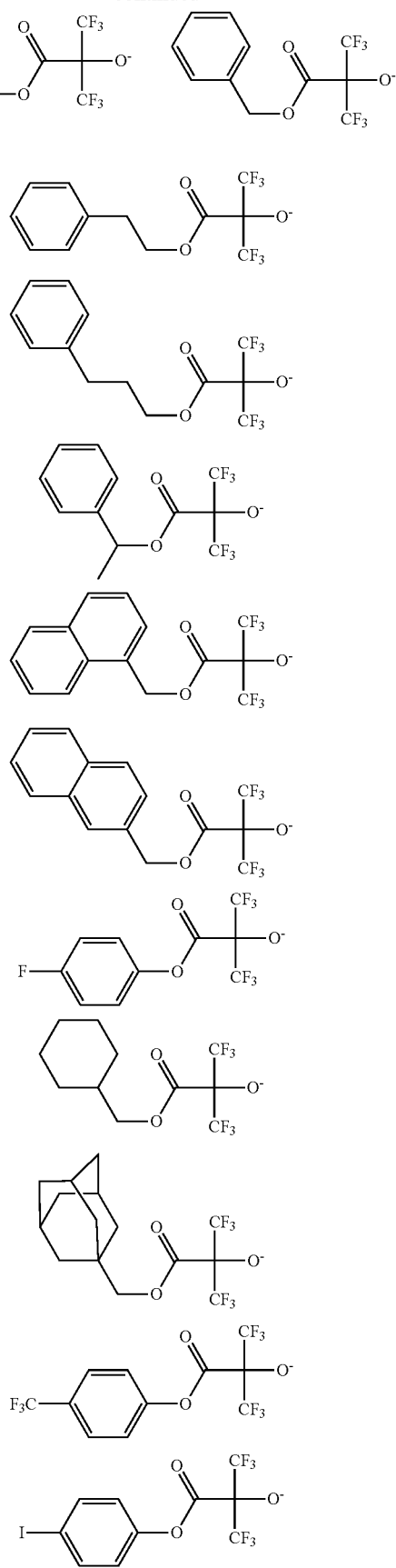

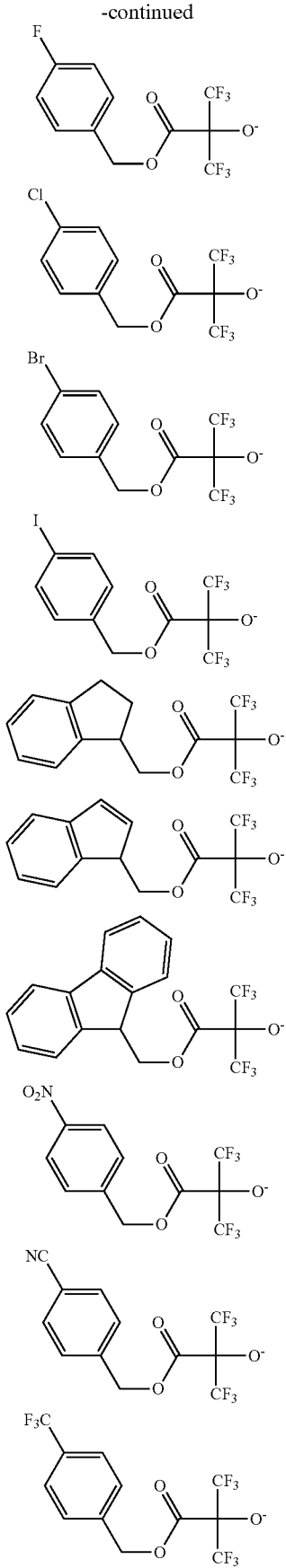
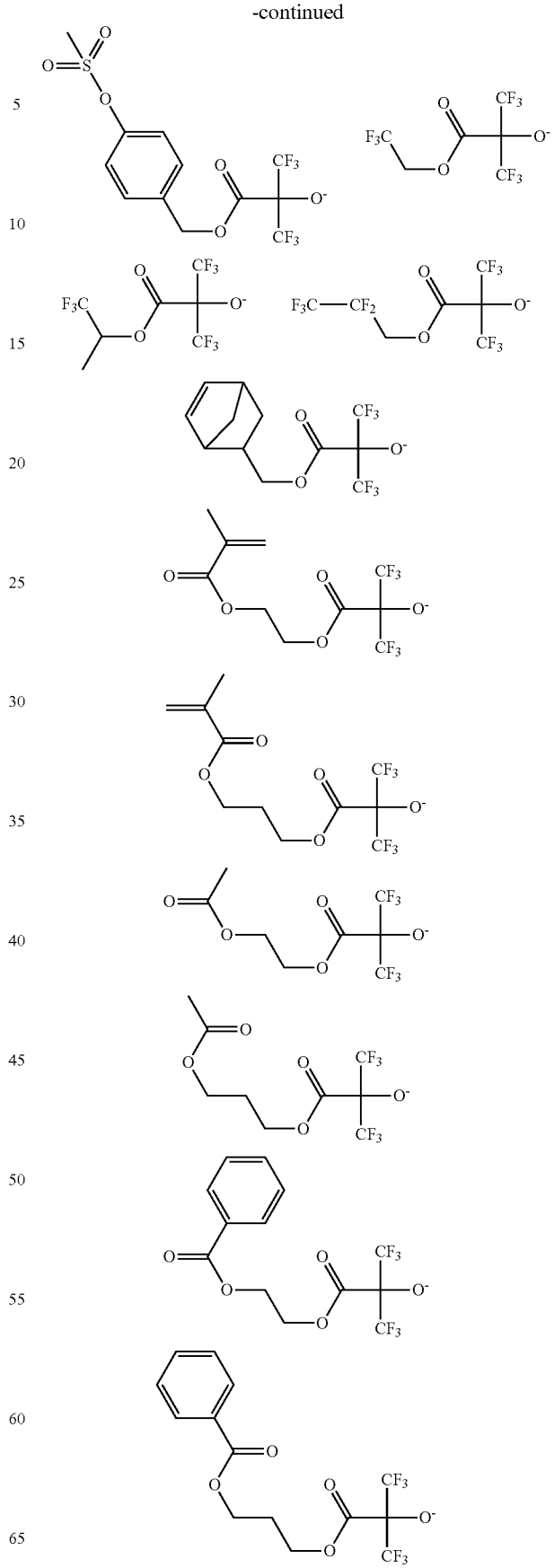

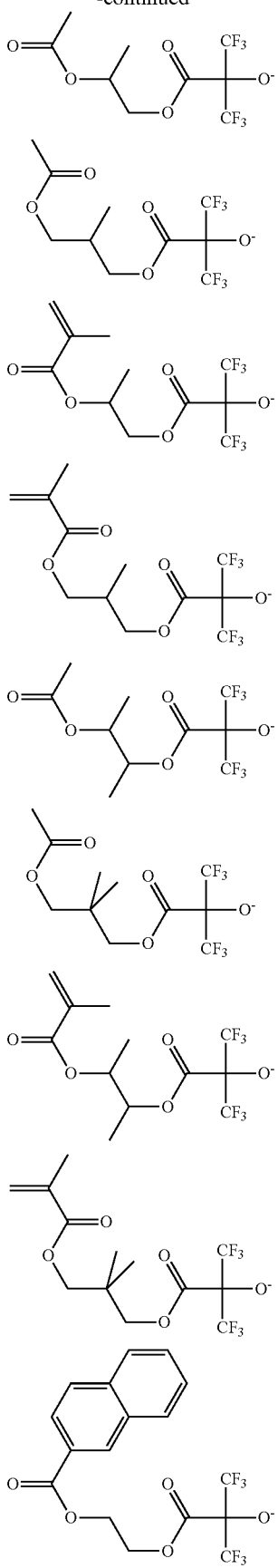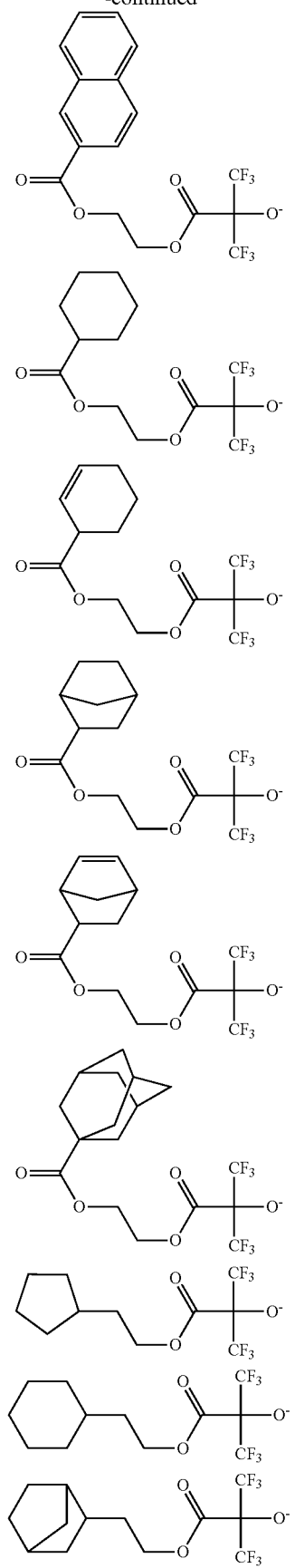

283
-continued
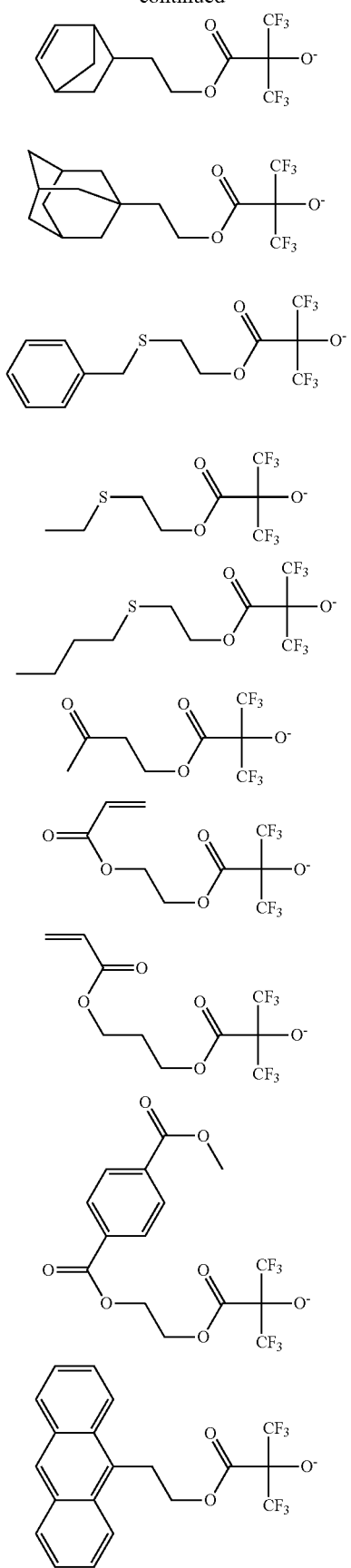
284
-continued
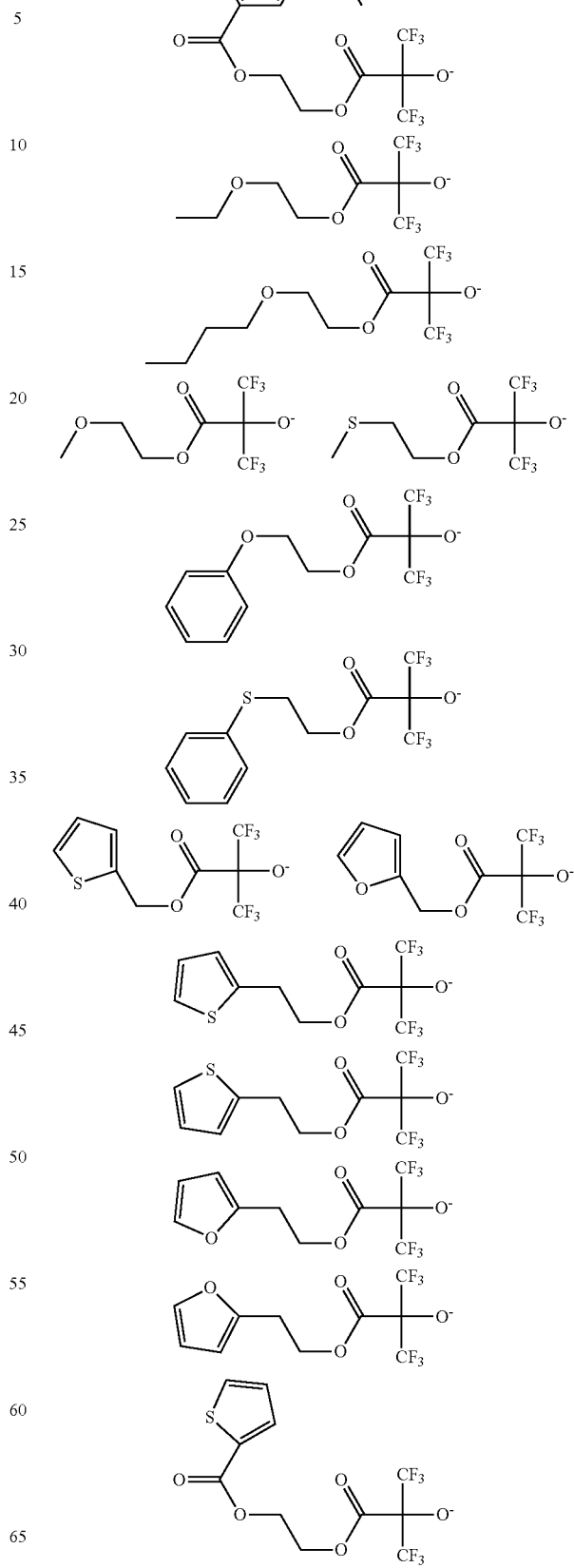

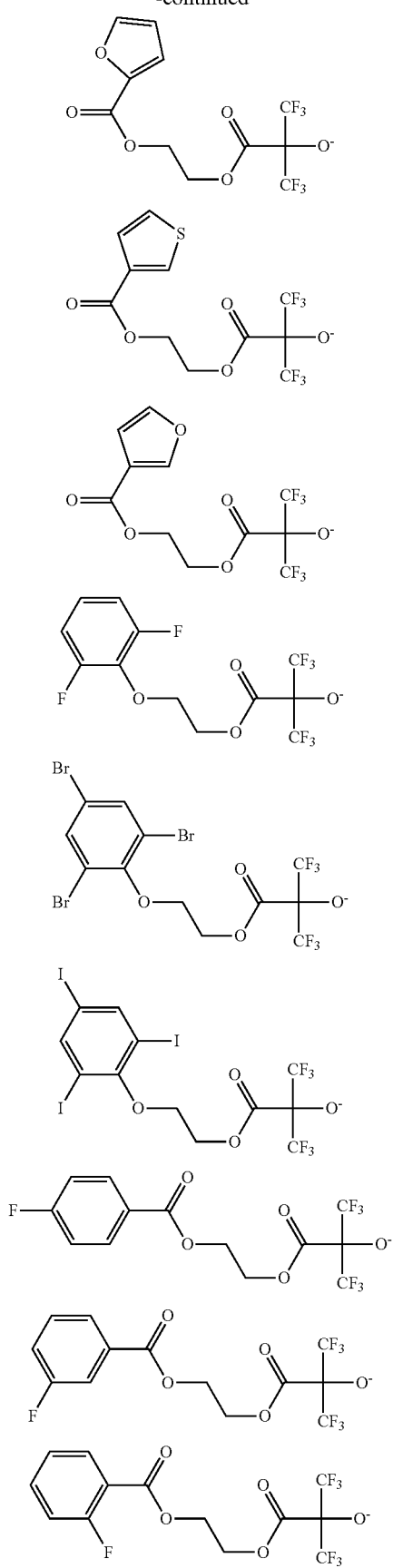
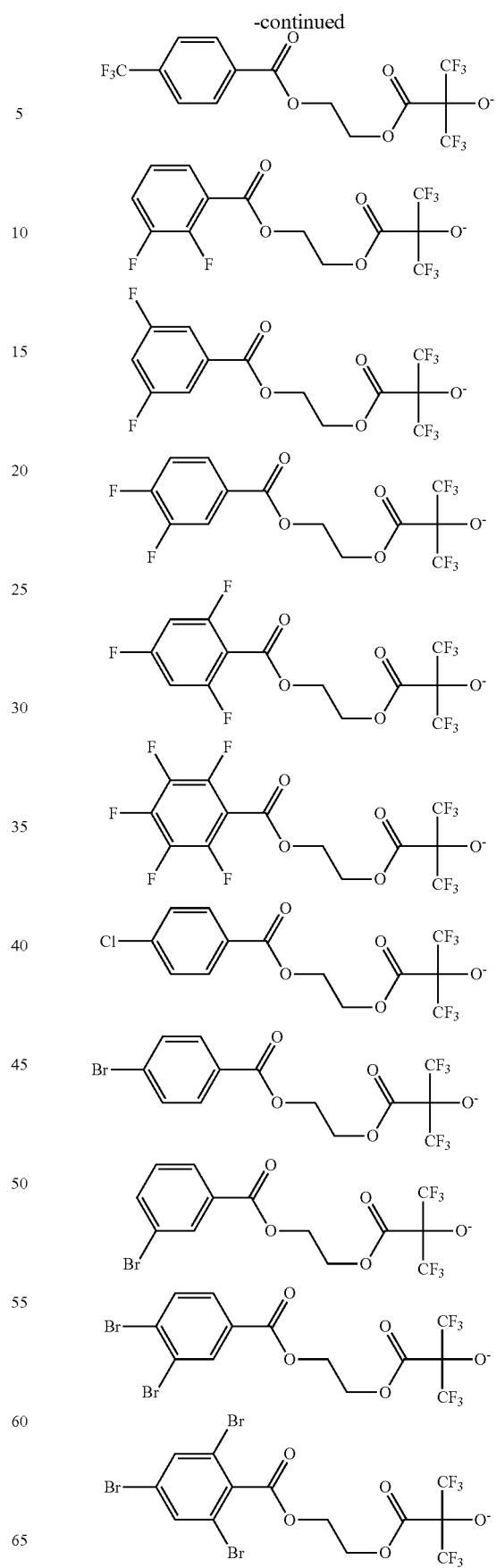

287
-continued
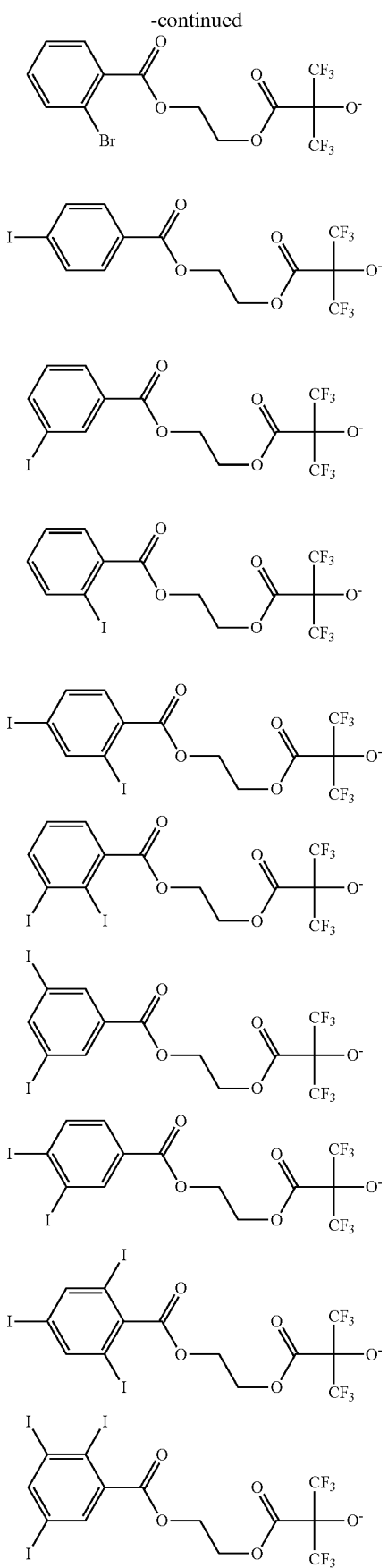
288
-continued
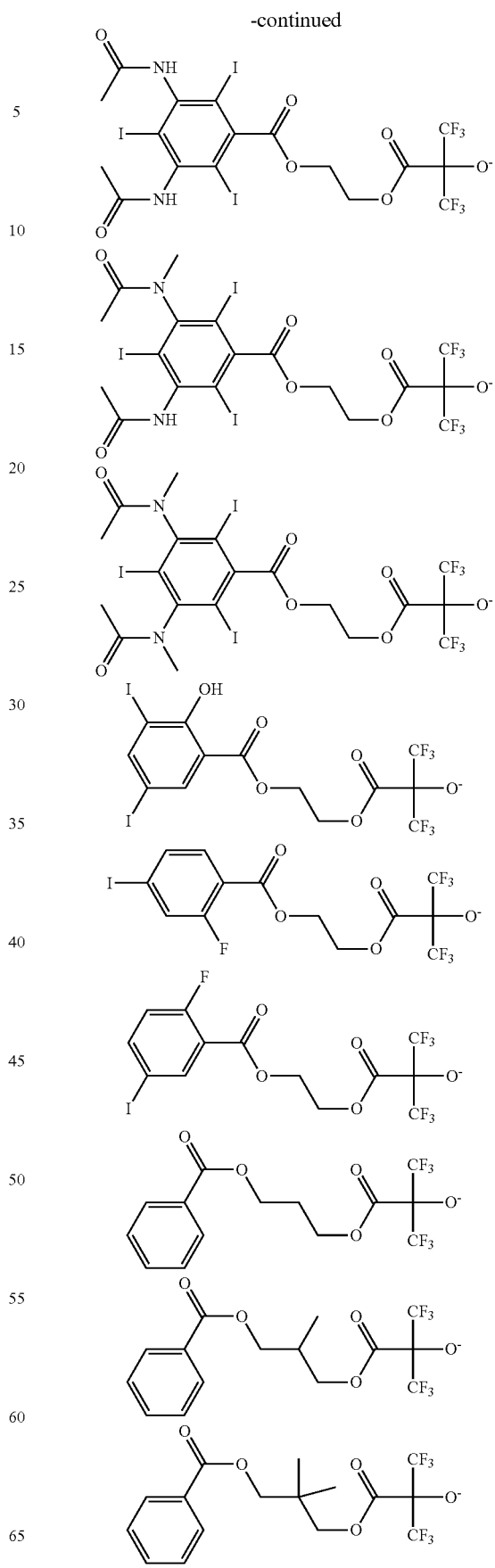

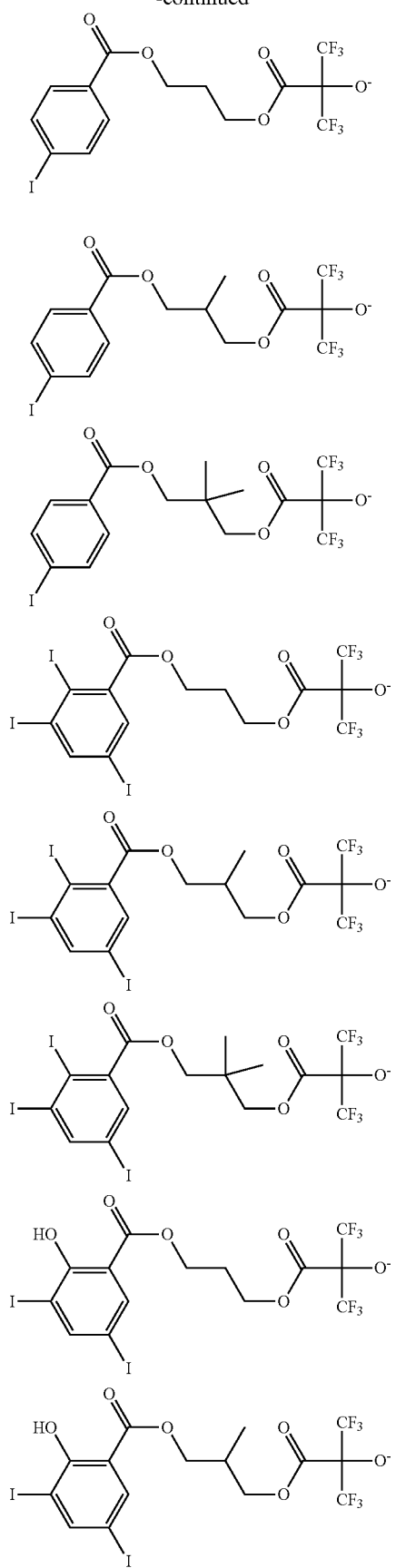
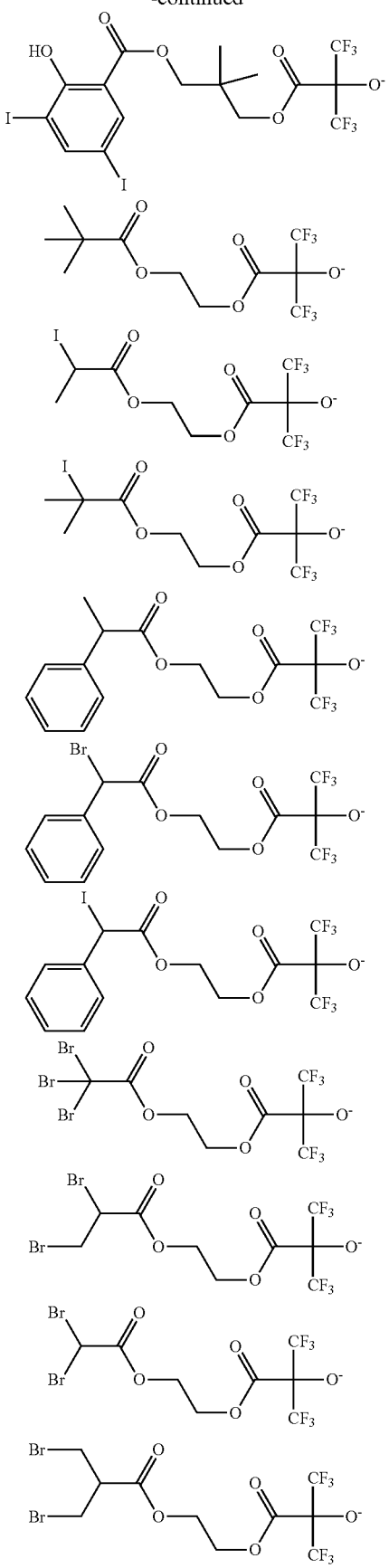

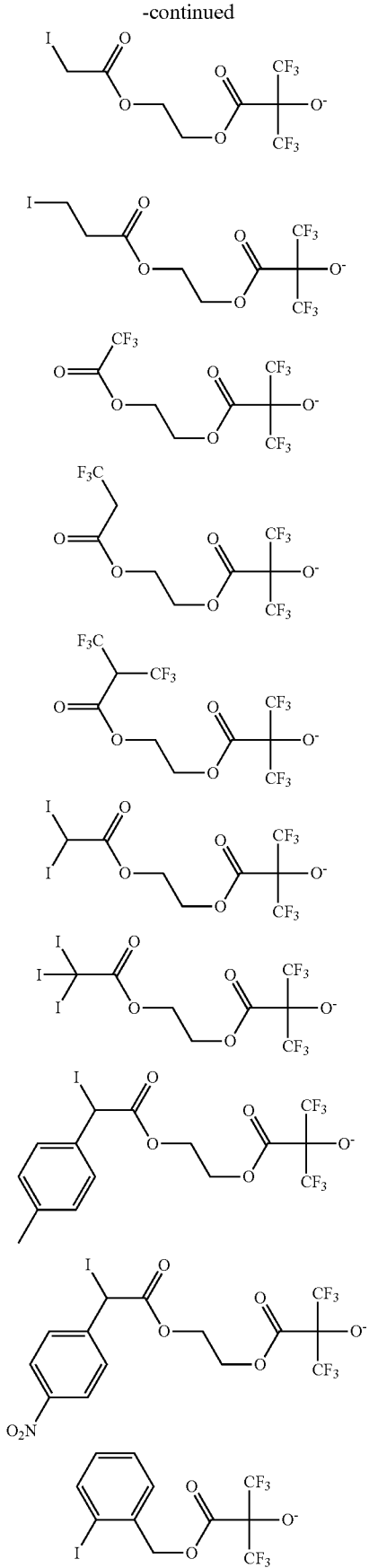
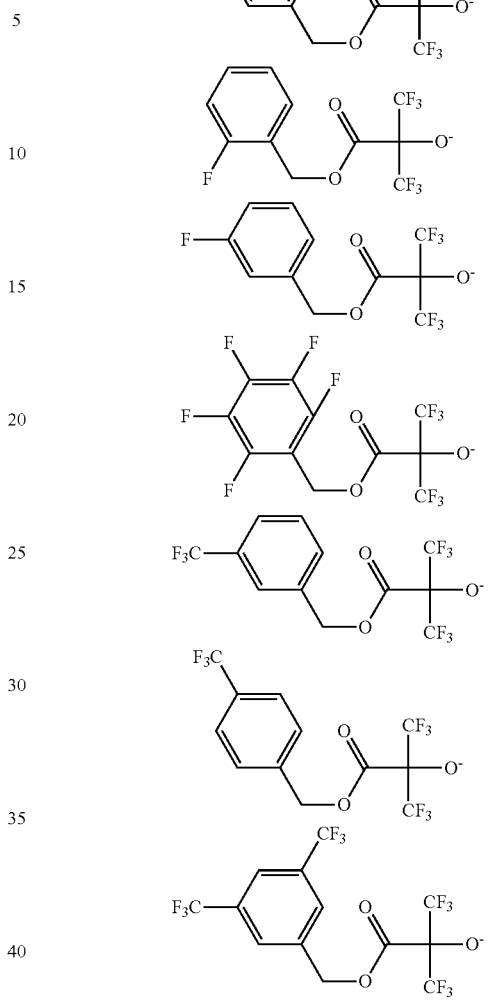

The cyclic ammonium salt compound may be synthesized, for example, by neutralization reaction of an amine compound having a tertiary ester group, which has been synthesized by esterification reaction of a carboxylic acid chloride compound with an amine compound having a tertiary hydroxyl group, with a compound having a 1,1,1,3,3,3-hexafluoro-2-propanol group (abbreviated as "HFA group"). The neutralization reaction is preferably carried out under the conditions that the amine compound having tertiary ester group and the compound having HFA group are in a molar ratio of 1:1 although either one of the compounds may be in excess.

The cyclic ammonium salt compound functions as a quencher for controlling acid diffusion in a resist composition. Since the salt compound has an acid-decomposable tertiary ester group, it is decomposed with an acid to a lower molecular weight. As the amino-containing compound reduces its molecular weight, the acid diffusion ability decreases and the acid reactivity increases. It occurs in the exposed region that the cyclic ammonium salt compound reduces its molecular weight under the action of acid. An acid diffusion controlling ability is retained high in the unexposed region whereas acid diffusion is promoted in the exposed region. The difference in reactivity between unexposed and exposed regions is exaggerated, leading to an improvement in reaction contrast. It is thus possible to improve a contrast while suppressing acid diffusion.

Since the anion possesses the HFA group, the electric repulsion of fluorine atoms prevents the quencher from agglomerating together. This enables uniform acid diffusion on a nanometer level, leading to improvements in LWR and CDU of resist patterns after development.

In the unexposed region or prior to acid decomposition, the cyclic ammonium salt compound is highly lipophilic and least dissolvable in alkaline developer. After acid decomposition, it is decomposed into a cyclic ammonium salt compound with a low molecular weight and a compound having HFA group, whereby alkaline solubility is increased. The cyclic ammonium salt compound is particularly effective in the case of alkaline development. That is, any pattern film thickness loss is restrained in the unexposed region whereas scum formation at the pattern bottom is prevented in the exposed region. The effect of preventing scum formation at the pattern bottom in the exposed region becomes outstanding particularly when the resist film has a thickness of 100 nm or more.

In the resist composition, the cyclic ammonium salt compound is preferably present in an amount of 0.001 to 50 parts by weight, more preferably 0.01 to 40 parts by weight per 100 parts by weight of the base polymer, as viewed from sensitivity and acid diffusion suppressing effect. The cyclic ammonium salt compound may be used alone or in admixture.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

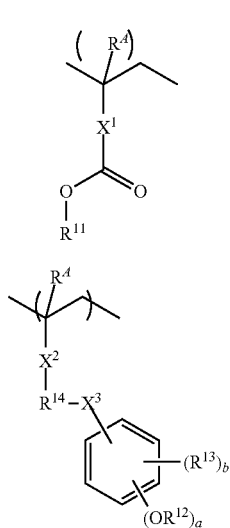

(a1)

(a2)

In formulae (a1) and (a2), $R^A$ is each independently hydrogen or methyl. $X^1$ is a single bond, phenylene or naphthylene group, or $C_1$-$C_{12}$ linking group containing at least one moiety selected from ester bond and lactone ring. $X^2$ is a single bond or ester bond. $X^3$ is a single bond, ether bond or ester bond. $R^{11}$ and $R^{12}$ are each independently an acid labile group. When the base polymer contains both recurring units (a1) and (a2). $R^1$ and $R^{12}$ may be the same or different. $R^{13}$ is fluorine, trifluoromethyl, cyano or $C_1$-$C_6$ saturated hydrocarbyl group. $R^{14}$ is a single bond or a C-CE alkanediyl group in which some carbon may be replaced by an ether bond or ester bond. The subscript "a" is 1 or 2, "b" is an integer of 0 to 4, and $1 \leq a+b \leq 5$.

Examples of the monomer from which the recurring units (a1) are derived are shown below, but not limited thereto. $R^A$ and $R^{11}$ are as defined above.

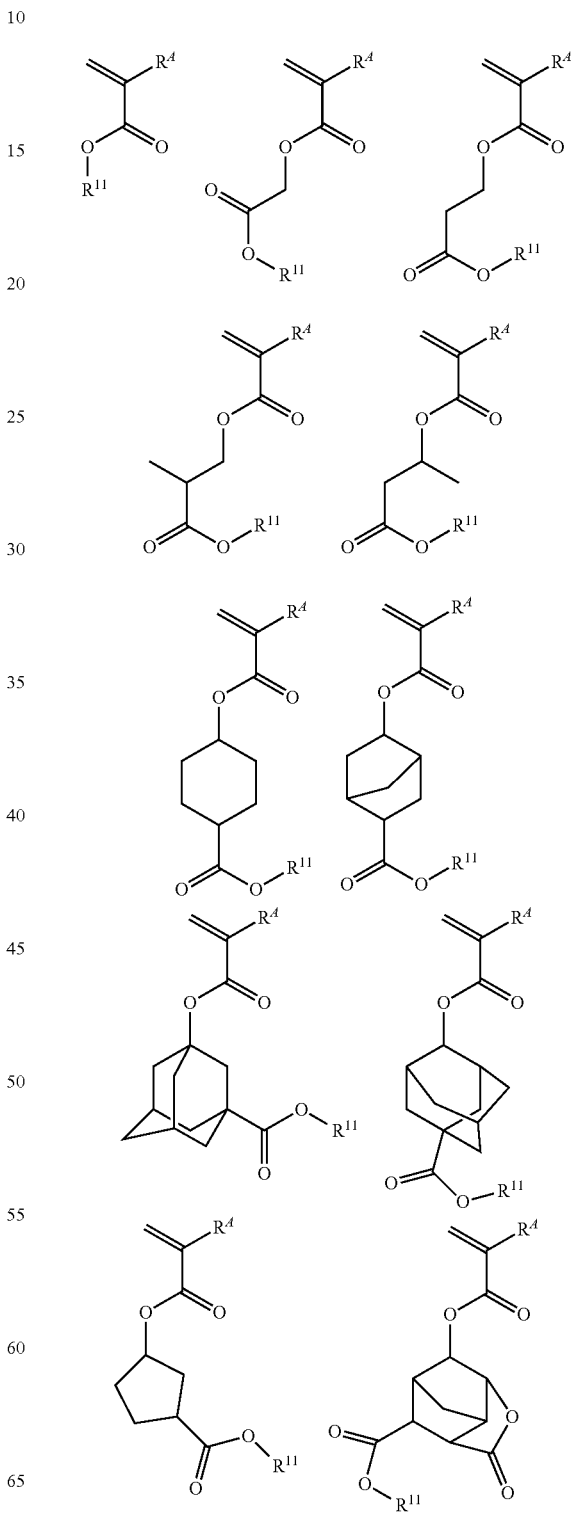

-continued

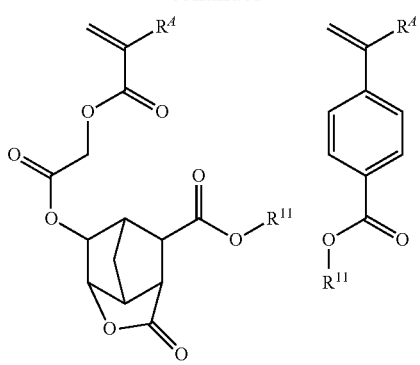

Examples of the monomer from which the recurring units (a2) are derived are shown below, but not limited thereto. $R^A$ and $R^{12}$ are as defined above.

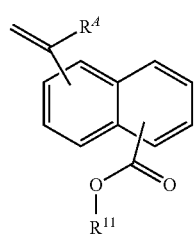

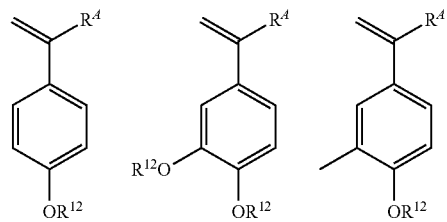

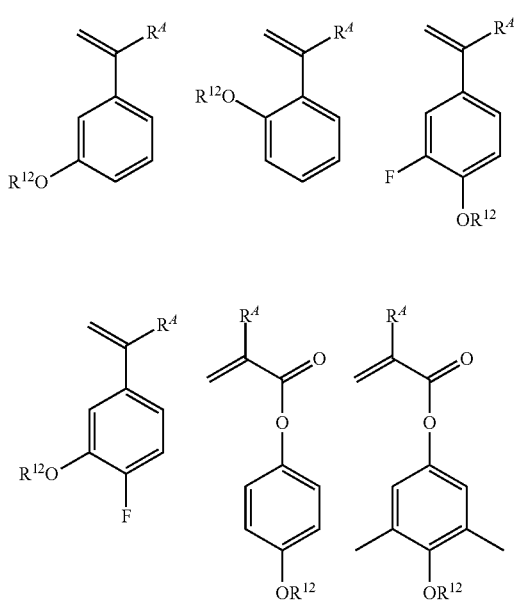

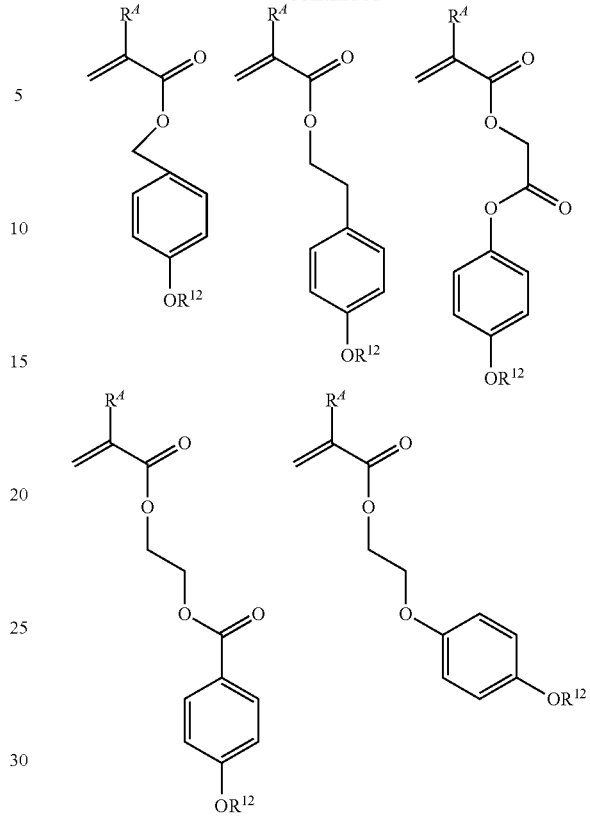

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3)

$$\text{-----}(CH_2)_c\text{---}\overset{\displaystyle O}{\underset{\displaystyle \|}{C}}\text{---}O\text{---}R^{L1} \quad (AL\text{-}1)$$

$$\text{----}\underset{\displaystyle R^{L4}}{\overset{\displaystyle R^{L3}}{C}}\text{---}O\text{---}R^{L2} \quad (AL\text{-}2)$$

$$\text{----}\underset{\displaystyle R^{L6}}{\overset{\displaystyle R^{L5}}{C}}\text{---}R^{L7} \quad (AL\text{-}3)$$

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ saturated hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached. The ring preferably contains 4 to 16 carbon atoms and is typically alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached. The ring preferably contains 4 to 16 carbon atoms and is typically alicyclic.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

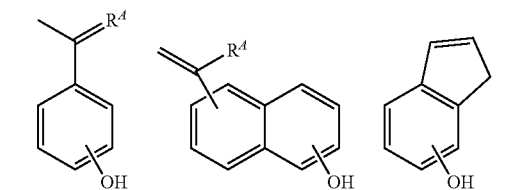

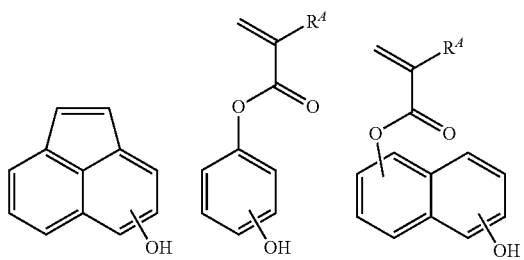

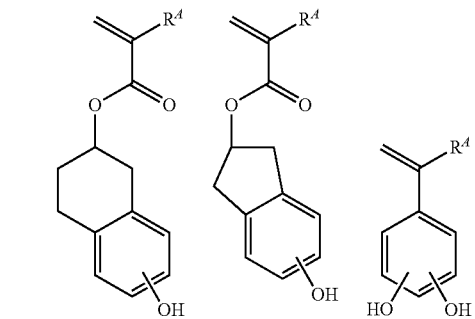

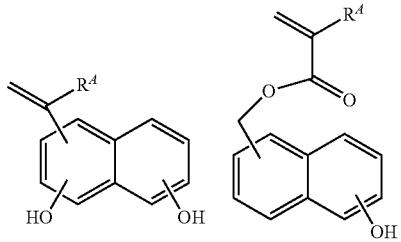

-continued

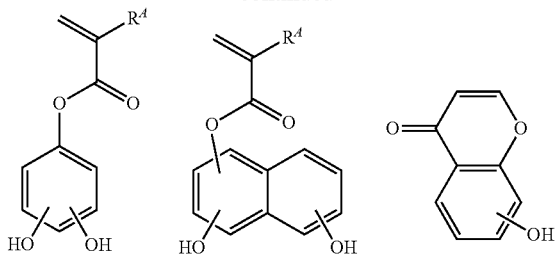

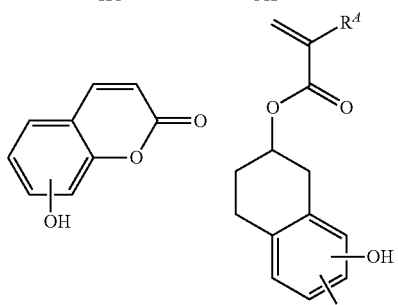

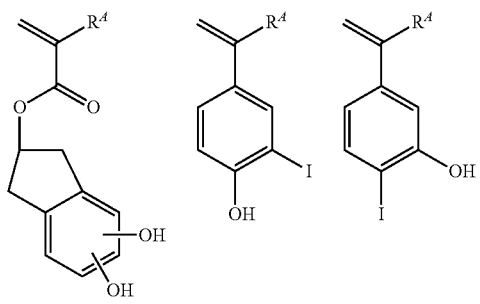

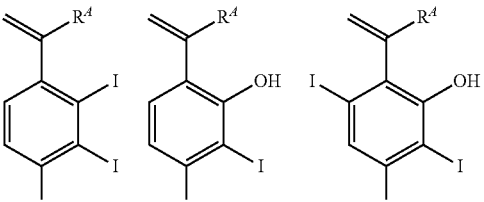

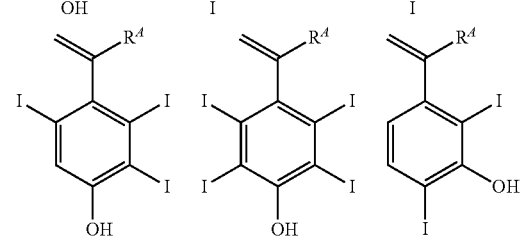

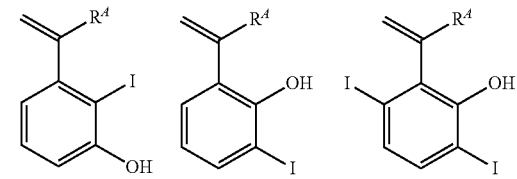

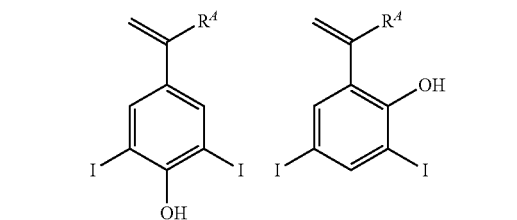

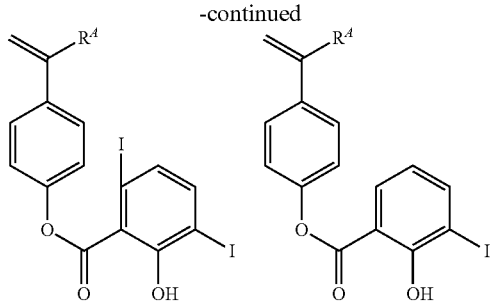
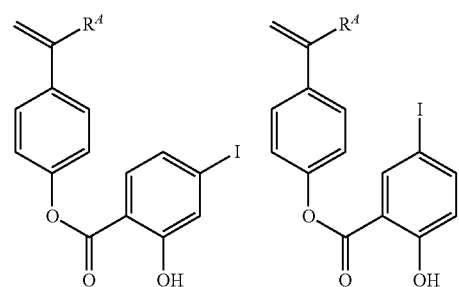
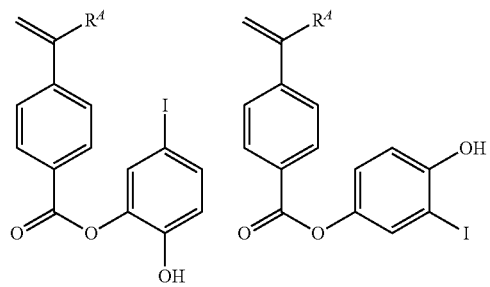
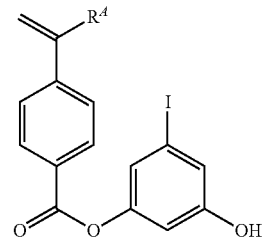

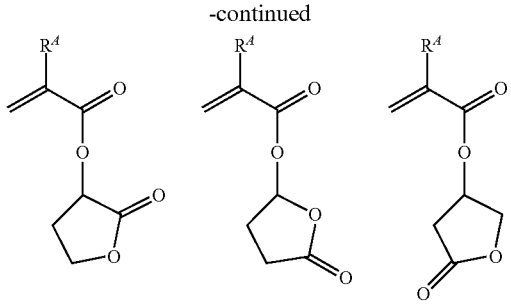
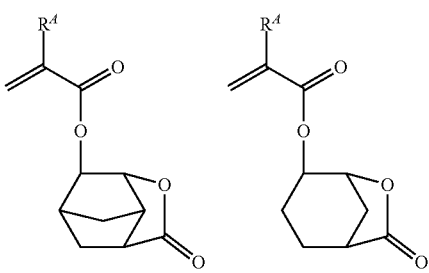
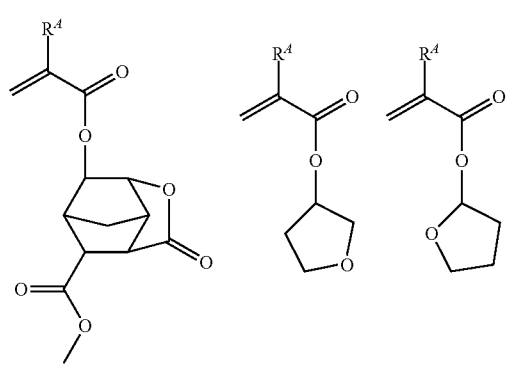
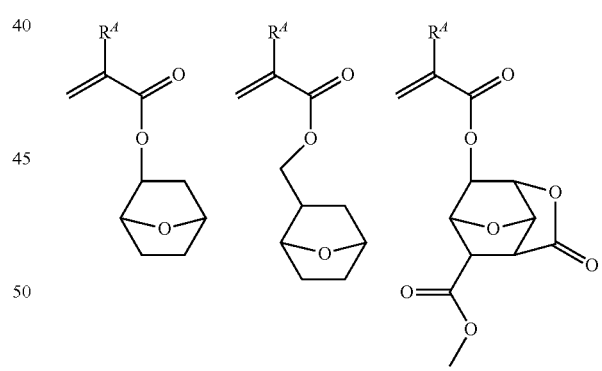
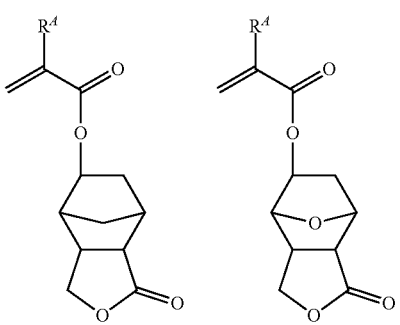

Further, recurring units (c) having another adhesive group selected from hydroxyl group (other than the foregoing phenolic hydroxyl), lactone ring, sultone ring, ether bond, ester bond, sulfonate bond, carbonyl group, sulfonyl group, cyano group, and carboxyl group may also be incorporated in the base polymer. Examples of suitable monomers from which recurring units (c) are derived are given below, but not limited thereto. Herein $R^A$ is as defined above.

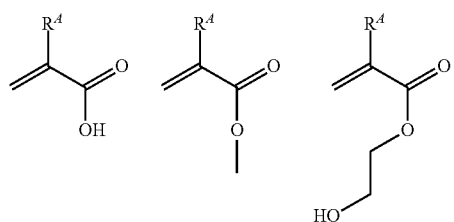

301
-continued
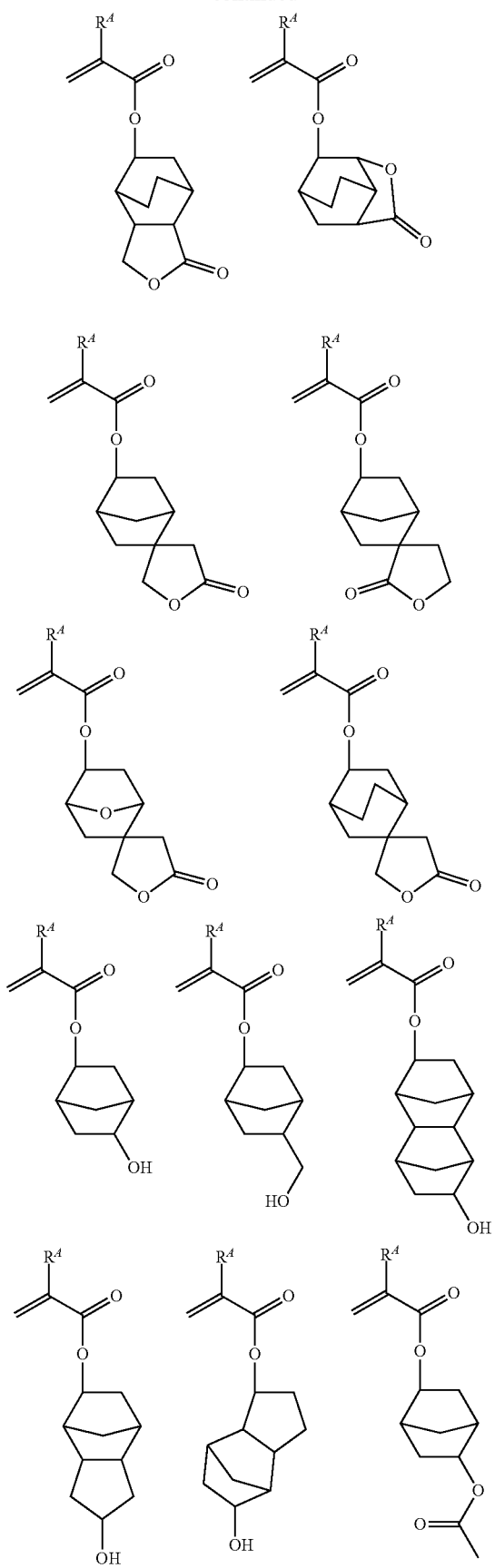
302
-continued
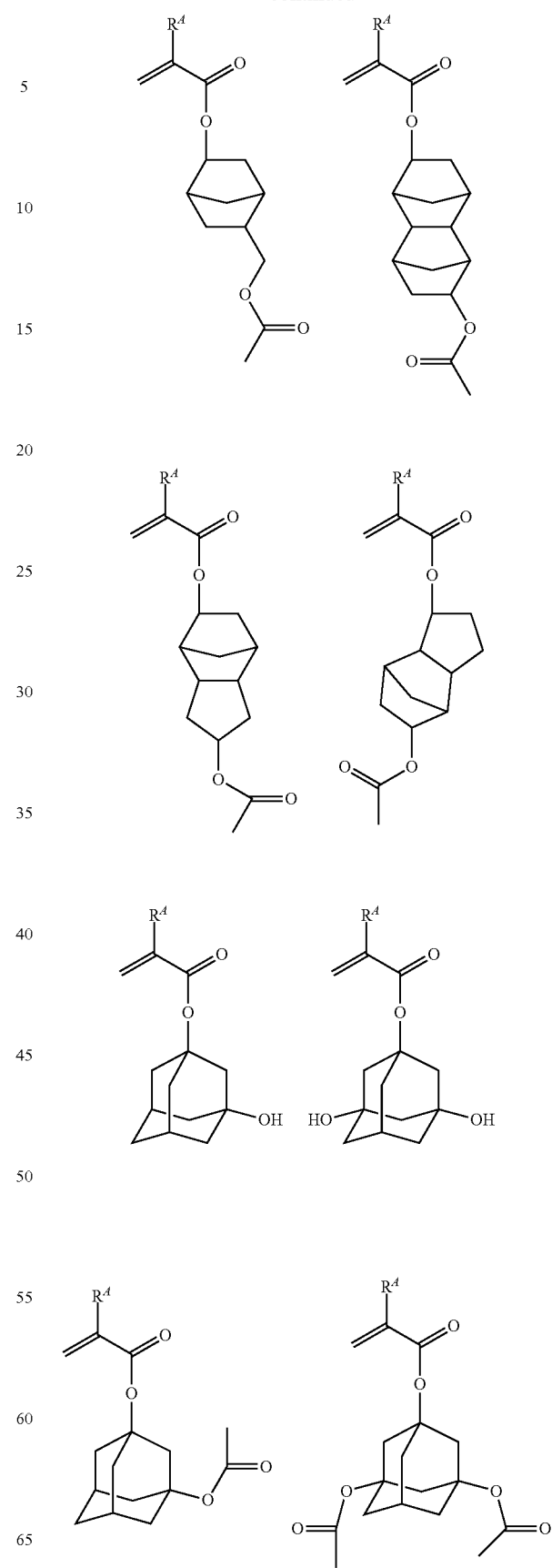

-continued
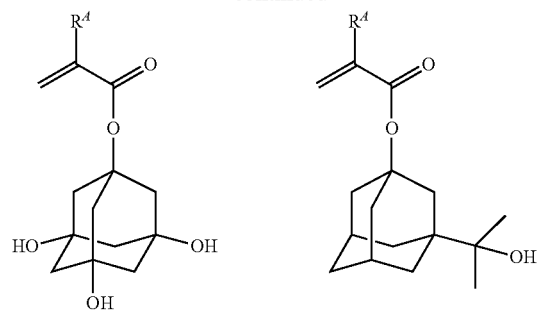
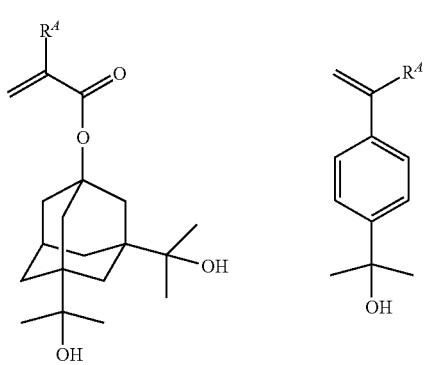
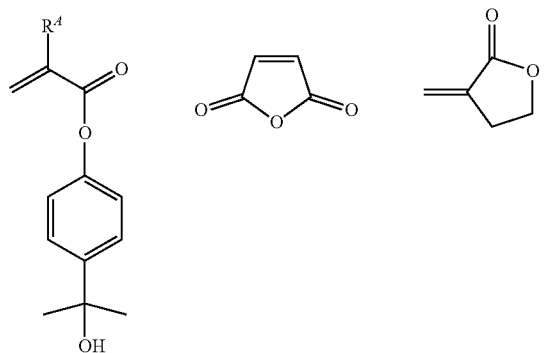
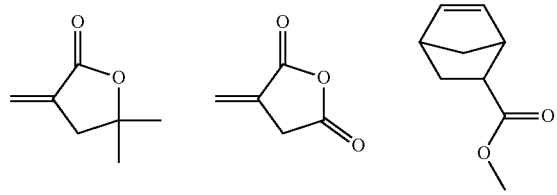
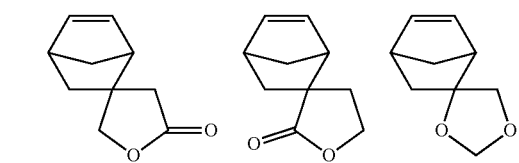
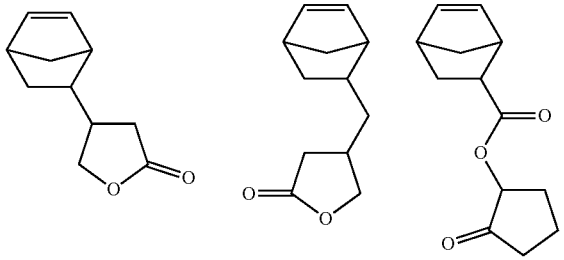
-continued
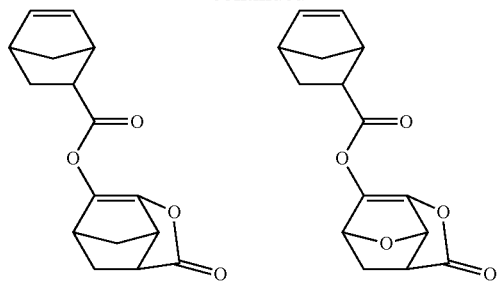
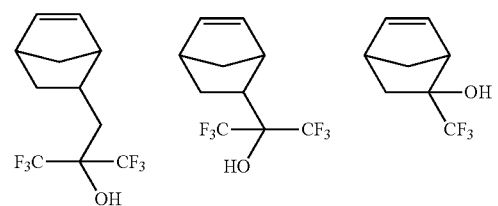
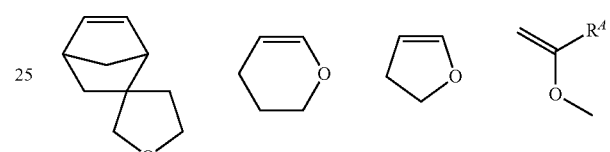
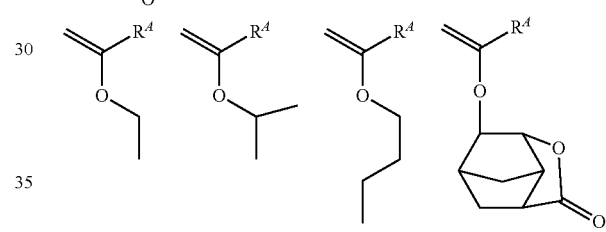
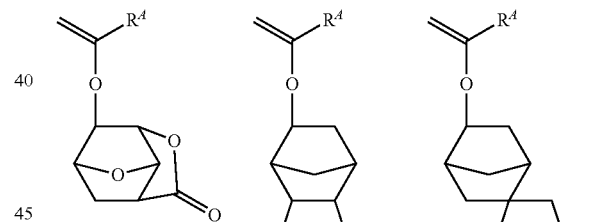
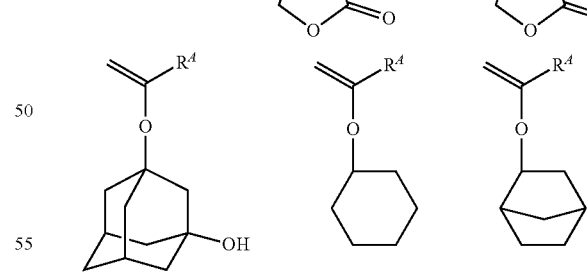
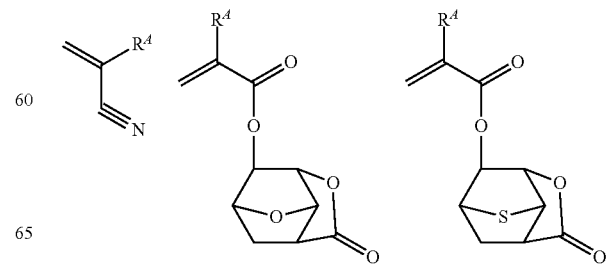

305
-continued
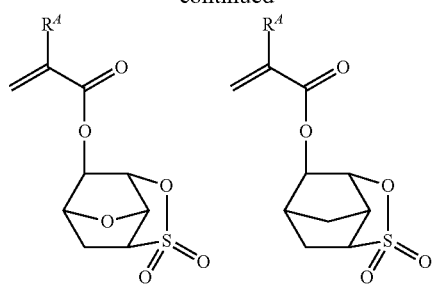
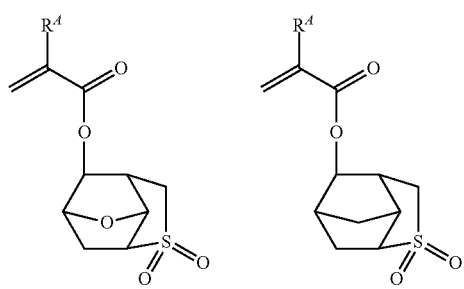
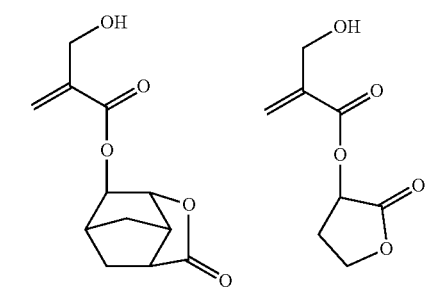
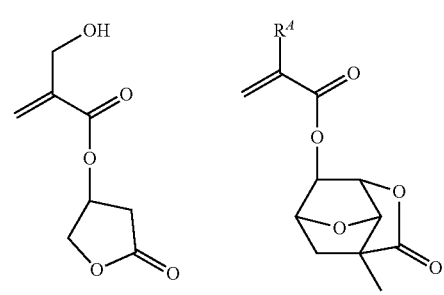
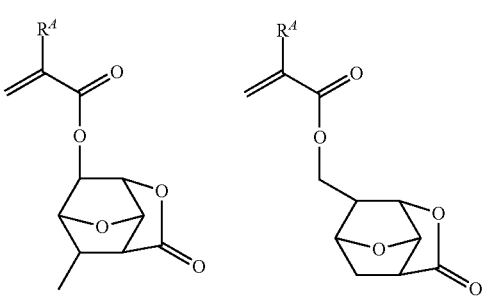
306
-continued
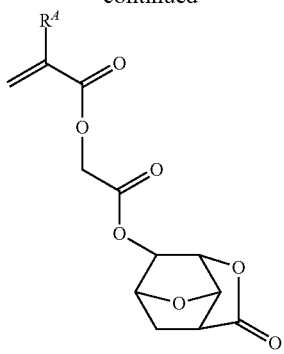
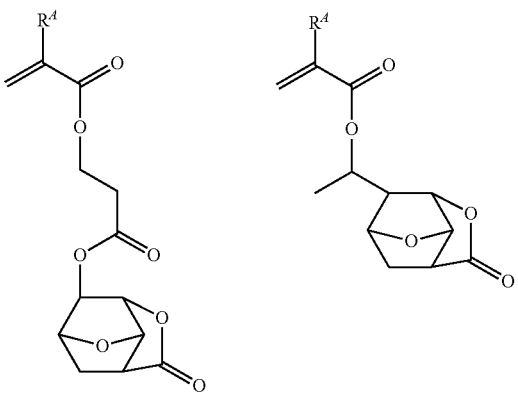
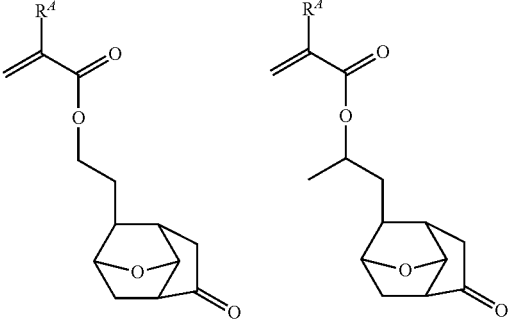
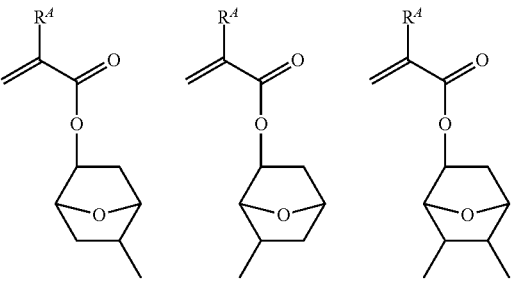
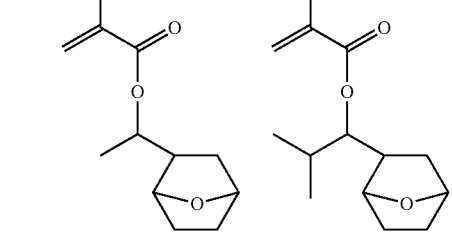

-continued
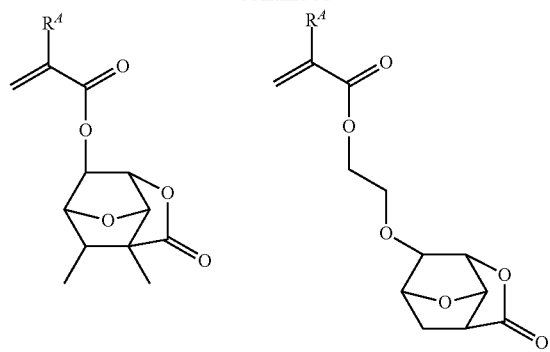
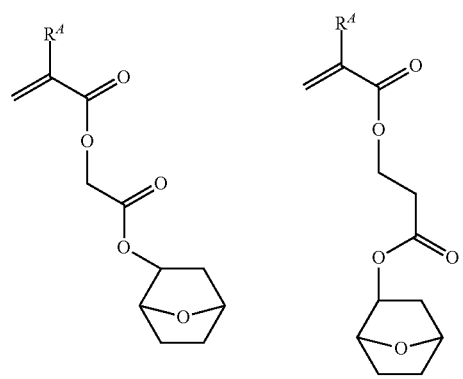
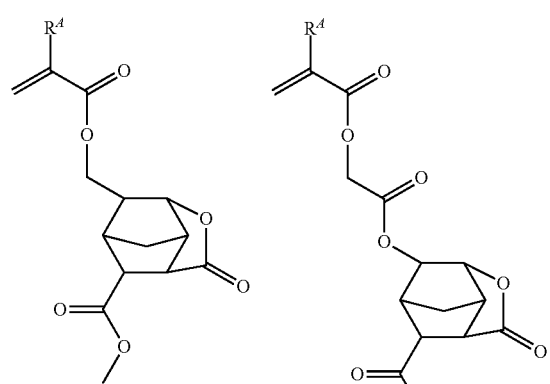
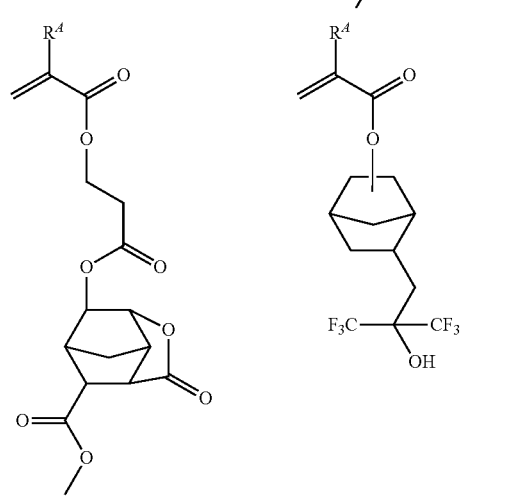
-continued
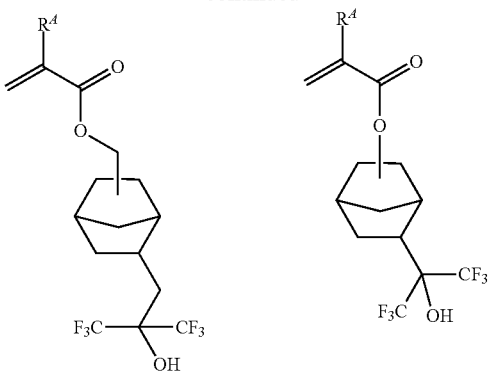
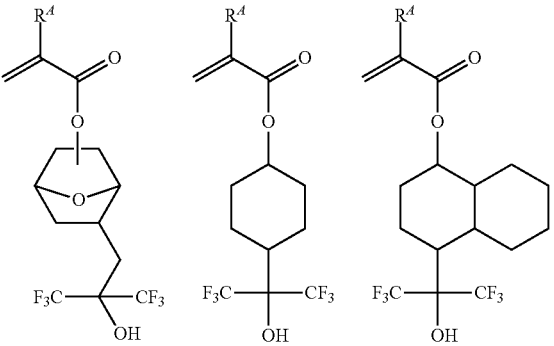
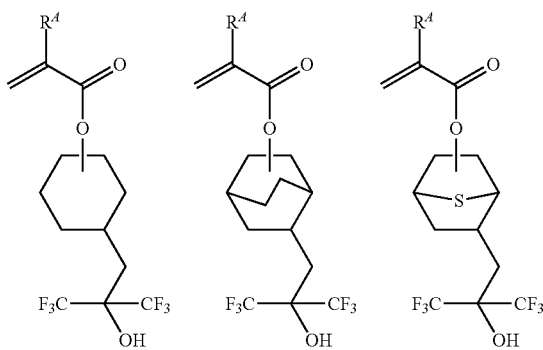
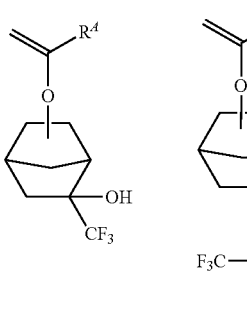

309
-continued
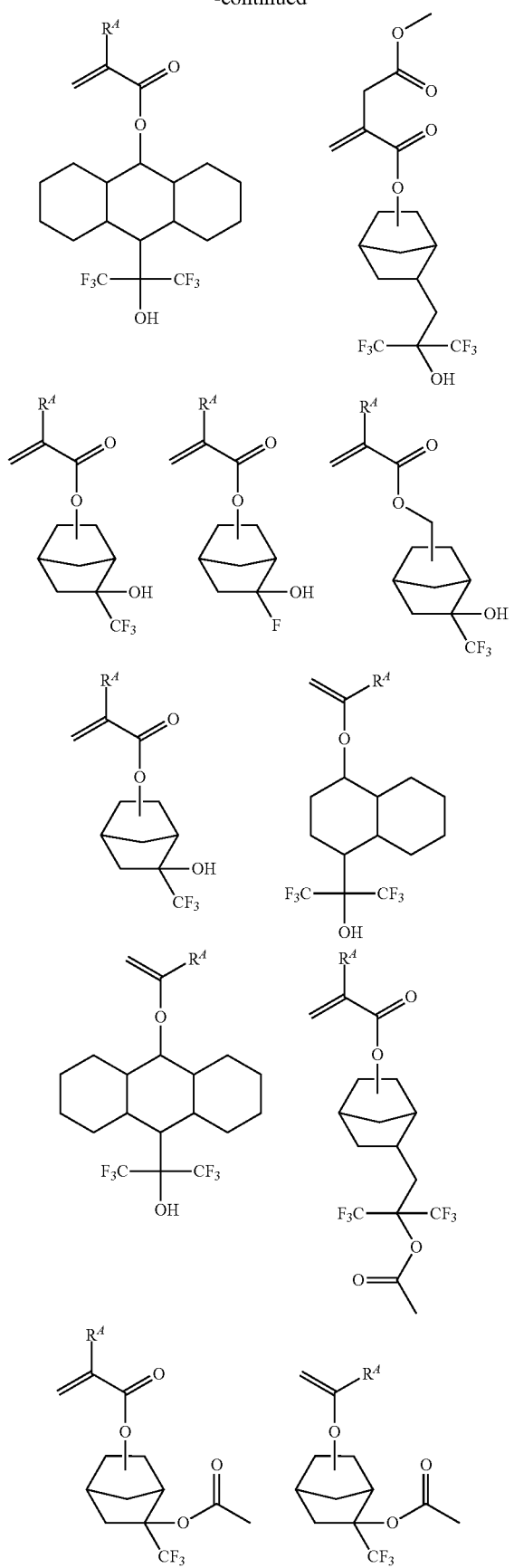
310
-continued
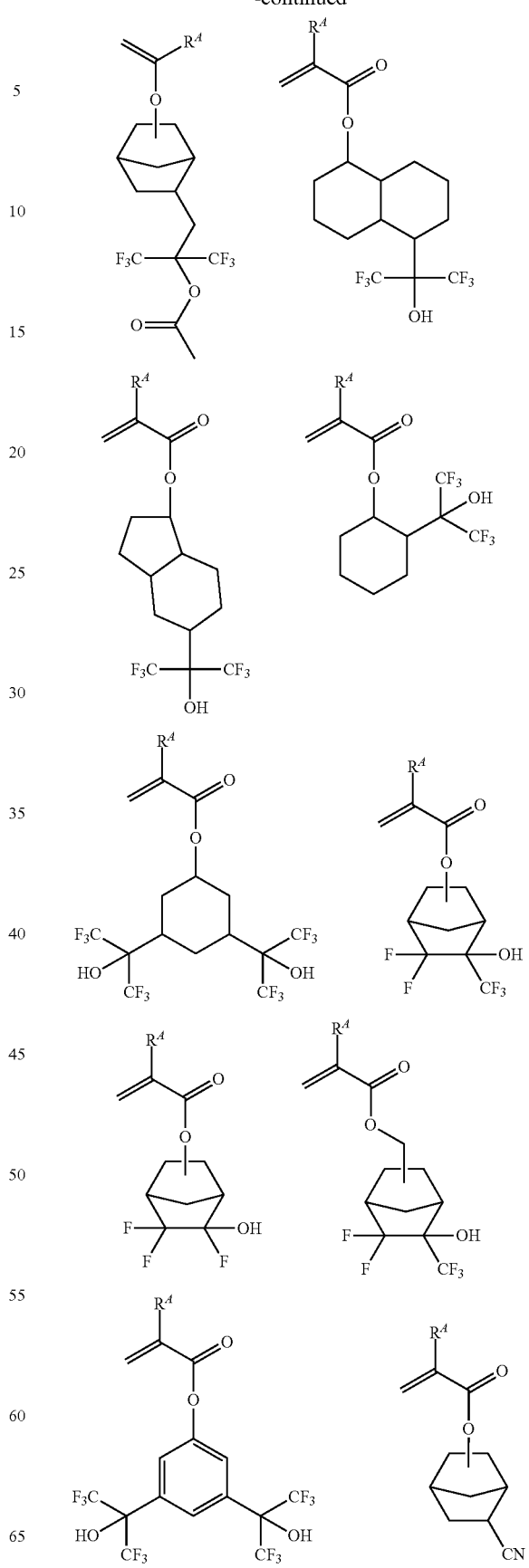

311
-continued
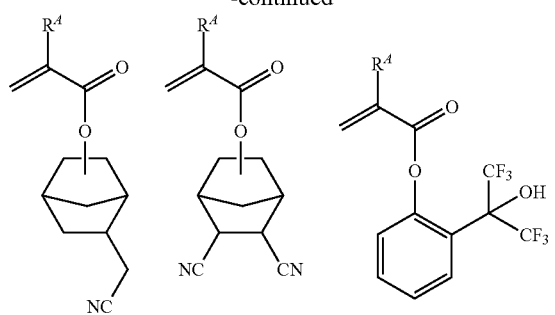
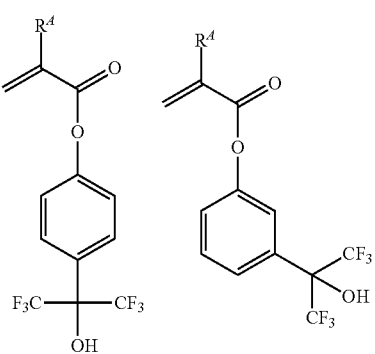
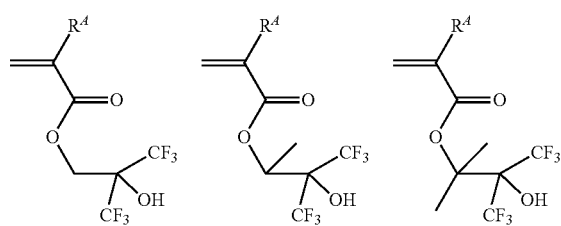
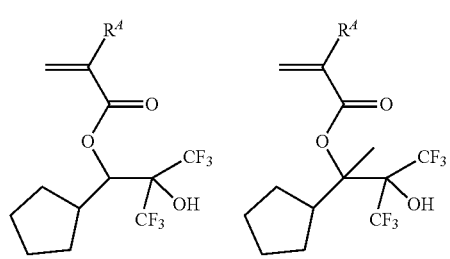
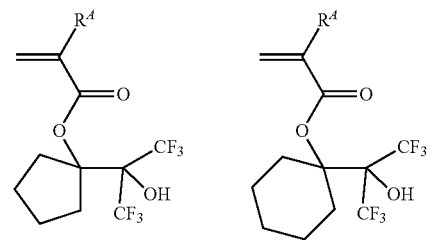
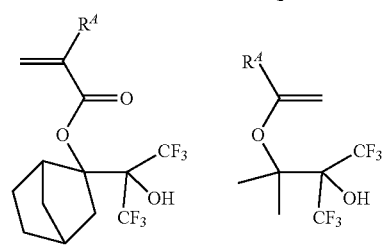
312
-continued
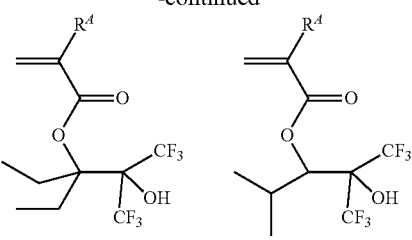
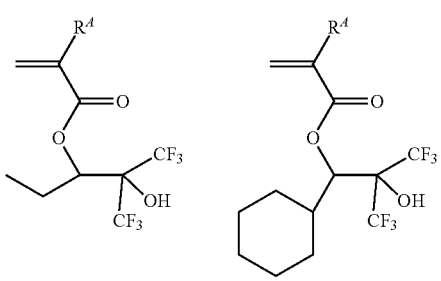
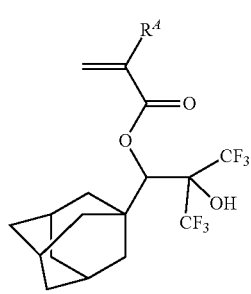
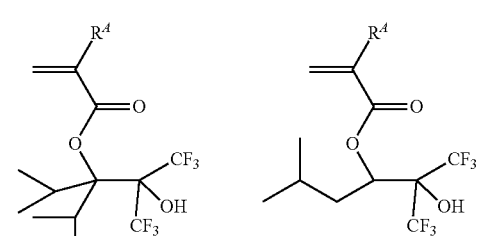
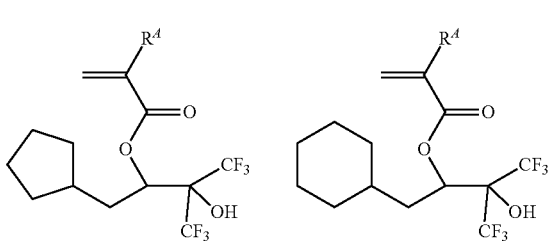
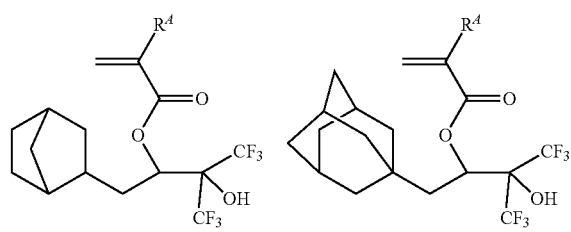

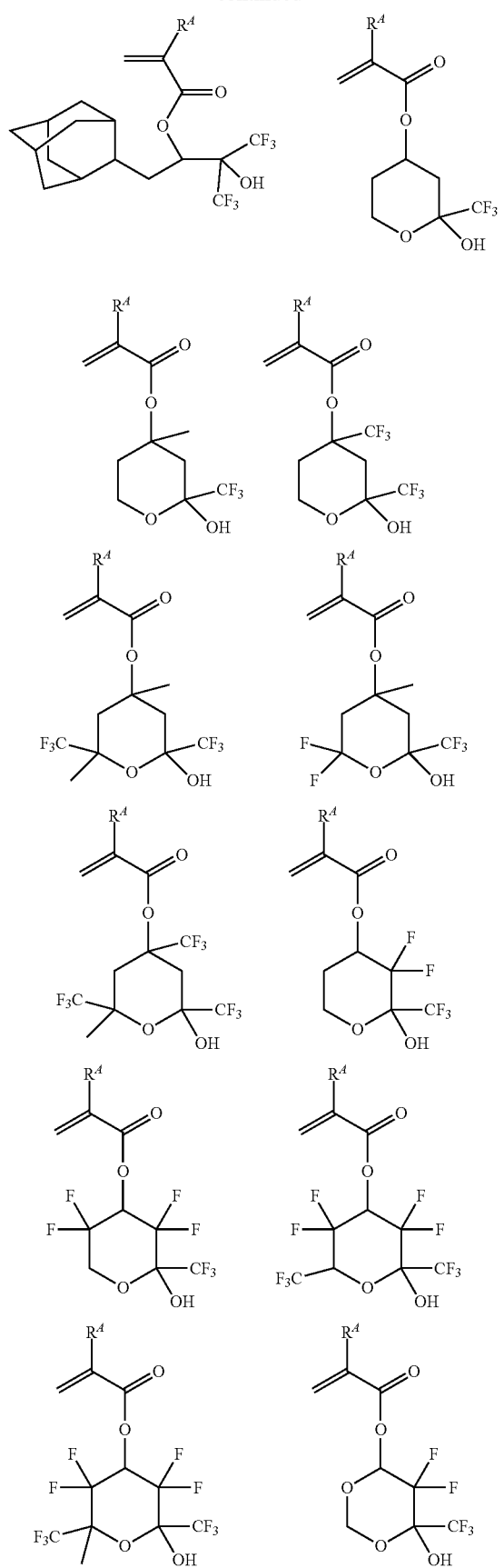
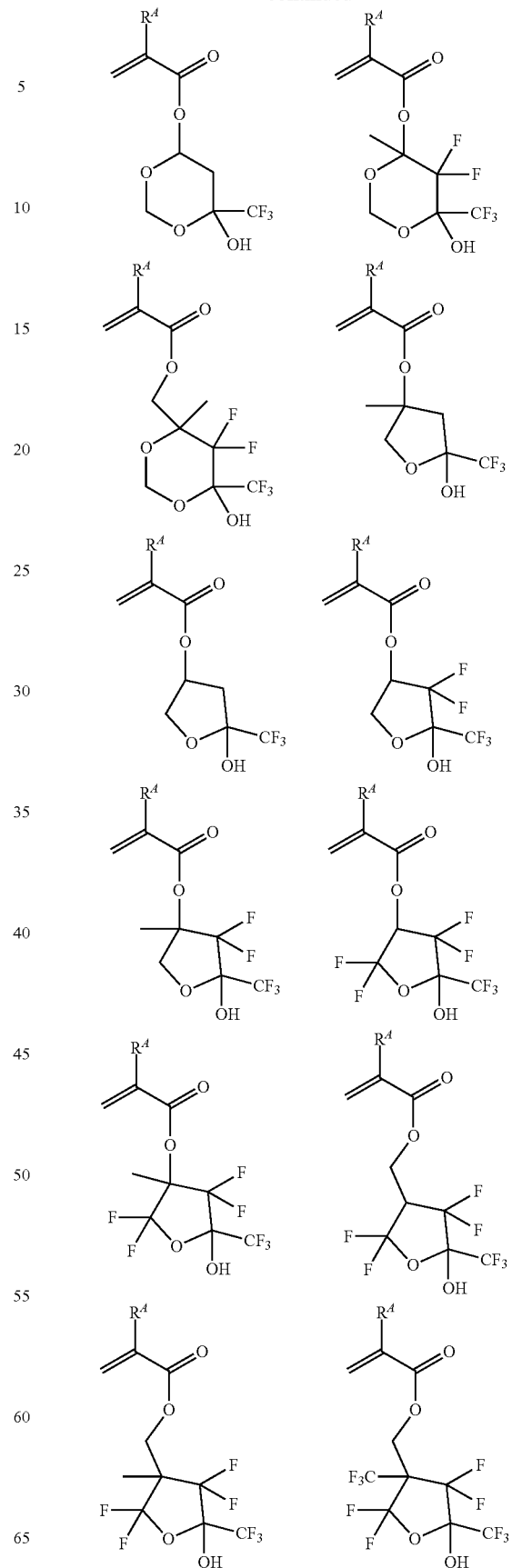

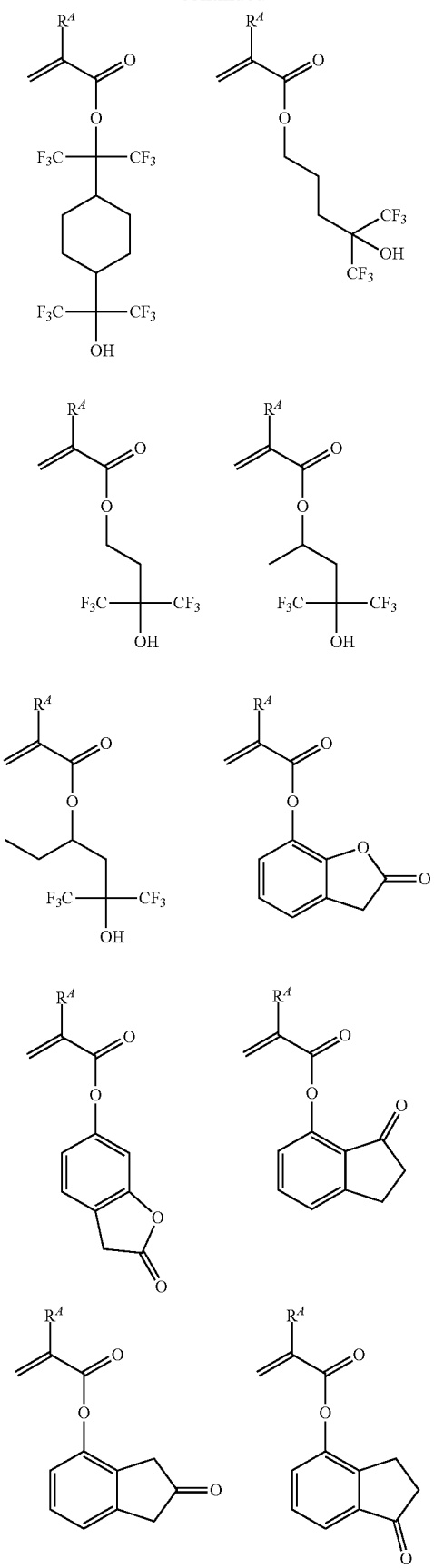
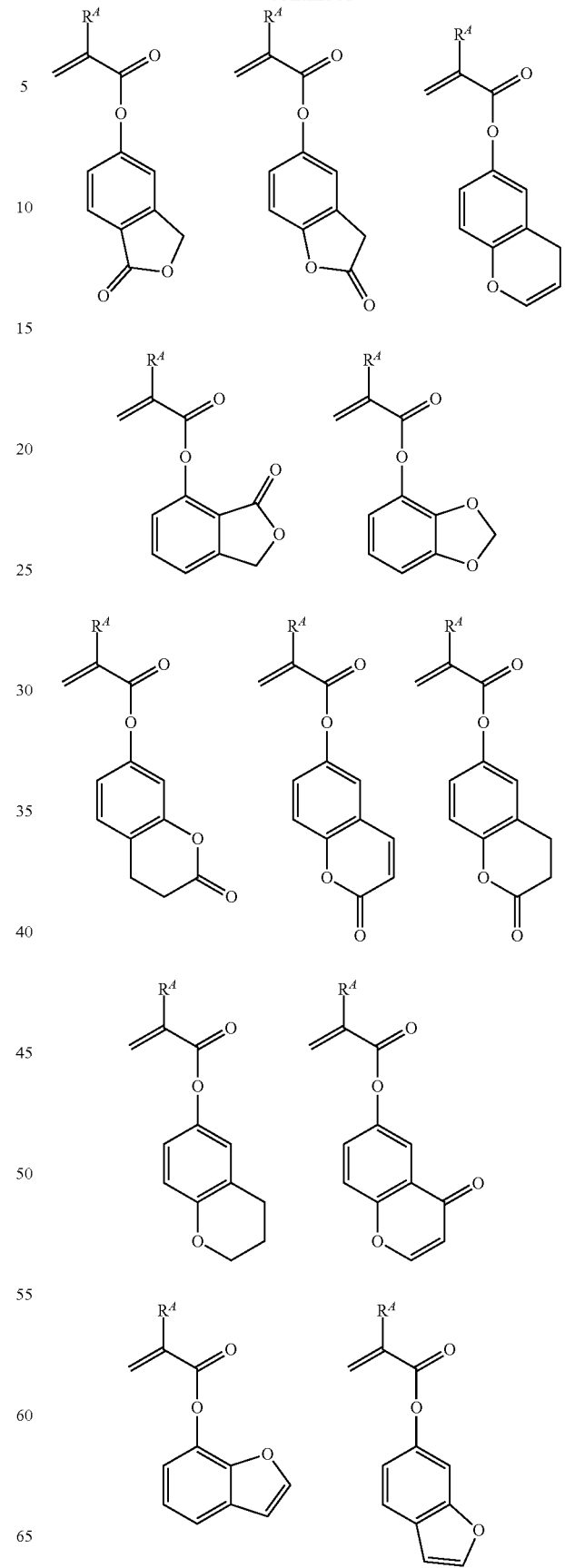

-continued
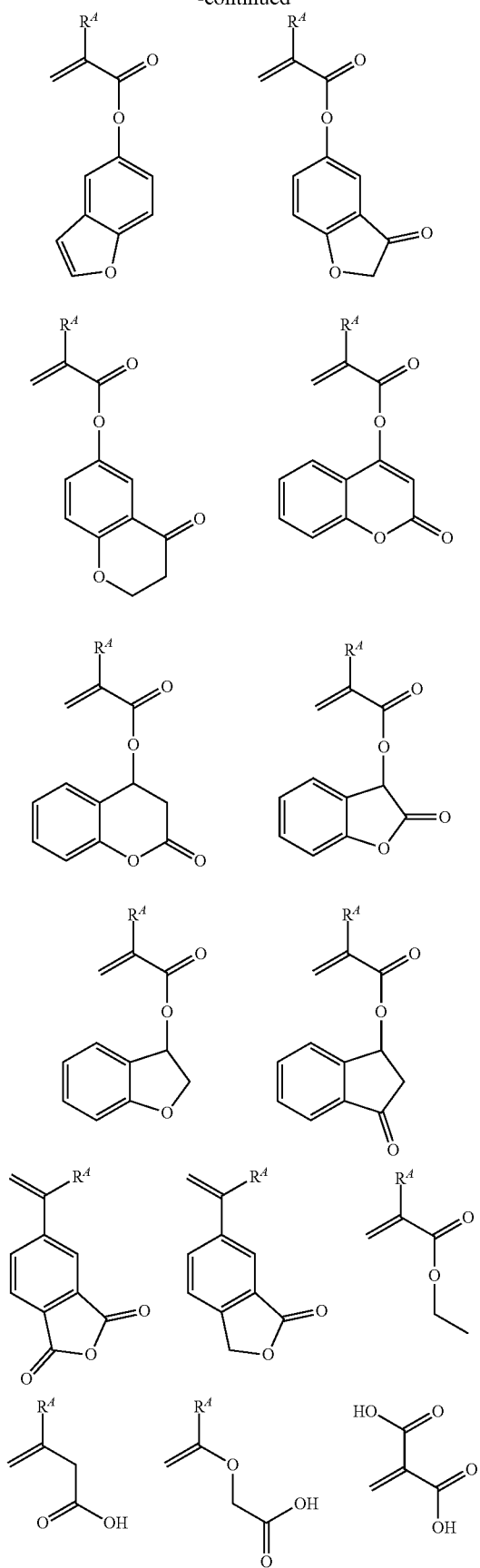
-continued
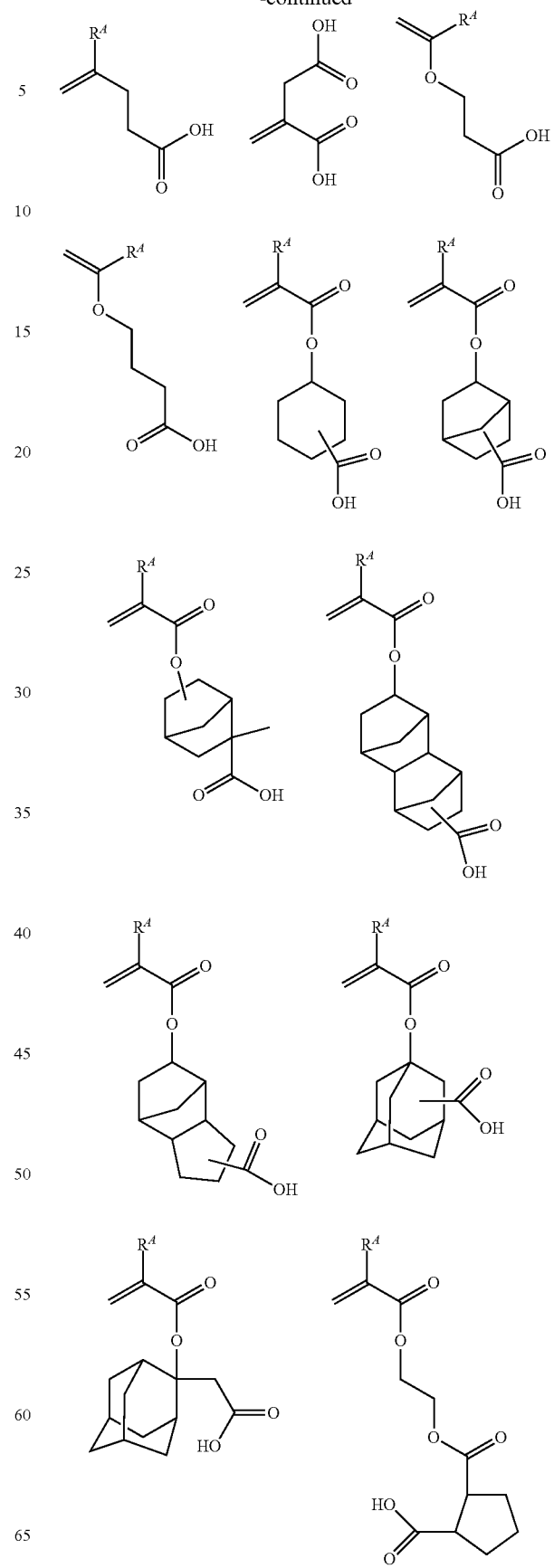

319
-continued
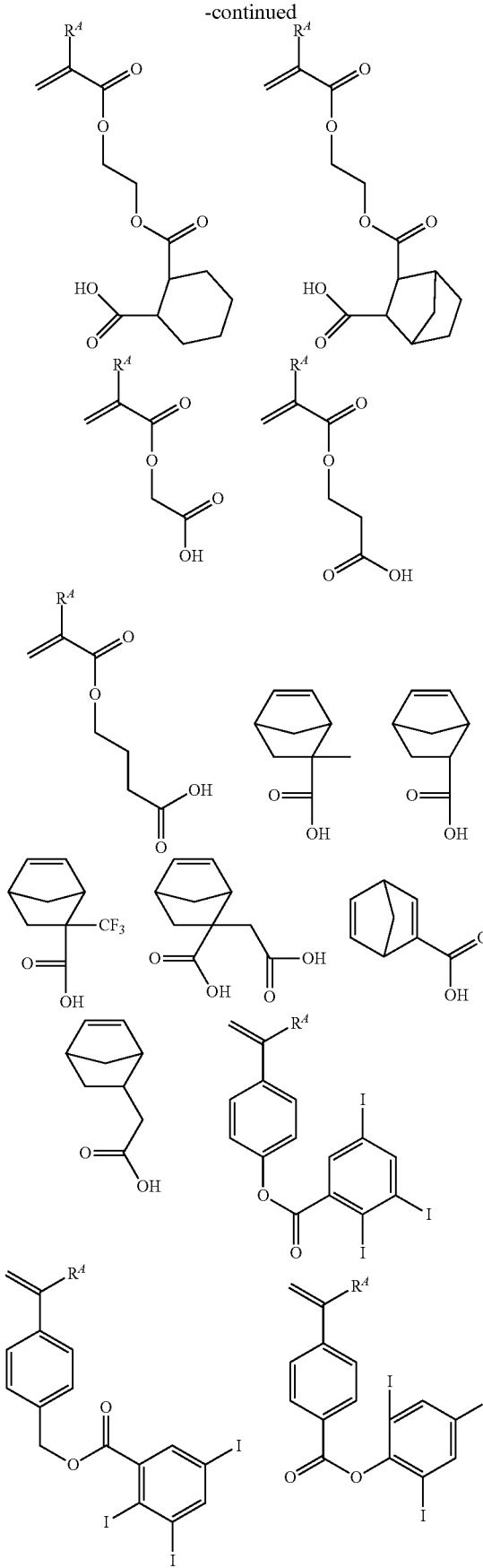
320
-continued
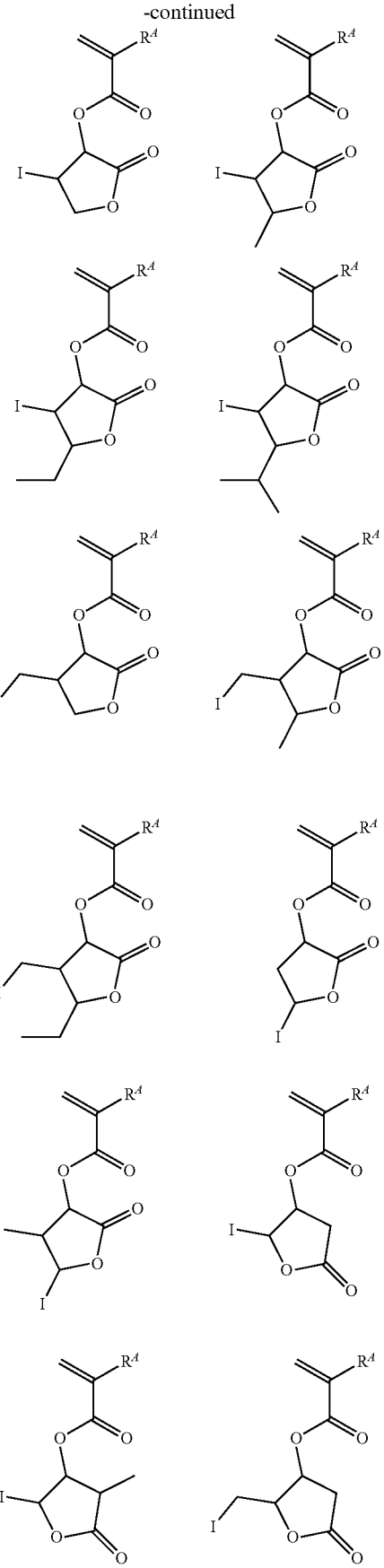

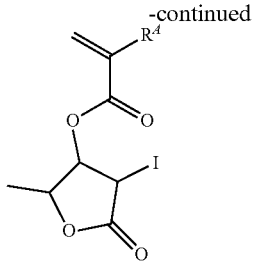
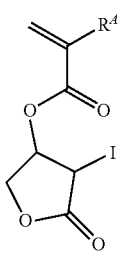

In another preferred embodiment, the base polymer may further comprise recurring units (d) derived from indene, benzofuran, benzothiophene, acenaphthylene, chromone, coumarin, and norbornadiene, or derivatives thereof. Suitable monomers are exemplified below.

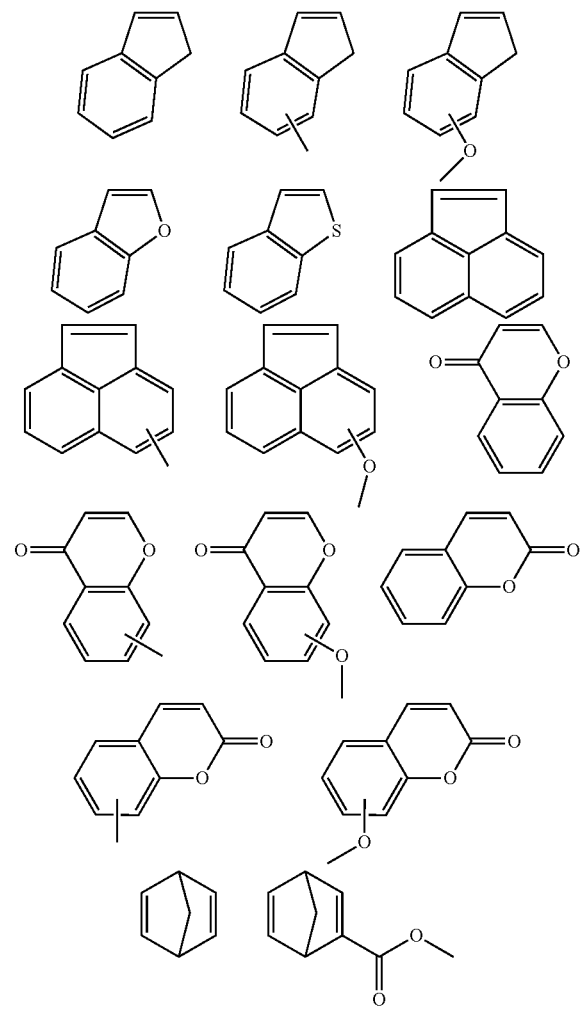

Furthermore, recurring units (e) may be incorporated in the base polymer, which are derived from styrene, vinylnaphthalene, vinylanthracene, vinylpyrene, methyleneindene, vinylpyridine, or vinylcarbazole.

In a further embodiment, recurring units (f) derived from an onium salt having a polymerizable unsaturated bond may be incorporated in the base polymer. Specifically, the base polymer may comprise recurring units of at least one type selected from recurring units having formulae (f1), (2) and (f3). These units are simply referred to as recurring units (f1), (f2) and (f3), which may be used alone or in combination of two or more types.

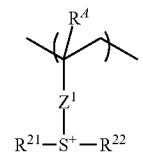

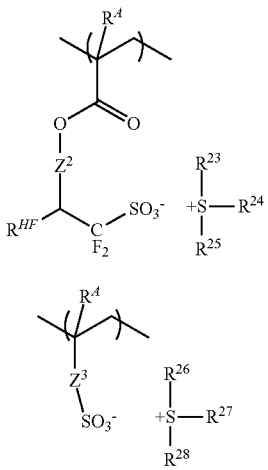

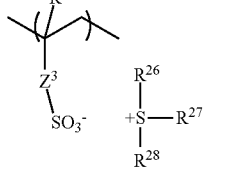

In formulae (f1) to (3), $R^A$ is independently hydrogen or methyl. $Z^1$ is a single bond, $C_1$-$C_6$ aliphatic hydrocarbylene group, phenylene group, naphthylene group, or $C_7$-$C_{18}$ group obtained by combining the foregoing, —O—$Z^{11}$—, —C(=O)—O—$Z^{11}$—, or —C(=O)—NH—$Z^{11}$—. $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—. $Z^{21}$ is a $C_1$-$C_{12}$ saturated hydrocarbylene group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety. The aliphatic hydrocarbylene groups $Z^{11}$ and $Z^{31}$ may be saturated or unsaturated and straight, branched or cyclic. The saturated hydrocarbylene group $Z^{21}$ may be straight, branched or cyclic.

In formulae (f1) to (f3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as will be exemplified later for $R^{101}$ to $R^{105}$ in formulae (1-1) and (1-2). In these groups, some or all of the hydrogen atoms may be substituted by a moiety containing a heteroatom such as oxygen, sulfur, nitrogen or halogen and some carbon may be replaced by a moiety containing a heteroatom such as oxygen, sulfur or nitrogen, so that the group may contain a hydroxyl moiety, cyano moiety, nitro moiety, mercapto moiety, carbonyl moiety, ether bond, ester bond, sulfonate bond, carbonate moiety, lactone ring, sultone ring, carboxylic anhydride, or haloalkyl moiety.

A pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In formula (2), $R^{HF}$ is hydrogen or trifluoromethyl.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate: arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl at β-position as represented by the formula (f1-2).

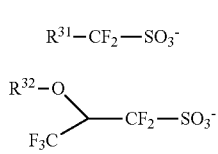

In formula (f1-1), $R^{31}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples of the hydrocarbyl group are as will be exemplified later for $R^{111}$ in formula (1A').

In formula (f1-2), $R^{32}$ is hydrogen, or a $C_1$-$C_{30}$ hydrocarbyl group or $C_2$-$C_{30}$ hydrocarbylcarbonyl group, which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic. Examples of the hydrocarbyl group are as will be exemplified later for $R^{111}$ in formula (1A').

Examples of the cation in the monomer from which recurring unit (f1) is derived are shown below, but not limited thereto. $R^A$ is as defined above.

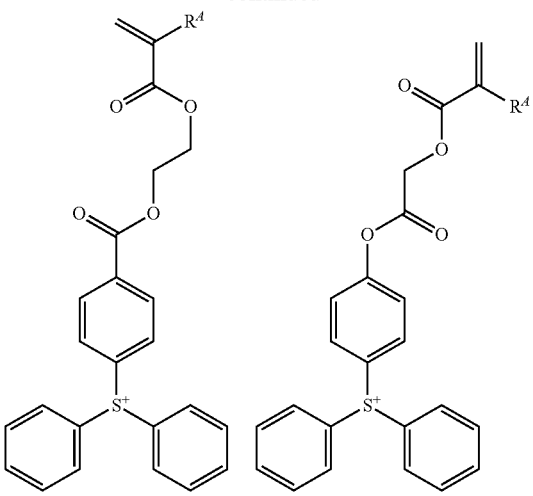

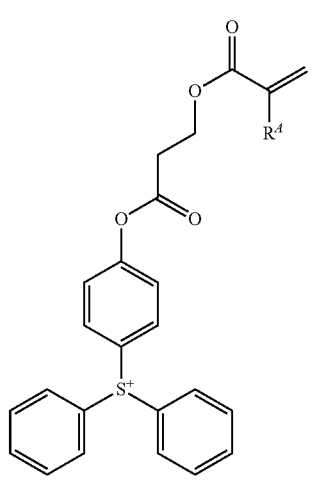

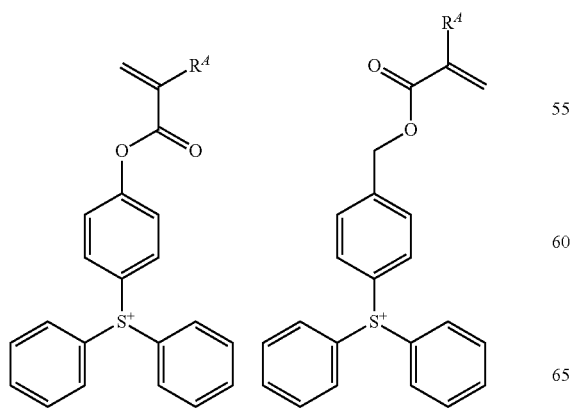

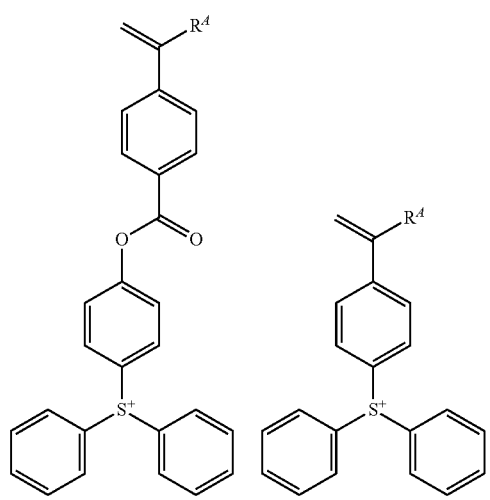

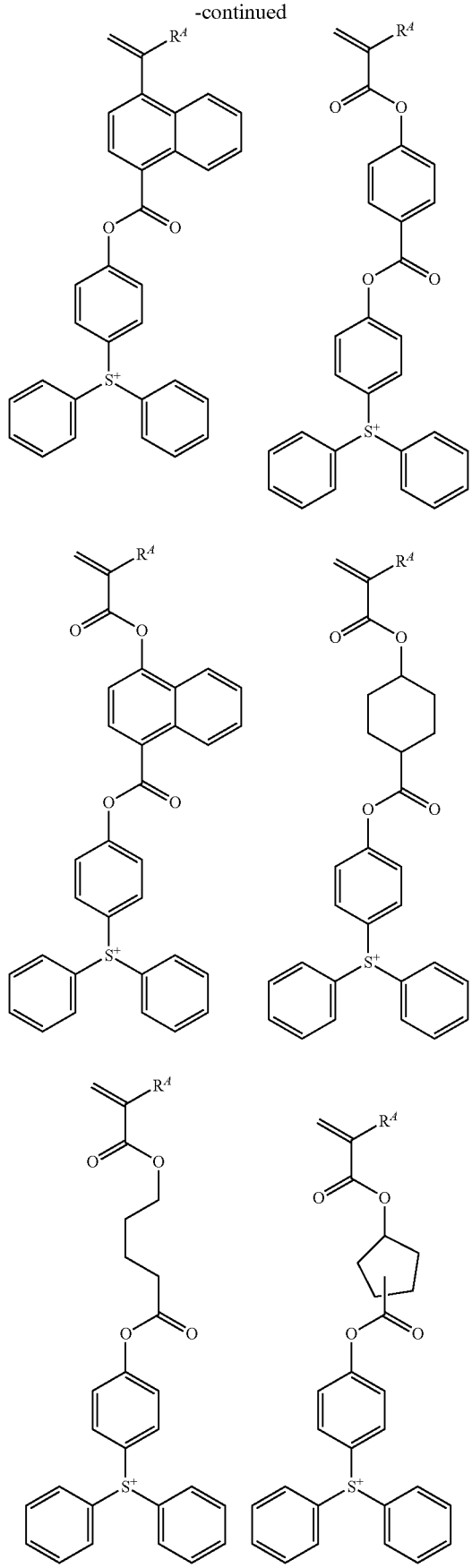
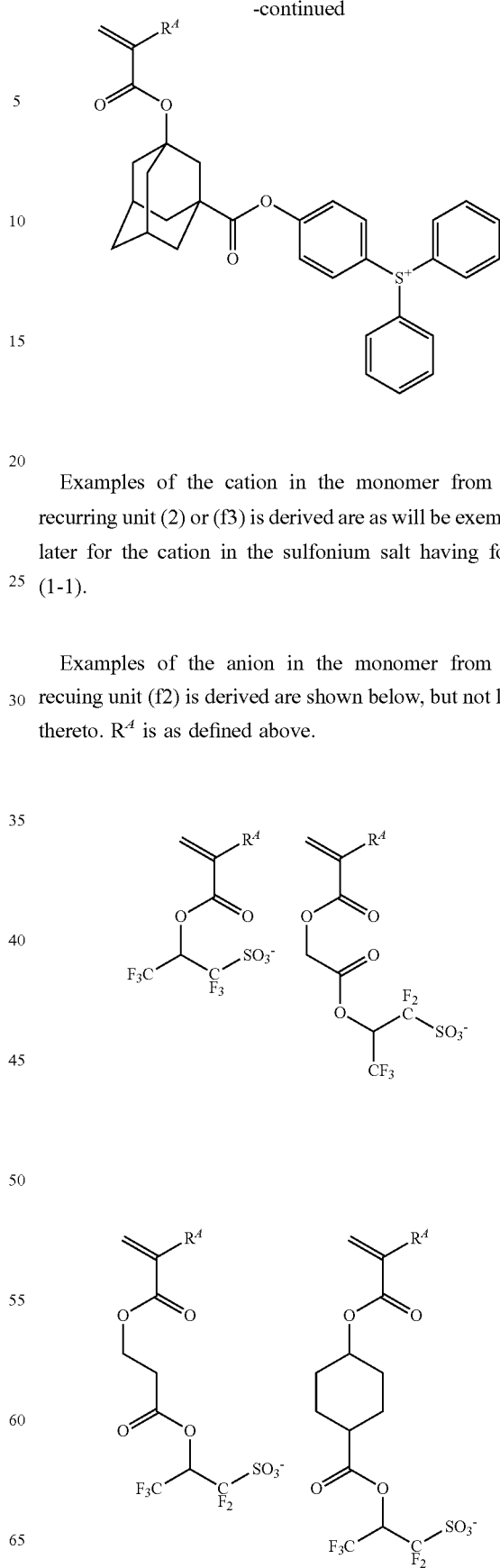
Examples of the cation in the monomer from which recurring unit (2) or (f3) is derived are as will be exemplified later for the cation in the sulfonium salt having formula (1-1).
Examples of the anion in the monomer from which recuing unit (f2) is derived are shown below, but not limited thereto. $R^A$ is as defined above.

327
-continued
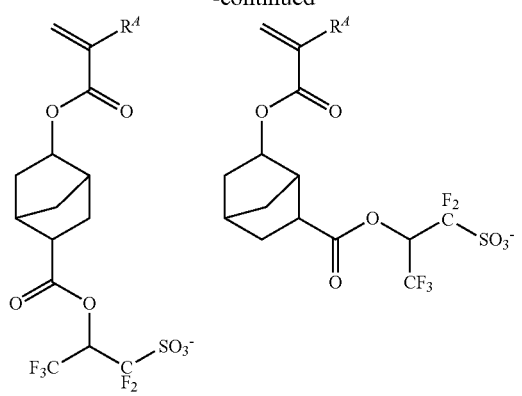
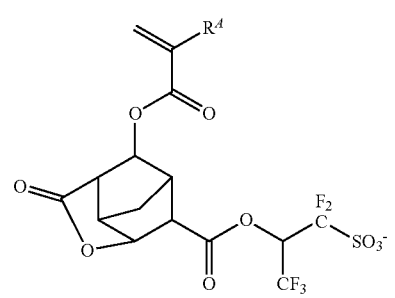
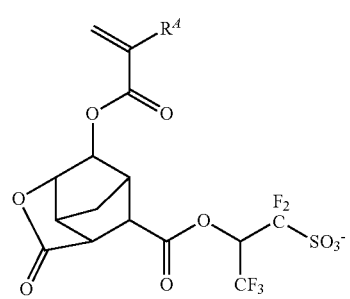
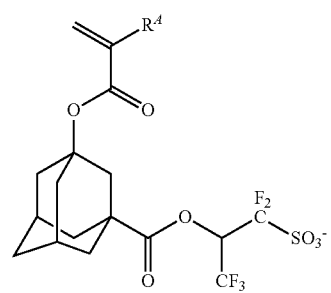
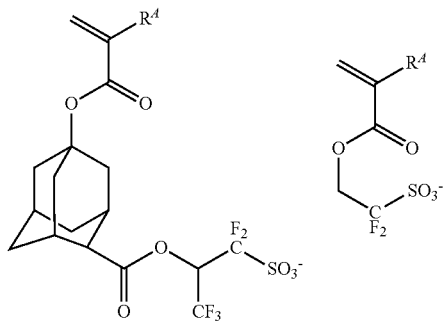
328
-continued
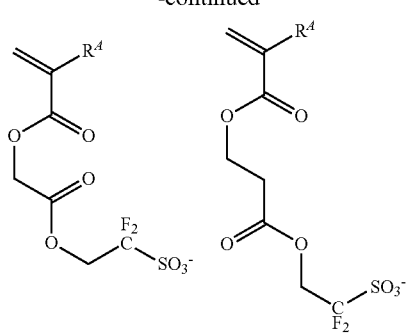
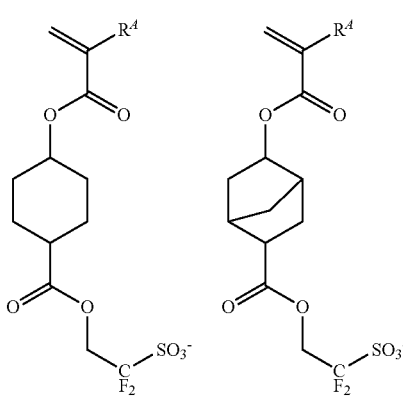
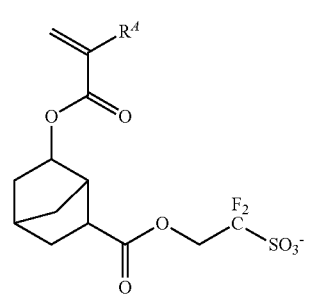
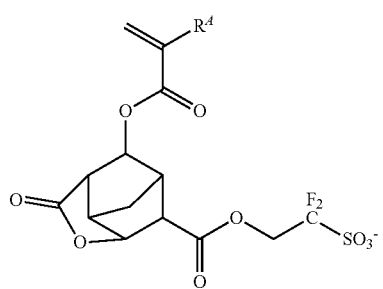
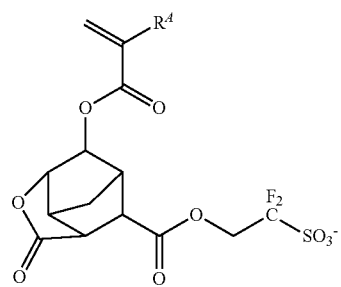

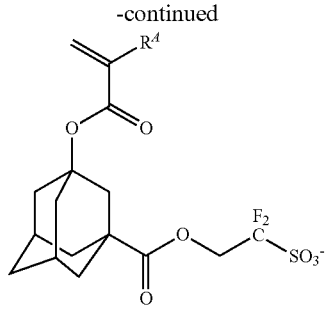
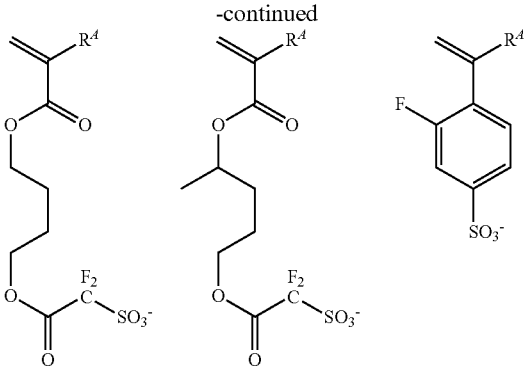
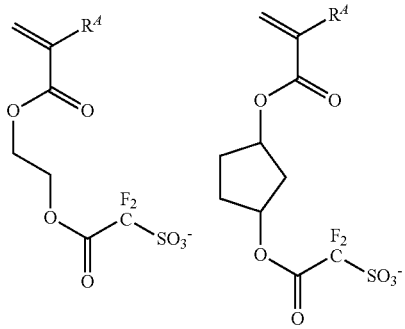
Examples of the anion in the monomer from which recurring unit (f3) is derived are shown below, but not limited thereto. $R^A$ is as defined above.
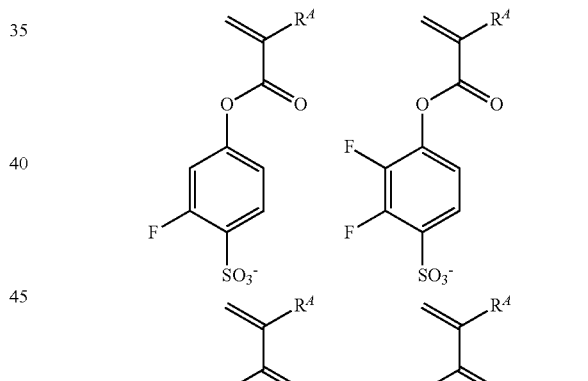
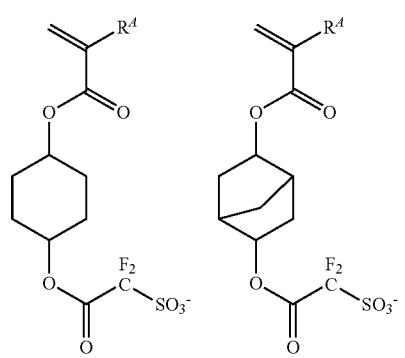
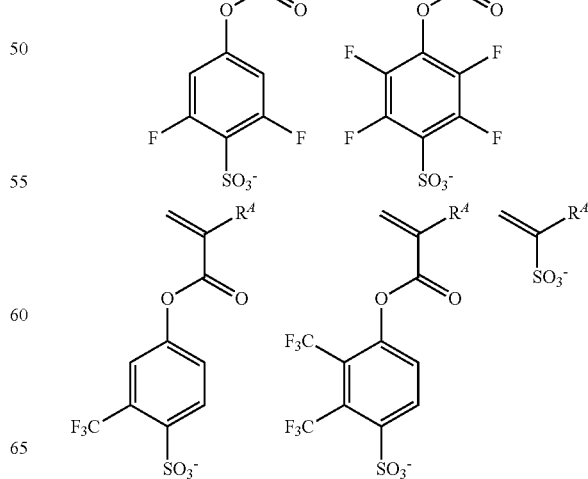

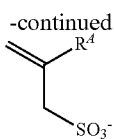

The attachment of an acid generator to the polymer main chain is effective in restraining acid diffusion, thereby preventing a reduction of resolution due to blur by acid diffusion. Also, LWR or CDU is improved since the acid generator is uniformly distributed. Where a base polymer containing recurring units (f), i.e., polymer-bound acid generator is used, the blending of an acid generator of addition type (to be described later) may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0<b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinyinaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the cyclic ammonium salt compound functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

(1-1)

(1-2)

In formulae (1-1) and (1-2), $R^{101}$ to $R^{105}$ are independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^{101}$ to $R^{105}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_2$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl and tert-butylnaphthyl; $C_7$-$C_{20}$ aralkyl groups such as benzyl and phenethyl; and combinations thereof.

Also included are substituted forms of the foregoing groups in which some or all of the hydrogen atoms are substituted by a moiety containing a heteroatom such as oxygen, sulfur, nitrogen or halogen, or some carbon is replaced by a moiety containing a heteroatom such as oxygen, sulfur or nitrogen, so that the group may contain a hydroxyl moiety, cyano moiety, nitro moiety, mercapto moiety, carbonyl moiety, ether bond, ester bond, sulfonic acid ester bond, carbonate moiety, lactone ring, sultone ring, carboxylic anhydride or haloalkyl moiety.

A pair of $R^{101}$ and $R^{102}$ may bond together to form a ring with the sulfur atom to which they are attached. Preferred are those rings of the structure shown below.

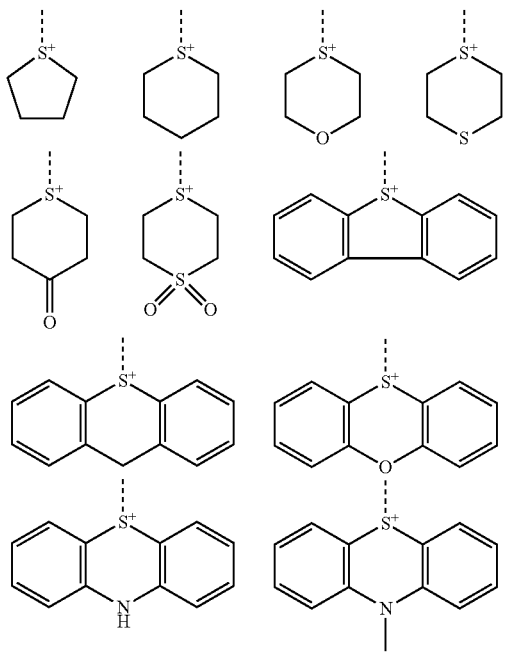

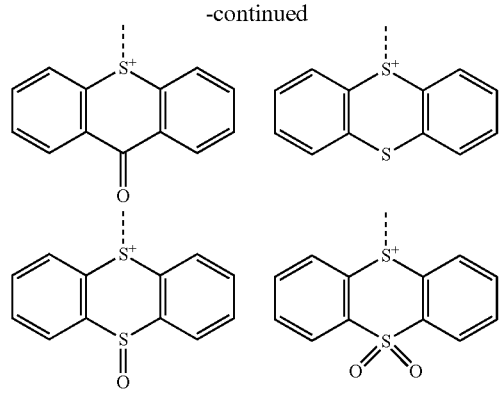

Herein, the broken line denotes a point of attachment to $R^{103}$.

Examples of the cation in the sulfonium salt having formula (1-1) are shown below, but not limited thereto.

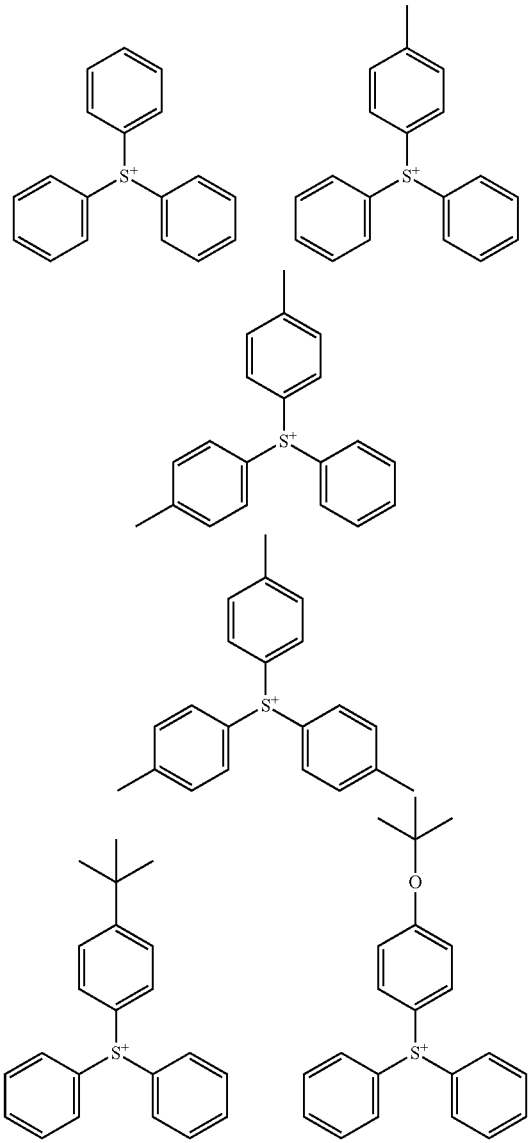

-continued
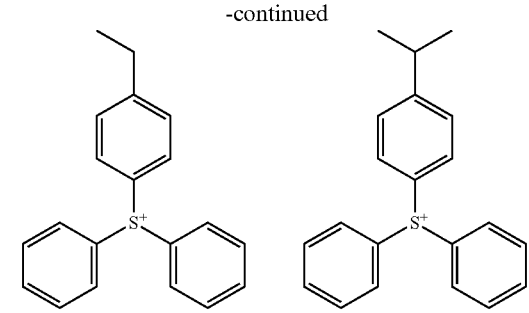
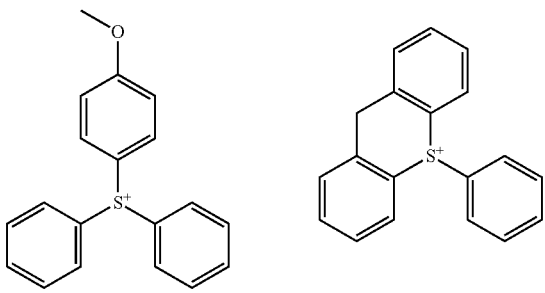
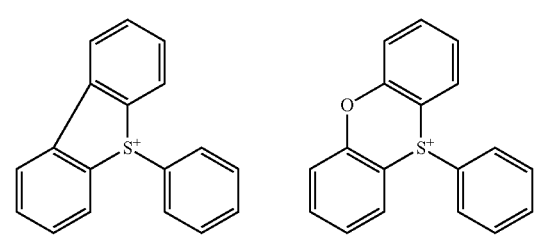
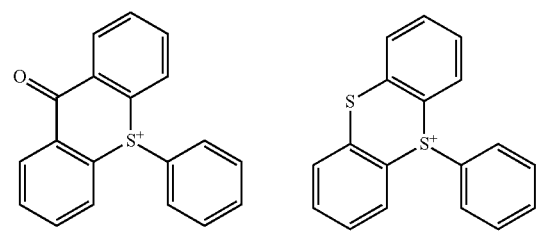
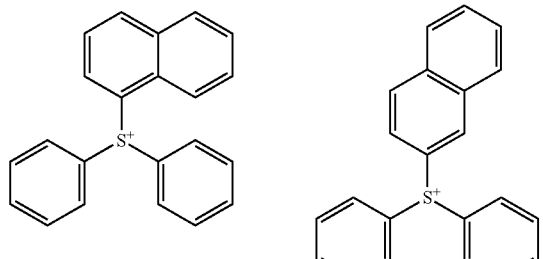
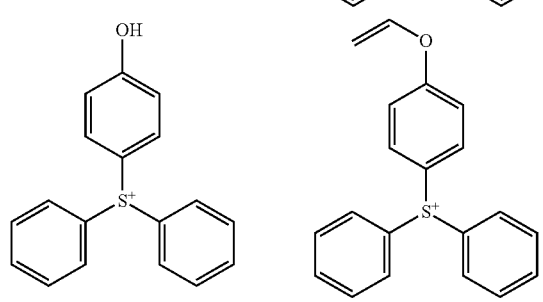
-continued
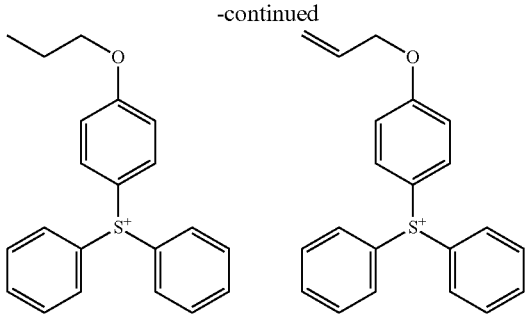
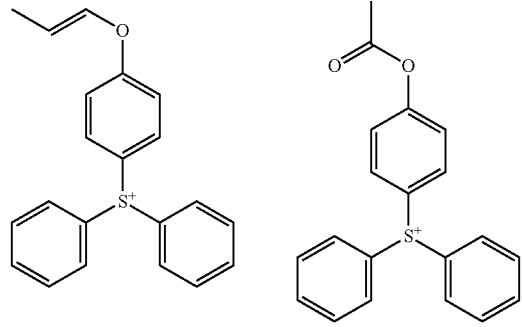
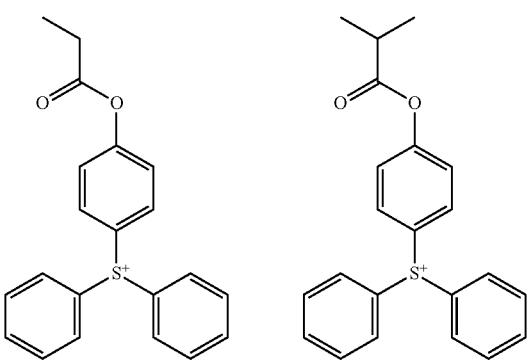
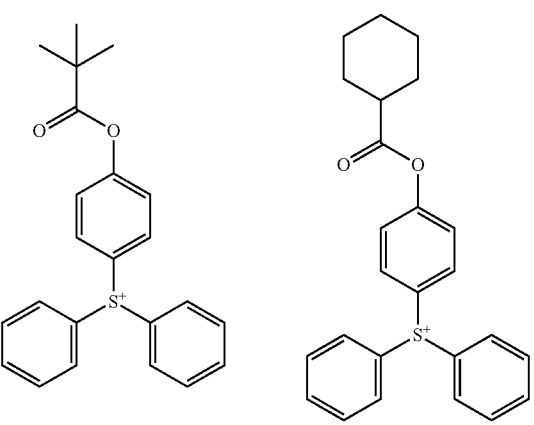

337
-continued
338
-continued
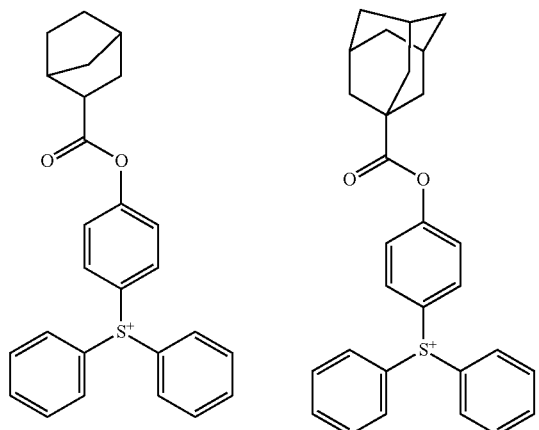
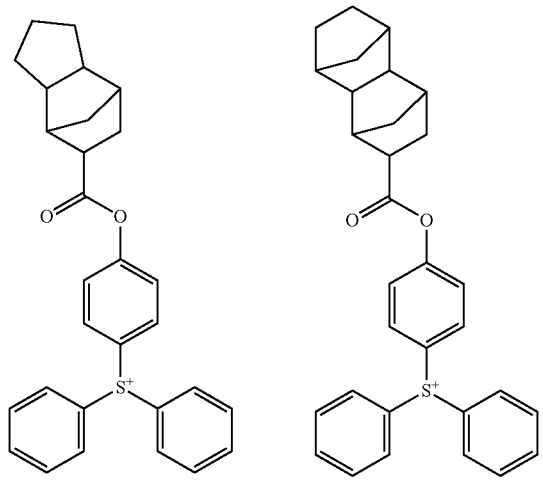
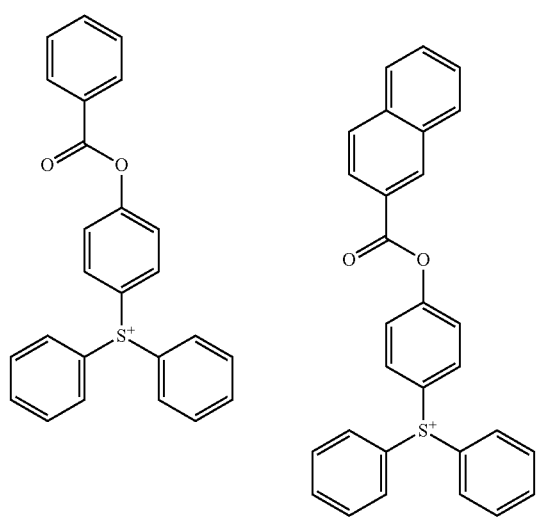
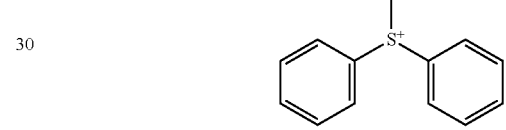
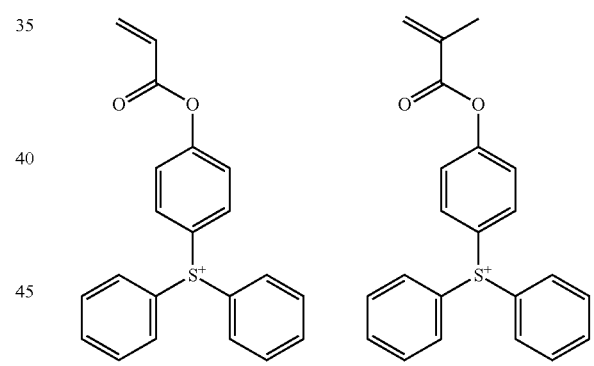
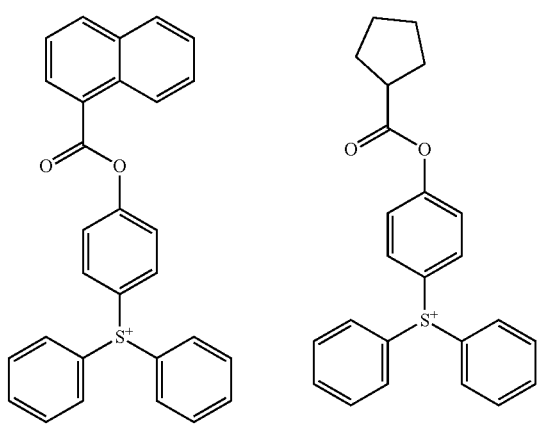
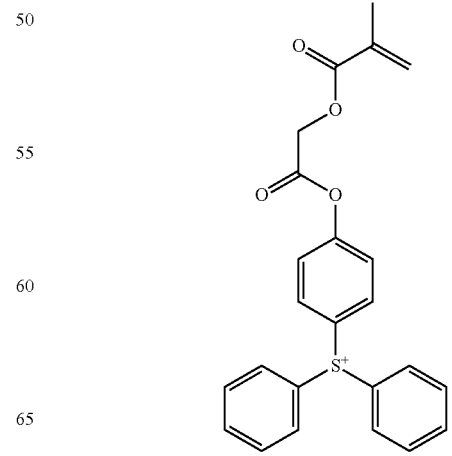

339
-continued
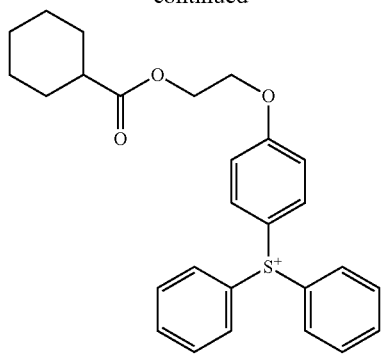
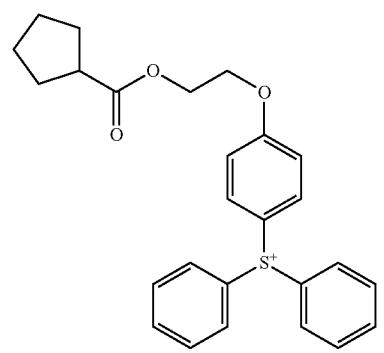
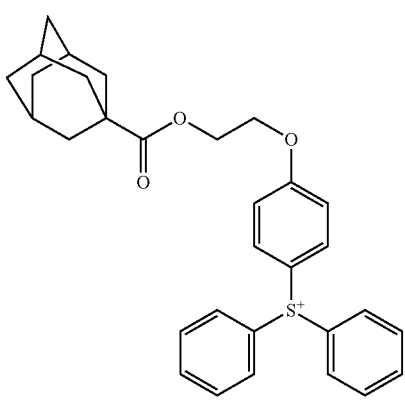
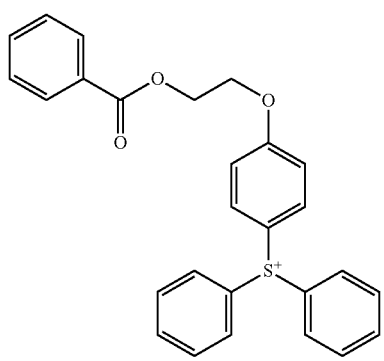
340
-continued
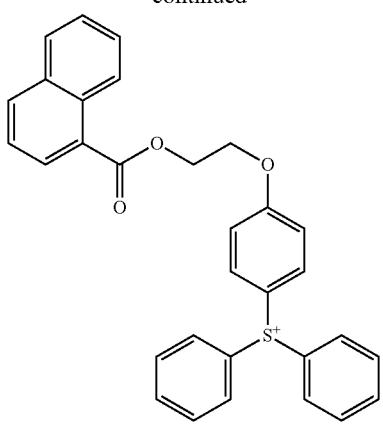
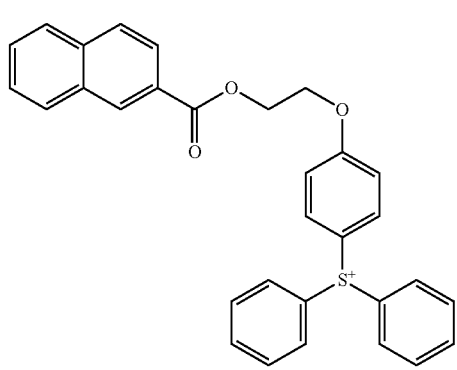
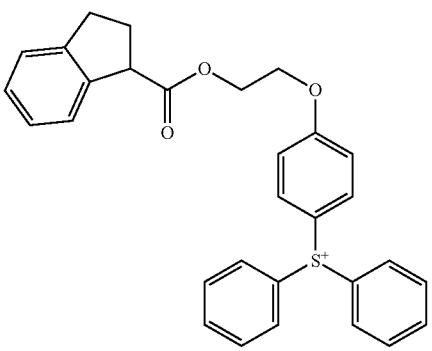
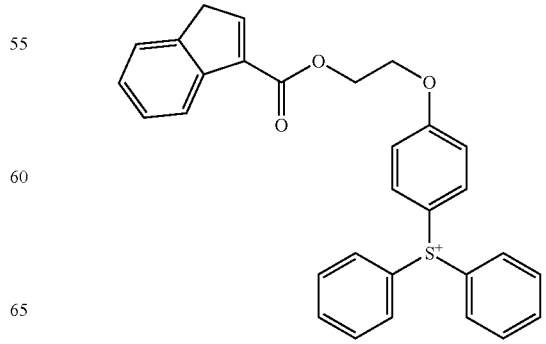

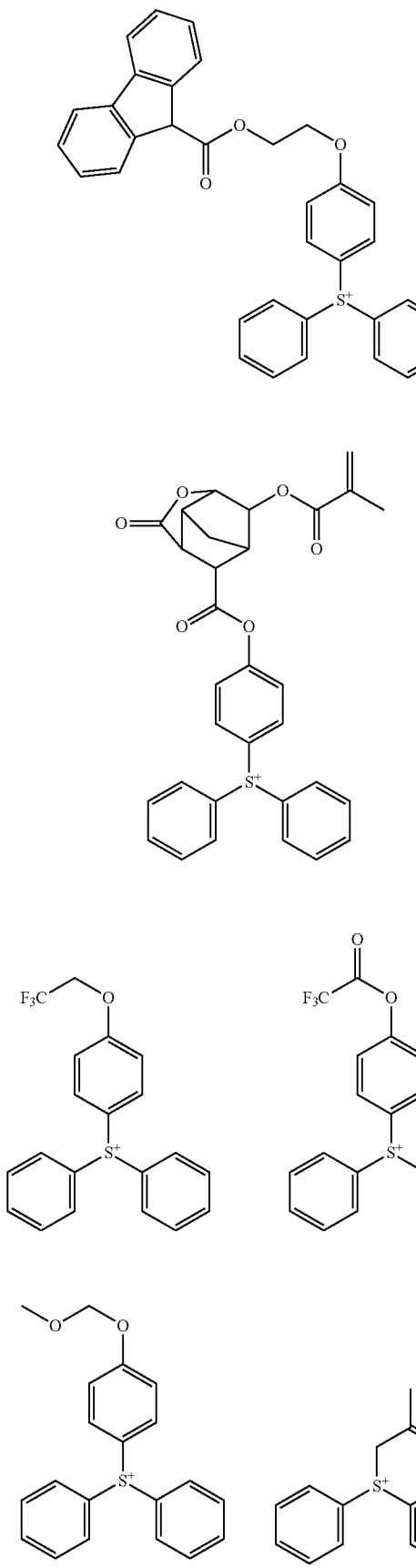
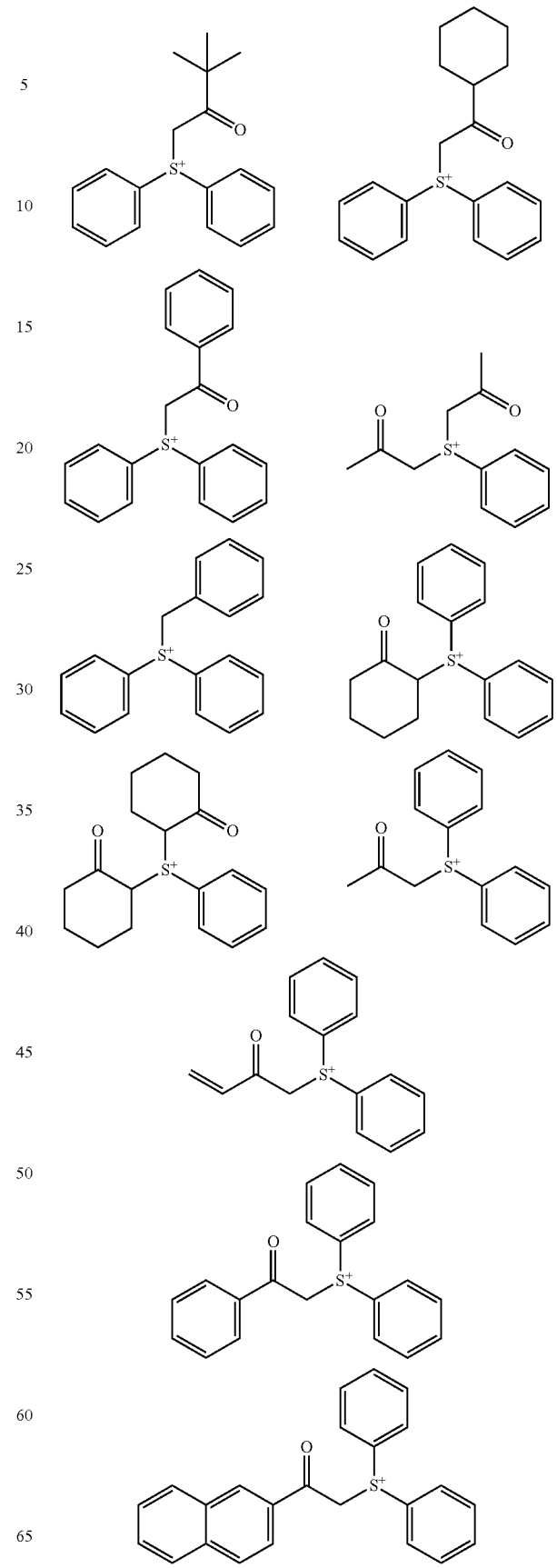

-continued
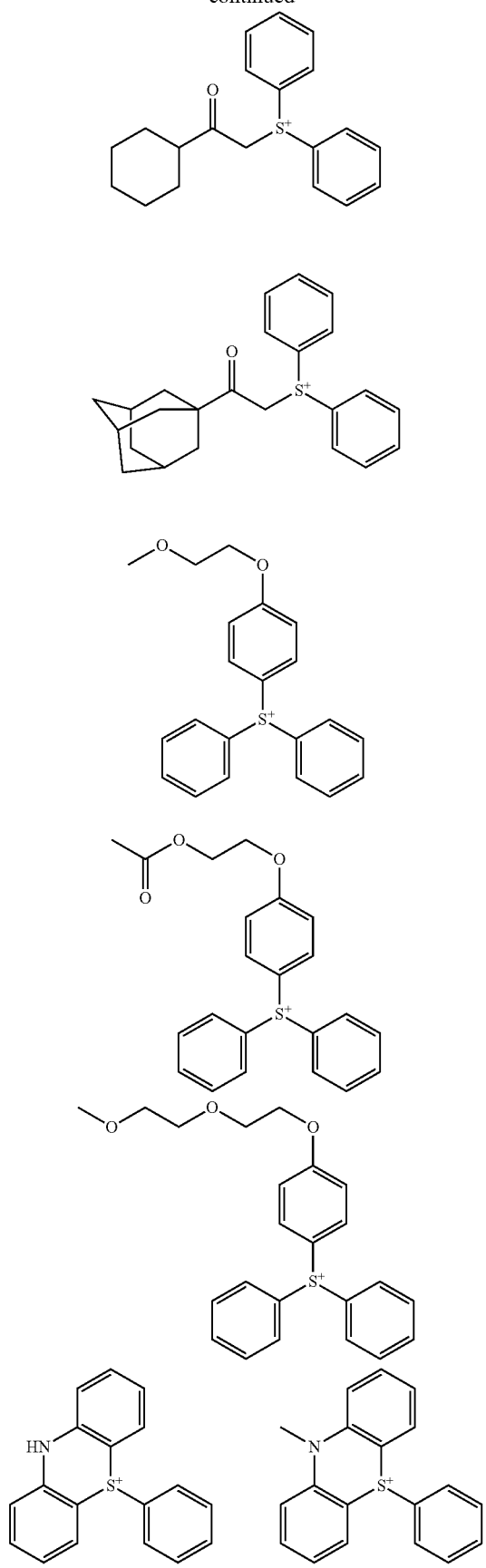
-continued
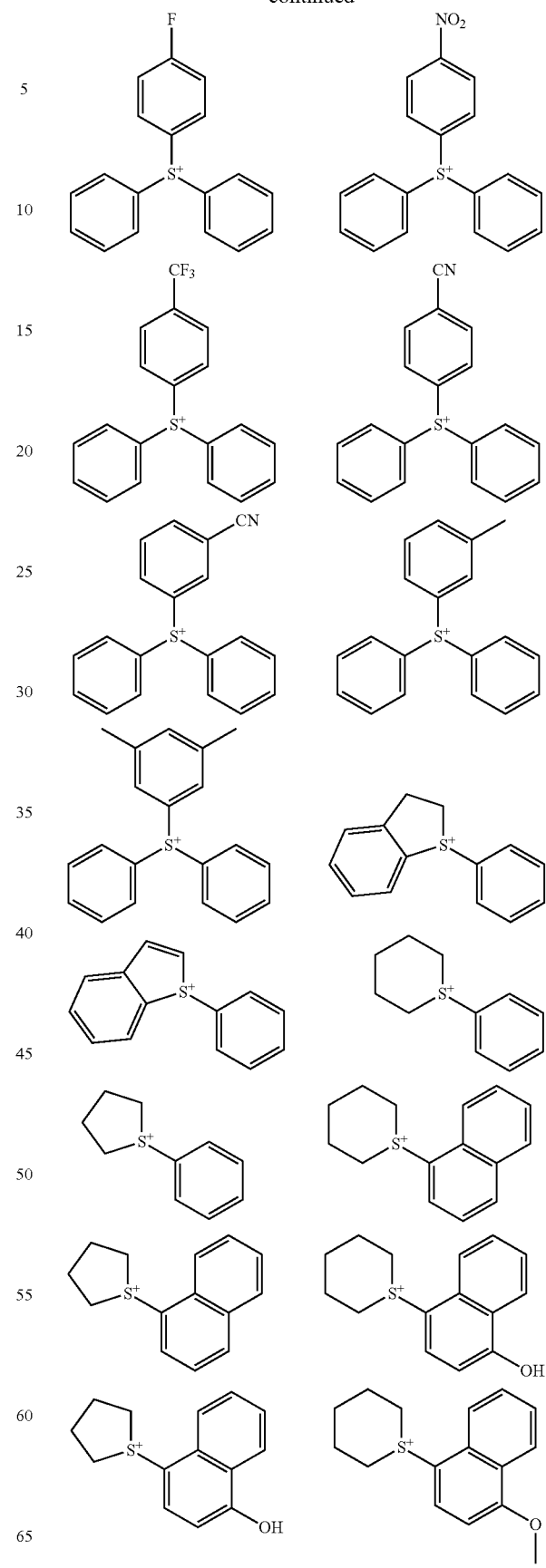

-continued
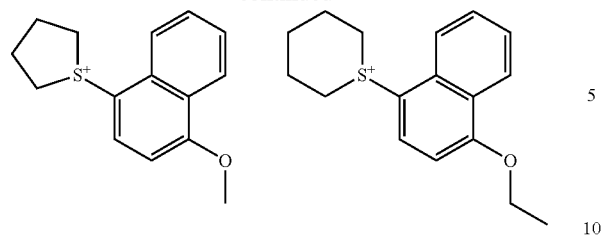
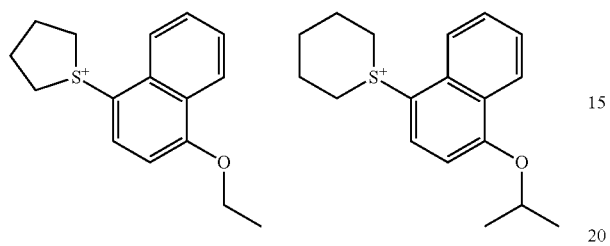
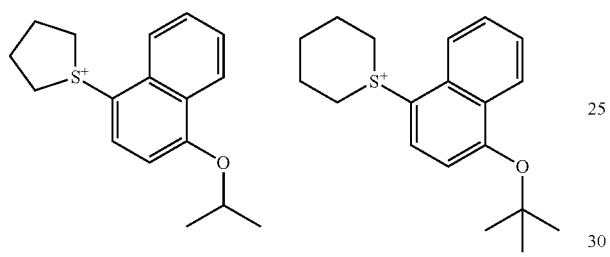
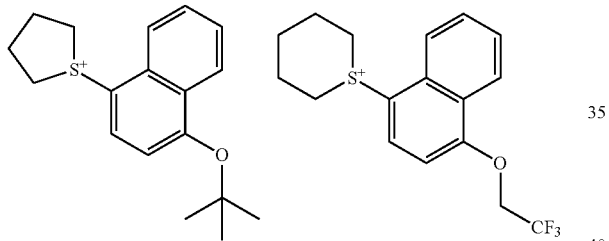
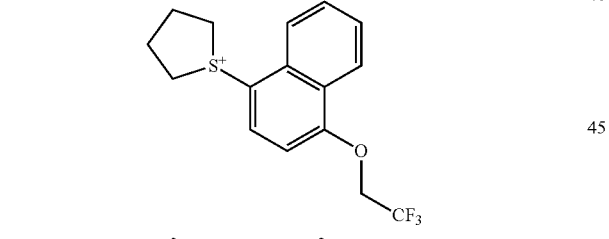
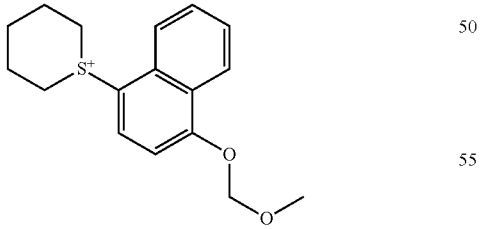
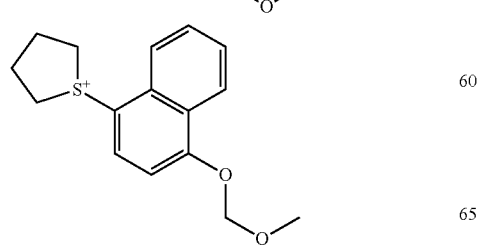
-continued
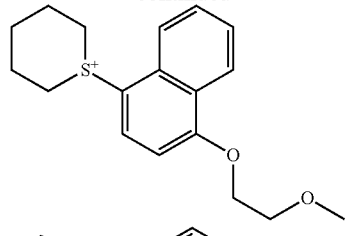
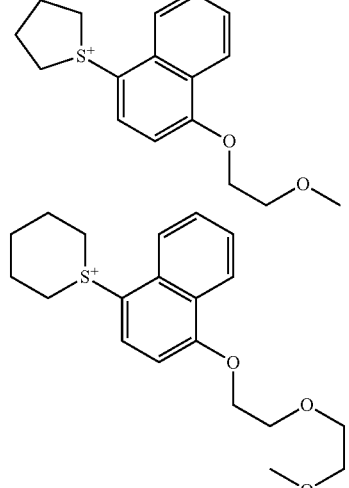
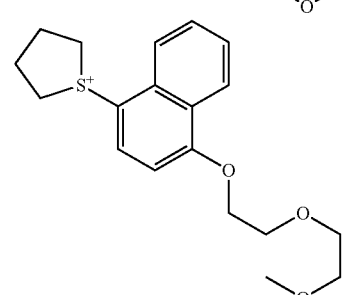
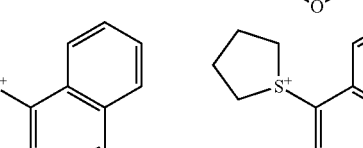
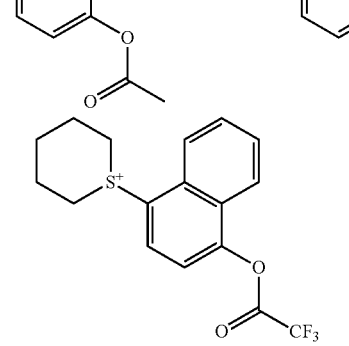
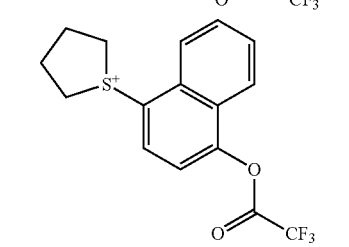

347
-continued
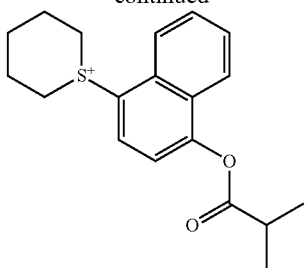
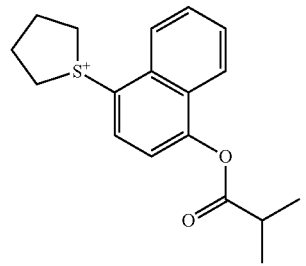
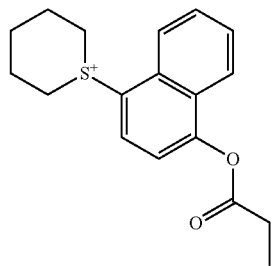
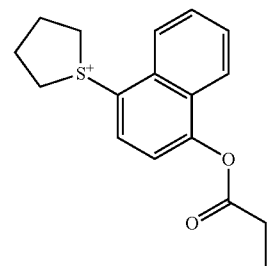
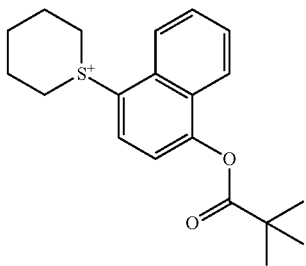
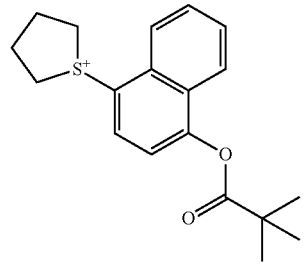
348
-continued
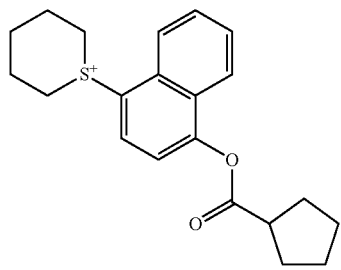
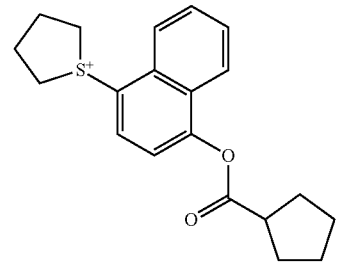
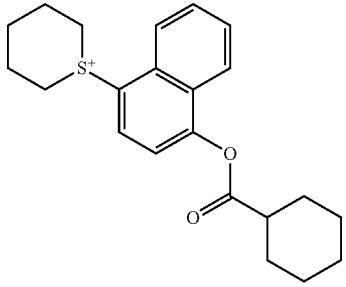
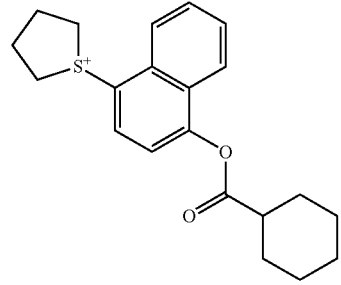
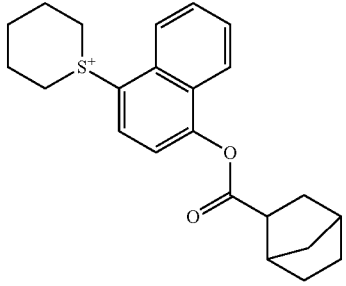
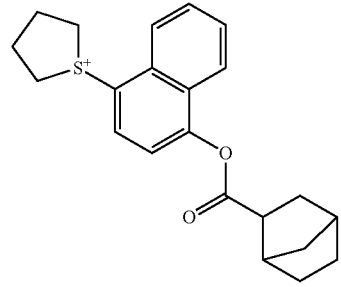

349
-continued
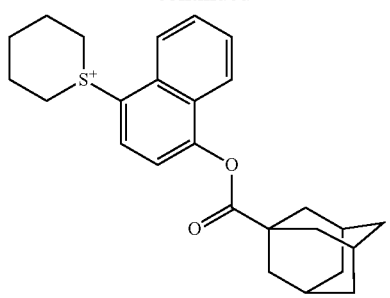
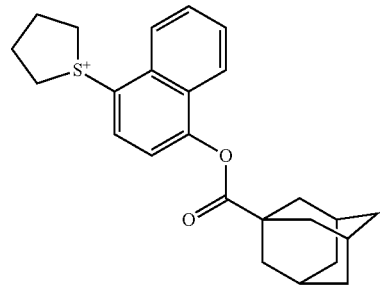
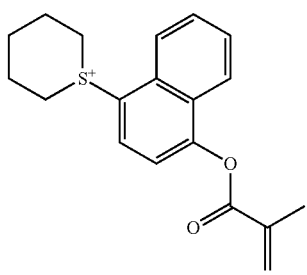
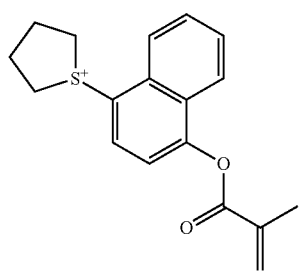
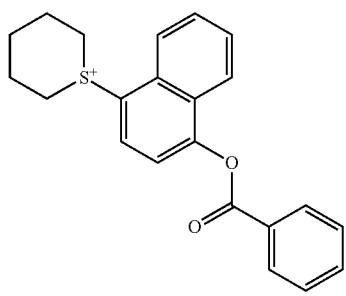
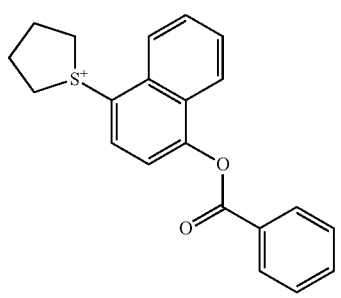
350
-continued
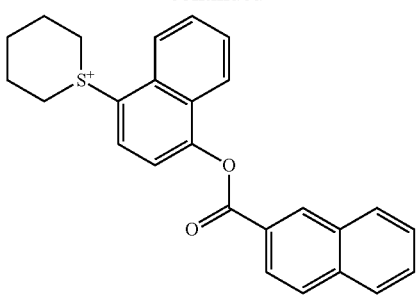
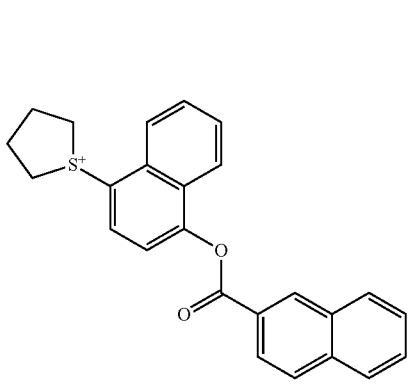
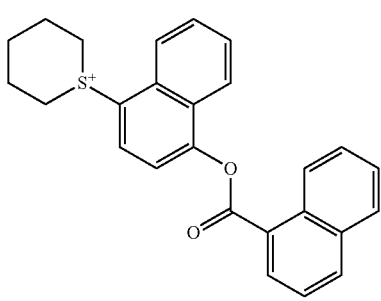
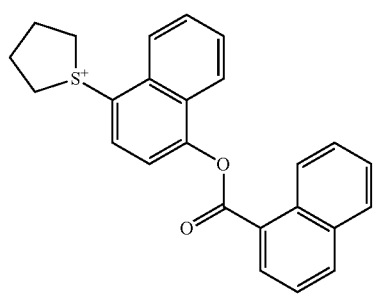
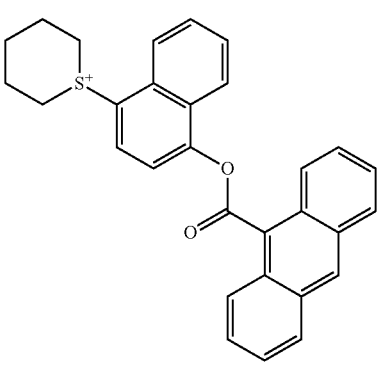

351
-continued
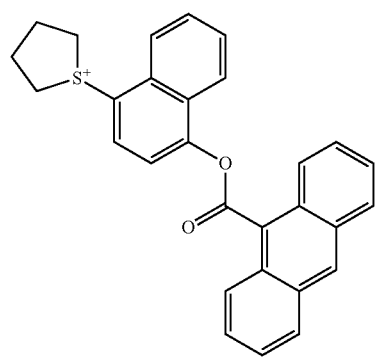
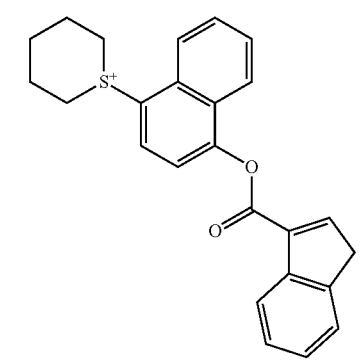
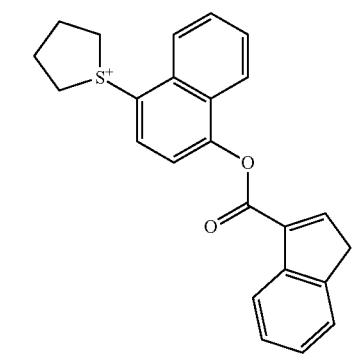
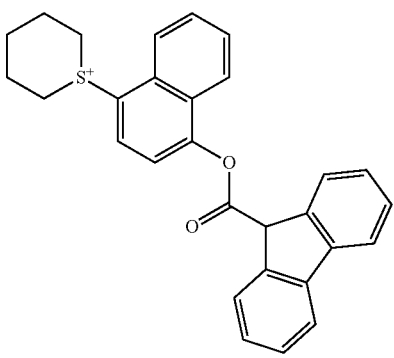
352
-continued
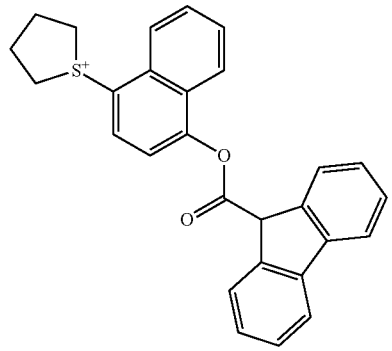
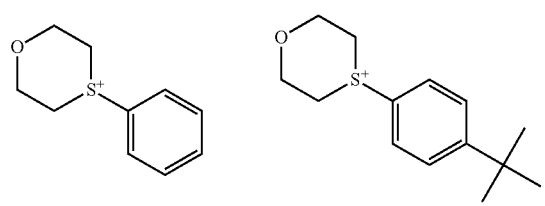
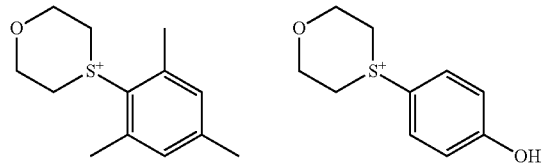
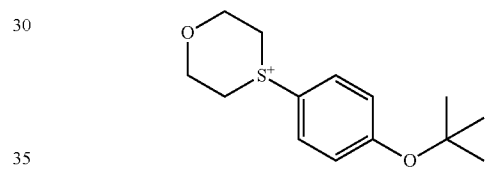
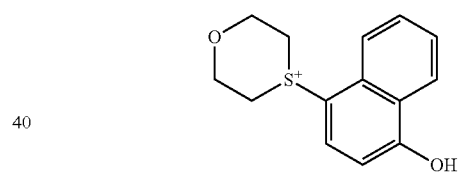
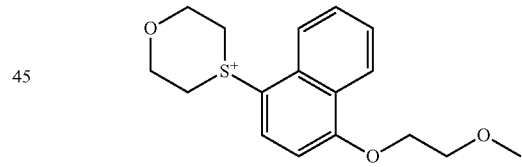
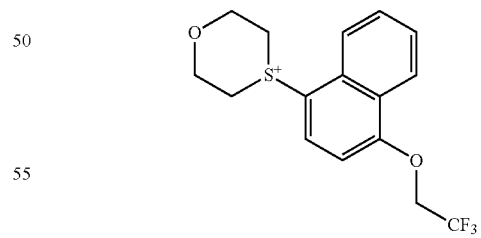
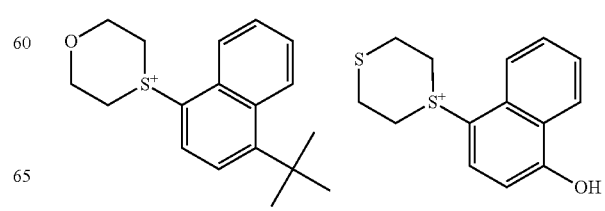

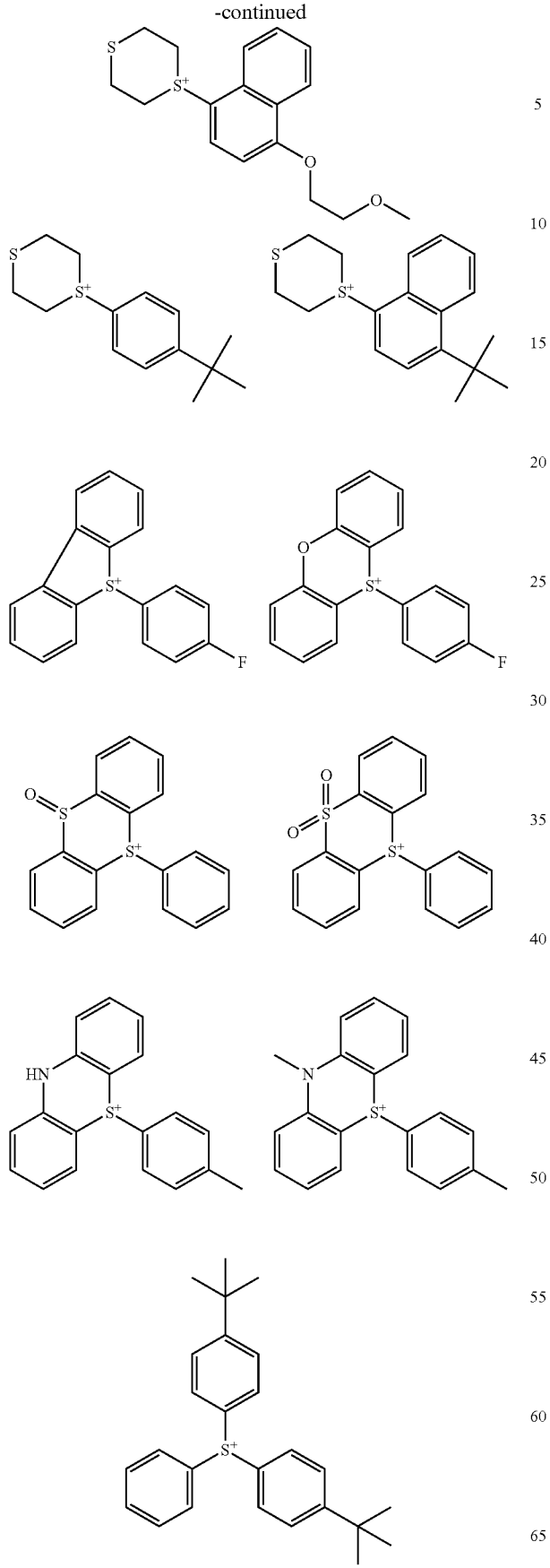
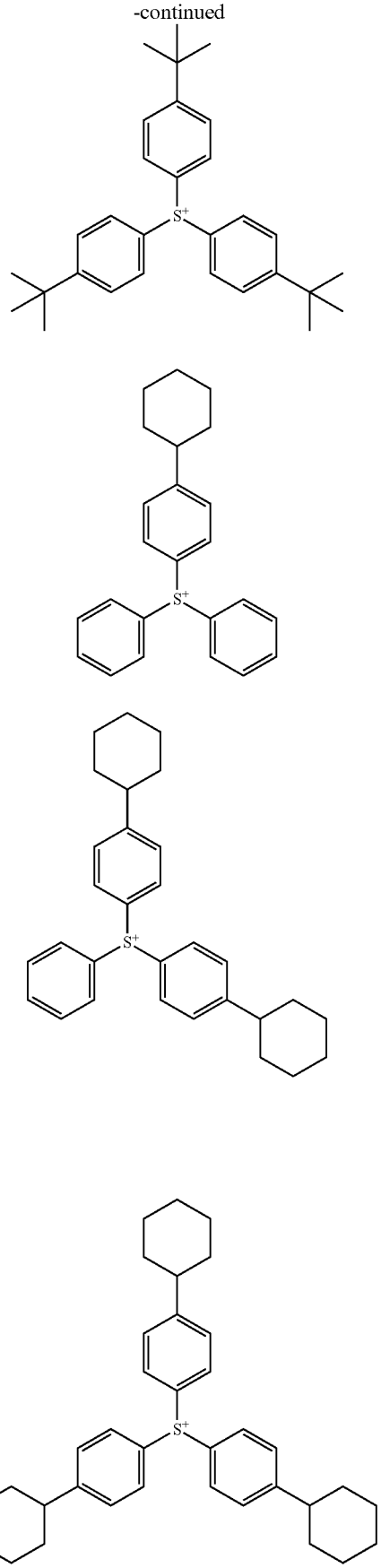

355
-continued
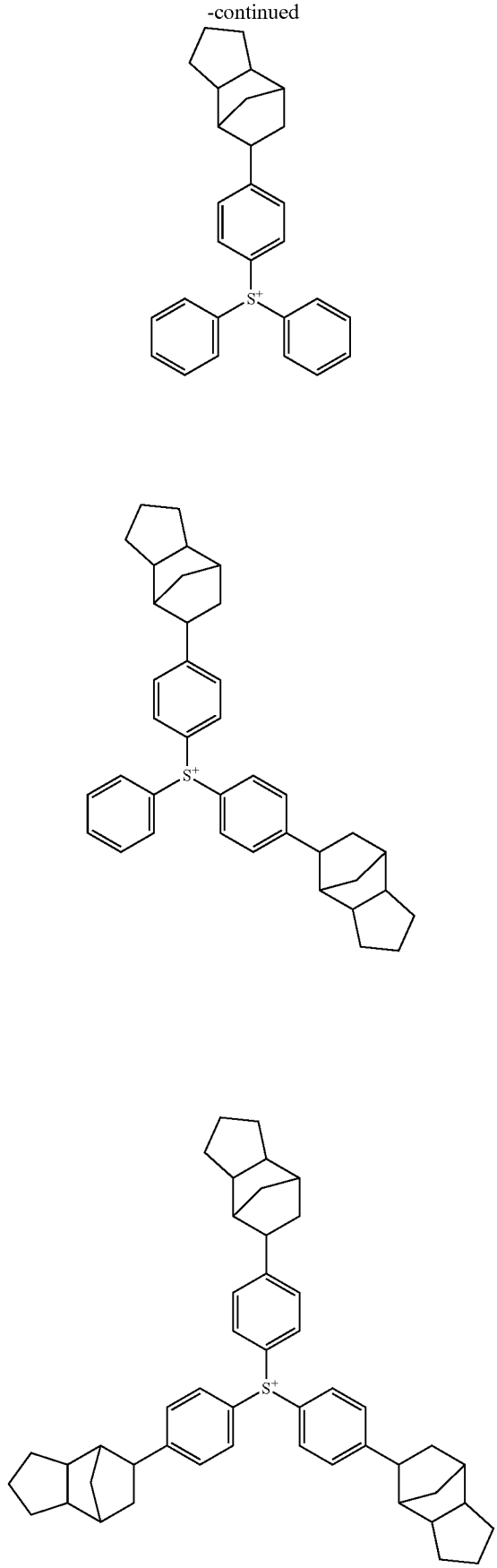
356
-continued
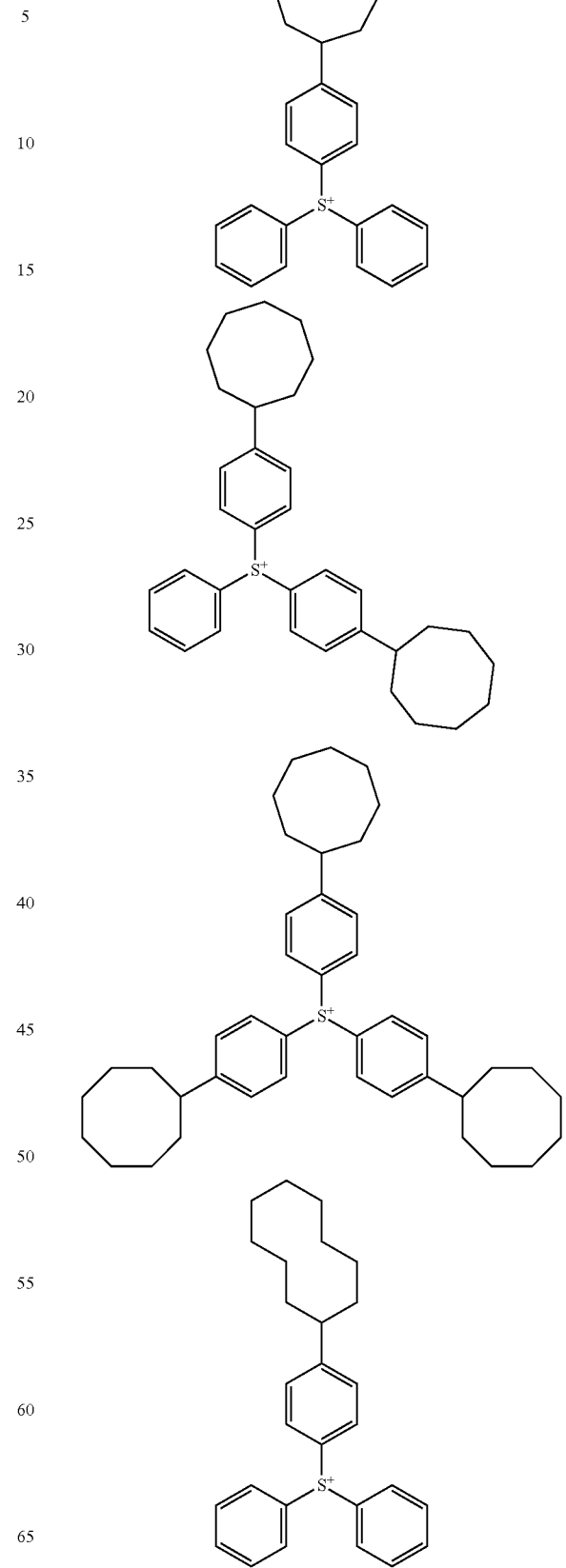

357
-continued
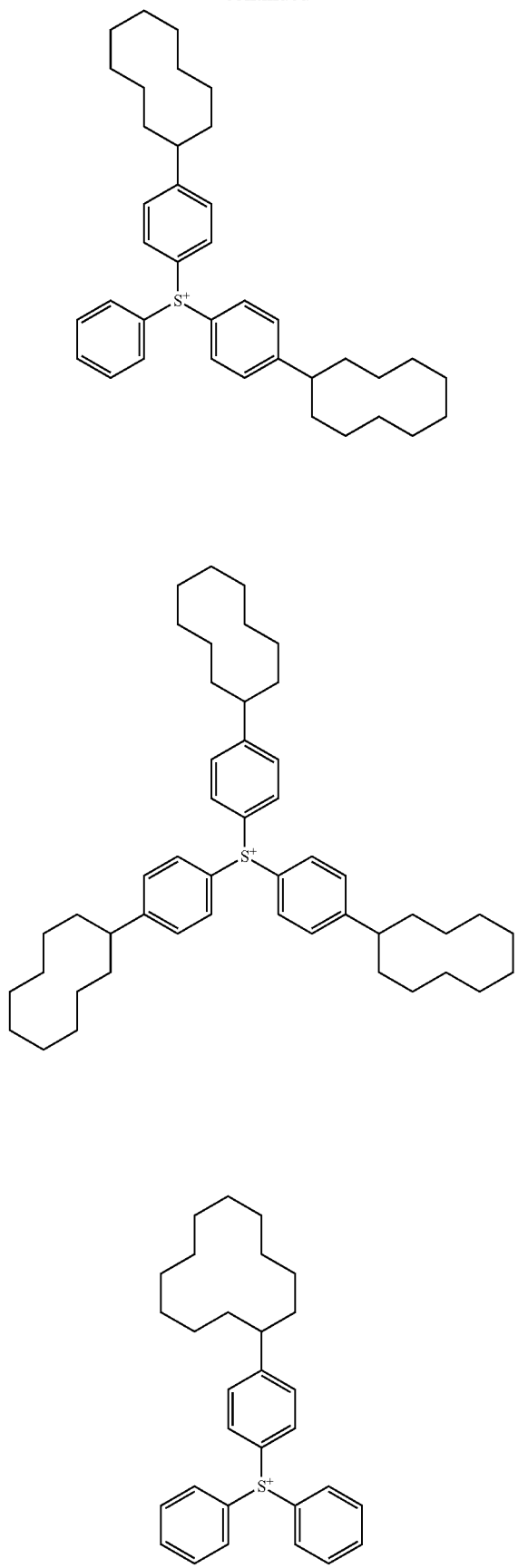
358
-continued
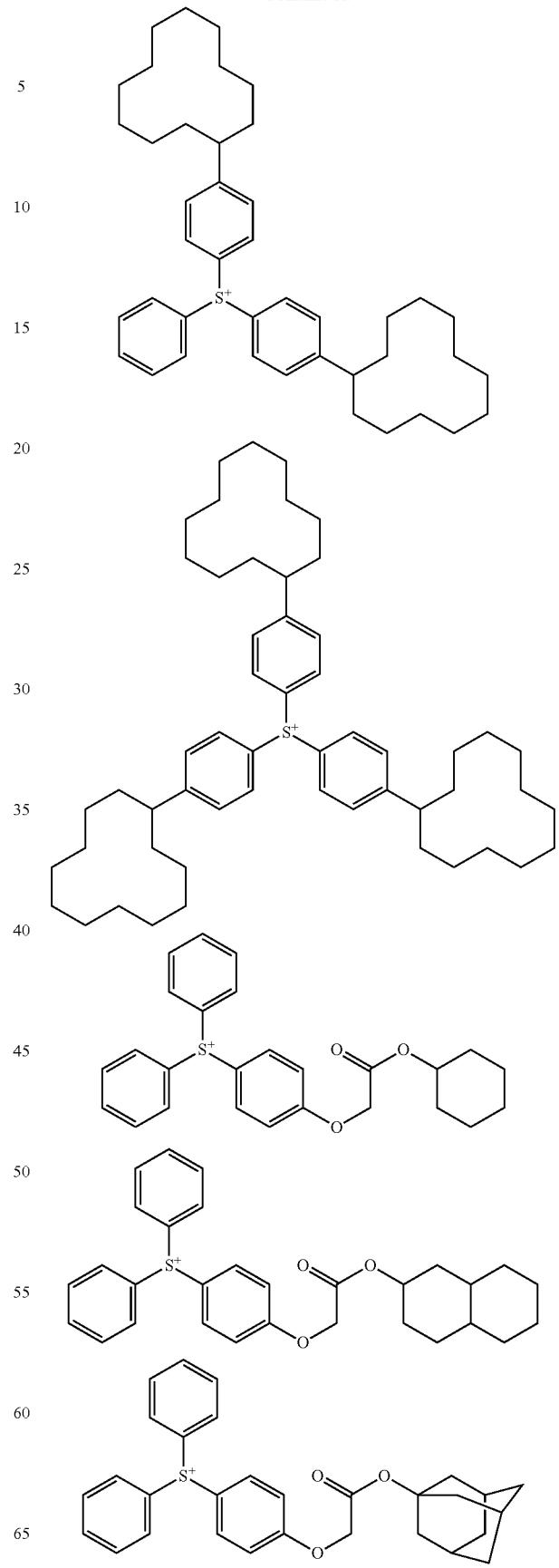

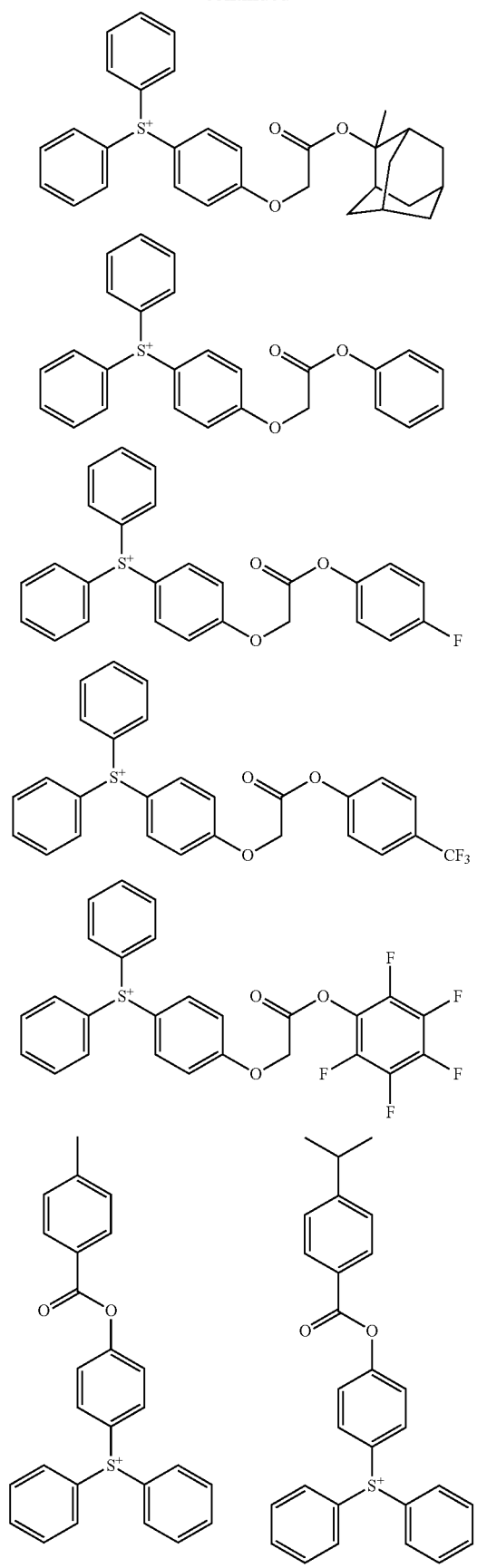
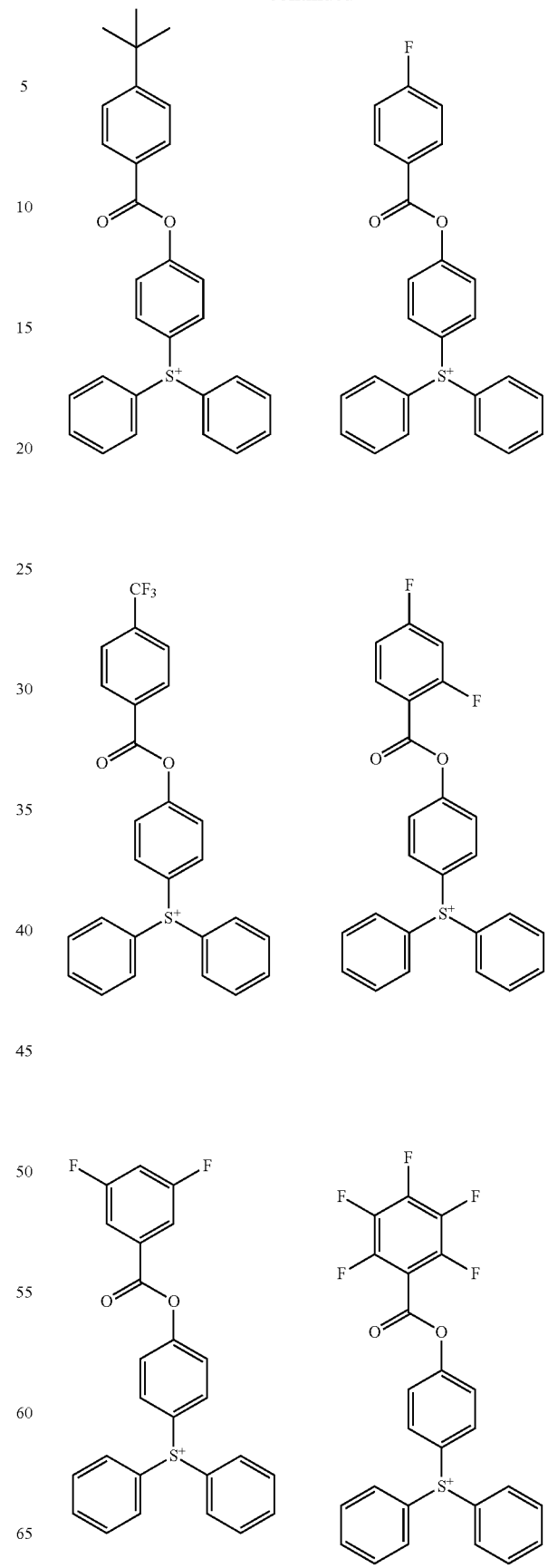

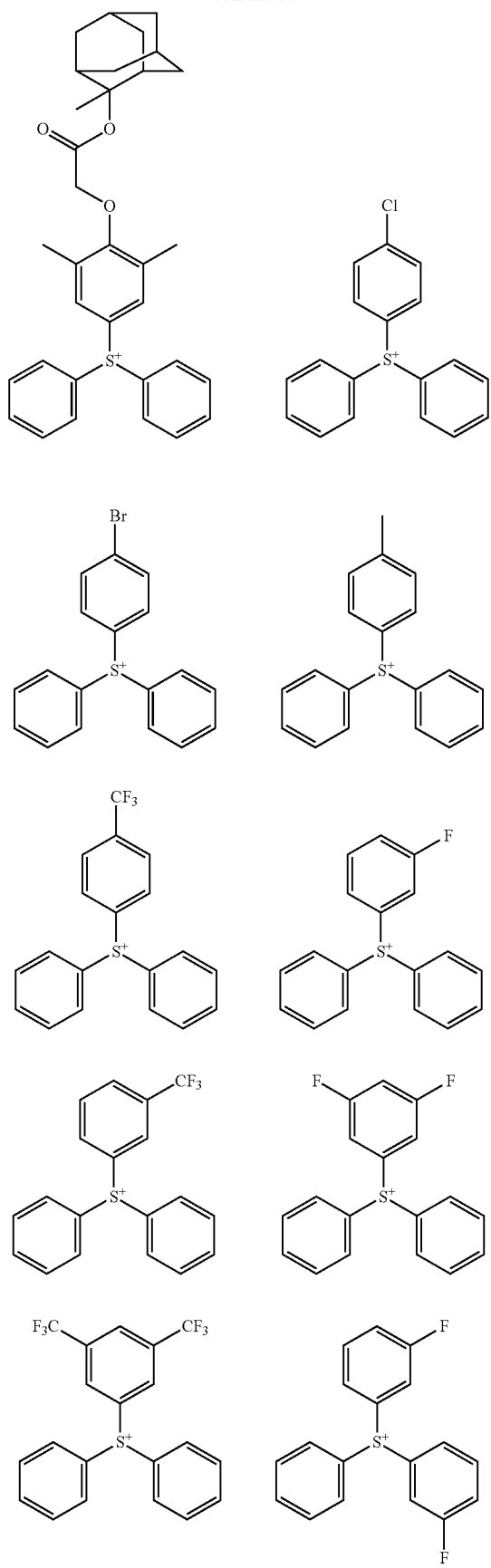
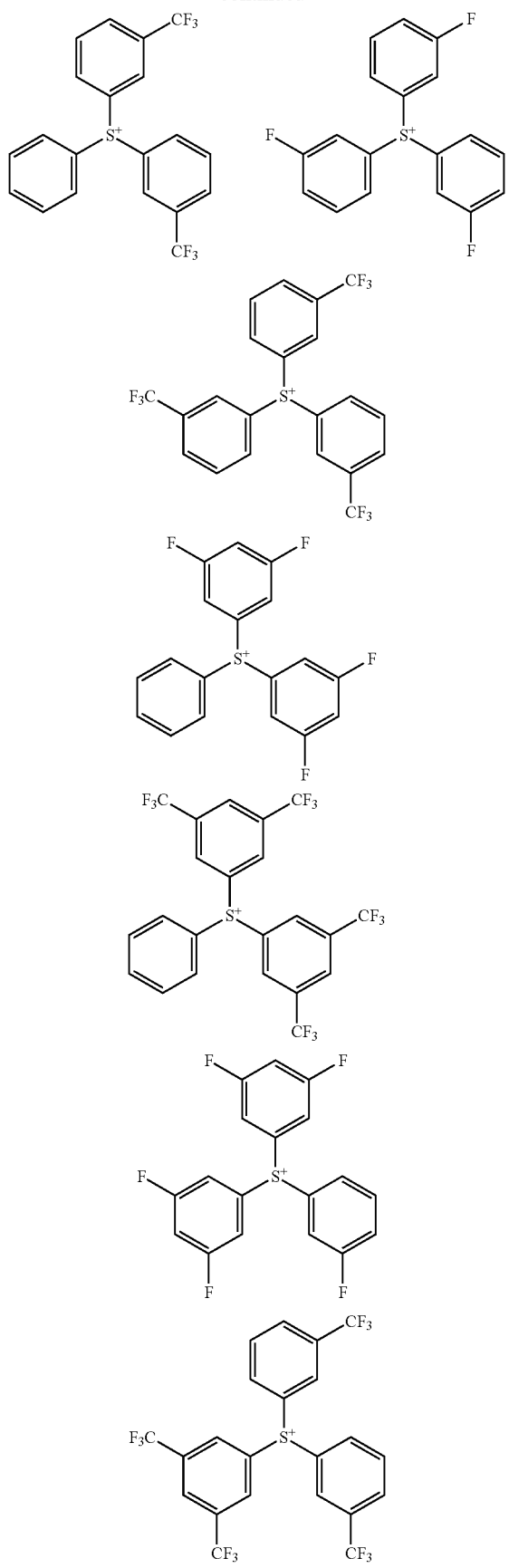

363
-continued
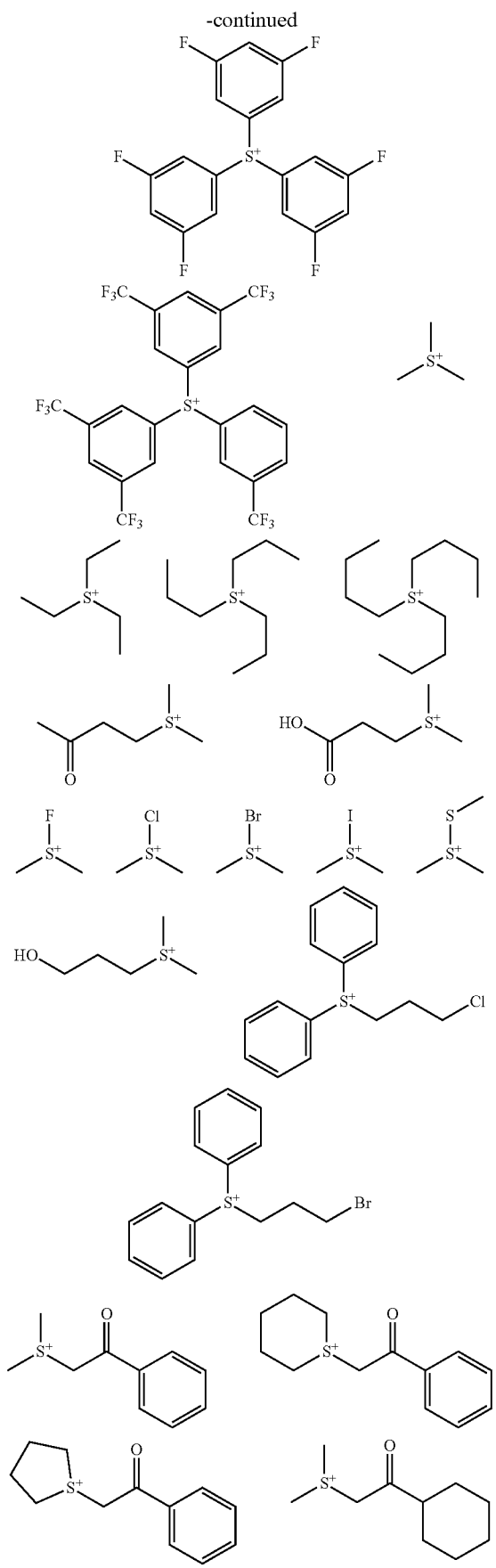
364
-continued
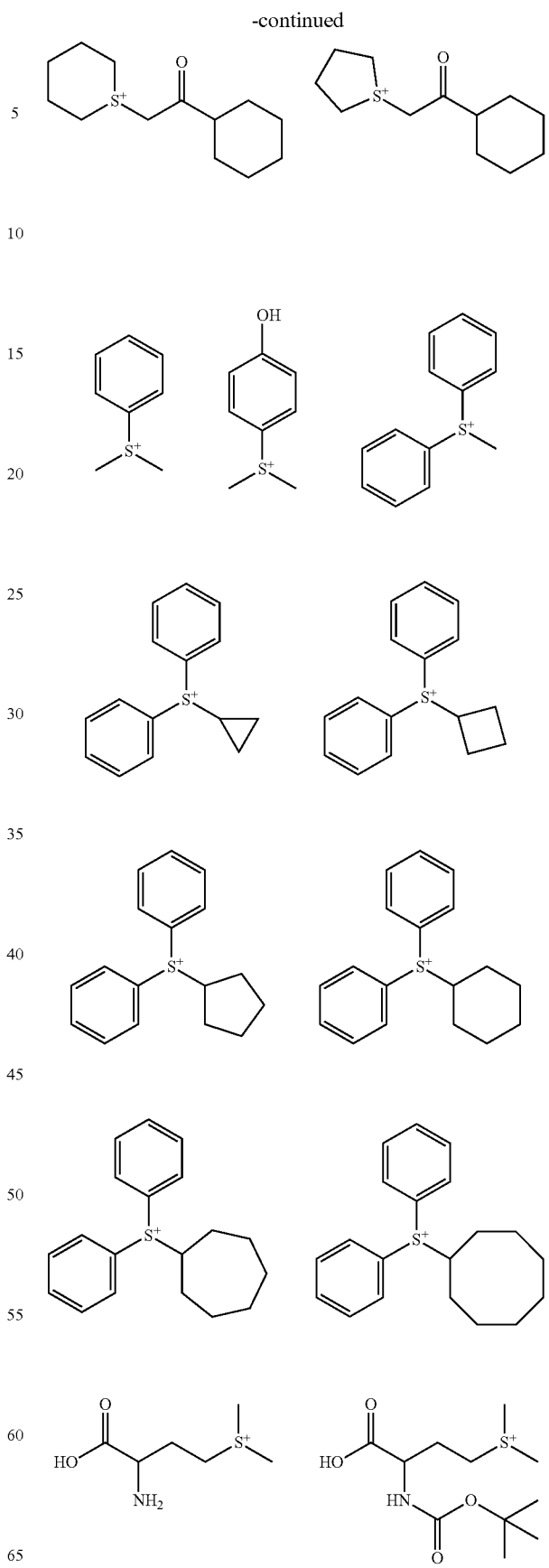

Examples of the cation in the iodonium salt having formula (1-2) are shown below, but not limited thereto.
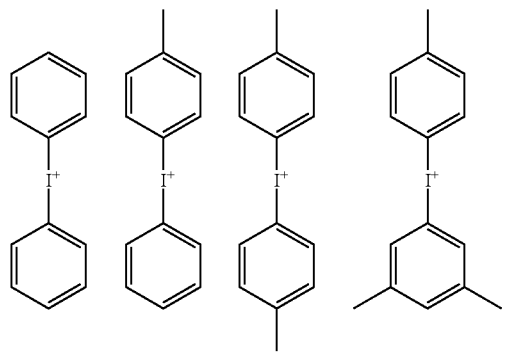
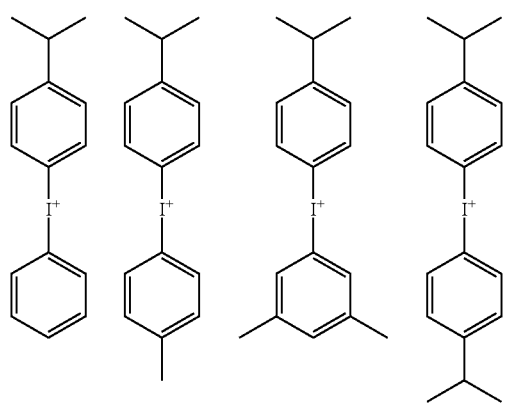
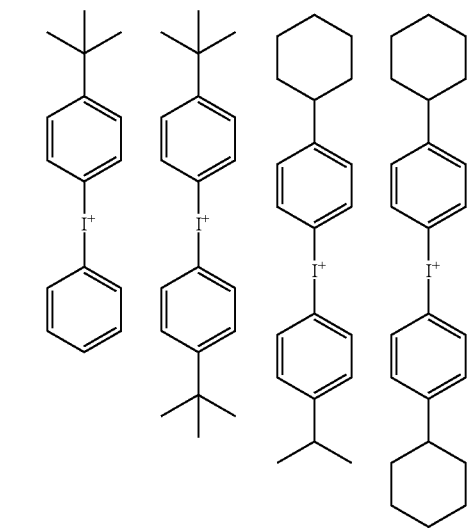
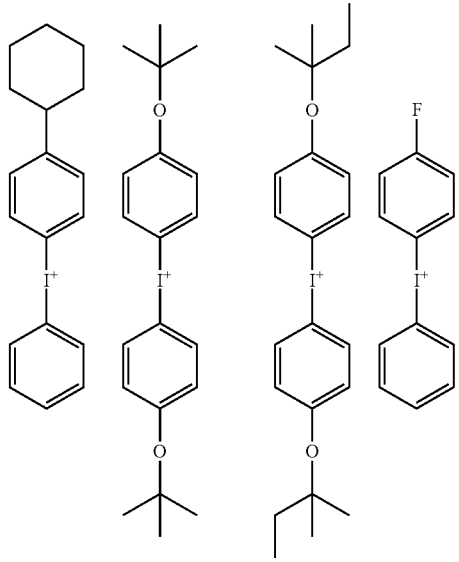
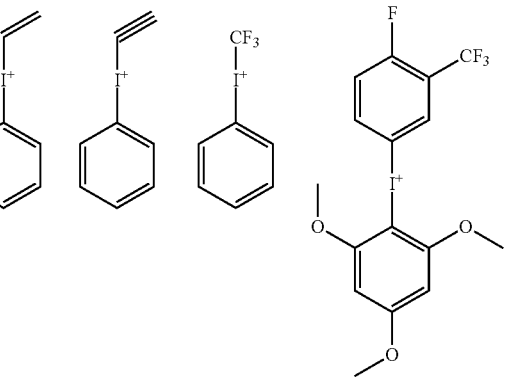
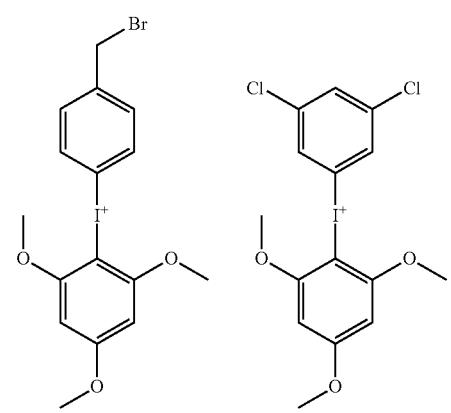

-continued

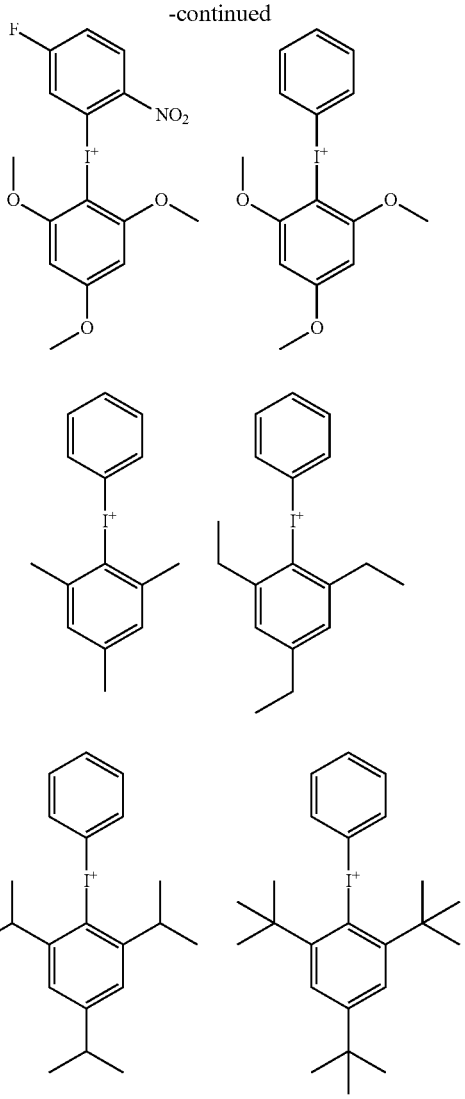

In formulae (1-1) and (1-2), $X_a^-$ is an anion of the following formula (1A), (1B), (1C) or (1D).

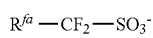
(1A)
$$R^{fa}-CF_2-SO_3^-$$

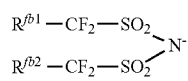
(1B)

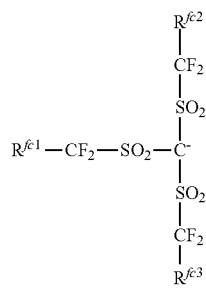
(1C)

-continued

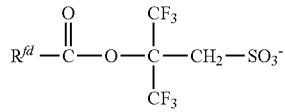
(1D)

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof areas will be exemplified later for hydrocarbyl group $R^{111}$ in formula (1A').

Of the anions of formula (1A), a structure having formula (1A') is preferred.

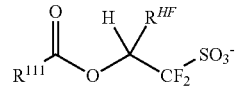
(1A')

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic. Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl; $C_7$-$C_{38}$ aralkyl groups such as benzyl and diphenylmethyl; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608. JP-A 2012-041320, JP-A 2012-106986, and JP-A 2012-153644.

Examples of the anion having formula (1A) are shown below, but not limited thereto.

369
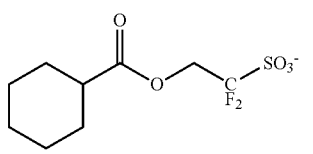
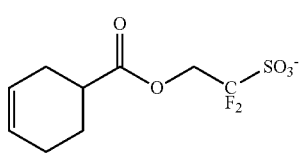
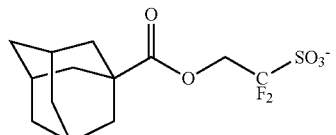
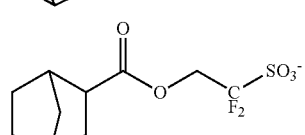
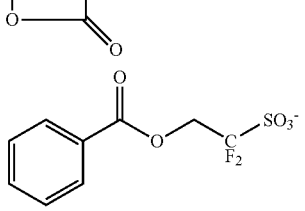
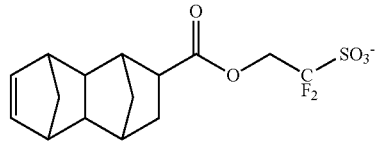
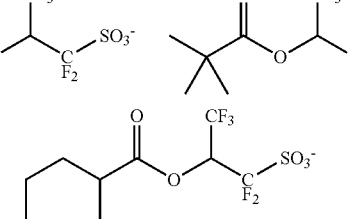
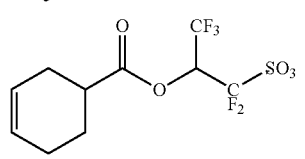
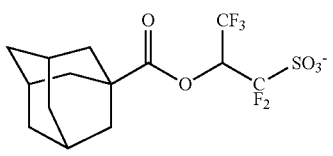
370
-continued
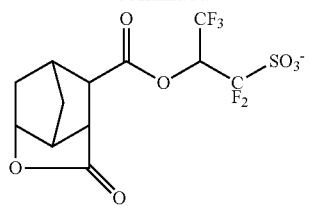
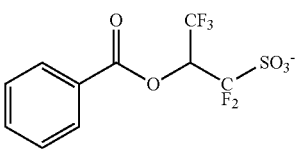
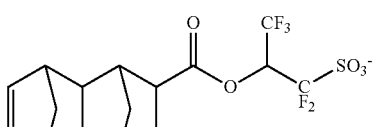
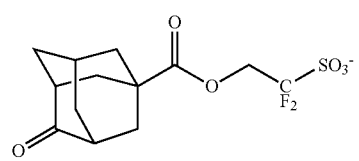
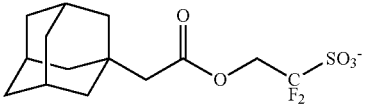
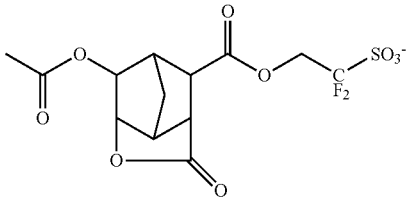
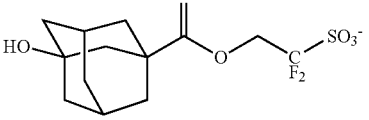
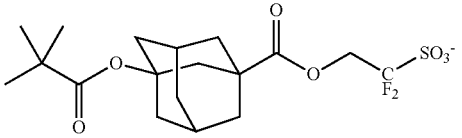
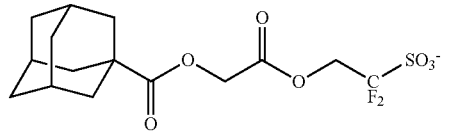
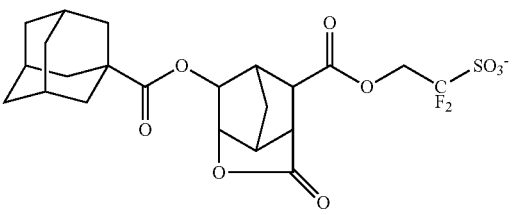

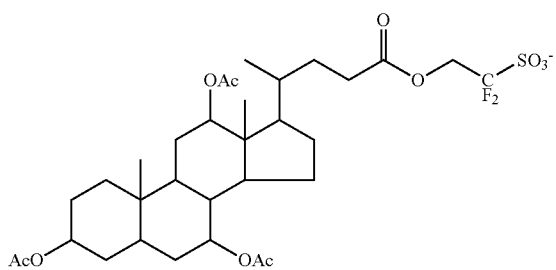

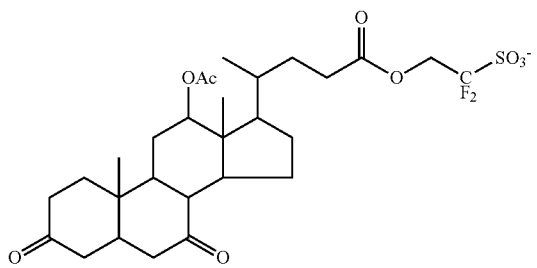

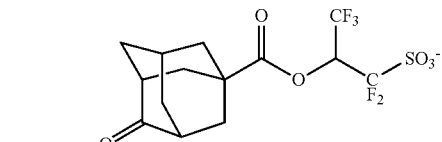

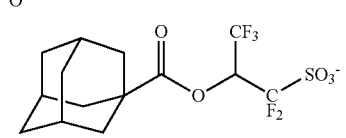

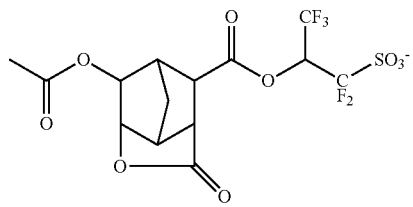

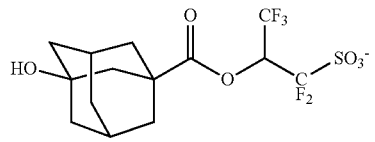

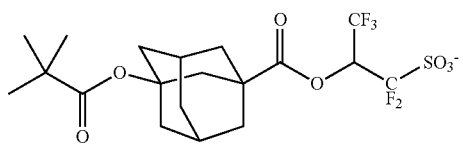

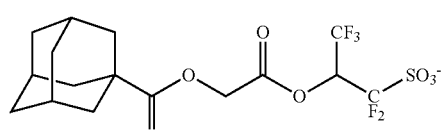

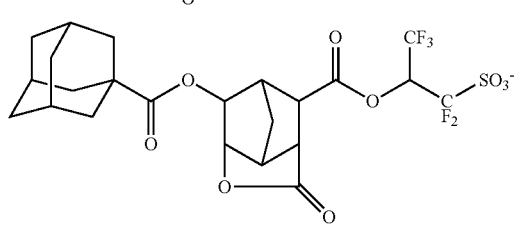

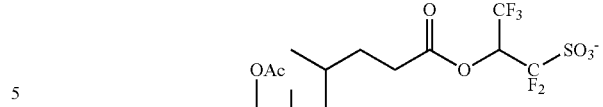

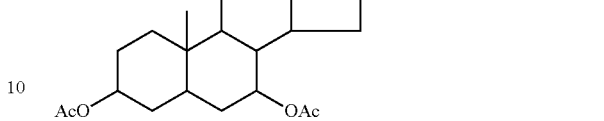

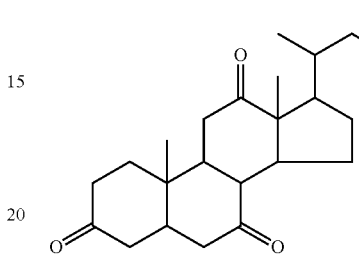

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C$—$SO_2$—$CF_2$—) to which they are attached, and the ring-forming pair is preferably a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

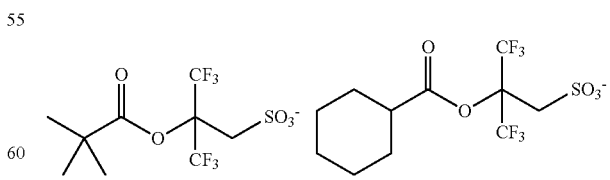

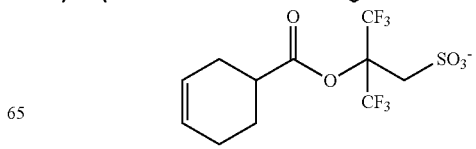

-continued

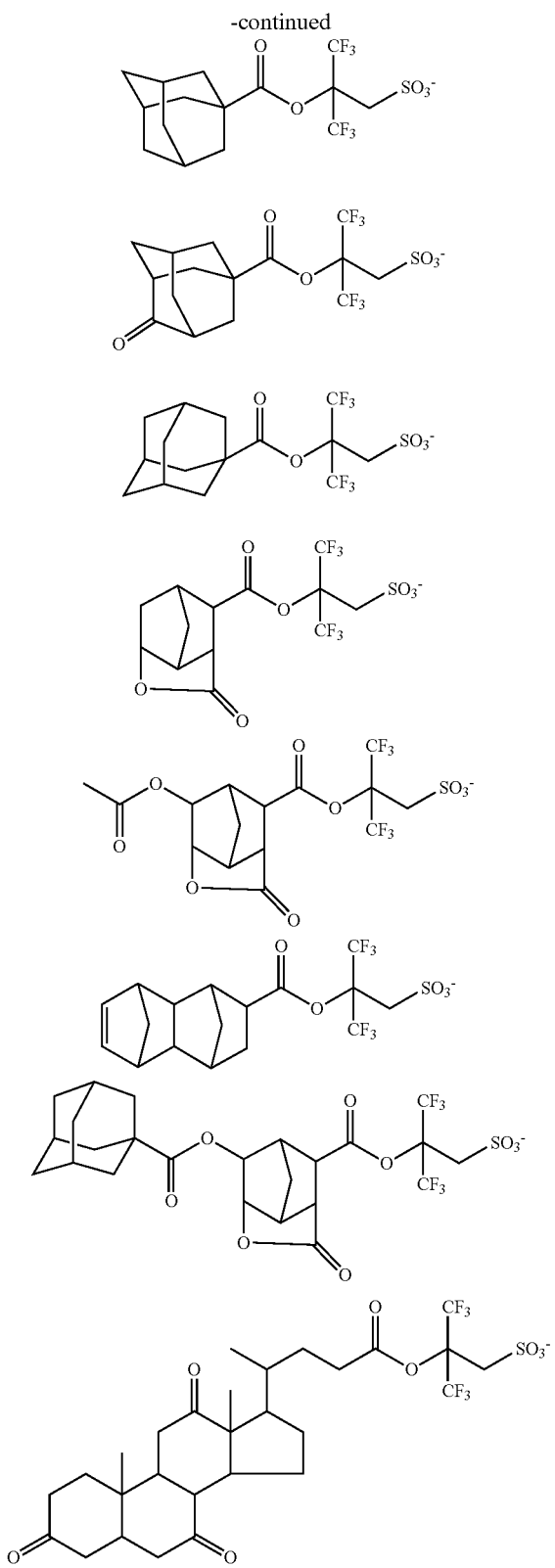

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

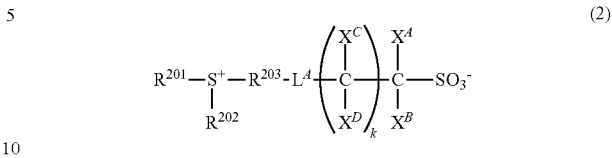

(2)

In formula (2), $R^{201}$ and $R^{202}$ are each independently halogen or a $C_1$-$C_{30}$ hydrocarbyl group which may contain a heteroatom. $R^{03}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2.6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutyhnaphthyl, sea-butylnaphthyl, tert-butylnaphthyl, and anthracenyl; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

The hydrocarbylene group $R^0$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_3$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene and tert-butylnaphthylene; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Of the heteroatoms, oxygen is preferred.

In formula (2), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), k is an integer of 0 to 3.

Of the PAGs having formula (2), those having formula (2') are preferred.

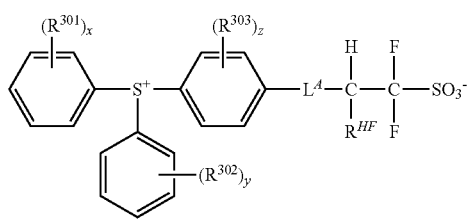

(2')

In formula (2'), $L^A$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the solvent. Also those having an anion of formula (2') are especially preferred because of extremely reduced acid diffusion.

When the resist composition contains the acid generator of addition type, its content is preferably 0.1 to 50 parts by weight, and more preferably 1 to 40 parts by weight per 100 parts by weight of the base polymer. When the base polymer contains recurring units (f) and/or the resist composition contains the acid generator of addition type, the resist composition functions as a chemically amplified resist composition.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, crosslinker, and quencher other than the cyclic ammonium salt compound may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

In the case of negative resist compositions, a negative pattern may be formed by adding a crosslinker to reduce the dissolution rate of a resist film in exposed area. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer. The crosslinker may be used alone or in admixture.

The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer. The water repellency improver may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohol may be used alone or in admixture.

Pattern Forming Process

The resist composition is used in the fabrication of various integrated circuits. Pattern formation using the resist composition may be performed by well-known lithography processes. The process generally involves the steps of applying the resist composition to form a resist film on a substrate, exposing the resist film to high-energy radiation, and developing the exposed resist film in a developer. If necessary, any additional steps may be added.

Specifically, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, MoSi$_2$, or SiO$_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 µm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 mJ/cm$^2$, more preferably about 10 to 100 mJ/cm$^2$. When EB is used as the high-energy radiation, the resist film is exposed thereto directly or through a mask having a desired pattern in a dose of preferably about 0.1 to 100 µC/cm$^2$, more preferably about 0.5 to 50 µC/cm$^2$. It is appreciated that the inventive resist composition is suited in micropatterning using i-line of wavelength 365 nm, KrF excimer laser, ArF excimer laser, EB, EUV, x-ray, soft x-ray, γ-ray or synchrotron radiation, especially in micropatterning using EB or EUV.

Besides the standard exposure, the immersion lithography technique of exposing the resist film while interposing a liquid having a refractive index of at least 1.0, typically water, between the resist film and a projection lens is also applicable. In this case, a water-insoluble protective film may be formed on the resist film.

After the exposure, the resist film may be baked (PEB) on a hot plate or in an oven at 30 to 150° C. for 10 seconds to 30 minutes, preferably at 50 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In the case of positive resist, the resist film in the exposed area is dissolved in the developer whereas the resist film in the unexposed area is not dissolved. In this way, the desired positive pattern is formed on the substrate. Inversely in the case of negative resist, the exposed area of resist film is insolubilized whereas the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Quenchers Q-1 to Q-43 used in resist compositions have the structure shown below. They were synthesized by mixing a compound, which was obtained by esterification reaction of a compound having a carboxyl group providing the cation shown below with an amine compound having a tertiary hydroxyl group, with a compound having a 1,1,1,3,3,3-hexafluoro-2-propanol (HFA) group bonded to a trifluoromethyl, hydrocarbylcarbonyl or hydrocarbyloxycarbonyl group providing the anion shown below.

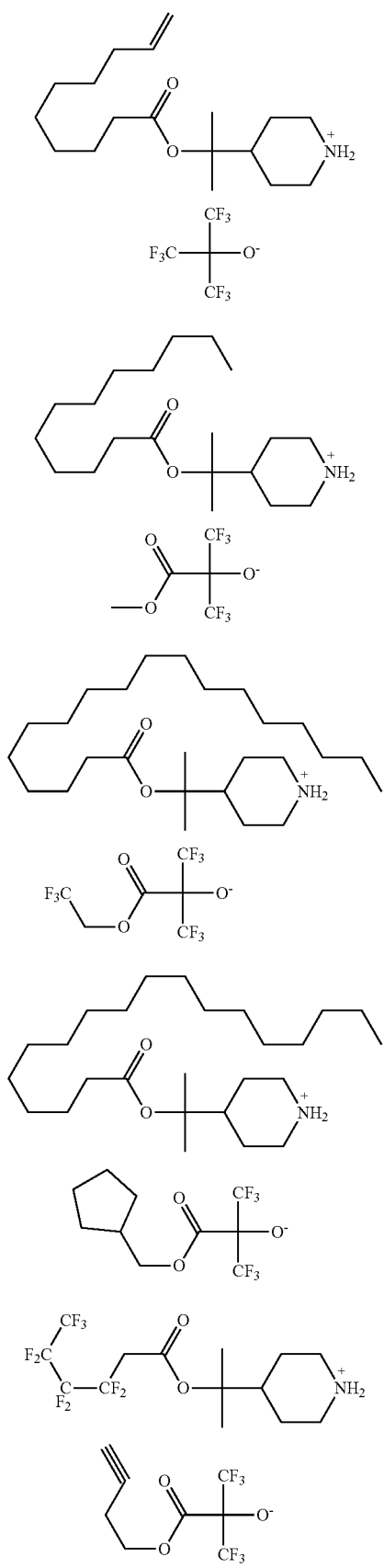
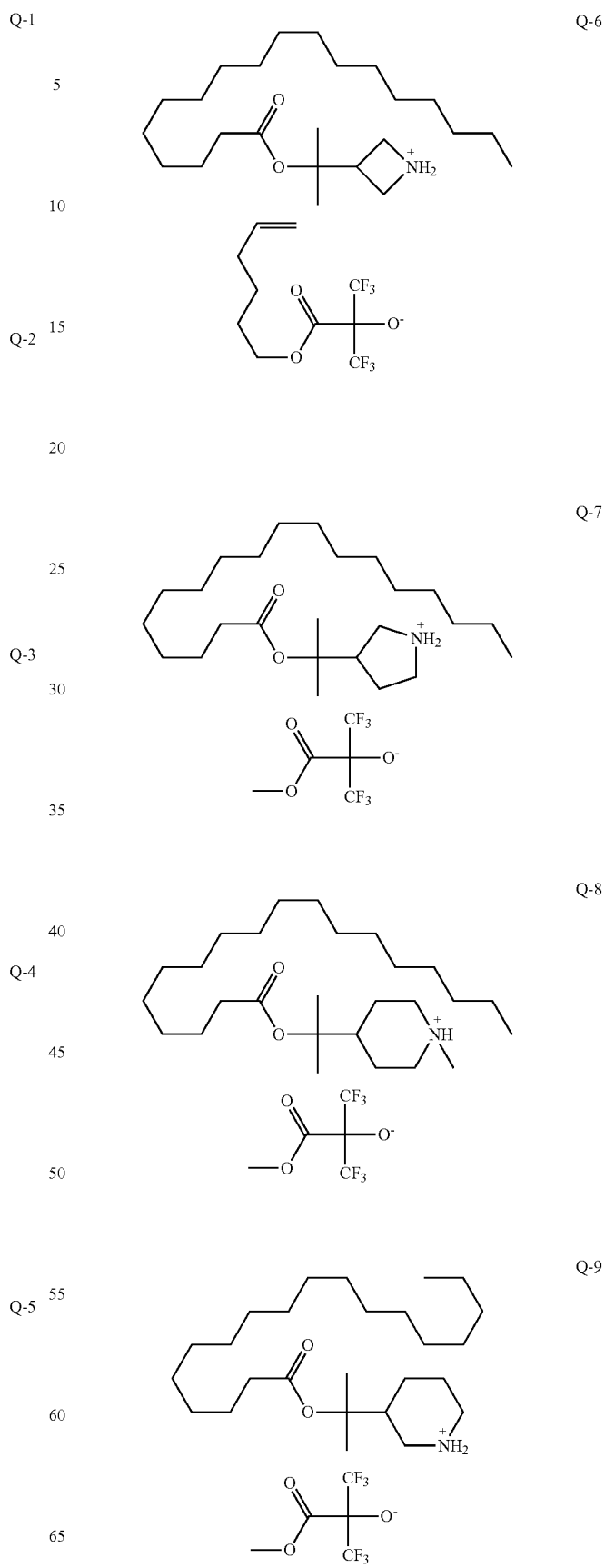

-continued
Q-10
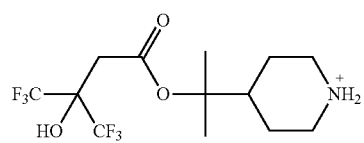
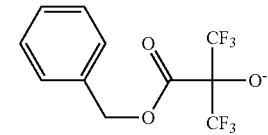
Q-11
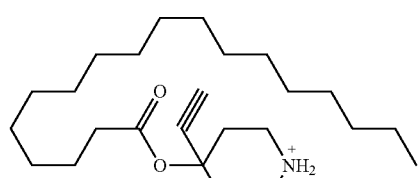
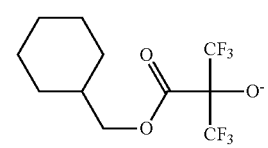
Q-12
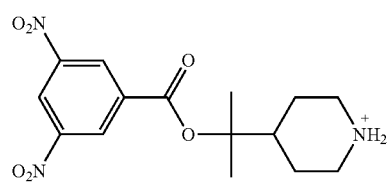
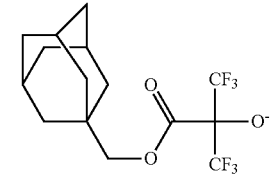
Q-13
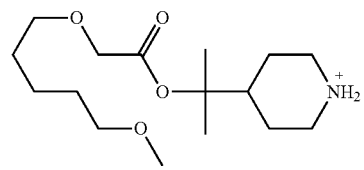
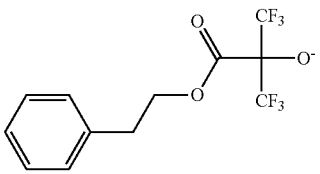
-continued
Q-14
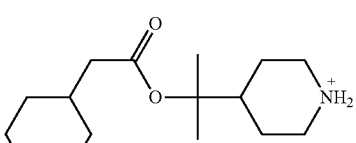
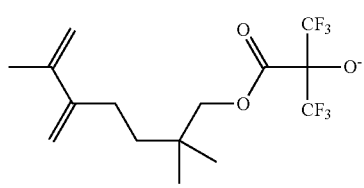
Q-15
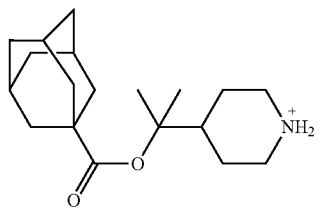
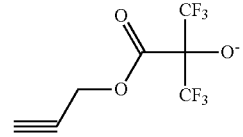
Q-16
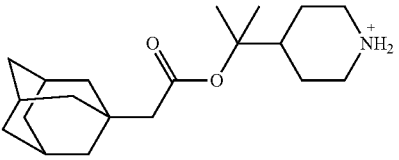
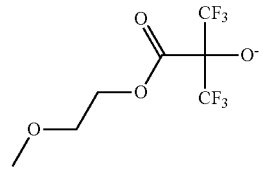
Q-17
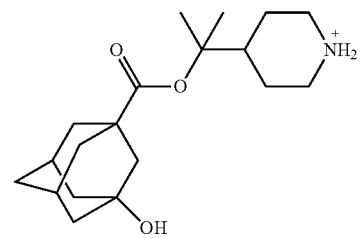
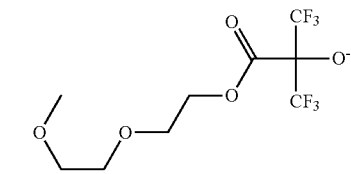

Q-18
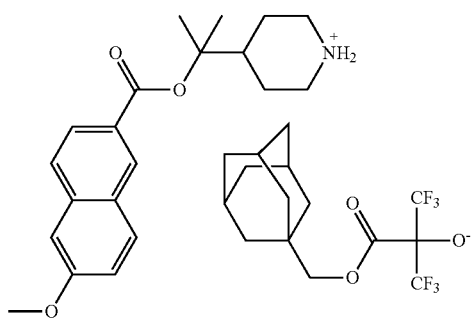
Q-19
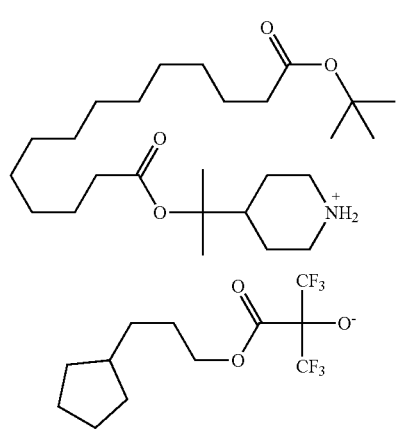
Q-20
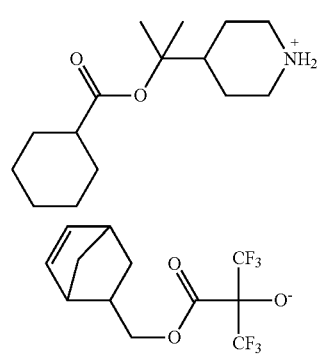
Q-21
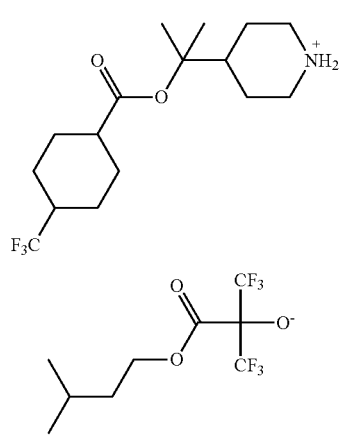
Q-22
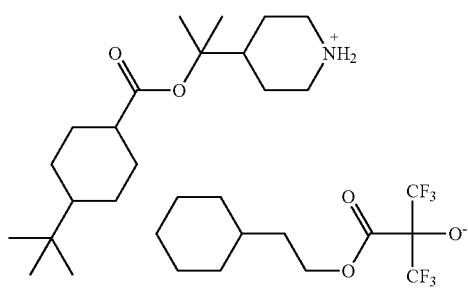
Q-23
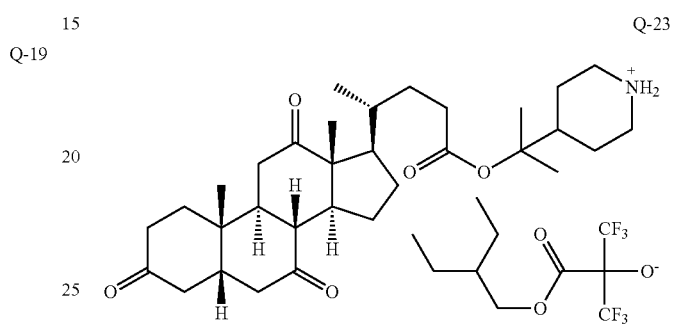
Q-24
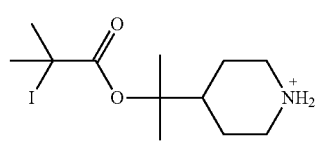
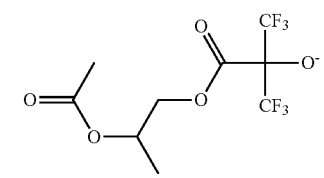
Q-25
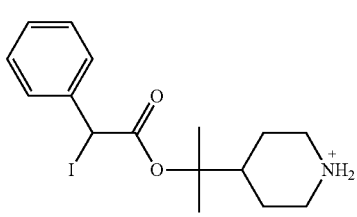
Q-26
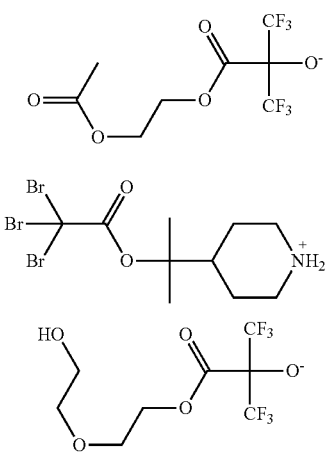

Q-27
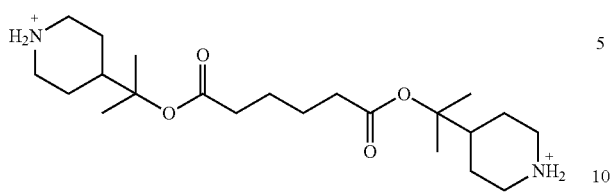
Q-28
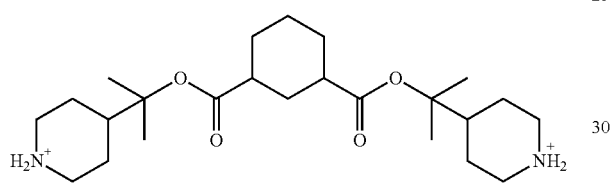
Q-29
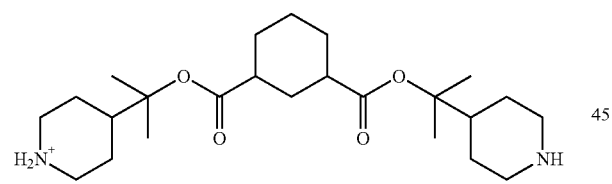
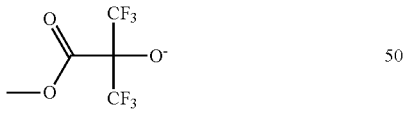
Q-30
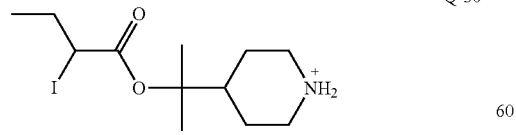
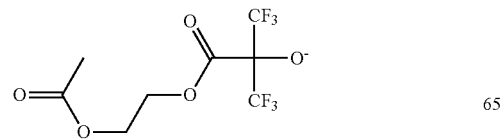
Q-31
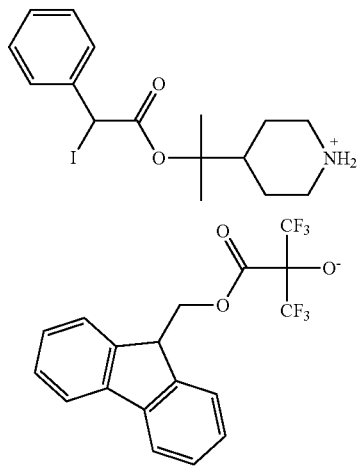
Q-32
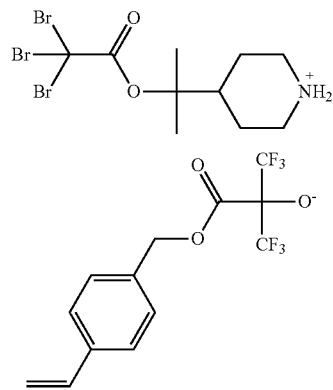
Q-33
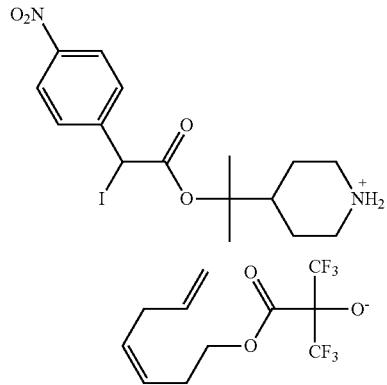
Q-34
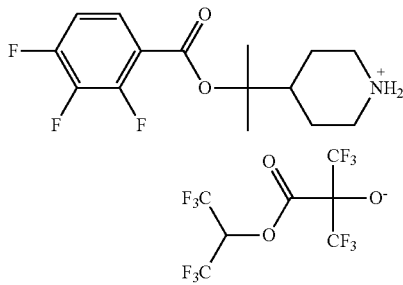

Q-35
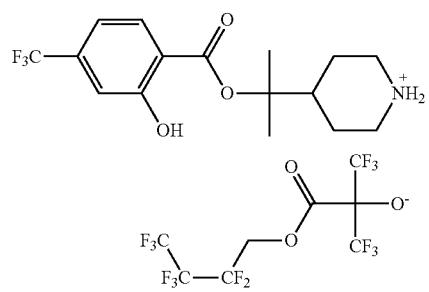
Q-36
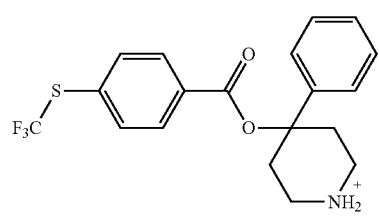
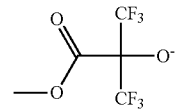
Q-37
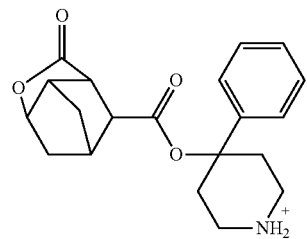
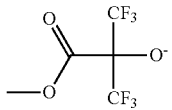
Q-38
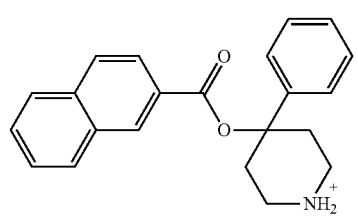
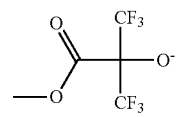
Q-39
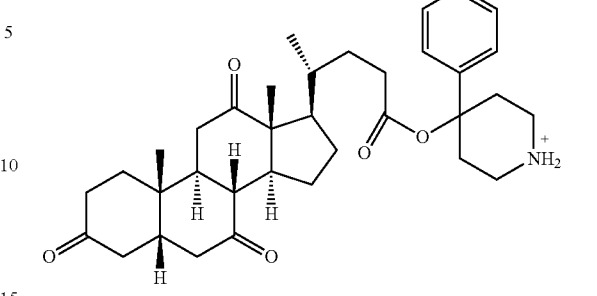
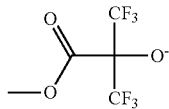
Q-40
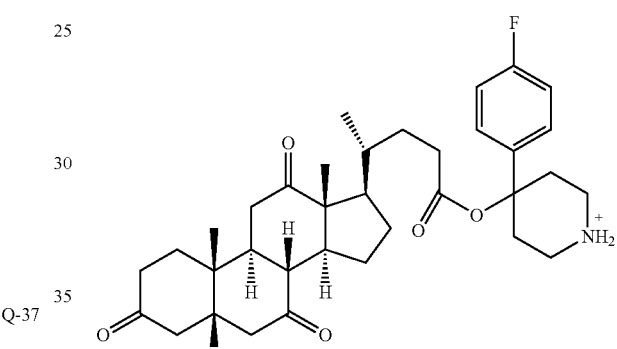
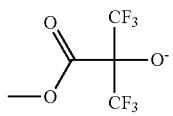
Q-41
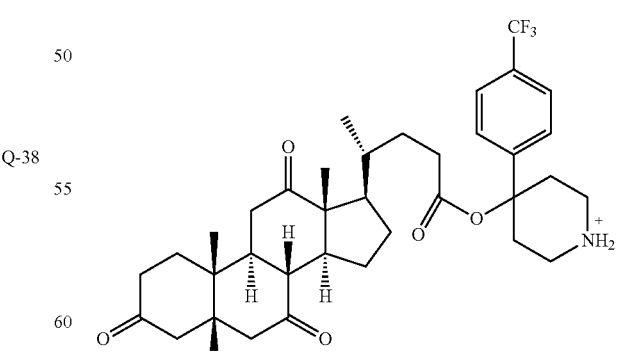
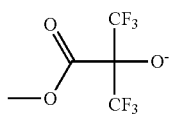

-continued

Q-42

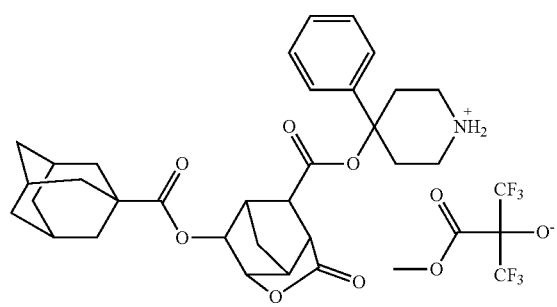

Q-43

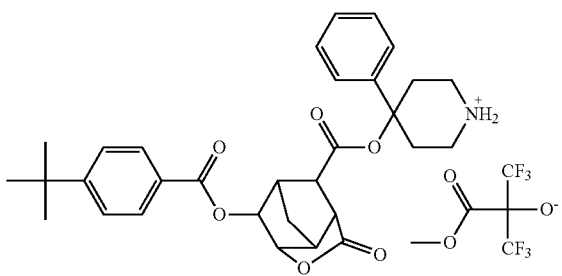

An amine compound (designated Amine-1) and a HFA group-containing compound (designated HFA-1) used in resist compositions have the structure shown below.

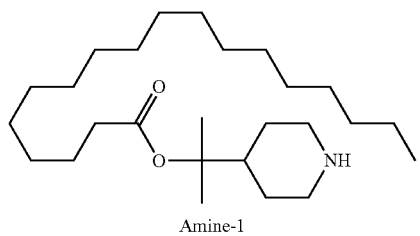
Amine-1

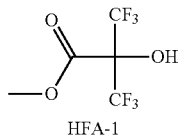
HFA-1

Synthesis Example

Synthesis of Base Polymer P-1

A base polymer P-1 was prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymer was analyzed for composition by $^1$H-NMR spectroscopy, and for Mw and Mw/Mn by GPC versus polystyrene standards using THF solvent.

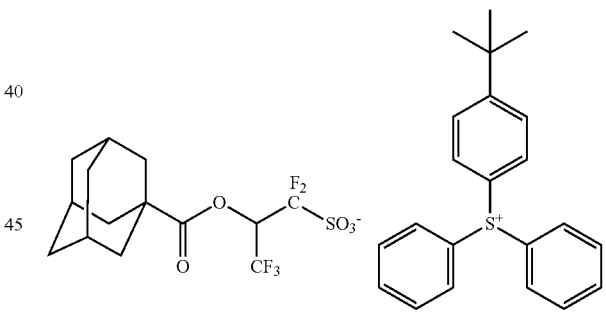

P-1
Mw = 8,300
Mw/Mn = 1.70

Examples 1 to 47 and Comparative Examples 1 to 6

(1) Preparation of Resist Compositions

Resist compositions were prepared by dissolving various components in a solvent in accordance with the recipe shown in Tables 1 to 3, and filtering through a filter having a pore size of 0.2 μm. The solvent contained 100 ppm of surfactant Polyfox PF-636 (Omnova Solutions Inc.).

The components in Tables 1 to 3 are as identified below.

Organic Solvent:

PGMEA (propylene glycol monomethyl ether acetate)

Acid Generator: PAG-1 of the Following Structural Formula

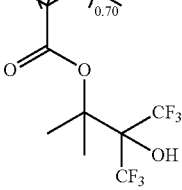
PAG-1

Water Repellency Improver: FP-1 of the Following Structural Formula

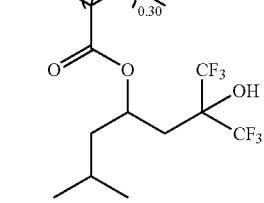

FP-1
Mw = 10,200
Mw/Mn = 1.67

Comparative Quenchers cQ-1 to cQ-6 of the Following Structural Formulae

Blend Quenchers bQ-1 to bQ-3 of the Following Structural Formulae

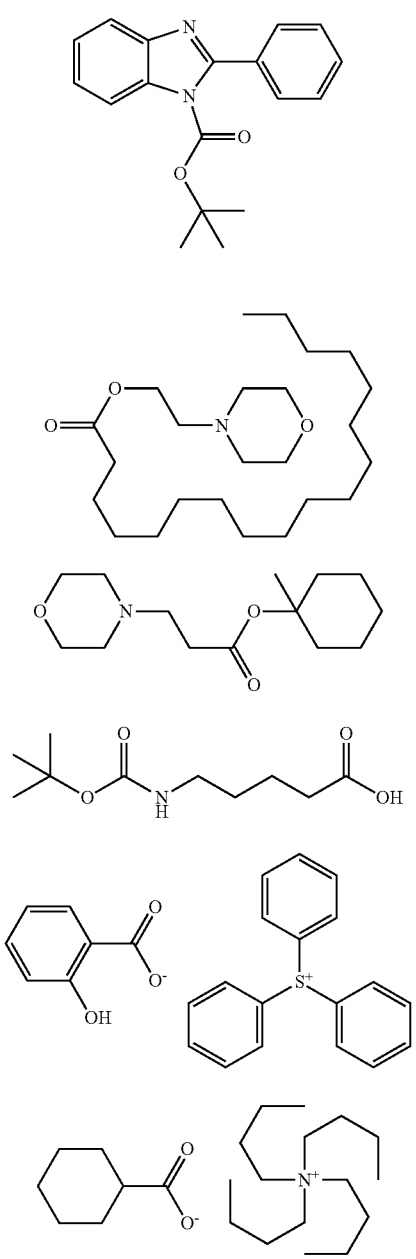

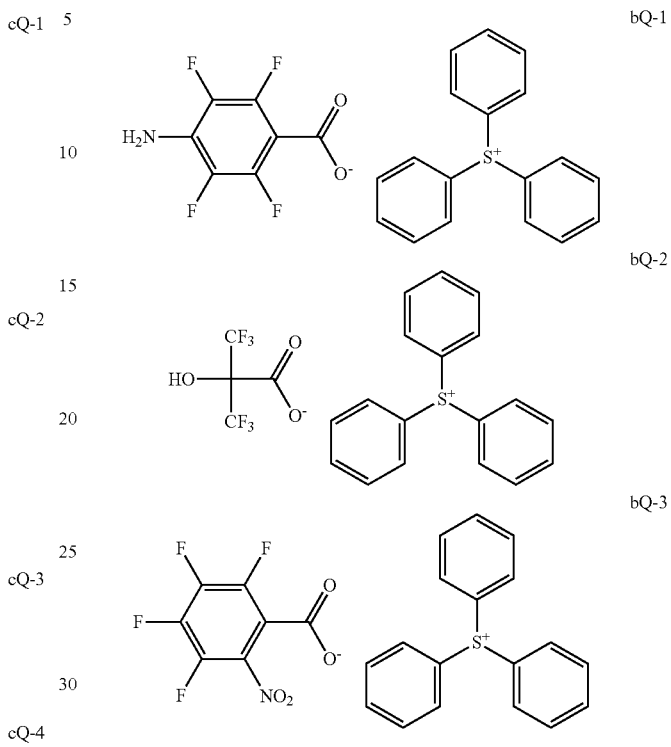

(2) Evaluation by ArF Immersion Lithography

Each of the resist compositions in Tables 1 to 3 was spin coated on a silicon wafer having an antireflective coating of 78 nm thick (ARC-29A by Nissan Chemical Industries. Ltd.), and baked on a hotplate at 100'C for 60 seconds to form a resist film of 170 nm thick. Using an ArF excimer laser immersion lithography scanner NSR-S610C (Nikon Corp., NA 1.10, σ0.98/0.78, 35° dipole illumination), the resist film was exposed to ArF radiation through a 6% halftone phase shift mask bearing a 1:1 line-and-space (LS) pattern with a size of 60 nm (on-wafer size). Water was used as the immersion liquid. The resist film was baked (PEB) at the temperature shown in Tables 1 to 3 for 60 seconds and developed in a 2.38 wt % tetramethylammonium hydroxide aqueous solution, yielding a 1:1 LS pattern with a size of 60 nm.

The LS pattern was observed under CD-SEM (CG6300 by Hitachi High-Technologies Corp.). The exposure dose (md/cm$^2$) to form a 1:1 LS pattern with a size of 60 nm was determined and reported as sensitivity. The LWR of the pattern was also measured. The results are also shown in Tables 1 to 3.

TABLE 1

| | | Polymer (pbw) | Acid generator (pbw) | Quencher (pbw) | Water repellency improver (pbw) | Organic solvent (pbw) | PEB temp. (° C.) | Sensitivity (mJ/cm$^2$) | LWR (nm) |
|---|---|---|---|---|---|---|---|---|---|
| Example | 1 | P-1 (100) | PAG-1 (6.0) | Q-1 (2.65) | FP-1 (4.0) | PGMEA (1,500) | 90 | 42 | 2.1 |
| | 2 | P-1 (100) | PAG-1 (6.0) | Q-2 (2.76) | FP-1 (4.0) | PGMEA (1,500) | 90 | 38 | 2.2 |
| | 3 | P-1 (100) | PAG-1 (6.0) | Q-3 (3.51) | FP-1 (4.0) | PGMEA (1,500) | 90 | 37 | 2.1 |

TABLE 1-continued

| | | Polymer (pbw) | Acid generator (pbw) | Quencher (pbw) | Water repellency improver (pbw) | Organic solvent (pbw) | PEB temp. (° C.) | Sensitivity (mJ/cm$^2$) | LWR (nm) |
|---|---|---|---|---|---|---|---|---|---|
| | 4 | P-1 (100) | PAG-1 (6.0) | Q-4 (3.51) | FP-1 (4.0) | PGMEA (1,500) | 90 | 42 | 2.4 |
| | 5 | P-1 (100) | PAG-1 (6.0) | Q-5 (3.33) | FP-1 (4.0) | PGMEA (1,500) | 90 | 46 | 2.4 |
| | 6 | P-1 (100) | PAG-1 (6.0) | Q-6 (3.37) | FP-1 (4.0) | PGMEA (1,500) | 90 | 45 | 2.3 |
| | 7 | P-1 (100) | PAG-1 (6.0) | Q-7 (3.11) | FP-1 (4.0) | PGMEA (1,500) | 90 | 40 | 2.2 |
| | 8 | P-1 (100) | PAG-1 (6.0) | Q-8 (3.25) | FP-1 (4.0) | PGMEA (1,500) | 90 | 41 | 2.6 |
| | 9 | P-1 (100) | PAG-1 (6.0) | Q-9 (3.18) | FP-1 (4.0) | PGMEA (1,500) | 90 | 42 | 2.5 |
| | 10 | P-1 (100) | PAG-1 (6.0) | Q-10 (3.27) | FP-1 (4.0) | PGMEA (1,500) | 90 | 38 | 2.3 |
| | 11 | P-1 (100) | PAG-1 (6.0) | Q-11 (3.50) | FP-1 (4.0) | PGMEA (1,500) | 90 | 41 | 2.2 |
| | 12 | P-1 (100) | PAG-1 (6.0) | Q-12 (3.49) | FP-1 (4.0) | PGMEA (1,500) | 90 | 46 | 2.4 |
| | 13 | P-1 (100) | PAG-1 (6.0) | Q-13 (3.10) | FP-1 (4.0) | PGMEA (1,500) | 90 | 41 | 2.6 |
| | 14 | P-1 (100) | PAG-1 (6.0) | Q-14 (3.17) | FP-1 (4.0) | PGMEA (1,500) | 90 | 44 | 2.5 |
| | 15 | P-1 (100) | PAG-1 (6.0) | Q-15 (2.78) | FP-1 (4.0) | PGMEA (1,500) | 90 | 45 | 2.6 |
| | 16 | P-1 (100) | PAG-1 (6.0) | Q-16 (2.95) | FP-1 (4.0) | PGMEA (1,500) | 90 | 44 | 2.6 |
| | 17 | P-1 (100) | PAG-1 (6.0) | Q-17 (3.18) | FP-1 (4.0) | PGMEA (1,500) | 90 | 47 | 2.4 |
| | 18 | P-1 (100) | PAG-1 (6.0) | Q-18 (3.44) | FP-1 (4.0) | PGMEA (1,500) | 90 | 46 | 2.4 |
| | 19 | P-1 (100) | PAG-1 (6.0) | Q-19 (3.81) | FP-1 (4.0) | PGMEA (1,500) | 90 | 42 | 2.3 |
| | 20 | P-1 (100) | PAG-1 (6.0) | Q-20 (2.86) | FP-1 (4.0) | PGMEA (1,500) | 90 | 44 | 2.4 |
| | 21 | P-1 (100) | PAG-1 (6.0) | Q-21 (3.02) | FP-1 (4.0) | PGMEA (1,500) | 90 | 43 | 2.2 |
| | 22 | P-1 (100) | PAG-1 (6.0) | Q-22 (3.16) | FP-1 (4.0) | PGMEA (1,500) | 90 | 45 | 2.3 |
| | 23 | P-1 (100) | PAG-1 (6.0) | Q-23 (4.12) | FP-1 (4.0) | PGMEA (1,500) | 90 | 47 | 2.3 |
| | 24 | P-1 (100) | PAG-1 (6.0) | Q-24 (3.26) | FP-1 (4.0) | PGMEA (1,500) | 90 | 44 | 2.6 |
| | 25 | P-1 (100) | PAG-1 (6.0) | Q-25 (3.43) | FP-1 (4.0) | PGMEA (1,500) | 90 | 41 | 2.4 |

TABLE 2

| | | Polymer (pbw) | Acid generator (pbw) | Quencher (pbw) | Water repellency improver (pbw) | Organic solvent (pbw) | PEB temp. (° C.) | Sensitivity (mJ/cm$^2$) | LWR (nm) |
|---|---|---|---|---|---|---|---|---|---|
| Example | 26 | P-1 (100) | PAG-1 (6.0) | Q-26 (3.61) | FP-1 (4.0) | PGMEA (1,500) | 90 | 44 | 2.6 |
| | 27 | P-1 (100) | PAG-1 (6.0) | Q-27 (2.65) | FP-1 (4.0) | PGMEA (1,500) | 90 | 39 | 2.7 |
| | 28 | P-1 (100) | PAG-1 (6.0) | Q-28 (2.73) | FP-1 (4.0) | PGMEA (1,500) | 90 | 39 | 2.6 |
| | 29 | P-1 (100) | PAG-1 (6.0) | Q-29 (2.02) | FP-1 (4.0) | PGMEA (1,500) | 90 | 38 | 2.8 |
| | 30 | P-1 (100) | PAG-1 (6.0) | Q-30 (3.19) | FP-1 (4.0) | PGMEA (1,500) | 90 | 43 | 2.3 |
| | 31 | P-1 (100) | PAG-1 (6.0) | Q-31 (3.89) | FP-1 (4.0) | PGMEA (1,500) | 90 | 41 | 2.7 |
| | 32 | P-1 (100) | PAG-1 (6.0) | Q-32 (3.75) | FP-1 (4.0) | PGMEA (1,500) | 90 | 40 | 2.5 |
| | 33 | P-1 (100) | PAG-1 (6.0) | Q-33 (3.69) | FP-1 (4.0) | PGMEA (1,500) | 90 | 42 | 2.4 |
| | 34 | P-1 (100) | PAG-1 (6.0) | Q-34 (3.32) | FP-1 (4.0) | PGMEA (1,500) | 90 | 41 | 2.2 |

TABLE 2-continued

| | Polymer (pbw) | Acid generator (pbw) | Quencher (pbw) | Water repellency improver (pbw) | Organic solvent (pbw) | PEB temp. (°C.) | Sensitivity (mJ/cm$^2$) | LWR (nm) |
|---|---|---|---|---|---|---|---|---|
| 35 | P-1 (100) | PAG-1 (6.0) | Q-35 (3.63) | FP-1 (4.0) | PGMEA (1,500) | 90 | 42 | 2.2 |
| 36 | P-1 (100) | PAG-1 (6.0) | Amine-1 (2.05) HFA-1 (1.13) | FP-1 (4.0) | PGMEA (1,500) | 90 | 42 | 2.7 |
| 37 | P-1 (100) | PAG-1 (6.0) | bQ-1 (2.35) Q-4 (1.76) | FP-1 (4.0) | PGMEA (1,500) | 90 | 39 | 2.0 |
| 38 | P-1 (100) | PAG-1 (6.0) | bQ-2 (2.37) Q-21 (1.51) | FP-1 (4.0) | PGMEA (1,500) | 90 | 37 | 2.1 |
| 39 | P-1 (100) | PAG-1 (6.0) | bQ-3 (2.51) Q-21 (1.51) | FP-1 (4.0) | PGMEA (1,500) | 90 | 39 | 2.1 |
| 40 | P-1 (100) | PAG-1 (6.0) | Q-36 (3.04) | FP-1 (4.0) | PGMEA (1,500) | 90 | 40 | 2.2 |
| 41 | P-1 (100) | PAG-1 (6.0) | Q-37 (2.84) | FP-1 (4.0) | PGMEA (1,500) | 90 | 42 | 2.4 |
| 42 | P-1 (100) | PAG-1 (6.0) | Q-38 (2.78) | FP-1 (4.0) | PGMEA (1,500) | 90 | 41 | 2.2 |
| 43 | P-1 (100) | PAG-1 (6.0) | Q-39 (3.94) | FP-1 (4.0) | PGMEA (1,500) | 90 | 45 | 2.3 |
| 44 | P-1 (100) | PAG-1 (6.0) | Q-40 (4.02) | FP-1 (4.0) | PGMEA (1,500) | 90 | 42 | 2.2 |
| 45 | P-1 (100) | PAG-1 (6.0) | Q-41 (4.27) | FP-1 (4.0) | PGMEA (1,500) | 90 | 42 | 2.1 |
| 46 | P-1 (100) | PAG-1 (6.0) | Q-42 (3.73) | FP-1 (4.0) | PGMEA (1,500) | 90 | 44 | 2.2 |
| 47 | P-1 (100) | PAG-1 (6.0) | Q-43 (3.72) | FP-1 (4.0) | PGMEA (1,500) | 90 | 45 | 2.1 |

TABLE 3

| | | Polymer (pbw) | Acid generator (pbw) | Quencher (pbw) | Water repellency improver (pbw) | Organic solvent (pbw) | PEB temp. (°C.) | Sensitivity (mJ/cm$^2$) | LWR (nm) |
|---|---|---|---|---|---|---|---|---|---|
| Comparative Example | 1 | P-1 (100) | PAG-1 (6.0) | cQ-1 (1.47) | FP-1 (4.0) | PGMEA (1,500) | 90 | 42 | 3.8 |
| | 2 | P-1 (100) | PAG-1 (6.0) | cQ-2 (1.99) | FP-1 (4.0) | PGMEA (1,500) | 90 | 43 | 3.6 |
| | 3 | P-1 (100) | PAG-1 (6.0) | cQ-3 (1.28) | FP-1 (4.0) | PGMEA (1,500) | 90 | 42 | 3.8 |
| | 4 | P-1 (100) | PAG-1 (6.0) | cQ-4 (1.09) | FP-1 (4.0) | PGMEA (1,500) | 90 | 40 | 3.6 |
| | 5 | P-1 (100) | PAG-1 (6.0) | cQ-5 (2.00) | FP-1 (4.0) | PGMEA (1,500) | 90 | 38 | 3.1 |
| | 6 | P-1 (100) | PAG-1 (6.0) | cQ-6 (1.85) | FP-1 (4.0) | PGMEA (1,500) | 90 | 37 | 3.2 |

It is evident from Tables 1 to 3 that the inventive resist compositions comprising a cyclic ammonium salt compound having a tertiary ester structure exhibit reduced values of LWR.

Japanese Patent Application No. 2020-109898 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, said quencher comprising a salt compound consisting of a cyclic ammonium cation having the formula (A-1) or (A-2) and a 1,1,1,3,3,3-hexafluoro-2-propoxide anion having bonded thereto a group selected from trifluoromethyl, hydrocarbylcarbonyl and hydrocarbyloxycarbonyl,

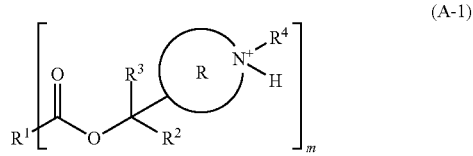

(A-1)

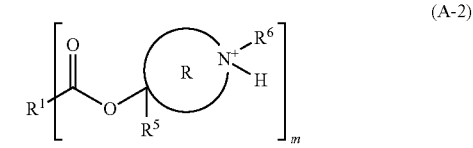

(A-2)

wherein m is an integer of 1 to 6,

R¹ is a $C_1$-$C_{30}$ hydrocarbyl group when m=1, a single bond or $C_1$-$C_{30}$ hydrocarbylene group when m=2, and a m-valent $C_1$-$C_{30}$ hydrocarbon group when m is an integer of 3 to 6, the hydrocarbyl, hydrocarbylene and m-valent hydrocarbon groups may contain at least one moiety selected from hydroxyl, thiol, ester bond, thioester bond, thionoester bond, ether bond, sulfide bond, halogen, nitro, amino, amide bond, sulfonyl, sulfonate bond, sultone ring, lactam ring, and carbonate, exclusive of an aromatic hydrocarbon group having iodine bonded to the aromatic ring, $R^2$ and $R^3$ are each independently a $C_1$-$C_6$ saturated hydrocarbyl group, $R^2$ and $R^3$ may bond together to form a ring with the carbon atom to which they are attached, $R^4$ and $R^6$ are each independently hydrogen, a $C_1$-$C_4$ alkyl group or $C_2$-$C_{12}$ alkoxycarbonyl group, $R^5$ is a $C_1$-$C_6$ aliphatic hydrocarbyl group or $C_6$-$C_{12}$ aryl group, which may be substituted with halogen or trifluoromethyl, the ring R is a $C_2$-$C_{10}$ alicyclic group containing the nitrogen atom.

2. The resist composition of claim 1 wherein the 1,1,1,3,3,3-hexafluoro-2-propoxide anion having bonded thereto a group selected from trifluoromethyl, hydrocarbylcarbonyl and hydrocarbyloxycarbonyl has the formula (B):

(B)

wherein $R^7$ is a trifluoromethyl group, $C_1$-$C_{20}$ hydrocarbyloxy group or $C_2$-$C_{21}$ hydrocarbyloxycarbonyl group, the hydrocarbyl moiety in the hydrocarbyloxy group or hydrocarbyloxycarbonyl group may contain at least one moiety selected from ether bond, ester bond, thiol, cyano, nitro, hydroxyl, sultone, sulfonate bond, amide bond, and halogen.

3. The resist composition of claim 1, further comprising an acid generator capable of generating a sulfonic acid, imide acid or methide acid.

4. The resist composition of claim 1, further comprising an organic solvent.

5. The resist composition of claim 1 wherein the base polymer comprises recurring units having the formula (a1) or recurring units having the formula (a2):

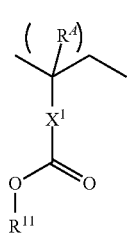

(a1)

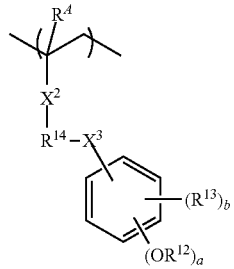

(a2)

wherein $R^A$ is each independently hydrogen or methyl, $X^1$ is a single bond, phenylene, naphthylene, or a $C_1$-$C_{12}$ linking group containing an ester bond and/or lactone ring, $X^2$ is a single bond or ester bond, $X^3$ is a single bond, ether bond or ester bond, $R^{11}$ and $R^{12}$ are each independently an acid labile group, $R^{13}$ is fluorine, trifluoromethyl, cyano or $C_1$-$C_6$ saturated hydrocarbyl group, $R^{14}$ is a single bond or a $C_1$-$C_6$ alkanediyl group in which some carbon may be replaced by an ether bond or ester bond, a is 1 or 2, b is an integer of 0 to 4, and 1≤a+b≤5.

6. The resist composition of claim 5 which is a chemically amplified positive resist composition.

7. The resist composition of claim 1 wherein the base polymer is free of an acid labile group.

8. The resist composition of claim 7 which is a chemically amplified negative resist composition.

9. The resist composition of claim 1, further comprising a surfactant.

10. The resist composition of claim 1 wherein the base polymer comprises recurring units of at least one type selected from recurring units having the formulae (f1) to (f3):

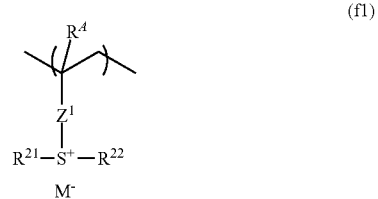

(f1)

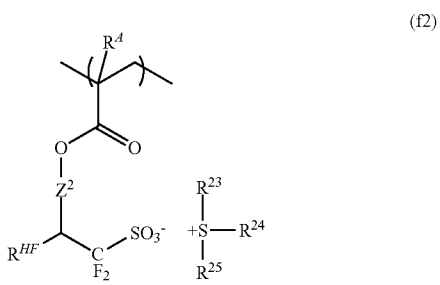

(f2)

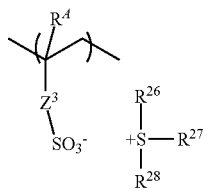

(f3)

wherein $R^A$ is each independently hydrogen or methyl, $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ saturated hydrocarbylene group which may contain a carbonyl moiety, ester bond or ether bond, $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety, $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, $R^{HF}$ is hydrogen or trifluoromethyl, and $M^-$ is a non-nucleophilic counter ion.

11. A pattern forming process comprising the steps of applying the resist composition of claim 1 to form a resist film on a substrate, exposing the resist film to high-energy radiation, and developing the exposed resist film in a developer.

12. The process of claim 11 wherein the high-energy radiation is i-line of wavelength 365 nm, ArF excimer laser of wavelength 193 nm or KrF excimer laser of wavelength 248 m.

13. The process of claim 11 wherein the high-energy radiation is EB or EUV of wavelength 3 to 15 nm.

* * * * *